United States Patent
Van Den Eynde et al.

(10) Patent No.: US 12,180,501 B2
(45) Date of Patent: Dec. 31, 2024

(54) VIRAL VECTORS ENCODING CANCER/TESTIS ANTIGENS FOR USE IN A METHOD OF PREVENTION OR TREATMENT OF CANCER

(71) Applicant: LUDWIG INSTITUTE FOR CANCER RESEARCH LTD., Zurich (CH)

(72) Inventors: Benoit J. Van Den Eynde, Oxford (GB); Carol S. Leung, Oxford (GB); Adrian V. S. Hill, Oxford (GB); Irina Redchenko, Oxford (GB)

(73) Assignee: Ludwig Institute for Cancer Research Ltd, Zurich (CH)

( * ) Notice: Subject to any disclaimer, the term of this patent is extended or adjusted under 35 U.S.C. 154(b) by 955 days.

(21) Appl. No.: 17/250,561

(22) PCT Filed: Jul. 30, 2019

(86) PCT No.: PCT/EP2019/070555
§ 371 (c)(1),
(2) Date: Feb. 3, 2021

(87) PCT Pub. No.: WO2020/025642
PCT Pub. Date: Feb. 6, 2020

(65) Prior Publication Data
US 2021/0171981 A1    Jun. 10, 2021

(30) Foreign Application Priority Data

Aug. 3, 2018   (GB) .................................. 1812647

(51) Int. Cl.
*C12N 15/863* (2006.01)
*A61K 39/00* (2006.01)
*A61P 35/00* (2006.01)
*C07K 14/74* (2006.01)
*C07K 16/28* (2006.01)
*C12N 15/86* (2006.01)

(52) U.S. Cl.
CPC ........ *C12N 15/86* (2013.01); *A61K 39/00118* (2018.08); *A61K 39/001186* (2018.08); *A61K 39/001188* (2018.08); *A61P 35/00* (2018.01); *C07K 14/70539* (2013.01); *C07K 16/2818* (2013.01); *C07K 16/2827* (2013.01); *A61K 2039/545* (2013.01); *A61K 2039/585* (2013.01); *C07K 2319/02* (2013.01); *C12N 2710/10043* (2013.01); *C12N 2710/24043* (2013.01)

(58) Field of Classification Search
None
See application file for complete search history.

(56) References Cited

U.S. PATENT DOCUMENTS

| | | | |
|---|---|---|---|
| 2003/0138454 A1 | 7/2003 | Hill et al. | |
| 2012/0027788 A1* | 2/2012 | Colloca | A61K 39/235 435/235.1 |

FOREIGN PATENT DOCUMENTS

| | | |
|---|---|---|
| WO | 2005/071093 A2 | 8/2005 |
| WO | 2011/128704 A1 | 10/2011 |
| WO | 2014141176 A1 | 9/2014 |
| WO | 2015/082922 A1 | 6/2015 |
| WO | 2015/092710 A1 | 6/2015 |

OTHER PUBLICATIONS

Cappuccini et al, "5T4 oncofoetal glycoprotein: an old Target for a novel prostate cancer immunotherapy", Oncotarget, 2017, pp. 1-16.
Kou et al., "Tissue plasminogen activator ((PA) signal sequence enhances immunogenicity of MVA-based vaccine against tuberculosis", Immunology Letters, vol. 190, 2017, pp. 51-57.
Thomas et al., "NY-ES0-1 Based Immunotherapy of Cancer. Current Perspectives", Frontiers in Immunology, vol. 9, 2018.
Cappuccini et al., "Immunogenicity and efficacy of the novel cancer vaccine based on simian adenovirus and MVA vectors alone and in combination with PD-1 mAb in a mouse model of prostate cancer", Cancer Immunology, Immunotherapy, NIH author manuscript, vol. 65, No. 6, 2016, pp. 701-713.
English Translation of Japanese Office Action for Application No. 2021-505666 dated Jul. 3, 2023, 13 pages.

* cited by examiner

*Primary Examiner* — Michael D Burkhart
(74) *Attorney, Agent, or Firm* — Fox Rothschild LLP

(57) ABSTRACT

Chimpanzee adenovirus (ChAd) and MVA virus vectors containing polynucleotide sequences encoding cancer antigens are administered sequentially to a subject in a suitable adjuvant in order to achieve a prime boost effect. The polynucleotides are expressed in situ following administration to provide a MAGEA3/linker/NY-ESO-1 fusion protein and variants thereof. Also, a hli/MAGEA3/linker/NY-ESO-1 fusion protein and variants thereof. An improved T cell response is found. In a particular synergistic therapeutic approach a triple combination of ChAdOx and MVA vectors together with chemotherapeutic agent and checkpoint inhibitor results in depleted myeloid derived suppressor cells (MDSC) and dramatically improves survival time in a mouse model of cancer.

28 Claims, 41 Drawing Sheets

Specification includes a Sequence Listing.

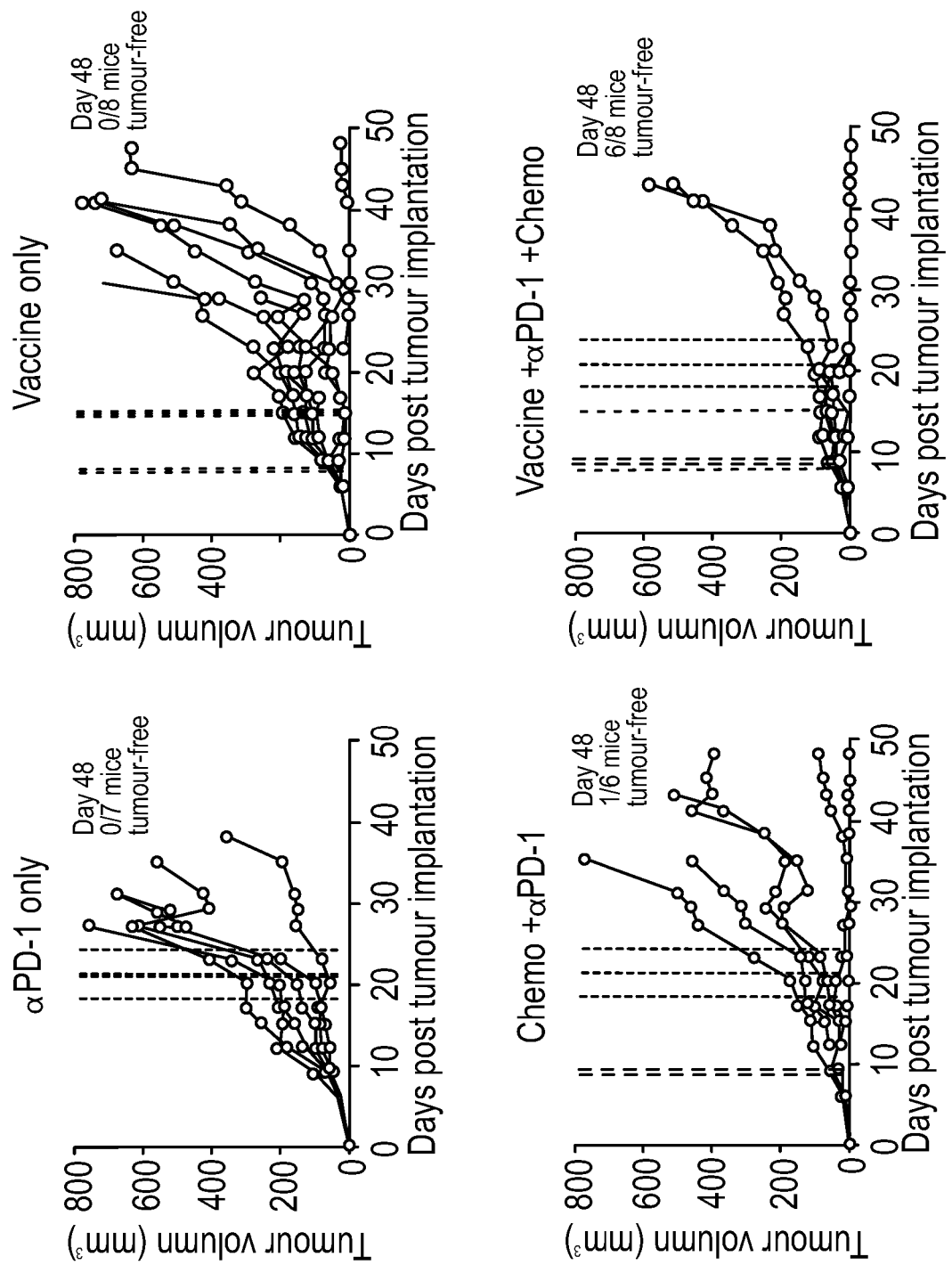
FIG.20 Continue.

PD1 expression on T cells

PD1 expression on P1A-specific T cells

SEQUENCE LISTING

```
<160> NUMBER OF SEQ ID NOS: 31

<210> SEQ ID NO 1
<211> LENGTH: 314
<212> TYPE: PRT
<213> ORGANISM: Homo sapiens

<400> SEQUENCE: 1

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205
```

Ile Ala Arg Glu Gly Asp Cys Ala Pro Glu Glu Lys Ile Trp Glu Glu
210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
            245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
290                 295                 300

His Glu Trp Val Leu Arg Glu Gly Glu Glu
305                 310

<210> SEQ ID NO 2
<211> LENGTH: 1753
<212> TYPE: PRT
<213> ORGANISM: Homo sapiens

<400> SEQUENCE: 2

Gly Ala Gly Ala Thr Thr Cys Thr Cys Gly Cys Cys Thr Gly Ala
1               5                   10                  15

Gly Cys Ala Ala Cys Gly Ala Gly Cys Gly Ala Cys Gly Cys Cys
                20                  25                  30

Thr Gly Ala Cys Gly Thr Cys Gly Gly Cys Gly Gly Ala Gly Gly
            35                  40                  45

Ala Ala Gly Cys Cys Gly Gly Cys Cys Ala Gly Gly Cys Thr Cys
        50                  55                  60

Gly Gly Thr Gly Ala Gly Gly Ala Gly Gly Cys Ala Ala Gly Thr
65                  70                  75                  80

Thr Cys Thr Gly Ala Gly Gly Gly Ala Cys Ala Ala Gly Cys Thr
                85                  90                  95

Gly Ala Cys Cys Thr Gly Gly Ala Gly Gly Ala Cys Cys Ala Gly Ala
                100                 105                 110

Gly Gly Cys Cys Cys Cys Cys Gly Gly Ala Gly Gly Ala Gly Cys Ala
            115                 120                 125

Cys Thr Gly Ala Ala Gly Gly Ala Ala Ala Gly Ala Thr Cys Thr
        130                 135                 140

Gly Cys Cys Ala Gly Thr Gly Gly Gly Thr Cys Thr Cys Cys Ala Thr
145                 150                 155                 160

Thr Gly Cys Cys Cys Ala Gly Cys Thr Cys Thr Gly Cys Cys Cys
                165                 170                 175

Ala Cys Ala Cys Thr Cys Cys Cys Gly Cys Cys Thr Gly Thr Thr Gly
                180                 185                 190

Cys Cys Cys Thr Gly Ala Cys Cys Ala Gly Ala Gly Thr Cys Ala Thr
            195                 200                 205

Cys Ala Thr Gly Cys Cys Thr Cys Thr Thr Gly Ala Gly Cys Ala Gly
        210                 215                 220

Ala Gly Gly Ala Gly Thr Cys Ala Gly Cys Thr Gly Cys Ala
225                 230                 235                 240

Ala Gly Cys Cys Thr Gly Ala Ala Gly Ala Gly Gly Cys Cys Thr
                245                 250                 255

Thr Gly Ala Gly Gly Cys Cys Cys Gly Ala Gly Gly Ala Gly Ala Gly

-continued

```
            260                 265                 270

Gly Cys Cys Cys Thr Gly Gly Gly Cys Cys Thr Gly Gly Thr Gly Gly
        275                 280                 285

Gly Thr Gly Cys Gly Cys Ala Gly Gly Cys Thr Cys Cys Thr Gly Cys
    290                 295                 300

Thr Ala Cys Thr Gly Ala Gly Gly Ala Gly Cys Ala Gly Gly Ala Gly
305                 310                 315                 320
Gly Cys Thr Gly Cys Cys Thr Cys Cys Thr Cys Cys Thr Cys Thr Thr
                325                 330                 335
Cys Thr Ala Cys Thr Cys Thr Ala Gly Thr Thr Gly Ala Ala Gly Thr
            340                 345                 350

Cys Ala Cys Cys Cys Thr Gly Gly Gly Gly Gly Ala Gly Gly Thr Gly
        355                 360                 365

Cys Cys Thr Gly Cys Thr Gly Cys Cys Gly Ala Gly Thr Cys Ala Cys
    370                 375                 380

Cys Ala Gly Ala Thr Cys Cys Thr Cys Cys Cys Cys Ala Gly Ala Gly
385                 390                 395                 400

Thr Cys Cys Thr Cys Ala Gly Gly Gly Ala Gly Cys Cys Thr Cys Cys
                405                 410                 415

Ala Gly Cys Cys Thr Cys Cys Cys Cys Ala Cys Thr Ala Cys Cys Ala
            420                 425                 430

Thr Gly Ala Ala Cys Thr Ala Cys Cys Cys Thr Cys Thr Cys Thr Gly
        435                 440                 445

Gly Ala Gly Cys Cys Ala Ala Thr Cys Cys Thr Ala Thr Gly Ala Gly
    450                 455                 460

Gly Ala Cys Thr Cys Cys Ala Gly Cys Ala Ala Cys Cys Ala Ala Gly
465                 470                 475                 480

Ala Ala Gly Ala Gly Gly Ala Gly Gly Gly Gly Cys Cys Ala Ala Gly
                485                 490                 495

Cys Ala Cys Cys Thr Thr Cys Cys Cys Thr Gly Ala Cys Cys Thr Gly
            500                 505                 510

Gly Ala Gly Thr Cys Cys Gly Ala Gly Thr Thr Cys Cys Ala Ala Gly
        515                 520                 525

Cys Ala Gly Cys Ala Cys Thr Cys Ala Gly Thr Ala Gly Gly Ala Ala
    530                 535                 540

Gly Gly Thr Gly Gly Cys Cys Gly Ala Gly Thr Thr Gly Gly Thr Thr
545                 550                 555                 560

Cys Ala Thr Thr Thr Thr Cys Thr Gly Cys Thr Cys Cys Thr Cys Ala
                565                 570                 575

Ala Gly Thr Ala Thr Cys Gly Ala Gly Cys Cys Ala Gly Gly Gly Ala
            580                 585                 590

Gly Cys Cys Gly Gly Thr Cys Ala Cys Ala Ala Ala Gly Gly Cys Ala
        595                 600                 605

Gly Ala Ala Ala Thr Gly Cys Thr Gly Gly Gly Gly Ala Gly Thr Gly
    610                 615                 620

Thr Cys Gly Thr Cys Gly Gly Ala Ala Ala Thr Thr Gly Gly Cys Ala
625                 630                 635                 640

Gly Thr Ala Thr Thr Thr Cys Thr Thr Thr Cys Cys Thr Gly Thr Gly
                645                 650                 655

Ala Thr Cys Thr Thr Cys Ala Gly Cys Ala Ala Ala Gly Cys Thr Thr
            660                 665                 670

Cys Cys Ala Gly Thr Thr Cys Cys Thr Thr Gly Cys Ala Gly Cys Thr
        675                 680                 685
```

-continued

Gly Gly Thr Cys Thr Thr Thr Gly Gly Cys Ala Thr Cys Gly Ala Gly
    690             695                 700
Cys Thr Gly Ala Thr Gly Gly Ala Ala Gly Thr Gly Gly Ala Cys Cys
705                 710              715                 720
Cys Cys Ala Thr Cys Gly Gly Cys Cys Ala Cys Thr Gly Thr Gly Ala
                725                 730                 735
Cys Ala Thr Cys Thr Thr Thr Gly Cys Cys Ala Cys Cys Thr Gly Cys
                740                 745                 750
Cys Thr Gly Gly Gly Cys Cys Thr Cys Thr Cys Cys Thr Ala Cys Gly
        755                 760                 765
Ala Thr Gly Gly Cys Cys Thr Cys Thr Gly Gly Gly Thr Gly Ala
    770                 775                 780
Cys Ala Ala Thr Cys Ala Gly Ala Thr Cys Ala Thr Gly Cys Cys Cys
785                 790                 795                 800
Ala Ala Gly Gly Cys Ala Gly Gly Cys Cys Thr Cys Thr Gly Ala
        805                 810                 815
Thr Ala Ala Thr Cys Gly Thr Cys Cys Thr Gly Gly Cys Cys Ala Thr
            820                 825                 830
Ala Ala Thr Cys Gly Cys Ala Ala Gly Ala Gly Ala Gly Gly Gly Cys
        835                 840                 845
Gly Ala Cys Thr Gly Thr Gly Cys Cys Cys Thr Gly Ala Gly Gly
    850                 855                 860
Ala Gly Ala Ala Ala Ala Thr Cys Thr Gly Gly Gly Ala Gly Gly Ala
865                 870                 875                 880
Gly Cys Thr Gly Ala Gly Thr Gly Thr Gly Thr Thr Ala Gly Ala Gly
            885                 890                 895
Gly Thr Gly Thr Thr Thr Gly Ala Gly Gly Gly Ala Gly Gly Gly
        900                 905                 910
Ala Ala Gly Ala Cys Ala Gly Thr Ala Thr Cys Thr Thr Gly Gly Gly
        915                 920                 925
Gly Gly Ala Thr Cys Cys Cys Ala Ala Gly Ala Ala Gly Cys Thr Gly
    930                 935                 940
Cys Thr Cys Ala Cys Cys Cys Ala Ala Cys Ala Thr Thr Thr Cys Gly
945                 950                 955                 960
Thr Gly Cys Ala Gly Gly Ala Ala Ala Cys Thr Ala Cys Cys Thr
            965                 970                 975
Gly Gly Ala Gly Thr Ala Cys Cys Gly Gly Cys Ala Gly Gly Thr Cys
        980                 985                 990
Cys Cys Cys Gly Gly Cys Ala Gly Thr Gly Ala Thr Cys Cys Thr Gly
        995                 1000                1005
Cys Ala Thr Gly Thr Thr Ala Thr Gly Ala Ala Thr Thr Cys Cys
    1010                1015                1020
Thr Gly Thr Gly Gly Gly Thr Cys Cys Ala Ala Gly Gly Gly
        1025                1030                1035
Cys Cys Cys Thr Cys Gly Thr Thr Gly Ala Ala Ala Cys Cys Ala
    1040                1045                1050
Gly Cys Thr Ala Thr Gly Thr Gly Ala Ala Ala Gly Thr Cys Cys
    1055                1060                1065
Thr Gly Cys Ala Cys Cys Ala Thr Ala Thr Gly Gly Thr Ala Ala
    1070                1075                1080
Ala Gly Ala Thr Cys Ala Gly Thr Gly Gly Ala Gly Gly Ala Cys
    1085                1090                1095

-continued

```
Cys Thr Cys Ala Cys Ala Thr Thr Cys Cys Thr Ala Cys Cys
    1100            1105            1110

Cys Ala Cys Cys Cys Cys Thr Gly Cys Ala Thr Gly Ala Gly Thr
    1115            1120            1125

Gly Gly Gly Thr Thr Thr Thr Gly Ala Gly Ala Gly Ala Gly Gly
    1130            1135            1140

Gly Gly Gly Ala Ala Gly Ala Gly Thr Gly Ala Gly Thr Cys Thr
    1145            1150            1155

Gly Ala Gly Cys Ala Cys Gly Ala Gly Thr Thr Gly Cys Ala Gly
    1160            1165            1170

Cys Cys Ala Gly Gly Gly Cys Ala Gly Thr Gly Gly Gly Ala
    1175            1180            1185

Gly Gly Gly Gly Gly Thr Cys Thr Gly Gly Gly Cys Cys Ala Gly
    1190            1195            1200

Thr Gly Cys Ala Cys Cys Thr Cys Cys Gly Gly Gly Gly Cys
    1205            1210            1215

Cys Gly Cys Ala Thr Cys Cys Cys Thr Ala Gly Thr Thr Thr
    1220            1225            1230

Cys Cys Ala Cys Thr Gly Cys Cys Thr Gly Thr Gly
    1235            1240            1245

Ala Cys Gly Thr Gly Ala Gly Gly Cys Cys Cys Ala Thr Thr Cys
    1250            1255            1260

Thr Thr Cys Ala Cys Thr Cys Thr Thr Gly Ala Ala Gly Cys
    1265            1270            1275

Gly Ala Gly Cys Ala Gly Thr Cys Ala Gly Cys Ala Thr Thr Cys
    1280            1285            1290

Thr Thr Ala Gly Thr Ala Gly Thr Gly Gly Thr Thr Thr Cys
    1295            1300            1305

Thr Gly Thr Thr Cys Thr Gly Thr Thr Gly Gly Ala Thr Gly Ala
    1310            1315            1320

Cys Thr Thr Thr Gly Ala Gly Ala Thr Thr Ala Thr Thr Cys Thr
    1325            1330            1335

Thr Thr Gly Thr Thr Thr Cys Cys Thr Gly Thr Thr Gly Gly Ala
    1340            1345            1350

Gly Thr Thr Gly Thr Thr Cys Ala Ala Ala Thr Gly Thr Thr Cys
    1355            1360            1365

Cys Thr Thr Thr Thr Ala Ala Cys Gly Gly Ala Thr Gly Gly Thr
    1370            1375            1380

Thr Gly Ala Ala Thr Gly Ala Gly Cys Gly Thr Cys Ala Gly Cys
    1385            1390            1395

Ala Thr Cys Cys Ala Gly Gly Thr Thr Thr Ala Thr Gly Ala Ala
    1400            1405            1410

Thr Gly Ala Cys Ala Gly Thr Ala Gly Thr Cys Ala Cys Ala Cys
    1415            1420            1425

Ala Thr Ala Gly Thr Gly Cys Thr Gly Thr Thr Thr Ala Thr Ala
    1430            1435            1440

Thr Ala Gly Thr Thr Thr Ala Gly Gly Ala Gly Thr Ala Ala Gly
    1445            1450            1455

Ala Gly Thr Cys Thr Thr Thr Gly Thr Thr Thr Thr Thr Ala Cys
    1460            1465            1470

Thr Cys Ala Ala Ala Thr Thr Gly Gly Gly Ala Ala Ala Thr Cys
    1475            1480            1485

Cys Ala Thr Thr Cys Cys Ala Thr Thr Thr Thr Gly Thr Gly Ala
```

-continued

```
                1490                1495                1500

Ala  Thr  Thr  Gly  Thr  Gly  Ala  Cys  Ala  Thr  Ala  Ala  Thr  Ala  Ala
       1505                1510                1515

Thr  Ala  Gly  Cys  Ala  Gly  Thr  Gly  Gly  Thr  Ala  Ala  Ala  Ala  Gly
       1520                1525                1530

Thr  Ala  Thr  Thr  Thr  Gly  Cys  Thr  Thr  Ala  Ala  Ala  Ala  Thr  Thr
       1535                1540                1545

Gly  Thr  Gly  Ala  Gly  Cys  Gly  Ala  Ala  Thr  Ala  Gly  Cys  Ala
       1550                1555                1560

Ala  Thr  Ala  Ala  Cys  Ala  Thr  Ala  Cys  Ala  Thr  Gly  Ala  Gly  Ala
       1565                1570                1575

Thr  Ala  Ala  Cys  Thr  Cys  Ala  Ala  Gly  Ala  Ala  Ala  Thr  Cys  Ala
       1580                1585                1590

Ala  Ala  Ala  Gly  Ala  Thr  Ala  Gly  Thr  Thr  Gly  Ala  Thr  Thr  Cys
       1595                1600                1605

Thr  Thr  Gly  Cys  Cys  Thr  Thr  Gly  Thr  Ala  Cys  Cys  Thr  Cys  Ala
       1610                1615                1620

Ala  Thr  Cys  Thr  Ala  Thr  Thr  Cys  Thr  Gly  Thr  Ala  Ala  Ala  Ala
       1625                1630                1635

Thr  Thr  Ala  Ala  Ala  Cys  Ala  Ala  Ala  Thr  Ala  Thr  Gly  Cys  Ala
       1640                1645                1650

Ala  Ala  Cys  Cys  Ala  Gly  Gly  Ala  Thr  Thr  Thr  Cys  Cys  Thr  Thr
       1655                1660                1665

Gly  Ala  Cys  Thr  Thr  Cys  Thr  Thr  Thr  Gly  Ala  Gly  Ala  Ala  Thr
       1670                1675                1680

Gly  Cys  Ala  Ala  Gly  Cys  Gly  Ala  Ala  Ala  Thr  Thr  Ala  Ala  Ala
       1685                1690                1695

Thr  Cys  Thr  Gly  Ala  Ala  Thr  Ala  Ala  Ala  Thr  Ala  Ala  Thr  Thr
       1700                1705                1710

Cys  Thr  Thr  Cys  Cys  Thr  Cys  Thr  Thr  Cys  Ala  Ala  Ala  Ala  Ala
       1715                1720                1725

Ala  Ala  Ala  Ala  Ala  Ala  Ala  Ala  Ala  Ala  Ala  Ala  Ala  Ala  Ala
       1730                1735                1740

Ala  Ala  Ala  Ala  Ala  Ala  Ala  Ala  Ala  Ala
       1745                1750

<210> SEQ ID NO 3
<211> LENGTH: 180
<212> TYPE: PRT
<213> ORGANISM: Homo sapiens

<400> SEQUENCE: 3

Met  Gln  Ala  Glu  Gly  Arg  Gly  Thr  Gly  Gly  Ser  Thr  Gly  Asp  Ala  Asp
  1                5                   10                  15

Gly  Pro  Gly  Gly  Pro  Gly  Ile  Pro  Asp  Gly  Pro  Gly  Gly  Asn  Ala  Gly
              20                  25                  30

Gly  Pro  Gly  Glu  Ala  Gly  Ala  Thr  Gly  Gly  Arg  Gly  Pro  Arg  Gly  Ala
          35                  40                  45

Gly  Ala  Ala  Arg  Ala  Ser  Gly  Pro  Gly  Gly  Gly  Ala  Pro  Arg  Gly  Pro
      50                  55                  60

His  Gly  Gly  Ala  Ala  Ser  Gly  Leu  Asn  Gly  Cys  Cys  Arg  Cys  Gly  Ala
 65                  70                  75                  80

Arg  Gly  Pro  Glu  Ser  Arg  Leu  Leu  Glu  Phe  Tyr  Leu  Ala  Met  Pro  Phe
                  85                  90                  95
```

```
Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 4
<211> LENGTH: 752
<212> TYPE: DNA
<213> ORGANISM: Homo sapiens

<400> SEQUENCE: 4
atcctcgtgg gccctgacct tctctctgag agccgggcag aggctccgga gccatgcagg      60
ccgaaggccg gggcacaggg ggttcgacgg gcgatgctga tggcccagga ggccctggca     120
ttcctgatgg cccagggggc aatgctggcg gcccaggaga ggcgggtgcc acgggcggca     180
gaggtccccg ggcgcagggg cagcaaggg cctcggggcc gggaggaggc ccccgcggg      240 gtccgcatgg cggcgcggct cagggctga atggatgctg cagatgcggg gccagggggc     300
cggagagccg cctgcttgag ttctacctcg ccatgccttt cgcgacaccc atggaagcag     360
agctggcccg caggagcctg gcccaggatg ccccaccgct tcccgtgcca ggggtgcttc     420
tgaaggagtt cactgtgtcc ggcaacatac tgactatccg actgactgct gcagaccacc     480
gccaactgca gctctccatc agctcctgtc tccagcagct ttccctgttg atgtggatca     540
cgcagtgctt tctgcccgtg tttttggctc agcctcccct agggcagagg cgctaagccc     600
agcctggcgc cccttcctag gtcatgcctc ctcccctagg gaatggtccc agcacgagtg     660
gccagttcat tgtgggggcc tgattgtttg tcgctggagg aggacggctt acatgtttgt     720
ttctgtagaa aataaaactg agctacgaaa aa                                   752

<210> SEQ ID NO 5
<211> LENGTH: 180
<212> TYPE: PRT
<213> ORGANISM: Homo sapiens

<400> SEQUENCE: 5

Met Gln Ala Glu Gly Gln Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Gln Leu His Ile Thr Met Pro Phe
                85                  90                  95

Ser Ser Pro Met Glu Ala Glu Leu Val Arg Arg Ile Leu Ser Arg Asp
```

```
            100                 105                 110
Ala Ala Pro Leu Pro Arg Pro Gly Ala Val Leu Lys Asp Phe Thr Val
        115                 120                 125

Ser Gly Asn Leu Leu Phe Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Ala Pro Ser
                165                 170                 175

Gly Gln Arg Arg
            180

<210> SEQ ID NO 6
<211> LENGTH: 296
<212> TYPE: PRT
<213> ORGANISM: Homo sapiens

<400> SEQUENCE: 6

Met His Arg Arg Arg Ser Arg Ser Cys Arg Glu Asp Gln Lys Pro Val
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Val Leu Thr Lys Cys Gln Glu Glu Val Ser His Ile Pro Ala Val His
    210                 215                 220

Pro Gly Ser Phe Arg Pro Lys Cys Asp Glu Asn Gly Asn Tyr Leu Pro
225                 230                 235                 240

Leu Gln Cys Tyr Gly Ser Ile Gly Tyr Cys Trp Cys Val Phe Pro Asn
                245                 250                 255

Gly Thr Glu Val Pro Asn Thr Arg Ser Arg Gly His His Asn Cys Ser
            260                 265                 270

Glu Ser Leu Glu Leu Glu Asp Pro Ser Ser Gly Leu Gly Val Thr Lys
        275                 280                 285
```

```
Gln Asp Leu Gly Pro Val Pro Met
    290                 295

<210> SEQ ID NO 7
<211> LENGTH: 26
<212> TYPE: PRT
<213> ORGANISM: Homo sapiens

<400> SEQUENCE: 7

Gly Ala Leu Tyr Thr Gly Phe Ser Ile Leu Val Thr Leu Leu Leu Ala
1               5                   10                  15

Gly Gln Ala Thr Thr Ala Tyr Phe Leu Tyr
            20                  25

<210> SEQ ID NO 8
<211> LENGTH: 562
<212> TYPE: PRT
<213> ORGANISM: Homo sapiens

<400> SEQUENCE: 8

Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
        35                  40                  45

Ile Tyr Gln Gln His Gln Ser Trp Leu Arg Pro Val Leu Arg Ser Asn
    50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
            100                 105                 110

Gly Phe Ala Gly Lys Cys Cys Glu Ile Asp Thr Arg Ala Thr Cys Tyr
        115                 120                 125

Glu Asp Gln Gly Ile Ser Tyr Arg Gly Thr Trp Ser Thr Ala Glu Ser
    130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
            180                 185                 190

Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
    210                 215                 220

Gly Thr His Ser Leu Thr Glu Ser Gly Ala Ser Cys Leu Pro Trp Asn
225                 230                 235                 240

Ser Met Ile Leu Ile Gly Lys Val Tyr Thr Ala Gln Asn Pro Ser Ala
                245                 250                 255

Gln Ala Leu Gly Leu Gly Lys His Asn Tyr Cys Arg Asn Pro Asp Gly
            260                 265                 270

Asp Ala Lys Pro Trp Cys His Val Leu Lys Asn Arg Arg Leu Thr Trp
        275                 280                 285
```

```
Glu Tyr Cys Asp Val Pro Ser Cys Ser Thr Cys Gly Leu Arg Gln Tyr
    290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
                325                 330                 335

Gly Glu Arg Phe Leu Cys Gly Gly Ile Leu Ile Ser Ser Cys Trp Ile
                340                 345                 350

Leu Ser Ala Ala His Cys Phe Gln Glu Arg Phe Pro Pro His His Leu
        355                 360                 365

Thr Val Ile Leu Gly Arg Thr Tyr Arg Val Val Pro Gly Glu Glu Glu
    370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
                405                 410                 415

Ser Arg Cys Ala Gln Glu Ser Ser Val Val Arg Thr Val Cys Leu Pro
                420                 425                 430

Pro Ala Asp Leu Gln Leu Pro Asp Trp Thr Glu Cys Glu Leu Ser Gly
        435                 440                 445

Tyr Gly Lys His Glu Ala Leu Ser Pro Phe Tyr Ser Glu Arg Leu Lys
    450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
                485                 490                 495

Arg Ser Gly Gly Pro Gln Ala Asn Leu His Asp Ala Cys Gln Gly Asp
                500                 505                 510

Ser Gly Gly Pro Leu Val Cys Leu Asn Asp Gly Arg Met Thr Leu Val
        515                 520                 525

Gly Ile Ile Ser Trp Gly Leu Gly Cys Gly Gln Lys Asp Val Pro Gly
    530                 535                 540

Val Tyr Thr Lys Val Thr Asn Tyr Leu Asp Trp Ile Arg Asp Asn Met
545                 550                 555                 560

Arg Pro

<210> SEQ ID NO 9
<211> LENGTH: 21
<212> TYPE: PRT
<213> ORGANISM: Homo sapiens

<400> SEQUENCE: 9

Asp Ala Met Lys Arg Gly Leu Cys Cys Val Leu Leu Leu Cys Gly Ala
1               5                   10                  15

Val Phe Val Ser Pro
            20

<210> SEQ ID NO 10
<211> LENGTH: 1506
<212> TYPE: DNA
<213> ORGANISM: Artificial Sequence
<220> FEATURE:
<223> OTHER INFORMATION: Polynucleotide construct for vector
      ChAdOx1_MAGE_NYESO

<400> SEQUENCE: 10
atgcccctgg aacagcggag ccagcactgc aagcctgagg aaggcctgga agccagaggc      60
```

```
gaagctctgg gactcgtggg agcacaggct ccagccaccg aagaacagga agccgccagc    120
agcagctcca ccctggtgga agtgacactg ggcgaagtgc ctgccgccga gtctcctgat    180
cctcctcagt ctcctcaggg cgccagctct ctgcccacca ccatgaacta ccccctgtgg    240
tcccagtcct acgaggacag cagcaaccag gaagaagagg gccccagcac cttccccgac    300
ctggaatctg aattccaggc cgccctgagc cggaaggtgg ccgaactggt gcacttcctg    360
ctgctgaagt accgggccag agaacccgtg accaaggccg agatgctggg cagcgtcgtg    420
ggcaactggc agtacttctt ccccgtgatc ttctccaagg ccagctccag cctgcagctg    480
gtgttcggca tcgagctgat ggaagtggac cccatcggac acctgtacat cttcgccacc    540
tgtctgggcc tgagctacga tggcctgctg ggcgacaacc agatcatgcc caaagccggc    600
ctgctgatca tcgtgctggc catcattgcc cgcgagggcg attgtgcccc cgaggaaaag    660
atctgggagg aactgagcgt gctggaagtg ttcgagggaa gagaggactc catcctgggc    720 gacccccaaga agctgctgac ccagcacttc gtgcaggaaa actacctgga gtatagacag    780
gtgcccggca gcgaccctgc ctgctacgaa tttctgtggg gccctagagc actggtggaa    840
accagctacg tgaaagtgct gcaccacatg gtcaagatca gcggcggacc ccacatcagc    900
tacccccctc tgcatgaatg ggtgctgaga gagggcgagg aaggcggagg acctggcgga    960
ggaatgcagg ctgaaggcag aggcacaggc ggctctacag cgacgctga tggaccaggc   1020 ggacccggaa ttccagatgg ccctggcgga aatgctggcg ggcctggcga agctggcgct   1080
acaggcggaa aggacctag aggcgctggc gccgctagag cttctggacc aggggggaggc   1140 gctcctagag gacctcatgg cggagctgcc tctggcctga acggctgctg tagatgtggc   1200
gccagaggcc ccgaaagcag actgctggaa ttctacctgg ccatgccttt cgccacccc   1260 atggaagctg agctggccag aagaagcctg gcccaggacg ctcctccact gcctgtgcca   1320
ggcgtgctgc tgaaagaatt caccgtgtcc ggcaacatcc tgaccatccg gctgacagcc   1380
gccgaccaca gacagctgca gctgagcatc agcagctgcc tgcagcagct gtccctgctg   1440
atgtggatca cccagtgctt tctgcccgtg tttctggccc agcctcctag cggacagcgg   1500
agatga                                                              1506
```

<210> SEQ ID NO 11
<211> LENGTH: 501
<212> TYPE: PRT
<213> ORGANISM: Artificial Sequence
<220> FEATURE:
<223> OTHER INFORMATION: Translated protein of ChAdOx1_MAGE_NYESO

<400> SEQUENCE: 11

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95
```

```
Thr Phe Pro Asp Leu Glu Ser Glu Phe Gln Ala Ala Leu Ser Arg Lys
                100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
        130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
            245                 250                 255

Glu Tyr Arg Gln Val Pro Gly Ser Asp Pro Ala Cys Tyr Glu Phe Leu
        260                 265                 270

Trp Gly Pro Arg Ala Leu Val Glu Thr Ser Tyr Val Lys Val Leu His
            275                 280                 285

His Met Val Lys Ile Ser Gly Gly Pro His Ile Ser Tyr Pro Pro Leu
        290                 295                 300

His Glu Trp Val Leu Arg Glu Gly Glu Glu Gly Gly Pro Gly Gly Gly
305                 310                 315                 320

Gly Met Gln Ala Glu Gly Arg Gly Thr Gly Gly Ser Thr Gly Asp Ala
            325                 330                 335

Asp Gly Pro Gly Gly Pro Gly Ile Pro Asp Gly Pro Gly Gly Asn Ala
        340                 345                 350

Gly Gly Pro Gly Glu Ala Gly Ala Thr Gly Gly Arg Gly Pro Arg Gly
            355                 360                 365

Ala Gly Ala Ala Arg Ala Ser Gly Pro Gly Gly Gly Ala Pro Arg Gly
        370                 375                 380

Pro His Gly Gly Ala Ala Ser Gly Leu Asn Gly Cys Cys Arg Cys Gly
385                 390                 395                 400

Ala Arg Gly Pro Glu Ser Arg Leu Leu Glu Phe Tyr Leu Ala Met Pro
            405                 410                 415

Phe Ala Thr Pro Met Glu Ala Glu Leu Ala Arg Arg Ser Leu Ala Gln
        420                 425                 430

Asp Ala Pro Pro Leu Pro Val Pro Gly Val Leu Leu Lys Glu Phe Thr
        435                 440                 445

Val Ser Gly Asn Ile Leu Thr Ile Arg Leu Thr Ala Ala Asp His Arg
        450                 455                 460

Gln Leu Gln Leu Ser Ile Ser Ser Cys Leu Gln Gln Leu Ser Leu Leu
465                 470                 475                 480

Met Trp Ile Thr Gln Cys Phe Leu Pro Val Phe Leu Ala Gln Pro Pro
            485                 490                 495

Ser Gly Gln Arg Arg
            500
```

<210> SEQ ID NO 12
<211> LENGTH: 1584
<212> TYPE: DNA
<213> ORGANISM: Artificial Sequence
<220> FEATURE:
<223> OTHER INFORMATION: Polynucleotide construct for vector
ChAdOx1_hIi_MAGE_NY-ESO-1

<400> SEQUENCE: 12

| | |
|---|---|
| atgggcgccc tgtacaccgg ctttagcatc ctcgtgaccc tgctgctggc cggacaggct | 60 |
| accaccgcct actttctgta ccccctggaa cagcggagcc agcactgcaa gcctgaggaa | 120 |
| ggcctggaag ccagaggcga agctctggga ctcgtgggag cacaggctcc agccaccgaa | 180 |
| gaacaggaag ccgccagcag ctctagcacc ctggtggaag tgacactggg cgaagtgcct | 240 |
| gccgccgagt ctcctgatcc tcctcagtct cctcagggcg ccagctctct gcccaccacc | 300 |
| atgaactacc ccctgtggtc ccagtcctac gaggacagca gcaaccagga agaagagggc | 360 |
| cccagcacct tccccgacct ggaatctgaa ttccaggccg ccctgagccg gaaggtggcc | 420 |
| gaactggtgc actttctgct gctgaagtac cgggccagag aacccgtgac caaggccgag | 480 |
| atgctgggca cgtcgtggg caactggcag tacttcttcc ccgtgatctt ctccaaggcc | 540 |
| agctccagcc tgcagctggt gttcggcatc gagctgatgg aagtggaccc catcggacac | 600 |
| ctgtacatct tcgccacctg tctgggcctg agctacgatg gcctgctggg cgacaaccag | 660 |
| atcatgccca agccggcct gctgatcatc gtgctggcca tcattgcccg cgagggcgat | 720 |
| tgtgccccccg aggaaaagat ctgggaggaa ctgagcgtgc tggaagtgtt cgaggaagat | 780 |
| gaggactcca tcctgggcga ccccaagaag ctgctgaccc agcacttcgt gcaggaaaac | 840 |
| tacctggagt atagacaggt gcccggcagc gaccctgcct gctacgaatt tctgtggggc | 900 |
| cctagagcac tggtggaaac cagctacgtg aaagtgctgc accacatggt caagatcagc | 960 |
| ggcgaccccc acatcagcta cccccctctg catgaatggg tgctgagaga gggcgaggaa | 1020 |
| ggcgaggac ctggcggagg aatgcaggct gaaggcagag cacaggcgg ctctacaggc | 1080 |
| gacgctgatg gaccaggcgg acccggaatt ccagatggcc ctggcggaaa tgctggcggg | 1140 |
| cctggcgaag ctggcgctac aggcggaaga ggacctagag cgctggcgc cgctagcagca | 1200 |
| tctggaccag ggggaggcgc tcctagagga cctcatggcg gagctgcctc tggcctgaac | 1260 |
| ggctgctgta gatgtggcgc cagaggcccc gaaagcagac tgctggaatt ctacctggcc | 1320 |
| atgcctttcg ccacccccat ggaagctgag ctggccagaa gaagcctggc ccaggacgct | 1380 |
| cctccactgc ctgtgccagg cgtgctgctg aaagaattca ccgtgtccgg caacatcctg | 1440 |
| accatccggc tgacagccgc cgaccacaga cagctgcagc tgagcatcag cagctgcctg | 1500 |
| cagcagctgt ccctgctgat gtggatcacc cagtgctttc tgcccgtgtt tctggcccag | 1560 |
| cctcctagcg gacagcggag atga | 1584 |

<210> SEQ ID NO 13
<211> LENGTH: 527
<212> TYPE: PRT
<213> ORGANISM: Artificial Sequence
<220> FEATURE:
<223> OTHER INFORMATION: Translated protein sequence of
ChAdOx1_hIi_MAGE_NY-ESO-1

<400> SEQUENCE: 13

Met Gly Ala Leu Tyr Thr Gly Phe Ser Ile Leu Val Thr Leu Leu Leu
1               5                   10                  15

Ala Gly Gln Ala Thr Thr Ala Tyr Phe Leu Tyr Pro Leu Glu Gln Arg

```
            20                  25                  30
Ser Gln His Cys Lys Pro Glu Glu Gly Leu Glu Ala Arg Gly Glu Ala
                35                  40                  45
Leu Gly Leu Val Gly Ala Gln Ala Pro Ala Thr Glu Gln Glu Ala
    50                  55                  60
Ala Ser Ser Ser Thr Leu Val Glu Val Thr Leu Gly Glu Val Pro
65                  70                  75                  80
Ala Ala Glu Ser Pro Asp Pro Pro Gln Ser Pro Gln Gly Ala Ser Ser
                85                  90                  95
Leu Pro Thr Thr Met Asn Tyr Pro Leu Trp Ser Gln Ser Tyr Glu Asp
                100                 105                 110
Ser Ser Asn Gln Glu Glu Gly Pro Ser Thr Phe Pro Asp Leu Glu
            115                 120                 125
Ser Glu Phe Gln Ala Ala Leu Ser Arg Lys Val Ala Glu Leu Val His
            130                 135                 140
Phe Leu Leu Leu Lys Tyr Arg Ala Arg Glu Pro Val Thr Lys Ala Glu
145                 150                 155                 160
Met Leu Gly Ser Val Val Gly Asn Trp Gln Tyr Phe Phe Pro Val Ile
                165                 170                 175
Phe Ser Lys Ala Ser Ser Ser Leu Gln Leu Val Phe Gly Ile Glu Leu
                180                 185                 190
Met Glu Val Asp Pro Ile Gly His Leu Tyr Ile Phe Ala Thr Cys Leu
                195                 200                 205
Gly Leu Ser Tyr Asp Gly Leu Leu Gly Asp Asn Gln Ile Met Pro Lys
            210                 215                 220
Ala Gly Leu Leu Ile Ile Val Leu Ala Ile Ile Ala Arg Glu Gly Asp
225                 230                 235                 240
Cys Ala Pro Glu Glu Lys Ile Trp Glu Glu Leu Ser Val Leu Glu Val
                245                 250                 255
Phe Glu Gly Arg Glu Asp Ser Ile Leu Gly Asp Pro Lys Lys Leu Leu
                260                 265                 270
Thr Gln His Phe Val Gln Glu Asn Tyr Leu Glu Tyr Arg Gln Val Pro
            275                 280                 285
Gly Ser Asp Pro Ala Cys Tyr Glu Phe Leu Trp Gly Pro Arg Ala Leu
            290                 295                 300
Val Glu Thr Ser Tyr Val Lys Val Leu His His Met Val Lys Ile Ser
305                 310                 315                 320
Gly Gly Pro His Ile Ser Tyr Pro Pro Leu His Glu Trp Val Leu Arg
                325                 330                 335
Glu Gly Glu Glu Gly Gly Pro Gly Gly Met Gln Ala Glu Gly
            340                 345                 350
Arg Gly Thr Gly Gly Ser Thr Gly Asp Ala Asp Gly Pro Gly Gly Pro
            355                 360                 365
Gly Ile Pro Asp Gly Pro Gly Gly Asn Ala Gly Gly Pro Gly Glu Ala
            370                 375                 380
Gly Ala Thr Gly Gly Arg Gly Pro Arg Gly Ala Gly Ala Ala Arg Ala
385                 390                 395                 400
Ser Gly Pro Gly Gly Gly Ala Pro Arg Gly Pro His Gly Gly Ala Ala
                405                 410                 415
Ser Gly Leu Asn Gly Cys Cys Arg Cys Gly Ala Arg Gly Pro Glu Ser
                420                 425                 430
Arg Leu Leu Glu Phe Tyr Leu Ala Met Pro Phe Ala Thr Pro Met Glu
            435                 440                 445
```

Ala Glu Leu Ala Arg Arg Ser Leu Ala Gln Asp Ala Pro Pro Leu Pro
    450                 455                 460

Val Pro Gly Val Leu Leu Lys Glu Phe Thr Val Ser Gly Asn Ile Leu
465                 470                 475                 480

Thr Ile Arg Leu Thr Ala Ala Asp His Arg Gln Leu Gln Leu Ser Ile
                485                 490                 495

Ser Ser Cys Leu Gln Gln Leu Ser Leu Leu Met Trp Ile Thr Gln Cys
            500                 505                 510

Phe Leu Pro Val Phe Leu Ala Gln Pro Pro Ser Gly Gln Arg Arg
            515                 520                 525

<210> SEQ ID NO 14
<211> LENGTH: 1569
<212> TYPE: DNA
<213> ORGANISM: Artificial Sequence
<220> FEATURE:
<223> OTHER INFORMATION: Polynucleotide construct for vector
      ChAdOx1_tPA_MAGE_NY-ESO-1

<400> SEQUENCE: 14
atggacgcca tgaagcgggg cctgtgttgc gtgctgctgc tgtgtggcgc tgtgttcgtg      60 tccccccac tggaacagag aagccagcac tgcaagcccg aggaaggcct ggaagccaga     120
ggcgaagctc tgggactcgt gggagcacag gctccagcca ccgaagaaca ggaagccgcc     180
agcagctcta gcaccctggt ggaagtgaca ctgggcgaag tgcctgccgc cgagtctcct     240
gatcctcctc agtctcctca gggcgccagc tctctgccca ccaccatgaa ctacccctg     300 tggtcccagt cctacgagga cagcagcaac caggaagaag agggccccag caccttcccc     360
gacctggaat ctgaattcca ggccgccctg agcggaagg tggccgaact ggtgcacttc     420
ctgctgctga gtaccgggc cagagaaccc gtgaccaagg ccgagatgct gggcagcgtc     480
gtgggcaact ggcagtactt cttccccgtg atcttctcca aggccagctc cagcctgcag     540
ctggtgttcg gcatcgagct gatggaagtg accccatcg acacctgta catcttcgcc     600 acctgtctgg gcctgagcta cgatggcctc ctgggcgaca accagatcat gcccaaagcc     660
ggcctgctga tcatcgtgct ggccatcatt gcccgcgagg gcgattgtgc ccccgaggaa     720
aagatctggg aggaactgag cgtgctggaa gtgttcgagg gaagagagga ctccatcctg     780
ggcgacccca agaagctgct gacccagcac ttcgtgcagg aaaactacct ggagtataga     840
caggtgcccg gcagcgaccc tgcctgctac gaatttctgt ggggccctag agcactggtg     900
gaaaccagct acgtgaaagt gctgcaccac atggtcaaga tcagcggcgg accccacatc     960
agctacccac ctctgcacga atgggtgctg agagagggcg aagaaggcgg aggacctggc    1020
ggaggaatgc aggctgaagg cagaggcaca ggcggctcta caggcgacgc tgatggacca    1080
ggcggacccg gaattccaga tggccctggc ggaaatgctg gcgggcctgg cgaagctggc    1140
gctacaggcg gaagaggacc tagaggcgct ggcgccgcta gcatctggg ccaggggga    1200 ggcgctccta gaggacctca tggcggagct gcctctggcc tgaatggctg ctgtagatgt    1260
ggcgccagag gccccgaaag cagactgctg gaatttctacc tggccatgcc tttcgccacc    1320
cccatggaag ctgagctggc cagaagaagc ctggcccagg acgctcctcc actgcctgtg    1380
ccaggggtgc tgctgaaaga attcaccgtg tccggcaaca tcctgaccat ccggctgaca    1440
gccgccgacc acagacagct gcagctgagc atcagcagct gctgcagca gctgtccctg    1500 ctgatgtgga tcacccagtg ctttctgccc gtgtttctgg cccagcctcc tagcggacag    1560

```
cggagatga                                                             1569
```

<210> SEQ ID NO 15
<211> LENGTH: 522
<212> TYPE: PRT
<213> ORGANISM: Artificial Sequence
<220> FEATURE:
<223> OTHER INFORMATION: Translated protein of ChAdOx1_tPA_MAGE_NY-ESO-1

<400> SEQUENCE: 15

```
Met Asp Ala Met Lys Arg Gly Leu Cys Cys Val Leu Leu Leu Cys Gly
1               5                   10                  15

Ala Val Phe Val Ser Pro Pro Leu Glu Gln Arg Ser Gln His Cys Lys
            20                  25                  30

Pro Glu Glu Gly Leu Glu Ala Arg Gly Glu Ala Leu Gly Leu Val Gly
        35                  40                  45

Ala Gln Ala Pro Ala Thr Glu Glu Gln Glu Ala Ala Ser Ser Ser Ser
    50                  55                  60

Thr Leu Val Glu Val Thr Leu Gly Glu Val Pro Ala Ala Glu Ser Pro
65                  70                  75                  80

Asp Pro Pro Gln Ser Pro Gln Gly Ala Ser Ser Leu Pro Thr Thr Met
                85                  90                  95

Asn Tyr Pro Leu Trp Ser Gln Ser Tyr Glu Asp Ser Ser Asn Gln Glu
            100                 105                 110

Glu Glu Gly Pro Ser Thr Phe Pro Asp Leu Glu Ser Glu Phe Gln Ala
        115                 120                 125

Ala Leu Ser Arg Lys Val Ala Glu Leu Val His Phe Leu Leu Leu Lys
    130                 135                 140

Tyr Arg Ala Arg Glu Pro Val Thr Lys Ala Glu Met Leu Gly Ser Val
145                 150                 155                 160

Val Gly Asn Trp Gln Tyr Phe Phe Pro Val Ile Phe Ser Lys Ala Ser
                165                 170                 175

Ser Ser Leu Gln Leu Val Phe Gly Ile Glu Leu Met Glu Val Asp Pro
            180                 185                 190

Ile Gly His Leu Tyr Ile Phe Ala Thr Cys Leu Gly Leu Ser Tyr Asp
        195                 200                 205

Gly Leu Leu Gly Asp Asn Gln Ile Met Pro Lys Ala Gly Leu Leu Ile
    210                 215                 220

Ile Val Leu Ala Ile Ile Ala Arg Glu Gly Asp Cys Ala Pro Glu Glu
225                 230                 235                 240

Lys Ile Trp Glu Glu Leu Ser Val Leu Glu Val Phe Glu Gly Arg Glu
                245                 250                 255

Asp Ser Ile Leu Gly Asp Pro Lys Lys Leu Leu Thr Gln His Phe Val
            260                 265                 270

Gln Glu Asn Tyr Leu Glu Tyr Arg Gln Val Pro Gly Ser Asp Pro Ala
        275                 280                 285

Cys Tyr Glu Phe Leu Trp Gly Pro Arg Ala Leu Val Glu Thr Ser Tyr
    290                 295                 300

Val Lys Val Leu His His Met Val Lys Ile Ser Gly Gly Pro His Ile
305                 310                 315                 320

Ser Tyr Pro Pro Leu His Glu Trp Val Leu Arg Glu Gly Glu Glu Gly
                325                 330                 335

Gly Gly Pro Gly Gly Gly Met Gln Ala Glu Gly Arg Gly Thr Gly Gly
            340                 345                 350

Ser Thr Gly Asp Ala Asp Gly Pro Gly Gly Pro Gly Ile Pro Asp Gly
```

```
                  355                 360                 365
Pro Gly Gly Asn Ala Gly Gly Pro Gly Glu Ala Gly Ala Thr Gly Gly
            370                 375                 380

Arg Gly Pro Arg Gly Ala Gly Ala Ala Arg Ala Ser Gly Pro Gly Gly
385                 390                 395                 400

Gly Ala Pro Arg Gly Pro His Gly Gly Ala Ala Ser Gly Leu Asn Gly
                405                 410                 415

Cys Cys Arg Cys Gly Ala Arg Gly Pro Glu Ser Arg Leu Leu Glu Phe
            420                 425                 430

Tyr Leu Ala Met Pro Phe Ala Thr Pro Met Glu Ala Glu Leu Ala Arg
                435                 440                 445

Arg Ser Leu Ala Gln Asp Ala Pro Pro Leu Pro Val Pro Gly Val Leu
            450                 455                 460

Leu Lys Glu Phe Thr Val Ser Gly Asn Ile Leu Thr Ile Arg Leu Thr
465                 470                 475                 480

Ala Ala Asp His Arg Gln Leu Gln Leu Ser Ile Ser Ser Cys Leu Gln
                485                 490                 495

Gln Leu Ser Leu Leu Met Trp Ile Thr Gln Cys Phe Leu Pro Val Phe
            500                 505                 510

Leu Ala Gln Pro Pro Ser Gly Gln Arg Arg
            515                 520

<210> SEQ ID NO 16
<211> LENGTH: 945
<212> TYPE: DNA
<213> ORGANISM: Artificial Sequence
<220> FEATURE:
<223> OTHER INFORMATION: Polynucleotide construct for vector MVA_MAGEA3

<400> SEQUENCE: 16 atgccctgg aacagcggag ccagcactgc aagcctgagg aaggcctgga agccagaggc      60
gaagctctgg gactcgtggg agcacaggct ccagccaccg aagaacagga agccgccagc    120
agcagctcca ccctggtgga agtgacactg ggcgaagtgc ctgccgccga gtctcctgat    180
cctcctcagt ctcctcaggg cgccagctct ctgcccacca ccatgaacta ccccctgtgg    240
tcccagtcct acgaggacag cagcaaccag gaagaagagg gccccagcac cttccccgac    300
ctggaatctg aattccaggc cgccctgagc cggaaggtgg ccgaactggt gcacttcctg    360
ctgctgaagt accgggccag agaacccgtg accaaggccg agatgctggg cagcgtcgtg    420
ggcaactggc agtacttctt ccccgtgatc ttctccaagg ccagctccag cctgcagctg    480
gtgttcggca tcgagctgat ggaagtggac cccatcggac acctgtacat cttcgccacc    540
tgtctgggcc tgagctacga tggcctgctg ggcgacaacc agatcatgcc aaagccggc    600 ctgctgatca tcgtgctggc catcattgcc cgcgagggcg attgtgcccc cgaggaaaag    660
atctgggagg aactgagcgt gctggaagtg ttcgagggaa gagaggactc catcctgggc    720
gaccccaaga agctgctgac ccagcacttc gtgcaggaaa actacctgga gtatagacag    780
gtgcccggca gcgaccctgc ctgctacgaa tttctgtggg gccctagagc actggtggaa    840
accagctacg tgaaagtgct gcaccacatg gtcaagatca gcggcggacc ccacatcagc    900 taccccctc tgcatgaatg ggtgctgcgg gaaggcgaag agtga                     945

<210> SEQ ID NO 17
<211> LENGTH: 314
<212> TYPE: PRT
<213> ORGANISM: Artificial Sequence
```

<220> FEATURE:
<223> OTHER INFORMATION: Translated protein of MVA_MAGEA3

<400> SEQUENCE: 17

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
                35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
        130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
            165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
            245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
290                 295                 300

His Glu Trp Val Leu Arg Glu Gly Glu Glu
305                 310
```

<210> SEQ ID NO 18
<211> LENGTH: 543
<212> TYPE: DNA
<213> ORGANISM: Artificial Sequence
<220> FEATURE:
<223> OTHER INFORMATION: Polynucleotide construct for vector MVA_NYESO

<400> SEQUENCE: 18

```
atgcaggccg agggcagagg caccggcgga tctactgggg atgctgatgg acctggcggc      60
cctggcattc cagatggccc aggcggaaat gctggcggac aggcgaagc tggcgctaca     120
```

```
ggcggaagag gacctagagg cgctggcgcc gctagagctt ctggacctgg gggaggcgct    180
cctagaggac ctcatggcgg agctgcctct ggcctgaatg gctgctgtag atgtggcgcc    240
agaggccccg aaagccggct gctggaattc tacctggcca tgcccttcgc cacccccatg    300
gaagctgagc tggccagaag aagcctggcc caggacgctc ctcctctgcc tgtgcctggc    360
gtgctgctga agaattcac cgtgtccggc aacatcctga ccatccggct gacagccgcc    420
gaccacagac agctgcagct gagcatcagc agctgcctgc agcagctgtc cctgctgatg    480
tggatcaccc agtgctttct gcccgtgttt ctggcccagc ctcctagcgg ccagcggcgc    540
taa                                                                  543
```

```
<210> SEQ ID NO 19
<211> LENGTH: 180
<212> TYPE: PRT
<213> ORGANISM: Artificial Sequence
<220> FEATURE:
<223> OTHER INFORMATION: Translated protein of MVA_NYESO

<400> SEQUENCE: 19

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180
```

```
<210> SEQ ID NO 20
<211> LENGTH: 1008
<212> TYPE: DNA
<213> ORGANISM: Artificial Sequence
<220> FEATURE:
<223> OTHER INFORMATION: Polynucleotide construct for vector
      MVA_tPA_MAGEA3

<400> SEQUENCE: 20
atggacgcca tgaagcgggg cctgtgctgc gtgctgctgc tgtgtggcgc tgtgttcgtg     60
tcccccccac tggaacagag aagccagcac tgcaagcccg aggaaggcct ggaagccaga    120
ggcgaagctc tgggactcgt gggagcacag gctccagcca ccgaagaaca ggaagccgcc    180
```

-continued

```
agcagctcta gcaccctggt ggaagtgaca ctgggcgaag tgcctgccgc cgagtctcct    240
gatcctcctc agtctcctca gggcgccagc tctctgccca ccaccatgaa ctaccccctg    300
tggtcccagt cctacgagga cagcagcaac caggaagaag agggcccag caccttcccc     360
gacctggaat ctgaattcca ggccgccctg agcggaagg tggccgaact ggtgcacttc     420
ctgctgctga agtaccgggc cagagaaccc gtgaccaagg ccgagatgct gggcagcgtc    480
gtgggcaact ggcagtactt cttccccgtg atcttctcca aggccagctc cagcctgcag    540
ctggtgttcg gcatcgagct gatggaagtg acccccatcg acacctgta catcttcgcc     600
acctgtctgg gcctgagcta cgatggcctg ctgggcgaca accagatcat gcccaaagcc    660
ggcctgctga tcatcgtgct ggccatcatt gcccgcgagg gcgattgtgc ccccgaggaa    720
aagatctggg aggaactgag cgtgctggaa gtgttcgagg gaagagagga ctccatcctg    780
ggcgaccca agaagctgct gacccagcac ttcgtgcagg aaaactacct ggagtataga    840
caggtgcccg gcagcgaccc tgcctgctac gaatttctgt ggggccctag agcactggtg    900
gaaaccagct acgtgaaagt gctgcaccac atggtcaaga tcagcggcgg accccacatc    960
agctacccac tctgcacga atgggtgctg cgggaaggcg aagagtga              1008
```

<210> SEQ ID NO 21
<211> LENGTH: 335
<212> TYPE: PRT
<213> ORGANISM: Artificial Sequence
<220> FEATURE:
<223> OTHER INFORMATION: Translated protein of MVA_tPA_MAGEA3

<400> SEQUENCE: 21

Met Asp Ala Met Lys Arg Gly Leu Cys Cys Val Leu Leu Cys Gly
1               5                   10                  15

Ala Val Phe Val Ser Pro Leu Glu Gln Arg Ser Gln His Cys Lys
            20                  25                  30

Pro Glu Glu Gly Leu Glu Ala Arg Gly Glu Ala Leu Gly Leu Val Gly
        35                  40                  45

Ala Gln Ala Pro Ala Thr Glu Glu Gln Glu Ala Ala Ser Ser Ser
    50                  55                  60

Thr Leu Val Glu Val Thr Leu Gly Glu Val Pro Ala Ala Glu Ser Pro
65                  70                  75                  80

Asp Pro Pro Gln Ser Pro Gln Gly Ala Ser Ser Leu Pro Thr Thr Met
                85                  90                  95

Asn Tyr Pro Leu Trp Ser Gln Ser Tyr Glu Asp Ser Ser Asn Gln Glu
            100                 105                 110

Glu Glu Gly Pro Ser Thr Phe Pro Asp Leu Glu Ser Glu Phe Gln Ala
        115                 120                 125

Ala Leu Ser Arg Lys Val Ala Glu Leu Val His Phe Leu Leu Leu Lys
    130                 135                 140

Tyr Arg Ala Arg Glu Pro Val Thr Lys Ala Glu Met Leu Gly Ser Val
145                 150                 155                 160

Val Gly Asn Trp Gln Tyr Phe Phe Pro Val Ile Phe Ser Lys Ala Ser
                165                 170                 175

Ser Ser Leu Gln Leu Val Phe Gly Ile Glu Leu Met Glu Val Asp Pro
            180                 185                 190

Ile Gly His Leu Tyr Ile Phe Ala Thr Cys Leu Gly Leu Ser Tyr Asp
        195                 200                 205

Gly Leu Leu Gly Asp Asn Gln Ile Met Pro Lys Ala Gly Leu Leu Ile
    210                 215                 220

```
Ile Val Leu Ala Ile Ile Ala Arg Glu Gly Asp Cys Ala Pro Glu Glu
225                 230                 235                 240

Lys Ile Trp Glu Glu Leu Ser Val Leu Glu Val Phe Glu Gly Arg Glu
                245                 250                 255

Asp Ser Ile Leu Gly Asp Pro Lys Lys Leu Leu Thr Gln His Phe Val
            260                 265                 270

Gln Glu Asn Tyr Leu Glu Tyr Arg Gln Val Pro Gly Ser Asp Pro Ala
        275                 280                 285

Cys Tyr Glu Phe Leu Trp Gly Pro Arg Ala Leu Val Glu Thr Ser Tyr
    290                 295                 300

Val Lys Val Leu His His Met Val Lys Ile Ser Gly Gly Pro His Ile
305                 310                 315                 320

Ser Tyr Pro Pro Leu His Glu Trp Val Leu Arg Glu Gly Glu Glu
                325                 330                 335

<210> SEQ ID NO 22
<211> LENGTH: 606
<212> TYPE: DNA
<213> ORGANISM: Artificial Sequence
<220> FEATURE:
<223> OTHER INFORMATION: Polynucleotide construct for vector
      MVA_tPA_NYESO

<400> SEQUENCE: 22
atggacgcca tgaagcgggg cctgtgctgc gtgctgctgc tgtgtggcgc tgtgttcgtg      60
agccctcagg ccgagggaag aggcacaggc ggatctacag gcgacgctga tggacctggc     120
ggccctggaa ttcctgatgg cccaggcgga atgctggcg accaggcga agctggcgct      180 acaggcggaa gaggacctag aggcgctggc gccgctagag cttctggacc tgggggaggc     240
gctcctagag gacctcatgg cggagctgcc tctggcctga atggctgctg tagatgtggc     300
gccagaggcc ccgaaaagcc gctgctggaa ttctacctgg ccatgcccct cgccacccc      360 atggaagctg agctggccag aagaagcctg gcccaggacg ctcctccact gcctgtgcca     420
ggggtgctgc tgaaagaatt caccgtgtcc ggcaacatcc tgaccatccg gctgacagcc     480
gccgaccaca gacagctgca gctgagcatc agcagctgcc tgcagcagct gtccctgctg     540
atgtggatca cccagtgctt tctgcccgtg tttctggccc agcctcctag cggccagcgg     600
cgctaa                                                                606

<210> SEQ ID NO 23
<211> LENGTH: 201
<212> TYPE: PRT
<213> ORGANISM: Artificial Sequence
<220> FEATURE:
<223> OTHER INFORMATION: Translated protein of MVA_tPA_NYESO

<400> SEQUENCE: 23

Met Asp Ala Met Lys Arg Gly Leu Cys Cys Val Leu Leu Leu Cys Gly
1               5                   10                  15

Ala Val Phe Val Ser Pro Gln Ala Glu Gly Arg Gly Thr Gly Gly Ser
            20                  25                  30

Thr Gly Asp Ala Asp Gly Pro Gly Gly Pro Gly Ile Pro Asp Gly Pro
        35                  40                  45

Gly Gly Asn Ala Gly Gly Pro Gly Glu Ala Gly Ala Thr Gly Gly Arg
    50                  55                  60

Gly Pro Arg Gly Ala Gly Ala Ala Arg Ala Ser Gly Pro Gly Gly Gly
65                  70                  75                  80
```

```
Ala Pro Arg Gly Pro His Gly Gly Ala Ala Ser Gly Leu Asn Gly Cys
                85                  90                  95

Cys Arg Cys Gly Ala Arg Gly Pro Glu Ser Arg Leu Leu Glu Phe Tyr
            100                 105                 110

Leu Ala Met Pro Phe Ala Thr Pro Met Glu Ala Glu Leu Ala Arg Arg
        115                 120                 125

Ser Leu Ala Gln Asp Ala Pro Pro Leu Pro Val Pro Gly Val Leu Leu
    130                 135                 140

Lys Glu Phe Thr Val Ser Gly Asn Ile Leu Thr Ile Arg Leu Thr Ala
145                 150                 155                 160

Ala Asp His Arg Gln Leu Gln Leu Ser Ile Ser Ser Cys Leu Gln Gln
                165                 170                 175

Leu Ser Leu Leu Met Trp Ile Thr Gln Cys Phe Leu Pro Val Phe Leu
            180                 185                 190

Ala Gln Pro Pro Ser Gly Gln Arg Arg
        195                 200

<210> SEQ ID NO 24
<211> LENGTH: 39593
<212> TYPE: DNA
<213> ORGANISM: Artificial Sequence
<220> FEATURE:
<223> OTHER INFORMATION: ChAdOx1 shuttle vector p2563

<400> SEQUENCE: 24
gtttaaacgc ggccgccagg cctacccact agtcaattcg ggaggatcga acggcagat      60 cgcaaaaaac agtacataca gaaggagaca tgaacatgaa catcaaaaaa attgtaaaac    120
aagccacagt tctgactttt acgactgcac ttctggcagg aggagcgact caagccttcg    180
cgaaagaaaa taccaaaaaa gcatacaaag aaacgtacgg cgtctctcat attacacgcc    240
atgatatgct gcagatccct aaacagcagc aaaacgaaaa ataccaagtg cctcaattcg    300
atcaatcaac gattaaaaat attgagtctg caaaaggact tgatgtgtgg acagctggc    360 cgctgcaaaa cgctgacgga acagtagctg aatacaacgg ctatcacgtt gtgtttgctc    420
ttgcgggaag cccgaaagac gctgatgaca catcaatcta catgttttat caaaaggtcg    480
gcgacaactc aatcgacagc tggaaaaacg cgggccgtgt ctttaaagac agcgataagt    540
tcgacgccaa cgatccgatc ctgaaagatc agacgcaaga atggtccggt tctgcaacct    600
ttacatctga cggaaaaatc cgtttattct acactgacta ttccggtaaa cattacggca    660
aacaaagcct gacaacagcg caggtaaatg tgtcaaaatc tgatgacaca ctcaaaatca    720
acggagtgga agatcacaaa acgattttg acggagacgg aaaaacatat cagaacgttc    780
agcagtttat cgatgaaggc aattatacat ccggcgacaa ccatacgctg agagaccctc    840
actacgttga agacaaaggc cataaatacc ttgtattcga agccaacacg ggaacagaaa    900
acggatacca aggcgaagaa tctttattta caaagcgta ctacggcggc ggcacgaact    960
tcttccgtaa agaaagccag aagcttcagc agagcgctaa aaaacgcgat gctgagttag   1020
cgaacggcgc cctcggtatc atagagttaa ataatgatta cacattgaaa aaagtaatga   1080
agccgctgat cacttcaaac acggtaactg atgaaatcga gcgcgcgaat gttttcaaaa   1140
tgaacggcaa atggtacttg ttcactgatt cacgcggttc aaaaatgacg atcgatggta   1200
ttaactcaaa cgatatttac atgcttggtt atgtatcaaa ctctttaacc ggcccttaca   1260
agccgctgaa caaaacaggg cttgtgctgc aaatgggtct tgatccaaac gatgtgacat   1320
```

```
tcacttactc tcacttcgca gtgccgcaag ccaaaggcaa caatgtggtt atcacaagct    1380
acatgacaaa cagaggcttc ttcgaggata aaaaggcaac atttgcgcca agcttcttaa    1440
tgaacatcaa aggcaataaa acatccgttg tcaaaaacag catcctggag caaggacagc    1500
tgacagtcaa ctaataacag caaaaagaaa atgccgatac ttcattggca ttttcttta    1560
tttctcaaca agatggtgaa ttgactagtg ggtagatcca caggacgggt gtggtcgcca    1620
tgatcgcgta gtcgatagtg gctccaagta gcgaagcgag caggactggg cggcggccaa    1680
agcggtcgga cagtgctccg agaacgggtg cgcatagaaa ttgcatcaac gcatatagcg    1740
ctagcagcac gccatagtga ctggcgatgc tgtcggaatg gacgatatcc cgcaagaggc    1800
ccggcagtac cggcataacc aagcctatgc ctacagcatc caggtgacg gtgccgagga    1860
tgacgatgag cgcattgtta gatttcatac acggtgcctg actgcgttag caatttaact    1920
gtgataaact accgcattaa agcttatcga tgataagctg tcaaacatga gaattgatcc    1980
ggaacccctta atataacttc gtataatgta tgctatacga agttattagg tccctcgact    2040
ataggggtcac cgtcgacagc gacacacttg catcggatgc agcccggtta acgtgccggc    2100
acggcctggg taaccaggta ttttgtccac ataaccgtgc gcaaaatgtt gtggataagc    2160
aggacacagc agcaatccac agcaggcata caaccgcaca ccgaggttac tccgttctac    2220
aggttacgac gacatgtcaa tacttgccct tgacaggcat tgatggaatc gtagtctcac    2280
gctgatagtc tgatcgacaa tacaagtggg accgtggtcc cagaccgata atcagaccga    2340
crayacgagt gggaycgtgg tcccagacta ataatcagac cgacgatacg agtgggaccg    2400
tggtcccaga ctaataatca gaccgacgat acgagtggga ccgtggtycc agwctratwa    2460
tcagaccgac gatacragtg gracmgtggk cccagasaka atawtcagrc cgagwtaygc    2520
wktckggcct gtaacaaagg acattaagta aagacagata mrmgtgrgac taaaacgtgg    2580
tcccagtctg attatcagac cgacgatacg agtgggaccg tggtcccaga ctaataatca    2640
gaccgacgat acgagtggga ccgtggtccc agactaataa tcagaccgac gatacgagtg    2700
ggaccgtggt cccagtctga ttatcagacc gacgatacaa gtggaacagt gggcccagag    2760
agaatattca ggccagttat gctttctggc ctgtaacaaa ggacattaag taaagacaga    2820
taaacgtaga ctaaaacgtg gtcgcatcag ggtgctggct tttcaagttc cttaagaatg    2880
gcctcaattt tctctataca ctcagttgga acacgagacc tgtccaggtt aagcaccatt    2940
ttatcgccct tatacaatac tgtcgctcca ggagcaaact gatgtcgtga gcttaaacta    3000
gttcttgatg cagatgacgt tttaagcaca gaagttaaaa gagtgataac ttcttcagct    3060
tcaaatatca ccccagcttt tttctgctca tgaaggttag atgcctgctg cttaagtaat    3120
tcctctttat ctgtaaaggc ttttgaagt gcatcacctg accgggcaga tagttcaccg    3180
gggtgagaaa aaagagcaac aactgattta ggcaatttgg cggtgttgat acagcgggta    3240
ataatcttac gtgaaatatt ttccgcatca gccagcgcag aaatatttcc agcaaattca    3300
ttctgcaatc ggcttgcata acgctgacca cgttcataag cacttgttgg gcgataatcg    3360
ttacccaatc tggataatgc agccatctgc tcatcatcca gctcgccaac cagaacacga    3420
taatcacttt cggtaagtgc agcagcttta cgacggcgac tcccatcggc aatttctatg    3480
acaccagata ctcttcgacc gaacgccggt gtctgttgac cagtcagtag aaaagaaggg    3540
atgagatcat ccagtgcgtc ctcagtaagc agctcctggt cacgttcatt acctgaccat    3600
acccgagagg tcttctcaac actatcaccc cggagcactt caagagtaaa cttcacatcc    3660
cgaccacata caggcaaagt aatggcatta ccgcgagcca ttactcctac gcgcgcaatt    3720
```

```
aacgaatcca ccatcggggc agctggtgtc gataacgaag tatcttcaac cggttgagta    3780
ttgagcgtat gttttggaat aacaggcgca cgcttcatta tctaatctcc cagcgtggtt    3840
taatcagacg atcgaaaatt tcattgcaga caggttccca aatagaaaga gcatttctcc    3900
aggcaccagt tgaagagcgt tgatcaatgg cctgttcaaa aacagttctc atccggatct    3960
gacctttacc aacttcatcc gtttcacgta caacattttt tagaaccatg cttccccagg    4020
catcccgaat ttgctcctcc atccacgggg actgagagcc attactattg ctgtatttgg    4080
taagcaaaat acgtacatca ggctcgaacc ctttaagatc aacgttcttg agcagatcac    4140
gaagcatatc gaaaaactgc agtgcggagg tgtagtcaaa caactcagca ggcgtgggaa    4200
caatcagcac atcagcagca catacgacat taatcgtgcc gatacccagg ttaggcgcgc    4260
tgtcaataac tatgacatca tagtcatgag caacagtttc aatggccagt cggagcatca    4320
ggtgtggatc ggtgggcagt ttaccttcat caaatttgcc cattaactca gtttcaatac    4380
ggtgcagagc cagacaggaa ggaataatgt caagccccgg ccagcaagtg ggctttattg    4440
cataagtgac atcgtccttt tccccaagat agaaaggcag gagagtgtct tctgcatgaa    4500
tatgaagatc tggtacccat ccgtgataca ttgaggctgt tccctggggg tcgttacctt    4560
ccacgagcaa aacacgtagc cccttcagag ccagatcctg agcaagatga acagaaactg    4620
aggttttgta aacgccacct ttatgggcag caaccccgat caccggtgga aatacgtctt    4680
cagcacgtcg caatcgcgta ccaaacacat cacgcatatg attaatttgt tcaattgtat    4740
aaccaacacg ttgctcaacc cgtcctcgaa tttccatatc cgggtgcggt agtcgccctg    4800 cttctcggc atctctgata gcctgagaag aaaccccaac taaatccgct gcttcaccta    4860
ttctccagcg ccggggttatt ttcctcgctt ccgggctgtc atcattaaac tgtgcaatgg    4920
cgatagcctt cgtcatttca tgaccagcgt ttatgcactg gttaagtgtt tccatgagtt    4980
tcattctgaa catcctttaa tcattgcttt gcgtttttt attaaatctt gcaatttact    5040
gcaaagcaac aacaaaatcg caaagtcatc aaaaaaccgc aaagttgttt aaaataagag    5100
caacactaca aaaggagata agaagagcac ataccctcagt cacttattat cactagcgct    5160
cgccgcagcc gtgtaaccga gcatagcgag cgaactggcg aggaagcaaa gaagaactgt    5220
tctgtcagat agctcttacg ctcagcgcaa gaagaaatat ccaccgtggg aaaaactcca    5280
ggtagaggta cacacgcgga tagccaattc agagtaataa actgtgataa tcaaccctca    5340
tcaatgatga cgaactaacc cccgatatca ggtcacatga cgaagggaaa gagaaggaaa    5400
tcaactgtga caaactgccc tcaaatttgg cttccttaaa aattacagtt caaaaagtat    5460
gagaaaatcc atgcaggctg aaggaaacag caaaactgtg acaaattacc ctcagtaggt    5520
cagaacaaat gtgacgaacc accctcaaat ctgtgacaga taaccctcag actatcctgt    5580
cgtcatggaa gtgatatcgc ggaaggaaaa tacgatatga gtcgtctggc ggcctttctt    5640
tttctcaatg tatgagaggc gcattggagt tctgctgttg atctcattaa cacagacctg    5700
caggaagcgg cggcggaagt caggcatacg ctggtaactt tgaggcagct ggtaacgctc    5760
tatgatccag tcgattttca gagagacgat gcctgagcca tccggcttac gatactgaca    5820
cagggattcg tataaacgca tggcatacgg attggtgatt tcttttgttt cactaagccg    5880
aaactgcgta aaccggttct gtaacccgat aaagaaggga atgagatatg ggttgatatg    5940
tacactgtaa agccctctgg atggactgtg cgcacgtttg ataaaccaag gaaaagattc    6000 atgcctttt tcatcgccgg catcctcttc agggcgataa aaaaccactt ccttccccgc    6060
```

-continued

```
gaaactcttc aatgcctgcc gtatatcctt actggcttcc gcagaggtca atccgaatat    6120
ttcagcatat ttagcaacat ggatctcgca gataccgtca tgttcctgta gggtgccatc    6180
agattttctg atctggtcaa cgaacagata cagcatacgt ttttgatccc gggagagact    6240
atatgccgcc tcagtgaggt cgtttgactg gacgattcgc gggctatttt tacgtttctt    6300
gtgattgata accgctgttt ccgccatgac agatccatgt gaagtgtgac aagtttttag    6360
attgtcacac taaataaaaa agagtcaata agcagggata actttgtgaa aaaacagctt    6420
cttctgaggg caatttgtca cagggttaag ggcaatttgt cacagacagg actgtcattt    6480
gagggtgatt tgtcacactg aaagggcaat ttgtcacaac accttctcta gaaccagcat    6540
ggataaaggc ctacaaggcg ctctaaaaaa gaagatctaa aaactataaa aaaaataatt    6600
ataaaaatat ccccgtggat aagtggataa ccccaaggga agttttttca ggcatcgtgt    6660
gtaagcagaa tatataagtg ctgttccctg gtgcttcctc gctcactcga gggcttcgcc    6720
ctgtcgctca actgcggcga gcactactgg ctgtaaaagg acagaccaca tcatggttct    6780
gtgttcatta ggttgttctg tccattgctg acataatccg ctccacttca acgtaacacc    6840
gcacgaagat ttctattgtt cctgaaggca tattcaaatc gttttcgtta ccgcttgcag    6900
gcatcatgac agaacactac ttcctataaa cgctacacag gctcctgaga ttaataatgc    6960
ggatctctac gataatggga gattttcccg actgtttcgt tcgcttctca gtggataaca    7020
gccagcttct ctgtttaaca gacaaaaaca gcatatccac tcagtccac  atttccatat    7080
aaaggccaag gcatttattc tcaggataat tgtttcagca tcgcaaccgc atcagactcc    7140
ggcatcgcaa actgcacccg gtgccgggca gccacatcca gcgcaaaaac cttcgtgtag    7200
acttccgttg aactgatgga cttatgtccc atcaggcttt gcagaacttt cagcggtata    7260
ccggcataca gcatgtgcat cgcataggaa tggcggaacg tatgtggtgt gaccggaaca    7320
gagaacgtca caccgtcagc agcagcggcg gcaaccgcct ccccaatcca ggtcctgacc    7380
gttctgtccg tcacttccca gatccgcgct ttctctgtcc ttcctgtgcg acggttacgc    7440
cgctccatga gcttatcgcg aataaatacc tgtgacggaa gatcacttcg cagaataaat    7500
aaatcctggt gtcccgttg  ataccgggaa gccctgggcc aacttttggc gaaaatgaga    7560
cgttgatcgg cacgtaagag gttccaactt tcaccataat gaaataagat cactaccggg    7620
cgtatttttt gagttatcga gattttcagg agctaaggaa gctaaaatgg agaaaaaaat    7680
cactggatat accaccgttg atatatccca atggcatcgt aaagaacatt ttgaggcatt    7740
tcagtcagtt gctcaatgta cctataacca gaccgttcag ctggatatta cggccttttt    7800
aaagaccgta agaaaaata agcacaagtt ttatccggcc tttattcaca ttcttgcccg    7860
cctgatgaat gctcatccgg agttccgtat ggcaatgaaa gacggtgagc tggtgatatg    7920
ggatagtgtt caccettgtt acaccgtttt ccatgagcaa actgaaacgt tttcatcgct    7980
ctggagtgaa taccacgacg atttccggca gtttctacac atatattcgc aagatgtggc    8040
gtgttacggt gaaaacctgg cctatttccc taaagggttt attgagaata tgttttcgt    8100
ctcagccaat ccctgggtga gtttcaccag ttttgattta aacgtggcca atatggacaa    8160
cttcttcgcc cccgttttca ccatgggcaa atattatacg caaggcgaca aggtgctgat    8220
gccgctggcg attcaggttc atcatgccgt ttgtgatggc ttccatgtcg cagaatgct    8280
taatgaatta caacagtact gcgatgagtg gcagggcggg gcgtaatttt tttaaggcag    8340
ttattggtgc ccttaaacgc ctggttgcta cgcctgaata agtgataata agcggatgaa    8400
tggcagaaat tcgatgataa gctgtcaaac atgagaattg gtcgacggcg cgccaaagct    8460
```

```
tgcatgcctg cagccgcgta acctggcaaa atcggttacg gttgagtaat aaatggatgc   8520
cctgcgtaag cggggcacat ttcattacct cttcctccgc acccgacata gataataact   8580
tcgtatagta tacattatac gaagttatct agtagactta atcgcgttta aacccatcat   8640
caataatata cctcaaactt tttgtgcgcg ttaatatgca aatgaggcgt ttgaatttgg   8700
gaagggagga aggtgattgg ccgagagaag ggcgaccgtt aggggcgggg cgagtgacgt   8760
tttgatgacg tgaccgcgag gaggagccag tttgcaagtt ctcgtgggaa aagtgacgtc   8820
aaacgaggtg tggtttgaac acggaaatac tcaattttcc cgcgctctct gacaggaaat   8880
gaggtgtttc taggcggatg caagtgaaaa cgggccattt tcgcgcgaaa actgaatgag   8940
gaagtgaaaa tctgagtaat ttcgcgttta tgacaggggag gagtatttgc cgagggccga   9000
gtagactttg accgattacg tgggggtttc gattaccgtg tttttcacct aaatttccgc   9060
gtacggtgtc aaagtccggt gttttacgt aggtgtcagc tgatcgccag ggtatttaaa   9120
cctgcgctct ccagtcaaga ggccactctt gagtgccagc gagaagagtt ttctcctccg   9180
cgcgcgagtc agatctacac tttgaaaggc gatcgctagc gacatcgatc acaagtttgt   9240
acaaaaaagc tgaacgagaa acgtaaaatg atataaatat caatatatta aattagattt   9300
tgcataaaaa acagactaca taatactgta aaacacaaca tatccagtca ctatggcggc   9360
cgccgattta ttcaacaaag ccacgttgtg tctcaaaatc tctgatgtta cattgcacaa   9420
gataaaaata tatcatcatg aacaataaaa ctgtctgctt acataaacag taatacaagg   9480
ggtgttatga gccatattca acgggaaacg tcttgctcga ggccgcgatt aaattccaac   9540
atggatgctg atttatatgg gtataaatgg gctcgtgata atgtcgggca atcaggtgcg   9600
acaatctatc gattgtatgg gaagcccgat gcgccagagt tgtttctgaa acatggcaaa   9660
ggtagcgttg ccaatgatgt tacagatgag atggtcagac taaactggct gacggaattt   9720
atgcctcttc cgaccatcaa gcattttatc cgtactcctg atgatgcatg ttactcacc   9780 actgcgatcc ccgggaaaac agcattccag gtattagaag aatatcctga ttcaggtgaa   9840
aatattgttg atgcgctggc agtgttcctg cgccggttgc attcgattcc tgtttgtaat   9900 tgtccttta acagcgatcg cgtatttcgt ctcgctcagg cgcaatcacg aatgaataac   9960
ggtttggttg atgcgagtga ttttgatgac gagcgtaatg gctggcctgt gaacaagtc  10020 tggaaagaaa tgcataagct tttgccattc tcaccggatt cagtcgtcac tcatggtgat  10080
ttctcacttg ataaccttat ttttgacgag gggaaattaa taggttgtat tgatgttgga  10140
cgagtcggaa tcgcagaccg ataccaggat cttgccatcc tatggaactg cctcggtgag  10200
ttttctcctt cattacagaa acggcttttt caaaaatatg gtattgataa tcctgatatg  10260
aataaattgc agtttcattt gatgctcgat gagttttct aatcagaatt ggttaattgg  10320
ttgtaacact ggcacgcgtg gatccggctt actaaaagcc agataacagt atgcgtattt  10380
gcgcgctgat ttttgcggta taagaatata tactgatatg tatacccgaa gtatgtcaaa  10440
aagaggtatg ctatgaagca gcgtattaca gtgacagttg acagcgacag ctatcagttg  10500
ctcaaggcat atatgatgtc aatatctccg gtctggtaag cacaaccatg cagaatgaag  10560
cccgtcgtct gcgtgccgaa cgctggaaag cggaaaatca ggaagggatg ctgaggtcg  10620 cccggtttat tgaaatgaac ggctcttttg ctgacgagaa caggggctgg tgaaatgcag  10680
tttaaggttt acacctataa aagagagagc cgttatcgtc tgtttgtgga tgtacagagt  10740
gatattattg acacgcccgg gcgacggatg gtgatccccc tggccagtgc acgtctgctg  10800
```

```
tcagataaag tctcccgtga actttacccg gtggtgcata tcggggatga aagctggcgc    10860
atgatgacca ccgatatggc cagtgtgccg gtctccgtta tcggggaaga agtggctgat    10920
ctcagccacc gcgaaaatga catcaaaaac gccattaacc tgatgttctg gggaatataa    10980
atgtcaggct cccttataca cagccagtct gcaggtcgac catagtgact ggatatgttg    11040
tgttttacag tattatgtag tctgtttttt atgcaaaatc taatttaata tattgatatt    11100
tatatcattt tacgtttctc gttcagcttt cttgtacaaa gtggtgatcg attcgacaga    11160
tcgcgatcgc agtgagtagt gttctggggc gggggaggac ctgcatgagg gccagaatga    11220
ctgaaatctg tgcttttctg tgtgttgcag catcatgagc ggaagcggct cctttgaggg    11280
aggggtattc agcccttatc tgacggggcg tctcccctcc tgggcgggag tgcgtcagaa    11340
tgtgatggga tccacggtgg acggccggcc cgtgcagccc gcgaactctt caaccctgac    11400
ctatgcaacc ctgagctctt cgtcggtgga cgcagctgcc gccgcagctg ctgcatccgc    11460
cgccagcgcc gtgcgcggaa tggccatggg cgccggctac tacggcactc tggtggccaa    11520
ctcgagttcc accaataatc ccgccagcct gaacgaggag aagctgctgc tgctgatggc    11580
ccagcttgag gccttgaccc agcgcctggg cgagctgacc cagcaggtgg ctcagctgca    11640
ggagcagacg cgggccgcgg ttgccacggt gaaatccaaa taaaaatga atcaataaat    11700 aaacggagac ggttgttgat tttaacacag agtctgaatc tttatttgat ttttcgcgcg    11760
cggtaggccc tggaccaccg gtctcgatca ttgagcaccc ggtggatctt tccaggacc    11820 cggtagaggt gggcttggat gttgaggtac atgggcatga gcccgtcccg ggggtggagg    11880
tagctccatt gcagggcctc gtgctcgggg gtggtgttgt aaatcaccca gtcatagcag    11940
gggcgcaggg cgtggtgttg cacaatatct tgaggagga gactgatggc cacgggcagc    12000
cctttggtgt aggtgtttac aaatctgttg agctgggagg gatgcatgcg gggggagatg    12060
aggtgcatct tggcctggat cttgagattg gcgatgttac cgcccagatc ccgcctgggg    12120
ttcatgttgt gcaggaccac cagcacggtg tatccggtgc acttgggaa tttatcatgc    12180 aacttggaag ggaaggcgtg aaagaatttg gcgacgccct tgtgtccgcc caggttttcc    12240
atgcactcat ccatgatgat ggcaatgggc ccgtgggcgg cggcctgggc aaagacgttt    12300
cgggggtcgg acacatcata gttgtggtcc tgggtgaggt catcataggc cattttaatg    12360 aatttgggc ggagggtgcc ggactggggg acaaaggtac cctcgatccc ggggggctag    12420
ttcccctcac agatctgcat ctcccaggct ttgagctcag agggggggat catgtccacc    12480
tgcggggcga taaagaacac ggtttccggg gcggggagga tgagctgggc cgaaagcaag    12540
ttccggagca gctgggactt gccgcagccg gtggggccgt aaatgacccc gatgaccggc    12600
tgcaggtggt agttgaggga gagacagctg ccgtcctccc ggaggagggg ggccacctcg    12660
ttcatcatct cgcgcacgtg catgttctcg cgcaccagtt ccgccaggag gcgctctccc    12720
cccagagata ggagctcctg gagcgaggcg aagttttca gcggcttgag tccgtcggcc    12780 atgggcatt tggagagggt ctgttgcaag agttccaagc ggtcccagag ctcggtgatg    12840
tgctctacgg catctcgatc cagcagacct cctcgtttcg cgggttggga cgactgcggg    12900
agtagggcac cagacgatgg gcgtccagcc cagccaggt ccgtccttc cagggccgca    12960 gcgtccgcgt cagggtggtc tccgtcacgg tgaagggtg cgcgccgggc tgggcgcttg    13020
cgagggtgcg cttcaggctc atccggctgg tcgaaaaccg ctcccgatcg gcgccctgcg    13080
cgtcggccag gtagcaattg accatgagtt cgtagttgag cgcctcggcc gcgtggcctt    13140
tggcgcggag cttaccttg gaagtctgcc cgcaggcggg acagaggagg gacttgaggg    13200
```

```
cgtagagctt gggggcgagg aagacggaat cggggggcgta ggcgtccgcg ccgcagtggg   13260
cgcagacggt ctcgcactcc acgagccagg tgaggtcggg ctggtcgggg tcaaaaacca   13320
gtttcccgcc gttcttttg atgcgtttct tacctttggt ctccatgagc tcgtgtcccc    13380
gctgggtgac aaagaggctg tccgtgtccc cgtagaccga ctttatgggc cggtcctcga   13440
gcggtgtgcc gcggtcctcc tcgtagagga accccgccca ctccgagacg aaagcccggg   13500
tccaggccag cacgaaggag gccacgtggg acgggtagcg gtcgttgtcc accagcgggt   13560
ccactttttc cagggtatgc aaacacatgt cccctcgtc cacatccagg aaggtgattg     13620
gcttgtaagt gtaggccacg tgaccggggg tcccggccgg gggggtataa aaggggggcgg  13680 gcccctgctc gtcctcactg tcttccggat cgctgtccag gagcgccagc tgttgggta    13740 ggtattccct ctcgaaggcg ggcatgacct cggcactcag gttgtcagtt tctagaaacg   13800
aggaggattt gatattgacg gtgccagcgg agatgccttt caagagcccc tcgtccatct   13860
ggtcagaaaa gacgattttt tgttgtcga gcttggtggc gaaggagccg tagagggcgt    13920 tggaaggag cttggcgatg gagcgcatgg tctggttttt ttccttgtcg gcgcgctcct    13980
tggccgcgat gttgagctgc acgtactcgc gcgccacgca cttccattcg gggaagacgg   14040
tggtcatctc gtcgggcacg attctgacct gccaacctcg attatgcagg gtgatgaggt   14100
ccacactggt ggccacctcg ccgcgcaggg gctcgttggt ccagcagagg cggccgccct   14160
tgcgcgagca aagggggggc agagggtcca gcatgacctc gtcgggggggg tcggcatcga   14220 tggtgaagat gccgggcagg agatcggggt cgaagtagct gatggaagtg gccagatcgt   14280
ccagggaagc ttgccattcg cgcacggcca gcgcgcgctc gtagggactg aggggcgtgc   14340
cccagggcat ggggtgggtg agcgcggagg cgtacatgcc gcagatgtcg tagacgtaga   14400
ggggctcctc gaggatgccg atgtaggtgg ggtagcagcg ccccccgcgg atgctggcgc   14460
gcacgtagtc atacagctcg tgcgagggcg cgaggagccc cgggcccagg ttggtgcgac   14520
tgggcttttc ggcgcggtag acgatctggc gaaagatggc atgcgagttg gaggagatgg   14580
tgggcctttg gaagatgttg aagtgggcgt gggggaggcc gaccgagtcg cggatgaagt   14640
gggcgtagga gtcttgcagt ttggcgacga gctcggcggt gacgaggacg tccagagcgc   14700
agtagtcgag ggtctcctgg atgatgtcat acttgagctg gcccttttgt ttccacagct   14760
cgcggttgag aaggaactct tcgcggtcct tccagtactc ttcgagggg aacccgtcct    14820 gatctgcacg gtaagagcct agcatgtaga actggttgac ggccttgtag gcgcagcagc    14880
ccttctccac gggagggcg taggcctggg cggccttgcg cagggaggtg tgcgtgaggg    14940
cgaaggtgtc cctgaccatg accttgagga actggtgctt gaaatcgata tcgtcgcagc   15000 cccctgctc ccagagctgg aagtccgtgc gcttcttgta ggcggggttg ggcaaagcga    15060
aagtaacatc gttgaaaagg atcttgcccg cgcggggcat aaagttgcga gtgatgcgga   15120
aaggctgggg cacctcggcc cggttgttga tgacctgggc ggcgagcacg atctcgtcga   15180
aaccgttgat gttgtggccc acgatgtaga gttccacgaa tcgcgggcgg cccttgacgt   15240
ggggcagctt cttgagctcc tcgtaggtga gctcgtcggg gtcgctgaga ccgtgctgct   15300
cgagcgccca gtcggcgaga tgggggttgg gcgcgaggaa ggaagtccag agatccacgg   15360
ccagggcggt ttgcagacgg tcccggtact gacggaactg ctgcccgacg gccatttttt    15420
cgggggtgac gcagtagaag gtgcgggggt ccccgtgcca gcggtcccat ttgagctgga   15480
gggcgagatc gagggcgagc tcgacgaggc ggtcgtcccc tgagagtttc atgaccagca   15540
```

-continued

```
tgaagggggac gagctgcttg ccgaaggacc ccatccaggt gtaggtttcc acatcgtagg    15600
tgaggaagag cctttcggtg cgaggatgcg agccgatggg gaagaactgg atctcctgcc    15660
accaattgga ggaatggctg ttgatgtgat ggaagtagaa atgccgacgg cgcgccgaac    15720
actcgtgctt gtgtttatac aagcggccac agtgctcgca acgctgcacg ggatgcacgt    15780
gctgcacgag ctgtacctga gttcctttga cgaggaattt cagtgggaag tggagtcgtg    15840
gcgcctgcat ctcgtgctgt actacgtcgt ggtggtcggc ctggccctct tctgcctcga    15900
tggtggtcat gctgacgagc ccgcgcggga ggcaggtcca gacctcggcg cgagcgggtc    15960
ggagagcgag gacgagggcg cgcaggccgg agctgtccag ggtcctgaga cgctgcggag    16020
tcaggtcagt gggcagcggc ggcgcgcggt tgacttgcag gagttttttcc agggcgcgcg    16080 ggaggtccag atggtacttg atctccaccg cgccgttggt ggcgacgtcg atggcttgca    16140
gggtcccgtg cccctggggt gtgaccaccg tcccccgttt cttcttgggc ggctggggcg    16200 acggggggcgg tgcctcttcc atggttagaa gcggcggcga ggacgcgcgc cgggcggcag    16260
aggcggctcg ggcccggag gcaggggcgg caggggcacg tcggcgccgc gcgcgggtag    16320
gttctggtac tgcgcccgga gaagactggc gtgagcgacg acgcgacggt tgacgtcctg    16380
gatctgacgc ctctgggtga aggccacggg acccgtgagt ttgaacctga aagagagttc    16440
gacagaatca atctcggtat cgttgacggc ggcctgccgc aggatctctt gcacgtcgcc    16500
cgagttgtcc tggtaggcga tctcggtcat gaactgctcg atctcctcct cctgaaggtc    16560
tccgcgaccg gcgcgctcca cggtggccgc gaggtcgttg gagatgcggc ccatgagctg    16620
cgagaaggcg ttcatgcccg cctcgttcca gacgcggctg tagaccacga cgcccctcggg    16680 atcgcgggcg cgcatgacca cctgggcgag gttgagctcc acgtggcgcg tgaagaccgc    16740
gtagttgcag aggcgctggt agaggtagtt gagcgtggtg gcgatgtgct cggtgacgaa    16800
gaaatacatg atccagcggc ggagcggcat ctcgctgacg tcgcccagcg cctccaagcg    16860
ttccatggcc tcgtaaaagt ccacggcgaa gttgaaaaac tgggagttgc gcgccgagac    16920
ggtcaactcc tcctccagaa gacggatgag ctcggcgatg tggcgcgca cctcgcgctc    16980 gaaggccccc gggagttcct ccacttcctc ctcttcttcc tcctccacta acatctcttc    17040
tacttcctcc tcaggcggtg gtggtggcgg gggagggggc ctgcgtcgcc ggcggcgcac    17100
gggcagacgg tcgatgaagc gctcgatggt ctcgccgcgc cggcgtcgca tggtctcggt    17160
gacggcgcgc ccgtcctcgc ggggccgcag cgtgaagacg ccgccgcgca tctccaggtg    17220 gccgggggg tccccgttgg gcagggagag ggcgctgacg atgcatctta tcaattgccc    17280
cgtagggact ccgcgcaagg acctgagcgt ctcgagatcc acgggatctg aaaaccgttg    17340
aacgaaggct tcgagccagt cgcagtcgca aggtaggctg agcacggttt cttctgccgg    17400
gtcatgttgg ggagcggggc gggcgatgct gctggtgatg aagttgaaat aggcggttct    17460 gagacgcgg atggtggcga ggagcaccag gtctttgggc ccggcttgct ggatgcgcag    17520
acggtcggcc atgcccagg cgtggtcctg acacctggcc aggtccttgt agtagtcctg    17580
catgagccgc tccacgggca cctcctcctc gcccgcgcgg ccgtgcatgc gcgtgagccc    17640
gaagccgcgc tggggctgga cgagcgccag gtcggcgacg acgcgctcgg cgaggatggc    17700
ctgctggatc tgggtgaggg tggtctggaa gtcgtcaaag tcgacgaagc ggtggtaggc    17760
tccggtgttg atggtgtagg agcagttggc catgacggac cagttgacgg tctggtggcc    17820
cggacgcacg agctcgtggt acttgaggcg cgagtaggcg cgcgtgtcga agatgtagtc    17880
gttgcaggtg cgcaccaggt actggtagcc gatgaggaag tgcggcggcg gctggcggta    17940
```

```
gagcggccat cgctcggtgg cgggggcgcc gggcgcgagg tcctcgagca tggtgcggtg    18000
gtagccgtag atgtacctgg acatccaggt gatgccggcg gcggtggtgg aggcgcgcgg    18060
gaactcgcgg acgcggttcc agatgttgcg cagcggcagg aagtagttca tggtgggcac    18120
ggtctggccc gtgaggcgcg cgcagtcgtg gatgctctat acgggcaaaa acgaaagcgg    18180
tcagcggctc gactccgtgg cctggaggct aagcgaacgg gttgggctgc gcgtgtaccc    18240
cggttcgaat ctcgaatcag gctggagccg cagctaacgt ggtactgcca ctcccgtctc    18300
gacccaagcc tgcaccaacc ctccaggata cggaggcggg tcgttttgca actttttttg    18360
gaggccggaa atgaaactag taagcgcgga aagcggccga ccgcgatggc tcgctgccgt    18420
agtctggaga agaatcgcca gggttgcgtt gcggtgtgcc ccggttcgag gccggccgga    18480
ttccgcggct aacgagggcg tggctgcccc gtcgtttcca agaccccata gccagccgac    18540
ttctccagtt acggagcgag cccctctttt gttttgtttg ttttgccag atgcatcccg    18600 tactgcggca gatgcgcccc caccaccctc caccgcaaca acagccccct cctccacagc    18660
cggcgcttct gccccgccc cagcagcagc agcaacttcc agccacgacc gccgcggccg    18720
ccgtgagcgg ggctggacag acttctcagt atgatcacct ggccttggaa gagggcgagg    18780
ggctggcgcg cctgggggcg tcgtcgccgg agcggcaccc gcgcgtgcag atgaaaaggg    18840
acgctcgcga ggcctacgtg cccaagcaga acctgttcag agacaggagc ggcgaggagc    18900
ccgaggagat gcgcgcggcc cggttccacg cggggcggga gctgcggcgc ggcctggacc    18960
gaaagagggt gctgagggac gaggatttcg aggcggacga gctgacgggg atcagccccg    19020
cgcgcgcgca cgtggccgcg gccaacctgg tcacggcgta cgagcagacc gtgaaggagg    19080
agagcaactt ccaaaaatcc ttcaacaacc acgtgcgcac cctgatcgcg cgcgaggagg    19140
tgaccctggg cctgatgcac ctgtgggacc tgctggaggc catcgtgcag aaccccacca    19200
gcaagccgct gacggcgcag ctgttcctgg tggtgcagca tagtcgggac aacgaggcgt    19260
tcagggaggc gctgctgaat atcaccgagc ccgagggccg ctggctcctg gacctggtga    19320
acattctgca gagcatcgtg gtgcaggagc gcgggctgcc gctgtccgag aagctggcgg    19380
ccatcaactt ctcggtgctg agtctgggca agtactacgc taggaagatc tacaagaccc    19440
cgtacgtgcc catagacaag gaggtgaaga tcgacgggtt ttacatgcgc atgaccctga    19500
aagtgctgac cctgagcgac gatctggggg tgtaccgcaa cgacaggatg caccgcgcgg    19560
tgagcgccag caggcggcgc gagctgagcg accaggagct gatgcacagc ctgcagcggg    19620
ccctgaccgg ggccgggacc gaggggggaga gctactttga catgggcgcg gacctgcact    19680
ggcagcccag ccgccgggcc ttggaggcgg caggcggtcc ccctacata gaagaggtgg    19740 acgatgaggt ggacgaggag ggcgagtacc tggaagactg atggcgcgac cgtatttttg    19800
ctagatgcaa caacagccac ctcctgatcc cgcgatgcgg gcggcgctgc agagccagcc    19860
gtccggcatt aactcctcgg acgattggac ccaggccatg caacgcatca tggcgctgac    19920
gacccgcaac cccgaagcct ttagacagca gccccaggcc aacggctctc cggccatcct    19980
ggaggccgtg gtgccctcgc gctccaaccc cacgcacgag aaggtcctgg ccatcgtgaa    20040
cgcgctggtg gagaacaagg ccatccgcgg cgacgaggcc ggcctggtgt acaacgcgct    20100
gctggagcgc gtggcccgct acaacagcac caacgtgcag accaacctgg accgcatggt    20160
gaccgacgtg cgcgaggccg tgcccagcg cgagcggttc caccgcgagt ccaacctggg    20220
atccatggtg gcgctgaacg ccttcctcag cacccagccc gccaacgtgc cccggggcca    20280
```

```
ggaggactac accaacttca tcagcgccct gcgcctgatg gtgaccgagg tgccccagag   20340
cgaggtgtac cagtccgggc cggactactt cttccagacc agtcgccagg gcttgcagac   20400
cgtgaacctg agccaggcgt tcaagaactt gcagggcctg tggggcgtgc aggccccggt   20460
cggggaccgc gcgacggtgt cgagcctgct gacgccgaac tcgcgcctgc tgctgctgct   20520
ggtggccccc ttcacggaca gcggcagcat caaccgcaac tcgtacctgg gctacctgat   20580
taacctgtac cgcgaggcca tcggccaggc gcacgtggac gagcagacct accaggagat   20640
cacccacgtg agccgcgccc tgggccagga cgacccgggc aatctggaag ccaccctgaa   20700
cttttttgctg accaaccggt cgcagaagat cccgccccag tacacgctca gcgccgagga   20760
ggagcgcatc ctgcgatacg tgcagcagag cgtgggcctg ttcctgatgc aggagggggc   20820
cacccccagc gccgcgctcg acatgaccgc gcgcaacatg gagcccagca tgtacgccag   20880
caaccgcccg ttcatcaata aactgatgga ctacttgcat cgggcggccg ccatgaactc   20940
tgactatttc accaacgcca tcctgaatcc ccactggctc ccgccgccgg ggttctacac   21000
gggcgagtac gacatgcccg accccaatga cgggttcctg tgggacgatg tggacagcag   21060
cgtgttctcc ccccgaccgg gtgctaacga gcgcccccttg tggaagaagg aaggcagcga   21120
ccgacgcccg tcctcggcgc tgtccggccg cgagggtgct gccgcggcgg tgcccgaggc   21180
cgccagtcct ttcccgagct tgcccttctc gctgaacagt attcgcagca gcgagctggg   21240
caggatcacg cgcccgcgct tgctgggcga ggaggagtac ttgaatgact cgctgttgag   21300
acccgagcgg gagaagaact tccccaataa cgggatagag agcctggtgg acaagatgag   21360
ccgctggaag acgtatgcgc aggagcacag ggacgatccg tcgcagggg ccacgagccg   21420
gggcagcgcc gcccgtaaac gccggtggca cgacaggcag cggggactga tgtgggacga   21480
tgaggattcc gccgacgaca gcagcgtgtt ggacttgggt gggagtggta acccgttcgc   21540
tcacctgcgc ccccgcatcg ggcgcatgat gtaagagaaa ccgaaaataa atgatactca   21600
ccaaggccat ggcgaccagc gtgcgttcgt ttcttctctg ttgttgtatc tagtatgatg   21660
aggcgtgcgt acccggaggg tcctcctccc tcgtacgaga gcgtgatgca gcaggcgatg   21720
gcggcggcgc cggcgatgca gccccgctg gaggctccctt acgtgccccc gcggtacctg   21780
gcgcctacgg aggggcggaa cagcattcgt tactcggagc tggcacccct gtacgatacc   21840
acccggttgt acctggtgga caacaagtcg gcggacatcg cctcgctgaa ctaccagaac   21900
gaccacagca acttcctgac caccgtggtg cagaacaatg acttcacccc cacggaggcc   21960
agcacccaga ccatcaactt tgacgagcgc tcgcggtggg gcggtcagct gaaaaccatc   22020
atgcacacca acatgcccaa cgtgaacgag ttcatgtaca gcaacaagtt caaggcgcgg   22080
gtgatggtct cccgcaagac ccccaacggg gtgacagtga cagatggtag tcaggatatc   22140
ttggagtatg aatgggtgga gtttgagctg cccgaaggca acttctcggt gaccatgacc   22200
atcgacctga tgaacaacgc catcatcgac aattacttgg cggtggggcg gcagaacggg   22260
gtcctggaga gcgatatcgg cgtgaagttc gacactagga acttcaggct gggctgggac   22320
cccgtgaccg agctggtcat gcccggggtg tacaccaacg aggccttcca ccccgatatt   22380
gtcttgctgc ccggctgcgg ggtggacttc accgagagcc gcctcagcaa cctgctgggc   22440
attcgcaaga ggcagcccctt ccaggagggc ttccagatca tgtacgagga tctggagggg   22500
ggcaacatcc ccgcgctcct ggatgtcgac gcctatgaga aaagcaagga ggagagcgcc   22560
gccgcggcga ctgcagctgt agccaccgcc tctaccgagg tcaggggcga taattttgcc   22620
agccctgcag cagtggcagc ggccgaggcg gctgaaaccg aaagtaagat agtcattcag   22680
```

```
ccggtggaga aggatagcaa ggacaggagc tacaacgtgc tgccggacaa gataaacacc    22740
gcctaccgca gctggtacct ggcctacaac tatggcgacc ccgagaaggg cgtgcgctcc    22800
tggacgctgc tcaccacctc ggacgtcacc tgcggcgtgg agcaagtcta ctggtcgctg    22860
cccgacatga tgcaagaccc ggtcaccttc cgctccacgc gtcaagttag caactacccg    22920
gtggtgggcg ccgagctcct gcccgtctac tccaagagct tcttcaacga gcaggccgtc    22980
tactcgcagc agctgcgcgc cttcacctcg ctcacgcacg tcttcaaccg cttccccgag    23040
aaccagatcc tcgtccgccc gcccgcgccc accattacca ccgtcagtga aaacgttcct    23100
gctctcacag atcacgggac cctgccgctg cgcagcagta tccggggagt ccagcgcgtg    23160
accgttactg acgccagacg ccgcacctgc ccctacgtct acaaggccct gggcatagtc    23220
gcgccgcgcg tcctctcgag ccgcaccttc taaaaaatgt ccattctcat ctcgcccagt    23280
aataacaccg gttggggcct gcgcgcgccc agcaagatgt acggaggcgc tcgccaacgc    23340
tccacgcaac accccgtgcg cgtgcgcggg cacttccgcg ctccctgggg cgccctcaag    23400
ggccgcgtgc ggtcgcgcac caccgtcgac gacgtgatcg accaggtggt ggccgacgcg    23460
cgcaactaca cccccgccgc cgcgcccgtc tccaccgtgg acgccgtcat cgacagcgtg    23520
gtggccgacg cgcgccggta cgcccgcgcc aagagccggc ggcggcgcat cgcccggcgg    23580
caccggagca cccccgccat gcgcgcgcg cgagccttgc tgcgcagggc caggcgcacg    23640
ggacgcaggg ccatgctcag ggcggccaga cgcgcggctt caggcgccag cgccggcagg    23700
acccggagac gcgcggccac ggcggcggca gcggccatcg ccagcatgtc ccgcccgcgg    23760
cgagggaacg tgtactgggt gcgcgacgcc gccaccggtg tgcgcgtgcc cgtgcgcacc    23820 cgccccctc gcacttgaag atgttcactt cgcgatgttg atgtgtccca gcggcgagga    23880
ggatgtccaa gcgcaaattc aaggaagaga tgctccaggt catcgcgcct gagatctacg    23940
gccccgcggt ggtgaaggag gaaagaaagc cccgcaaaat caagcgggtc aaaaaggaca    24000
aaaaggaaga agatgacgat ctggtggagt ttgtgcgcga gttcgccccc cggcggcgcg    24060
tgcagtggcg cgggcggaaa gtgcacccgg tgctgagacc cggcaccacc gtggtcttca    24120
cgcccggcga gcgctccggc agcgcttcca agcgctccta cgacgaggtg tacggggacg    24180
aggacatcct cgagcaggcg gccgagcgcc tgggcgagtt tgcttacgga aagcgcagcc    24240
gccccgccct gaaggaagag gcggtgtcca tcccgctgga ccacggcaac cccacgccga    24300
gcctcaagcc cgtgaccctg cagcaggtgc tgccgagcgc agcgccgcgc cgggggttca    24360
agcgcgaggg cgaggatctg taccccacca tgcagctgat ggtgcccaag cgccagaagc    24420
tggaagacgt gctggagacc atgaaggtgg acccggacgt gcagcccgag gtcaaggtgc    24480
ggcccatcaa gcaggtggcc ccgggcctgg gcgtgcagac cgtggacatc aagatccccc    24540
cggagcccat ggaaacgcag accgagccca tgatcaagcc cagcaccagc accatggagg    24600
tgcagacgga tccctggatg ccatcggctc ctagccgaag accccggcgc aagtacggcg    24660
cggccagcct gctgatgccc aactacgcgc tgcatccttc catcatcccc acgccgggct    24720 accgcgcac gcgcttctac cgcggtcata caaccagccg ccgccgcaag accaccaccc    24780
gccgccgccg tcgccgcaca gccgctgcat ctaccccctgc cgccctggtg cggagagtgt    24840
accgccgcgg ccgcgcgcct ctgaccctac cgcgcgcgcg ctaccacccg agcatcgcca    24900
tttaaacttt cgcctgcttt gcagatggcc ctcacatgcc gcctccgcgt tcccattacg    24960
ggctaccgag gaagaaaacc gcgccgtaga aggctggcgg ggaacgggat gcgtcgccac    25020
```

```
caccatcggc ggcggcgcgc catcagcaag cggttgggggg gaggcttcct gcccgcgctg   25080
atccccatca tcgccgcggc gatcggggcg atccccggca ttgcttccgt ggcggtgcag   25140
gcctctcagc gccactgaga cacttggaaa acatcttgta ataaaccaat ggactctgac   25200
gctcctggtc ctgtgatgtg ttttcgtaga cagatggaag acatcaattt ttcgtccctg   25260
gctccgcgac acggcacgcg gccgttcatg ggcacctgga gcgacatcgg caccagccaa   25320
ctgaacgggg gcgccttcaa ttggagcagt ctctggagcg ggcttaagaa tttcgggtcc   25380
acgcttaaaa cctatggcag caaggcgtgg aacagcacca cagggcaggc gctgagggat   25440
aagctgaaag agcagaactt ccagcagaag gtggtcgatg ggctcgcctc gggcatcaac   25500
ggggtggtgg acctggccaa ccaggccgtg cagcggcaga tcaacagccg cctggacccg   25560
gtgccgcccg ccggctccgt ggagatgccg caggtggagg aggagctgcc tcccctggac   25620
aagcggggcg agaagcgacc ccgccccgac gcggaggaga cgctgctgac gcacacggac   25680
gagccgcccc cgtacgagga ggcggtgaaa ctgggtctgc ccaccacgcg gcccatcgcg   25740
cccctggcca ccggggtgct gaaacccgaa agtaataagc ccgcgaccct ggacttgcct   25800
cctcccgctt cccgcccctc tacagtggct aagcccctgc cgccggtggc cgtggcccgc   25860
gcgcgacccg ggggctccgc ccgccctcat gcgaactggc agagcactct gaacagcatc   25920
gtgggtctgg gagtgcagag tgtgaagcgc cgccgctgct attaaaccta ccgtagcgct   25980
taacttgctt gtctgtgtgt gtatgtatta tgtcgccgct gtccgccaga aggaggagtg   26040
aagaggcgcg tcgccgagtt gcaagatggc cacccccatcg atgctgcccc agtgggcgta   26100
catgcacatc gccggacagg acgcttcgga gtacctgagt ccgggtctgg tgcagttcgc   26160
ccgcgccaca gacacctact tcagtctggg gaacaagttt aggaaccccca cggtggcgcc   26220
cacgcacgat gtgaccaccg accgcagcca gcggctgacg ctgcgcttcg tgcccgtgga   26280
ccgcgaggac aacacctact cgtacaaagt gcgctacacg ctggccgtgg gcgacaaccg   26340
cgtgctggac atgccagca cctactttga catccgcgcc gtgctggatc ggggcccctag   26400
cttcaaaccc tactccggca ccgcctacaa cagcctggct cccaagggag cgcccaattc   26460
cagccagtgg gagcaaaaaa aggcaggcaa tggtgacact atggaaacac acacatttgg   26520
tgtggcccca atgggcggtg agaatattac aatcgacgga ttacaaattg gaactgacgc   26580
tacagctgat caggataaac caatttatgc tgacaaaaca ttccagcctg aacctcaagt   26640
aggagaagaa aattggcaag aaactgaaag ctttttatggc ggtagggctc ttaaaaaaga   26700
cacaagcatg aaaccttgct atggctccta tgctagaccc accaatgtaa agggaggtca   26760
agctaaactt aaagttggag ctgatggagt tcctaccaaa gaatttgaca tagacctggc   26820
tttctttgat actcccggtg gcacagtgaa tggacaagat gagtataaag cagacattgt   26880
catgtatacc gaaaacacgt atctggaaac tccagacacg catgtggtat acaaaccagg   26940
caaggatgat gcaagttctg aaattaacct ggttcagcag tccatgccca atagacccaa   27000
ctatattggg ttcagagaca acttttattgg gctcatgtat tacaacagta ctggcaatat   27060
gggggtgctg gctggtcagg cctcacagct gaatgctgtg tcgacttgc aagacagaaa   27120
caccgagctg tcataccagc tcttgcttga ctctttgggt gacagaaccc ggtatttcag   27180
tatgtggaat caggcggtgg acagttatga tcctgatgtg cgcattattg aaaaccatgg   27240
tgtggaagac gaacttccca actattgctt cccccctggat gggtctggca ctaatgccgc   27300
ttaccaaggt gtgaaagtaa aaaatggtaa cgatggtgat gttgagagcg aatgggaaaa   27360
tgatgatact gtcgcagctc gaaatcaatt atgcaagggc aacattttg ccatggaaat   27420
```

```
taacctccaa gccaacctgt ggagaagttt cctctactcg aacgtggccc tgtacctgcc   27480
cgactcttac aagtacacgc cagccaacat caccctgccc accaacacca acacttatga   27540
ttacatgaac gggagagtgg tgcctccctc gctggtggac gcctacatca acatcggggc   27600
gcgctggtcg ctggacccca tggacaacgt caatcccttc aaccaccacc gcaacgcggg   27660
cctgcgctac cgctccatgc tcctgggcaa cgggcgctac gtgcccttcc acatccaggt   27720
gccccagaaa tttttcgcca tcaagagcct cctgctcctg cccgggtcct acacctacga   27780
gtggaacttc cgcaaggacg tcaacatgat cctgcagagc ccctcggca acgacctgcg    27840
cacgacggg gcctccatct ccttcaccag catcaacctc tacgccacct tcttccccat    27900
ggcgcacaac acggcctcca cgctcgaggc catgctgcgc aacgacacca acgaccagtc   27960
cttcaacgac tacctctcgg cggccaacat gctctacccc atcccggcca acgccaccaa   28020
cgtgcccatc tccatcccct cgcgcaactg gccgccttc cgcggctggt ccttcacgcg    28080
cctcaagacc aaggagacgc cctcgctggg ctccggggttc gacccctact tcgtctactc   28140
gggctccatc ccctacctcg acggcacctt ctacctcaac cacaccttca gaaggtctc    28200
catcaccttc gactcctccg tcagctggcc cggcaacgac cggctcctga cgcccaacga   28260
gttcgaaatc aagcgcaccg tcgacggcga gggatacaac gtggcccagt gcaacatgac   28320
caaggactgg ttcctggtcc agatgctggc ccactacaac atcggctacc agggcttcta   28380
cgtgcccgag ggctacaagg accgcatgta ctccttcttc cgcaacttcc agcccatgag   28440
ccgccaggtg gtggacgagg tcaactacaa ggactaccag gccgtcaccc tggcctacca   28500
gcacaacaac tcgggcttcg tcggctacct cgcgcccacc atgcgccagg ccagcccta    28560
ccccgccaac tacccgtacc cgctcatcgg caagagcgcc gtcaccagcg tcacccagaa   28620
aaagttcctc tgcgacaggg tcatgtgcg catccccttc tccagcaact tcatgtccat    28680
gggcgcgctc accgacctcg gccagaacat gctctatgcc aactccgccc acgcgctaga   28740
catgaatttc gaagtcgacc ccatggatga gtccacccctt ctctatgttg tcttcgaagt   28800
cttcgacgtc gtccgagtgc accagcccca ccgcggcgtc atcgaggccg tctacctgcg   28860
caccccctt tcggccggta acgccaccac ctaaattgct acttgcatga tggctgagcc   28920
cacaggctcc ggcgagcagg agctcagggc catcatccgc gacctgggct gcgggcccta   28980
cttcctgggc accttcgata gcgcttccc gggattcatg gccccgcaca agctggcctg   29040
cgccatcgtc aacacggccg gccgcgagac cggggggcgag cactggctgg ccttcgcctg   29100
gaacccgcgc tcgaacacct gctacctctt cgaccccttc gggttctcgg acgagcgcct   29160
caagcagatc taccagttcg agtacgaggg cctgctgcgc cgtagcgccc tggccaccga   29220
ggaccgctgc gtcaccctgg aaaagtccac ccagaccgtg cagggtccgc gctcggcgc    29280
ctgcgggctc ttctgctgca tgttcctgca cgccttcgtg cactggcccg accgcccat    29340
ggacaagaac cccaccatga acttgctgac ggggtgccc aacggcatgc tccagtcgcc    29400
ccaggtggaa cccacccctgc gccgcaacca ggaggcgctc taccgcttcc tcaactccca   29460
ctccgcctac tttcgctccc accgcgcgcg catcgagaag gccaccgcct tcgaccgcat   29520
gaacaatcaa gacatgtaaa ccgtgtgtgt atgtttaaaa tatcttttaa taaacagcac   29580
tttaatgtta cacatgcatc tgagatgatt ttatttttaga aatcgaaagg gttctgccgg   29640
gtctcggcat ggcccgcggg cagggacacg ttgcggaact ggtacttggc cagccacttg   29700
aactcgggga tcagcagttt gggcagcggg gtgtcgggga aggagtcggt ccacagcttc   29760
```

```
cgcgtcagct gcagggcgcc cagcaggtcg ggcgcggaga tcttgaaatc gcagttggga    29820
cccgcgttct gcgcgcgaga gttgcggtac acggggttgc agcactggaa caccatcagg    29880
gccgggtgct tcacgctcgc cagcaccgcc gcgtcggtga tgctctccac gtcgaggtcc    29940
tcggcgttgg ccatcccgaa gggggtcatc ttgcaggtct gccttcccat ggtgggcacg    30000
cacccgggct tgtggttgca atcgcagtgc agggggatca gcatcatctg ggcctggtcg    30060
gcgttcatcc ccgggtacat ggccttcatg aaagcctcca attgcctgaa cgcctgctgg    30120
gccttggctc cctcggtgaa gaagaccccg caggacttgc tagagaactg gttggtggca    30180
cagccggcat cgtgcacgca gcagcgcgcg tcgttgttgg ccagctgcac cacgctgcgc    30240
ccccagcggt tctgggtgat cttggcccgg tcggggttct ccttcagcgc gcgctgcccg    30300
ttctcgctcg ccacatccat ctcgatcatg tgctccttct ggatcatggt ggtcccgtgc    30360
aggcaccgca gtttgccctc ggcctcggtg cacccgtgca gccacagcgc gcacccggtg    30420
cactcccagt tcttgtgggc gatctgggaa tgcgcgtgca cgaacccttg caggaagcgg    30480
cccatcatgg tcgtcagggt cttgttgcta gtgaaggtca acgggatgcc gcggtgctcc    30540
tcgttgatgt acaggtggca gatgcggcgg tacacctcgc cctgctcggg catcagttgg    30600
aagttggctt tcaggtcggt ctccacgcgg tagcggtcca tcagcatagt catgatttcc    30660
atgcccttct cccaggccga gacgatgggc aggctcatag ggttcttcac catcatctta    30720
gcactagcag ccgcggccag ggggtcgctc tcatccaggg tctcaaagct ccgcttgccg    30780
tccttctcgg tgatccgcac cggggggtag ctgaagccca cggccgccag ctcctcctcg    30840
gcctgtcttt cgtcctcgct gtcctggctg acgtcctgca tgaccacatg cttggtcttg    30900
cggggtttct tcttgggcgg cagtggcggc ggagatgctt gtggcgaggg ggagcgcgag    30960
ttctcgctca ccactactat ctcttcctct tcttggtccg aggccacgcg gcggtaggta    31020
tgtctcttcg ggggcagagg cggaggcgac gggctctcgc cgccgcgact ggcggatgg     31080
ctggcagagc cccttccgcg ttcggggtg cgctcccggc ggcgtctga ctgacttcct      31140
ccgcggccgg ccattgtgtt ctcctaggga ggaacaacaa gcatggagac tcagccatcg    31200
ccaacctcgc catctgcccc caccgccggc gacgagaagc agcagcagca gaatgaaagc    31260
ttaaccgccc cgccgcccag ccccgcctcc gacgcagccg cggtcccaga catgcaagag    31320
atggaggaat ccatcgagat tgacctgggc tatgtgacgc ccgcggagca tgaggaggag    31380
ctggcagtgc gctttcaatc gtcaagccag gaagataaag aacagccaga gcaggaagca    31440
gagaacgagc agagtcaggc tgggctcgag catggcgact acctccacct gagcggggag    31500
gaggacgcgc tcatcaagca tctggcccgg caggccacca tcgtcaagga cgcgctgctc    31560
gaccgcaccg aggtgcccct cagcgtggag gagctcagcc gcgcctacga gctcaacctc    31620
ttctcgccgc gcgtgccccc caagcgccag cccaacggca cctgcgagcc caaccccgc    31680
ctcaacttct acccggtctt cgcggtgccc gaggccctgg ccacctacca catcttttc    31740
aagaaccaaa agatccccgt ctcctgccgc gccaaccgca cccgcgccga cgccctcttc    31800
aacctgggtc ccggcgcccg cctacctgat atcgcctcct ggaagaggt tcccaagatc    31860
ttcgagggtc tgggcagcga cgagactcgg gccgcgaacg ctctgcaagg agaaggagga    31920
ggagagcatg agcaccacag cgccctggtc gagttggaag gcgacaacgc gcggctggcg    31980
gtgctcaaac gcacggtcga gctgacccat ttcgcctacc cggctctgaa cctgcccccg    32040
aaaagtcatga gcgcggtcat ggaccaggtg ctcatcaagc gcgcgtcgcc catctccgag    32100
gacgagggca tgcaagactc cgaggagggc aagcccgtgg tcagcgacga gcagctggcc    32160
```

```
cggtggctgg gtcctaatgc taccccctcaa agtttggaag agcggcgcaa gctcatgatg   32220
gccgtggtcc tggtgaccgt ggagctggag tgcctgcgcc gcttcttcgc cgacgcggag   32280
accctgcgca aggtcgagga gaacctgcac tacctcttca ggcacgggtt cgtgcgccag   32340
gcctgcaaga tctccaacgt ggagctgacc aacctggtct cctacatggg catcttgcac   32400
gagaaccgcc tggggcagaa cgtgctgcac accaccctgc gcggggaggc ccgccgcgac   32460
tacatccgcg actgcgtcta cctctacctc tgccacacct ggcagacggg catgggcgtg   32520
tggcagcagt gtctggagga gcagaacctg aaagagctct gcaagctcct gcaaaagaac   32580
ctcaagggtc tgtggaccgg gttcgacgag cggaccaccg cctcggacct ggccgacctc   32640
atcttccccg agcgcctcag gctgacgctg cgcaacggcc tgcccgactt tatgagccaa   32700
agcatgttgc aaaactttcg ctctttcatc ctcgaacgct ccggaatcct gcccgccacc   32760
tgctccgcgc tgccctcgga cttcgtgccg ctgaccttcc gcgagtgccc ccgccgctg   32820 tggagccact gctacctgct gcgcctggcc aactacctgg cctaccactc ggacgtgatc   32880
gaggacgtca gcggcgaggg cctgctcgag tgccactgcc gctgcaacct ctgcacgccg   32940
caccgctccc tggcctgcaa ccccccagctg ctgagcgaga cccagatcat cggcaccttc   33000
gagttgcaag ggcccagcga gggcgaggga gccaaggggg gtctgaaact cacccccgggg   33060 ctgtggacct cggcctactt gcgcaagttc gtgcccgagg attacatcc cttcgagatc   33120 aggttctacg aggaccaatc ccagccgccc aaggccgagc tgtcggcctg cgtcatcacc   33180 caggggggcga tcctggccca attgcaagcc atccagaaat cccgccaaga attcttgctg   33240
aaaaagggcc gcggggtcta cctcgacccc cagaccggtg aggagctcaa ccccggcttc   33300
ccccaggatg ccccgaggaa acaagaagct gaaagtggag ctgccgcccg tggaggattt   33360
ggaggaagac tgggagaaca gcagtcaggc agaggagatg gaggaagact gggacagcac   33420
tcaggcagag gaggacagcc tgcaagacag tctggaggaa gacgaggagg aggcagagga   33480
ggaggtggaa gaagcagccg ccgccagacc gtcgtcctcg gcggggggaga aagcaagcag   33540 cacggatacc atctccgctc cgggtcgggg tcccgctcgg ccccacagta gatgggacga   33600
gaccgggcga ttcccgaacc ccaccaccca gaccggtaag aaggagcggc agggatacaa   33660
gtcctggcgg gggcacaaaa acgccatcgt ctcctgcttg caggcctgcg ggggcaacat   33720
ctccttcacc cggcgctacc tgctcttcca ccgcggggtg aacttccccc gcaacatctt   33780
gcattactac cgtcacctcc acagcccca ctacttccaa gaagaggcag cagcagcaga   33840
aaaagaccag aaaaccagct agaaaatcca cagcggcggc agcggcaggt ggactgagga   33900
tcgcggcgaa cgagccggcg cagacccggg agctgaggaa ccggatcttt cccaccctct   33960
atgccatctt ccagcagagt cggggggcagg agcaggaact gaaagtcaag aaccgttctc   34020
tgcgctcgct caccccgcagt tgtctgtatc acaagagcga agaccaactt cagcgcactc   34080
tcgaggacgc cgaggctctc ttcaacaagt actgcgcgct cactcttaaa gagtagcccg   34140
cgcccgccca gtcgcagaaa aaggcgggaa ttacgtcacc tgtgcccttc gccctagccg   34200
cctccaccca gcaccgccat gagcaaagag attcccacgc cttacatgtg gagctaccag   34260
ccccagatgg gcctggccgc cggcgccgcc caggactact ccaccccgcat gaattggctc   34320 agcgccgggc ccgcgatgat ctcacggggtg aatgacatcc gcgcccaccg aaaccagata   34380
ctcctagaac agtcagcgct caccgccacg ccccgcaatc acctcaatcc gcgtaattgg   34440
cccgccgccc tggtgtacca ggaaattccc cagcccacga ccgtactact tccgcgagac   34500
```

```
gcccaggccg aagtccagct gactaactca ggtgtccagc tggcgggcgg cgccaccctg   34560
tgtcgtcacc gccccgctca gggtataaag cggctggtga tccggggcag aggcacacag   34620
ctcaacgacg aggtggtgag ctcttcgctg gtctgcgac  ctgacggagt cttccaactc   34680
gccggatcgg ggagatcttc cttcacgcct cgtcaggcgg tcctgacttt ggagagttcg   34740
tcctcgcagc cccgctcggg cggcatcggc actctccagt tcgtggagga gttcactccc   34800
tcggtctact tcaaccccct ctccggctcc cccggccact acccggacga gttcatcccg   34860
aactttgacg ccatcagcga gtcggtggac ggctacgatt gattaattaa tcaactaacc   34920
ccttacccct ttaccctcca gtaaaaataa agattaaaaa tgattgaatt gatcaataaa   34980
gaatcactta cttgaaatct gaaaccaggt ctctgtccat gttttctgtc agcagcactt   35040
cactcccctc ttcccaactc tggtactgca ggccccggcg ggctgcaaac ttcctccaca   35100
ctctgaaggg gatgtcaaat tcctcctgtc cctcaatctt cattttatc  ttctatcaga   35160 tgtccaaaaa gcgcgcgcgg gtggatgatg gcttcgaccc cgtgtaccc  tacgatgcag   35220 acaacgcacc gactgtgccc ttcatcaacc ctcccttcgt ctcttcagat ggattccaag   35280
aaaagcccct gggggtgttg tccctgcgac tggccgaccc cgtcaccacc aagaatgggg   35340
ctgtcaccct caagctgggg gagggggtgg acctcgacga ctcgggaaaa ctcatctcca   35400
aaaatgccac caaggccact gcccctctca gtatttccaa cggcaccatt tcccttaaca   35460
tggctgcccc ttttttacaac aacaatggaa cgttaagtct caatgtttct acaccattag   35520
cagtatttcc cacttttaac actttaggta tcagtcttgg aaacggtctt caaacttcta   35580
ataagttgct gactgtacag ttaactcatc ctcttacatt cagctcaaat agcatcacag   35640
taaaaacaga caaaggactc tatattaatt ctagtggaaa cagagggctt gaggctaaca   35700
taagcctaaa aagaggactg attttgatg  gtaatgctat tgcaacatac cttggaagtg   35760
gtttagacta tggatcctat gatagcgatg ggaaaacaag acccatcatc accaaaattg   35820
gagcaggttt gaattttgat gctaataatg ccatggctgt gaagctaggc acaggtttaa   35880
gttttgactc tgccggtgcc ttaacagctg gaaacaaaga ggatgacaag ctaacacttt   35940
ggactacacc tgacccaagc cctaattgtc aattactttc agacagagat gccaaattta   36000
ccctatgtct tacaaaatgc ggtagtcaaa tactaggcac tgttgcagta gctgctgtta   36060
ctgtaggttc agcactaaat ccaattaatg acacagtaaa aagcgccata gtattcctta   36120
gatttgactc tgacggtgtg ctcatgtcaa actcatcaat ggtaggtgat tactggaact   36180
ttagggaagg acagaccacc caaagtgtgg cctatacaaa tgctgtggga ttcatgccca   36240
atctaggtgc atatcctaaa acccaaagca aaacaccaaa aaatagtata gtaagtcagg   36300
tatatttaaa tggagaaact actatgccaa tgacactgac aataactttc aatggcactg   36360
atgaaaaaga cacaacacct gtgagcactt actccatgac ttttacatgg cagtggactg   36420
gagactataa ggacaagaat attacctttg ctaccaactc cttttactttc tcctacatgg   36480 cccaagaata aaccctgcat gccaaccccca ttgttcccac cactatggaa aactctgaag   36540
cagaaaaaaa taaagttcaa gtgttttatt gattcaacag ttttctcaca gaaccctagt   36600
attcaacctg ccacctccct cccaacacac agagtacaca gtcctttctc cccggctggc   36660
cttaaaaagc atcatatcat gggtaacaga catattctta ggtgttatat tccacacggt   36720
ttcctgtcga gccaaacgct catcagtgat attaataaac tccccgggca gctcacttaa   36780
gttcatgtcg ctgtccagct gctgagccac aggctgctgt ccaacttgcg gttgcttaac   36840
gggcggcgaa ggagaagtcc acgcctacat gggggtagag tcataatcgt gcatcaggat   36900
```

```
agggcggtgg tgctgcagca gcgcgcgaat aaactgctgc cgccgccgct ccgtcctgca   36960
ggaatacaac atggcagtgg tctcctcagc gatgattcgc accgcccgca gcataaggcg   37020
ccttgtcctc cgggcacagc agcgcaccct gatctcactt aaatcagcac agtaactgca   37080
gcacagcacc acaatattgt tcaaaatccc acagtgcaag gcgctgtatc caaagctcat   37140
ggcggggacc acagaaccca cgtggccatc ataccacaag cgcaggtaga ttaagtggcg   37200
acccctcata aacacgctgg acataaacat tacctctttt ggcatgttgt aattcaccac   37260
ctcccggtac catataaacc tctgattaaa catggcgcca tccaccacca tcctaaacca   37320
gctggccaaa acctgcccgc cggctataca ctgcagggaa ccgggactgg aacaatgaca   37380
gtggagagcc caggactcgt aaccatggat catcatgctc gtcatgatat caatgttggc   37440
acaacacagg cacacgtgca tacacttcct caggattaca agctcctccc gcgttagaac   37500
catatcccag ggaacaaccc attcctgaat cagcgtaaat cccacactgc agggaagacc   37560
tcgcacgtaa ctcacgttgt gcattgtcaa agtgttacat tcgggcagca gcggatgatc   37620
ctccagtatg gtagcgcggg tttctgtctc aaaaggaggt agacgatccc tactgtacgg   37680
agtgcgccga gacaaccgag atcgtgttgg tcgtagtgtc atgccaaatg gaacgccgga   37740
cgtagtcata tttcctgaag caaaaccagg tgcgggcgtg acaaacagat ctgcgtctcc   37800
ggtctcgccg cttagatcgc tctgtgtagt agttgtagta tatccactct ctcaaagcat   37860
ccaggcgccc cctggcttcg ggttctatgt aaactccttc atgcgccgct gccctgataa   37920
catccaccac cgcagaataa gccacaccca gccaacctac acattcgttc tgcgagtcac   37980
acacgggagg agcgggaaga gctggaagaa ccatgattaa ctttattcca aacggtctcg   38040
gagcacttca aaatgcaggt cccggaggtg gcacctctcg cccccactgt gttggtggaa   38100
aataacagcc aggtcaaagg tgacacggtt ctcgagatgt tccacggtgg cttccagcaa   38160
agcctccacg cgcacatcca gaaacaagag gacagcgaaa gcgggagcgt tttctaattc   38220
ctcaatcatc atattacact cctgcaccat ccccagataa ttttcatttt tccagccttg   38280
aatgattcgt attagttcct gaggtaaatc caagccagcc atgataaaaa gctcgcgcag   38340
agcgccctcc accggcattc ttaagcacac cctcataatt ccaagagatt ctgctcctgg   38400
ttcacctgca gcagattaac aatgggaata tcaaaatctc tgccgcgatc cctaagctcc   38460
tccctcaaca ataactgtat gtaatctttc atatcatctc cgaaattttt agccataggg   38520
ccgccaggaa taagagcagg gcaagccaca ttacagataa agcgaagtcc tccccagtgw   38580
gcattgccaa atgtaagatt gaaataagca tgctggctag accctgtgat atcttccaga   38640
taactggaca gaaaatcagg caagcaattt ttaagaaaat caacaaaaga aaagtcgtcc   38700
aggtgcaggt ttagagcctc aggaacaacg atggaataag tgcaaggagt gcgttccagc   38760
atggttagtg ttttttttggt gatctgtaga acaaaaaata aacatgcaat attaaaccat   38820
gctagcctgg cgaacaggtg ggtaaatcac tcttttccagc accaggcagg ctacggggtc   38880
tccggcgcga ccctcgtaga agctgtcgcc atgattgaaa agcatcaccg agagaccttc   38940
ccggtggccg gcatggatga ttcgagaaga agcatacact ccgggaacat tggcatccgt   39000
gagtgaaaaa aagcgaccta taagcctcg gggcactaca atgctcaatc tcaattccag   39060
caaagccacc ccatgcggat ggagcacaaa attggcaggt gcgtaaaaaa tgtaattact   39120
cccctcctgc acaggcagca agccccgc tccctccaga aacacataca aagcctcagc   39180
gtccatagct taccgagcac ggcaggcgca agagtcagag aaaaggctga gctctaacct   39240
```

```
gactgcccgc tcctgtgctc aatatatagc cctaacctac actgacgtaa aggccaaagt    39300
ctaaaaatac cgccaaaat gacacacacg cccagcacac gcccagaaac cggtgacaca    39360
ctcaaaaaaa tacgtgcgct tcctcaaacg cccaaaccgg cgtcatttcc gggttcccac    39420
gctacgtcac cgctcagcga cttttcaaatt ccgtcgaccg ttaaaaacgt cactcgcccc    39480 gccctaacg gtcgcccttc tctcggccaa tcaccttcct cccttcccaa attcaaacgc    39540
ctcatttgca tattaacgcg cacaaaaagt ttgaggtata tatttgaatg atg          39593

<210> SEQ ID NO 25
<211> LENGTH: 39593
<212> TYPE: DNA
<213> ORGANISM: Artificial Sequence
<220> FEATURE:
<223> OTHER INFORMATION: MVA shuttle vector p4719

<400> SEQUENCE: 25
gtttaaacgc ggccgccagg cctacccact agtcaattcg ggaggatcga acggcagat      60 cgcaaaaaac agtacataca gaaggagaca tgaacatgaa catcaaaaaa attgtaaaac    120
aagccacagt tctgactttt acgactgcac ttctggcagg aggagcgact caagccttcg    180
cgaaagaaaa taaccaaaaa gcatacaaag aaacgtacgg cgtctctcat attacacgcc    240
atgatatgct gcagatccct aaacagcagc aaaacgaaaa ataccaagtg cctcaattcg    300
atcaatcaac gattaaaaat attgagtctg caaaggact tgatgtgtgg gacagctggc    360
cgctgcaaaa cgctgacgga acagtagctg aatacaacgg ctatcacgtt gtgtttgctc    420 ttgcggggaag cccgaaagac gctgatgaca catcaatcta catgttttat caaaaggtcg    480
gcgacaactc aatcgacagc tggaaaaacg cgggccgtgt cttttaaagac agcgataagt    540 tcgacgccaa cgatccgatc ctgaaagatc agacgcaaga atggtccggt tctgcaacct    600
ttacatctga cggaaaaatc cgtttattct acactgacta ttccggtaaa cattacggca    660
aacaaagcct gacaacagcg caggtaaatg tgtcaaaatc tgatgacaca ctcaaaatca    720
acggagtgga agatcacaaa acgattttg acggagacgg aaaaacatat cagaacgttc    780
agcagtttat cgatgaaggc aattatacat ccggcgacaa ccatacgctg agagaccctc    840
actacgttga agacaaaggc cataaatacc ttgtattcga agccaacacg ggaacagaaa    900 acggataacca aggcgaagaa tctttatttta acaaagcgta ctacggcggc ggcacgaact    960
tcttccgtaa agaaagccag aagcttcagc agagcgctaa aaaacgcgat gctgagttag   1020
cgaacggcgc cctcggtatc atagagttaa ataatgatta cacattgaaa aaagtaatga   1080
agccgctgat cacttcaaac acggtaactg atgaaatcga gcgcgcgaat gttttcaaaa   1140
tgaacggcaa atggtacttg ttcactgatt cacgcggttc aaaaatgacg atcgatggta   1200
ttaactcaaa cgatatttac atgcttggtt atgtatcaaa ctctttaacc ggcccttaca   1260
agccgctgaa caaacagggg cttgtgctgc aaatgggtct tgatccaaac gatgtgacat   1320
tcacttactc tcacttcgca gtgccgcaag ccaaaggcaa caatgtggtt atcacaagct   1380
acatgacaaa cagaggcttc ttcgaggata aaaaggcaac atttgcgcca agcttcttaa   1440
tgaacatcaa aggcaataaa acatccgttg tcaaaaacag catcctggag caaggacagc   1500
tgacagtcaa ctaataacag caaaaagaaa atgccgatac ttcattggca ttttcttttta   1560 tttctcaaca agatggtgaa ttgactagtg ggtagatcca caggacgggt gtggtcgcca   1620
tgatcgcgta gtcgatagtg gctccaagta gcgaagcgag caggactggg cggcggccaa   1680
agcggtcgga cagtgctccg agaacggtg cgcatagaaa ttgcatcaac gcatatagcg   1740
```

```
ctagcagcac gccatagtga ctggcgatgc tgtcggaatg gacgatatcc cgcaagaggc    1800
ccggcagtac cggcataacc aagcctatgc ctacagcatc cagggtgacg gtgccgagga    1860
tgacgatgag cgcattgtta gatttcatac acggtgcctg actgcgttag caatttaact    1920
gtgataaact accgcattaa agcttatcga tgataagctg tcaaacatga gaattgatcc    1980 ggaacccttta atataacttc gtataatgta tgctatacga agttattagg tccctcgact    2040 ataggggtcac cgtcgacagc gacacacttg catcggatgc agcccggtta acgtgccggc    2100
acggcctggg taaccaggta ttttgtccac ataaccgtgc gcaaaatgtt gtggataagc    2160
aggacacagc agcaatccac agcaggcata caaccgcaca ccgaggttac tccgttctac    2220
aggttacgac gacatgtcaa tacttgccct tgacaggcat tgatggaatc gtagtctcac    2280
gctgatagtc tgatcgacaa tacaagtggg accgtggtcc cagaccgata atcagaccga    2340
crayacgagt gggaycgtgg tcccagacta ataatcagac cgacgatacg agtgggaccg    2400
tggtcccaga ctaataatca gaccgacgat acgagtggga ccgtggtycc agwctratwa    2460
tcagaccgac gatacragtg gracmgtggk cccagasaka atawtcagrc cgagwtaygc    2520
wktckggcct gtaacaaagg acattaagta aagacagata mrmgtgrgac taaaacgtgg    2580
tcccagtctg attatcagac cgacgatacg agtgggaccg tggtcccaga ctaataatca    2640
gaccgacgat acgagtggga ccgtggtccc agactaataa tcagaccgac gatacgagtg    2700
ggaccgtggt cccagtctga ttatcagacc gacgatacaa gtggaacagt gggcccagag    2760
agaatattca ggccagttat gctttctggc ctgtaacaaa ggacattaag taaagacaga    2820
taaacgtaga ctaaaacgtg gtcgcatcag ggtgctggct tttcaagttc cttaagaatg    2880
gcctcaattt tctctataca ctcagttgga acacgagacc tgtccaggtt aagcaccatt    2940
ttatcgccct tatacaatac tgtcgctcca ggagcaaact gatgtcgtga gcttaaacta    3000
gttcttgatg cagatgacgt tttaagcaca gaagttaaaa gagtgataac ttcttcagct    3060
tcaaatatca ccccagcttt tttctgctca tgaaggttag atgcctgctg cttaagtaat    3120
tcctctttat ctgtaaaggc tttttgaagt gcatcacctg accgggcaga tagttcaccg    3180
gggtgagaaa aaagagcaac aactgattta ggcaatttgg cggtgttgat acagcgggta    3240
ataatcttac gtgaaatatt ttccgcatca gccagcgcag aaatatttcc agcaaattca    3300
ttctgcaatc ggcttgcata acgctgacca cgttcataag cacttgttgg gcgataatcg    3360
ttacccaatc tggataatgc agccatctgc tcatcatcca gctcgccaac cagaacacga    3420
taatcacttt cggtaagtgc agcagcttta cgacggcgac tcccatcggc aatttctatg    3480
acaccagata ctcttcgacc gaacgccggt gtctgttgac cagtcagtag aaaagaaggg    3540
atgagatcat ccagtgcgtc ctcagtaagc agctcctggt cacgttcatt acctgaccat    3600
acccgagagg tcttctcaac actatcaccc cggagcactt caagagtaaa cttcacatcc    3660
cgaccacata caggcaaagt aatggcatta ccgcagccca ttactcctac gcgcgcaatt    3720
aacgaatcca ccatcggggc agctggtgtc gataacgaag tatcttcaac cggttgagta    3780
ttgagcgtat gttttggaat aacaggcgca cgcttcatta tctaatctcc cagcgtggtt    3840
taatcagacg atcgaaaatt tcattgcaga caggttccca aatagaaaga gcatttctcc    3900
aggcaccagt tgaagagcgt tgatcaatgg cctgttcaaa aacagttctc atccggatct    3960
gacctttacc aacttcatcc gtttcacgta caacattttt tagaaccatg cttccccagg    4020
catcccgaat ttgctcctcc atccacgggg actgagagcc attactattg ctgtatttgg    4080
```

```
taagcaaaat acgtacatca ggctcgaacc ctttaagatc aacgttcttg agcagatcac   4140
gaagcatatc gaaaaactgc agtgcggagg tgtagtcaaa caactcagca ggcgtgggaa   4200
caatcagcac atcagcagca catacgacat taatcgtgcc gatacccagg ttaggcgcgc   4260
tgtcaataac tatgacatca tagtcatgag caacagtttc aatggccagt cggagcatca   4320
ggtgtggatc ggtgggcagt ttaccttcat caaatttgcc cattaactca gtttcaatac   4380
ggtgcagagc cagacaggaa ggaataatgt caagccccgg ccagcaagtg ggctttattg   4440
cataagtgac atcgtccttt tccccaagat agaaaggcag gagagtgtct tctgcatgaa   4500
tatgaagatc tggtacccat ccgtgataca ttgaggctgt tccctggggg tcgttacctt   4560
ccacgagcaa aacacgtagc cccttcagag ccagatcctg agcaagatga acagaaactg   4620
aggttttgta aacgccacct ttatgggcag caaccccgat caccggtgga aatacgtctt   4680
cagcacgtcg caatcgcgta ccaaacacat cacgcatatg attaatttgt tcaattgtat   4740
aaccaacacg ttgctcaacc cgtcctcgaa tttccatatc cgggtgcggt agtcgccctg   4800 cttttctcggc atctctgata gcctgagaag aaacccaac taaatccgct gcttcaccta   4860
ttctccagcg ccgggttatt ttcctcgctt ccgggctgtc atcattaaac tgtgcaatgg   4920
cgatagcctt cgtcatttca tgaccagcgt ttatgcactg gttaagtgtt tccatgagtt   4980
tcattctgaa catccttaa tcattgcttt gcgttttttt attaaatctt gcaatttact   5040
gcaaagcaac aacaaaatcg caaagtcatc aaaaaaccgc aaagttgttt aaaataagag   5100
caacactaca aaaggagata agaagagcac atacctcagt cacttattat cactagcgct   5160
cgccgcagcc gtgtaaccga gcatagcgag cgaactggcg aggaagcaaa gaagaactgt   5220
tctgtcagat agctcttacg ctcagcgcaa gaagaaatat ccaccgtggg aaaaactcca   5280
ggtagaggta cacacgcgga tagccaattc agagtaataa actgtgataa tcaaccctca   5340
tcaatgatga cgaactaacc cccgatatca ggtcacatga cgaagggaaa gagaaggaaa   5400
tcaactgtga caaactgccc tcaaatttgg cttccttaaa aattacagtt caaaaagtat   5460
gagaaaatcc atgcaggctg aaggaaacag caaaactgtg acaaattacc ctcagtaggt   5520
cagaacaaat gtgacgaacc accctcaaat ctgtgacaga taaccctcag actatcctgt   5580
cgtcatggaa gtgatatcgc ggaaggaaaa tacgatatga gtcgtctggc ggccttttctt   5640 tttctcaatg tatgagaggc gcattggagt tctgctgttg atctcattaa cacagacctg   5700
caggaagcgg cggcggaagt caggcatacg ctggtaactt tgaggcagct ggtaacgctc   5760
tatgatccag tcgattttca gagagacgat gcctgagcca tccggcttac gatactgaca   5820
cagggattcg tataaacgca tggcatacgg attggtgatt tcttttgttt cactaagccg   5880
aaactgcgta aaccggttct gtaacccgat aaagaaggga atgagatatg ggttgatatg   5940
tacactgtaa agccctctgg atggactgtg cgcacgtttg ataaaccaag gaaaagattc   6000
atagcctttt tcatcgccgg catcctcttc agggcgataa aaaaccactt ccttccccgc   6060
gaaactcttc aatgcctgcc gtatatcctt actggcttcc gcagaggtca atccgaatat   6120
ttcagcatat ttagcaacat ggatctcgca gataccgtca tgttcctgta gggtgccatc   6180
agattttctg atctggtcaa cgaacagata cagcatacgt ttttgatccc gggagagact   6240
atatgccgcc tcagtgaggt cgtttgactg gacgattcgc gggctatttt tacgtttctt   6300
gtgattgata accgctgttt ccgccatgac agatccatgt gaagtgtgac aagtttttag   6360
attgtcacac taaataaaaa agagtcaata agcaggata acttttgtgaa aaaacagctt   6420 cttctgaggg caatttgtca cagggttaag ggcaatttgt cacagacagg actgtcattt   6480
```

```
gagggtgatt tgtcacactg aaagggcaat ttgtcacaac accttctcta gaaccagcat    6540
ggataaaggc ctacaaggcg ctctaaaaaa gaagatctaa aaactataaa aaaataatt    6600 ataaaaatat ccccgtggat aagtggataa ccccaaggga agttttttca ggcatcgtgt    6660
gtaagcagaa tatataagtg ctgttccctg gtgcttcctc gctcactcga gggcttcgcc    6720
ctgtcgctca actgcggcga gcactactgg ctgtaaaagg acagaccaca tcatggttct    6780
gtgttcatta ggttgttctg tccattgctg acataatccg ctccacttca acgtaacacc    6840
gcacgaagat ttctattgtt cctgaaggca tattcaaatc gttttcgtta ccgcttgcag    6900
gcatcatgac agaacactac ttcctataaa cgctacacag gctcctgaga ttaataatgc    6960
ggatctctac gataatggga gattttcccg actgtttcgt tcgcttctca gtggataaca    7020
gccagcttct ctgtttaaca gacaaaaaca gcatatccac tcagttccac atttccatat    7080
aaaggccaag gcatttattc tcaggataat tgtttcagca tcgcaaccgc atcagactcc    7140
ggcatcgcaa actgcacccg gtgccgggca gccacatcca gcgcaaaaac cttcgtgtag    7200
acttccgttg aactgatgga cttatgtccc atcaggcttt gcagaacttt cagcggtata    7260
ccggcataca gcatgtgcat cgcataggaa tggcggaacg tatgtggtgt gaccggaaca    7320
gagaacgtca caccgtcagc agcagcggcg gcaaccgcct ccccaatcca ggtcctgacc    7380
gttctgtccg tcacttccca gatccgcgct ttctctgtcc ttcctgtgcg acggttacgc    7440
cgctccatga gcttatcgcg aataaatacc tgtgacggaa gatcacttcg cagaataaat    7500
aaatcctggt gtccctgttg ataccgggaa gccctgggcc aacttttggc gaaaatgaga    7560
cgttgatcgg cacgtaagag gttccaactt tcaccataat gaaataagat cactaccggg    7620 cgtattttt gagttatcga gattttcagg agctaaggaa gctaaaatgg agaaaaaat    7680 cactggatat accaccgttg atatatccca atggcatcgt aaagaacatt ttgaggcatt    7740
tcagtcagtt gctcaatgta cctataacca gaccgttcag ctggatatta cggcctttt    7800 aaagaccgta agaaaaata agcacaagtt ttatccggcc tttattcaca ttcttgcccg    7860
cctgatgaat gctcatccgg agttccgtat ggcaatgaaa gacggtgagc tggtgatatg    7920
ggatagtgtt cacccttgtt acaccgtttt ccatgagcaa actgaaacgt tttcatcgct    7980
ctggagtgaa taccacgacg atttccggca gtttctacac atatattcgc aagatgtggc    8040
gtgttacggt gaaaacctgg cctatttccc taaagggttt attgagaata tgttttcgt    8100 ctcagccaat ccctgggtga gtttcaccag ttttgattta aacgtggcca atatggacaa    8160
cttcttcgcc cccgttttca ccatgggcaa atattatacg caaggcgaca aggtgctgat    8220
gccgctggcg attcaggttc atcatgccgt ttgtgatggc ttccatgtcg cagaatgct    8280 taatgaatta caacagtact gcgatgagtg cagggcggg gcgtaatttt tttaaggcag    8340
ttattggtgc ccttaaacgc ctggttgcta cgcctgaata agtgataata agcggatgaa    8400
tggcagaaat tcgatgataa gctgtcaaac atgagaattg gtcgacgcg cgccaaagct    8460 tgcatgcctg cagccgcgta acctggcaaa atcggttacg gttgagtaat aaatggatgc    8520
cctgcgtaag cggggcacat ttcattacct ctttctccgc acccgacata gataataact    8580
tcgtatagta tacattatac gaagttatct agtagactta atcgcgttta aacccatcat    8640
caataatata cctcaaactt tttgtgcgcg ttaatatgca aatgaggcgt tgaatttgg    8700 gaagggagga aggtgattgg ccgagagaag ggcgaccgtt aggggcgggg cgagtgacgt    8760
tttgatgacg tgaccgcgag gaggagccag tttgcaagtt ctcgtgggaa aagtgacgtc    8820
```

-continued

```
aaacgaggtg tggtttgaac acggaaatac tcaattttcc cgcgctctct gacaggaaat    8880
gaggtgtttc taggcggatg caagtgaaaa cgggccattt tcgcgcgaaa actgaatgag    8940
gaagtgaaaa tctgagtaat ttcgcgttta tgacagggag gagtatttgc cgagggccga    9000
gtagactttg accgattacg tgggggtttc gattaccgtg tttttcacct aaatttccgc    9060
gtacggtgtc aaagtccggt gttttttacgt aggtgtcagc tgatcgccag ggtatttaaa    9120
cctgcgctct ccagtcaaga ggccactctt gagtgccagc gagaagagtt ttctcctccg    9180
cgcgcgagtc agatctacac tttgaaaggc gatcgctagc gacatcgatc acaagtttgt    9240
acaaaaaagc tgaacgagaa acgtaaaatg atataaatat caatatatta aattagattt    9300
tgcataaaaa acagactaca taatactgta aaacacaaca tatccagtca ctatggcggc    9360
cgccgattta ttcaacaaag ccacgttgtg tctcaaaatc tctgatgtta cattgcacaa    9420
gataaaaata tatcatcatg aacaataaaa ctgtctgctt acataaacag taatacaagg    9480
ggtgttatga gccatattca acgggaaacg tcttgctcga ggccgcgatt aaattccaac    9540
atggatgctg atttatatgg gtaaaatgg gctcgtgata atgtcgggca atcaggtgcg    9600
acaatctatc gattgtatgg gaagcccgat gcgccagagt tgtttctgaa acatggcaaa    9660
ggtagcgttg ccaatgatgt tacagatgag atggtcagac taaactggct gacggaattt    9720
atgcctcttc cgaccatcaa gcattttatc cgtactcctg atgatgcatg gttactcacc    9780
actgcgatcc ccgggaaaac agcattccag gtattagaag aatatcctga ttcaggtgaa    9840
aatattgttg atgcgctggc agtgttcctg cgccggttgc attcgattcc tgtttgtaat    9900
tgtccttttta acagcgatcg cgtatttcgt ctcgctcagg cgcaatcacg aatgaataac    9960
ggtttggttg atgcgagtga ttttgatgac gagcgtaatg gctggcctgt tgaacaagtc    10020
tggaaagaaa tgcataagct tttgccattc tcaccggatt cagtcgtcac tcatggtgat    10080
ttctcacttg ataaccttat ttttgacgag gggaaattaa taggttgtat tgatgttgga    10140
cgagtcggaa tcgcagaccg ataccaggat cttgccatcc tatggaactg cctcggtgag    10200
ttttctcctt cattacagaa acggcttttt caaaaatatg gtattgataa tcctgatatg    10260
aataaattgc agtttcattt gatgctcgat gagtttttct aatcagaatt ggttaattgg    10320
ttgtaacact ggcacgcgtg gatccggctt actaaaagcc agataacagt atgcgtattt    10380
gcgcgctgat ttttgcggta taagaatata tactgatatg tatacccgaa gtatgtcaaa    10440
aagaggtatg ctatgaagca gcgtattaca gtgacagttg acagcgacag ctatcagttg    10500
ctcaaggcat atatgatgtc aatatctccg gtctggtaag cacaaccatg cagaatgaag    10560
cccgtcgtct gcgtgccgaa cgctggaaag cggaaaatca ggaagggatg gctgaggtcg    10620
cccggtttat tgaaatgaac ggctcttttg ctgacgagaa caggggctgg tgaaatgcag    10680
tttaaggttt acacctataa aagagagagc cgttatcgtc tgtttgtgga tgtacagagt    10740
gatattattg acacgcccgg gcgacggatg gtgatccccc tggccagtgc acgtctgctg    10800
tcagataaag tctcccgtga actttacccg gtggtgcata tcgggatga aagctggcgc    10860
atgatgacca ccgatatggc cagtgtgccg gtctccgtta tcggggaaga agtggctgat    10920
ctcagccacc gcgaaaatga catcaaaaac gccattaacc tgatgttctg gggaatataa    10980
atgtcaggct cccttataca cagccagtct gcaggtcgac catagtgact ggatatgttg    11040
tgttttacag tattatgtag tctgttttt atgcaaaatc taatttaata tattgatatt    11100
tatatcattt tacgtttctc gttcagcttt cttgtacaaa gtggtgatcg attcgacaga    11160
tcgcgatcgc agtgagtagt gttctggggc gggggaggac ctgcatgagg gccagaatga    11220
```

```
ctgaaatctg tgcttttctg tgtgttgcag catcatgagc ggaagcggct cctttgaggg    11280
aggggtattc agcccttatc tgacggggcg tctcccctcc tgggcgggag tgcgtcagaa    11340
tgtgatggga tccacggtgg acggccggcc cgtgcagccc gcgaactctt caaccctgac    11400
ctatgcaacc ctgagctctt cgtcggtgga cgcagctgcc gccgcagctg ctgcatccgc    11460
cgccagcgcc gtgcgcggaa tggccatggg cgccggctac tacggcactc tggtggccaa    11520
ctcgagttcc accaataatc ccgccagcct gaacgaggag aagctgctgc tgctgatggc    11580
ccagcttgag gccttgaccc agcgcctggg cgagctgacc cagcaggtgg ctcagctgca    11640
ggagcagacg cgggccgcgg ttgccacggt gaaatccaaa taaaaaatga atcaataaat    11700
aaacggagac ggttgttgat tttaacacag agtctgaatc tttatttgat ttttcgcgcg    11760
cggtaggccc tggaccaccg gtctcgatca ttgagcaccc ggtggatctt ttccaggacc    11820
cggtagaggt gggcttggat gttgaggtac atgggcatga gcccgtcccg ggggtggagg    11880
tagctccatt gcagggcctc gtgctcgggg gtggtgttgt aaatcaccca gtcatagcag    11940
gggcgcaggg cgtggtgttg cacaatatct ttgaggagga gactgatggc cacgggcagc    12000
cctttggtgt aggtgtttac aaatctgttg agctgggagg gatgcatgcg ggggagatg     12060 aggtgcatct tggcctggat cttgagattg gcgatgttac cgcccagatc ccgcctgggg    12120
ttcatgttgt gcaggaccac cagcacggtg tatccggtgc acttgggaa tttatcatgc     12180 aacttggaag ggaaggcgtg aaagaatttg gcgacgccct tgtgtccgcc caggtttcc     12240 atgcactcat ccatgatgat ggcaatgggc ccgtgggcgg cggcctgggc aaagacgttt    12300 cggggtcgg acacatcata gttgtggtcc tgggtgaggt catcataggc cattttaatg     12360 aatttgggc ggagggtgcc ggactggggg acaaaggtac cctcgatccc ggggcgtag      12420 ttcccctcac agatctgcat ctcccaggct ttgagctcag aggggggat catgtccacc     12480 tgcggggcga taaagaacac ggtttccggg gcggggaga tgagctgggc cgaaagcaag     12540
ttccggagca gctgggactt gccgcagccg gtggggccgt aaatgacccc gatgaccggc    12600
tgcaggtggt agttgaggga gagacagctg ccgtcctccc ggaggagggg gccacctcg    12660 ttcatcatct cgcgcacgtg catgttctcg cgcaccagtt ccgccaggag gcgctctccc    12720
cccagagata ggagctcctg gagcgaggcg aagttttca gcggcttgag tccgtcggcc     12780
atgggcattt tggagagggt ctgttgcaag agttccaagc ggtcccagag ctcggtgatg    12840
tgctctacgg catctcgatc cagcagacct cctcgtttcg cggggttggga cgactgcggg   12900 agtagggcac cagacgatgg gcgtccagcg cagccagggt ccggtccttc cagggccgca    12960
gcgtccgcgt cagggtggtc tccgtcacgg tgaagggtg cgcgccgggc tgggcgcttg     13020
cgagggtgcg cttcaggctc atccggctgg tcgaaaaccg ctcccgatcg cgccctgcg     13080 cgtcggccag gtagcaattg accatgagtt cgtagttgag cgcctcggcc gcgtggcctt    13140
tggcgcggag cttacctttg gaagtctgcc cgcaggcggg acagaggagg acttgagggg    13200
cgtagagctt gggggcgagg aagacggaat cggggggcgta ggcgtccgcg ccgcagtggg   13260
cgcagacggt ctcgcactcc acgagccagg tgaggtcggg ctggtcgggg tcaaaaacca    13320
gtttcccgcc gttcttttg atgcgtttct tacctttggt ctccatgagc tcgtgtcccc    13380
gctgggtgac aaagaggctg tccgtgtccc cgtagaccga ctttatgggc cggtcctcga    13440
gcggtgtgcc gcggtcctcc tcgtagagga accccgccca ctccgagacg aaagcccggg    13500
tccaggccag cacgaaggag gccacgtggg acgggtagcg gtcgttgtcc accagcgggt    13560
```

```
ccactttttc cagggtatgc aaacacatgt cccctcgtc cacatccagg aaggtgattg    13620
gcttgtaagt gtaggccacg tgaccggggg tcccggccgg gggggtataa aaggggggcgg  13680 gcccctgctc gtcctcactg tcttccggat cgctgtccag gagcgccagc tgttgggta    13740 ggtattccct ctcgaaggcg ggcatgacct cggcactcag gttgtcagtt tctagaaacg   13800
aggaggattt gatattgacg gtgccagcgg agatgccttt caagagcccc tcgtccatct   13860
ggtcagaaaa gacgattttt tgttgtcga gcttggtggc gaaggagccg tagagggcgt    13920
tggaaaggag cttggcgatg gagcgcatgg tctggttttt ttccttgtcg gcgcgctcct   13980
tggccgcgat gttgagctgc acgtactcgc gcgccacgca cttccattcg gggaagacgg   14040
tggtcatctc gtcgggcacg attctgacct gccaacctcg attatgcagg gtgatgaggt   14100
ccacactggt ggccacctcg ccgcgcaggg gctcgttggt ccagcagagg cggccgccct   14160
tgcgcgagca aagggggggc agagggtcca gcatgacctc gtcgggggg tcggcatcga    14220 tggtgaagat gccgggcagg agatcggggt cgaagtagct gatggaagtg gccagatcgt   14280
ccagggaagc ttgccattcg cgcacggcca gcgcgcgctc gtaggactg aggggcgtgc    14340 cccagggcat ggggtgggtg agcgcggagg cgtacatgcc gcagatgtcg tagacgtaga   14400
ggggctcctc gaggatgccg atgtaggtgg ggtagcagcg ccccccgcgg atgctggcgc   14460
gcacgtagtc atacagctcg tgcgagggcg cgaggagccc cgggcccagg ttggtgcgac   14520 tgggctttc ggcgcggtag acgatctggc gaaagatggc atgcgagttg gaggagatgg    14580
tgggcctttg gaagatgttg aagtgggcgt gggggaggcc gaccgagtcg cggatgaagt   14640
gggcgtagga gtcttgcagt ttggcgacga gctcggcggt gacgaggacg tccagagcgc   14700
agtagtcgag ggtctcctgg atgatgtcat acttgagctg gccctttttgt ttccacagct   14760 cgcggttgag aaggaactct tcgcggtcct tccagtactc ttcgagggg aacccgtcct    14820 gatctgcacg gtaagagcct agcatgtaga actggttgac ggccttgtag gcgcagcagc   14880
ccttctccac ggggagggcg taggcctggg cggccttgcg cagggaggtg tgcgtgaggg   14940
cgaaggtgtc cctgaccatg accttgagga actggtgctt gaaatcgata tcgtcgcagc   15000 cccctgctc ccagagctgg aagtccgtgc gcttcttgta ggcggggttg ggcaaagcga    15060
aagtaacatc gttgaaaagg atcttgcccg cgcggggcat aaagttgcga gtgatgcgga   15120
aaggctgggg cacctcggcc cggttgttga tgacctgggc ggcgagcacg atctcgtcga   15180
aaccgttgat gttgtggccc acgatgtaga gttccacgaa tcgcgggcgg cccttgacgt   15240
ggggcagctt cttgagctcc tcgtaggtga gctcgtcggg gtcgctgaga ccgtgctgct   15300
cgagcgccca gtcggcgaga tgggggttgg cgcggaggaa ggaagtccag agatccacgg   15360
ccagggcggt ttgcagacgg tcccggtact gacggaactg ctgcccgacg gccatttttt   15420 cggggtgac gcagtagaag gtgcgggggt ccccgtgcca gcggtccat ttgagctgga     15480 gggcgagatc gagggcgagc tcgacgaggc ggtcgtcccc tgagagtttc atgaccagca   15540 tgaagggac gagctgcttg ccgaaggacc ccatccaggt gtaggtttcc acatcgtagg    15600
tgaggaagag cctttcggtg cgaggatgcg agccgatggg gaagaactgg atctcctgcc   15660
accaattgga ggaatggctg ttgatgtgat ggaagtagaa atgccgacgg cgcgccgaac   15720
actcgtgctt gtgttatac aagcggccac agtgctcgca acgctgcacg ggatgcacgt    15780
gctgcacgag ctgtacctga gttcctttga cgaggaattt cagtgggaag tggagtcgtg   15840
gcgcctgcat ctcgtgctgt actacgtcgt ggtggtcggc ctggccctct tctgcctcga   15900
tggtggtcat gctgacgagc ccgcgcggga ggcaggtcca gacctcggcg cgagcgggtc   15960
```

```
ggagagcgag gacgagggcg cgcaggccgg agctgtccag ggtcctgaga cgctgcggag   16020
tcaggtcagt gggcagcggc ggcgcgcggt tgacttgcag gagttttttcc agggcgcgcg   16080 ggaggtccag atggtacttg atctccaccg cgccgttggt ggcgacgtcg atggcttgca   16140
gggtcccgtg cccctggggt gtgaccaccg tcccccgttt cttcttgggc ggctggggcg   16200 acggggcgg tgcctcttcc atggttagaa gcggcggcga ggacgcgcgc cgggcggcag   16260
aggcggctcg gggcccggag gcaggggcgg caggggcacg tcggcgccgc gcgcgggtag   16320
gttctggtac tgcgcccgga gaagactggc gtgagcgacg acgcgacggt tgacgtcctg   16380
gatctgacgc ctctgggtga aggccacggg acccgtgagt ttgaacctga aagagagttc   16440
gacagaatca atctcggtat cgttgacggc ggcctgccgc aggatctctt gcacgtcgcc   16500
cgagttgtcc tggtaggcga tctcggtcat gaactgctcg atctcctcct cctgaaggtc   16560
tccgcgaccg gcgcgctcca cggtggccgc gaggtcgttg gagatgcggc ccatgagctg   16620
cgagaaggcg ttcatgcccg cctcgttcca gacgcggctg tagaccacga cgccctcggg   16680
atcgcgggcg cgcatgacca cctgggcgag gttgagctcc acgtggcgcg tgaagaccgc   16740
gtagttgcag aggcgctggt agaggtagtt gagcgtggtg gcgatgtgct cggtgacgaa   16800
gaaatacatg atccagcggc ggagcggcat ctcgctgacg tcgcccagcg cctccaagcg   16860
ttccatggcc tcgtaaaagt ccacggcgaa gttgaaaaac tgggagttgc gcgccgagac   16920
ggtcaactcc tcctccagaa gacggatgag ctcggcgatg gtggcgcgca cctcgcgctc   16980
gaaggccccc gggagttcct ccacttcctc ctcttcttcc tcctccacta acatctcttc   17040
tacttcctcc tcaggcggtg gtggtggcgg gggagggggc ctgcgtcgcc ggcggcgcac   17100
gggcagacgg tcgatgaagc gctcgatggt ctcgccgcgc cggcgtcgca tggtctcggt   17160
gacggcgcgc ccgtcctcgc ggggccgcag cgtgaagacg ccgccgcgca tctccaggtg   17220
gccggggggg tccccgttgg gcagggagag ggcgctgacg atgcatctta tcaattgccc   17280
cgtagggact ccgcgcaagg acctgagcgt ctcgagatcc acgggatctg aaaaccgttg   17340
aacgaaggct tcgagccagt cgcagtcgca aggtaggctg agcacggttt cttctgccgg   17400
gtcatgttgg ggagcgggc gggcgatgct gctggtgatg aagttgaaat aggcggttct   17460
gagacggcgg atggtggcga ggagcaccag gtctttgggc ccggcttgct ggatgcgcag   17520
acggtcggcc atgccccagg cgtggtcctg acacctggcc aggtccttgt agtagtcctg   17580
catgagccgc tccacgggca cctcctcctc gcccgcgcgg ccgtgcatgc gcgtgagccc   17640
gaagccgcgc tggggctgga cgagcgccag gtcggcgacg acgcgctcgg cgaggatggc   17700
ctgctggatc tgggtgaggg tggtctggaa gtcgtcaaag tcgacgaagc ggtggtaggc   17760
tccggtgttg atggtgtagg agcagttggc catgacggac cagttgacgg tctggtggcc   17820
cggacgcacg agctcgtggt acttgaggcg cgagtaggcg cgcgtgtcga agatgtagtc   17880
gttgcaggtg cgcaccaggt actggtagcc gatgaggaag tgcggcggcg gctggcggta   17940
gagcggccat cgctcggtgg cggggggcgcc gggcgcgagg tcctcgagca tggtgcggtg   18000
gtagccgtag atgtacctgg acatccaggt gatgccggcg gcggtggtgg aggcgcgcgg   18060
gaactcgcgc acgcggttcc agatgttgcg cagcggcagg aagtagttca tggtgggcac   18120
ggtctggccc gtgaggcgcg cgcagtcgtg gatgctctat acgggcaaaa acgaaagcgg   18180
tcagcggctc gactccgtgg cctggaggct aagcgaacgg gttgggctgc gcgtgtaccc   18240
cggttcgaat ctcgaatcag gctggagccg cagctaacgt ggtactggca ctcccgtctc   18300
```

```
gacccaagcc tgcaccaacc ctccaggata cggaggcggg tcgttttgca acttttttg    18360
gaggccggaa atgaaactag taagcgcgga aagcggccga ccgcgatggc tcgctgccgt    18420
agtctggaga agaatcgcca gggttgcgtt gcggtgtgcc ccggttcgag gccggccgga    18480
ttccgcggct aacgagggcg tggctgcccc gtcgtttcca agaccccata gccagccgac    18540
ttctccagtt acggagcgag cccctctttt gttttgtttg ttttgccag atgcatcccg    18600
tactgcggca gatgcgcccc caccaccctc caccgcaaca acagccccct cctccacagc    18660
cggcgcttct gcccccgccc cagcagcagc agcaacttcc agccacgacc gccgcggccg    18720
ccgtgagcgg ggctggacag acttctcagt atgatcacct ggccttggaa gagggcgagg    18780
ggctggcgcg cctgggggcg tcgtcgccgg agcggcaccc gcgcgtgcag atgaaaaggg    18840
acgctcgcga ggcctacgtg cccaagcaga acctgttcag agacaggagc ggcgaggagc    18900
ccgaggagat gcgcgcggcc cggttccacg cggggcggga gctgcggcgc ggcctggacc    18960
gaaagagggt gctgagggac gaggatttcg aggcggacga gctgacgggg atcagccccg    19020
cgcgcgcgca cgtggccgcg gccaacctgg tcacggcgta cgagcagacc gtgaaggagg    19080
agagcaactt ccaaaaatcc ttcaacaacc acgtgcgcac cctgatcgcg cgcgaggagg    19140
tgaccctggg cctgatgcac ctgtgggacc tgctggaggc catcgtgcag aaccccacca    19200
gcaagccgct gacggcgcag ctgttcctgg tggtgcagca tagtcgggac aacgaggcgt    19260
tcagggaggc gctgctgaat atcaccgagc ccgaggccg ctggctcctg gacctggtga    19320
acattctgca gagcatcgtg gtgcaggagc gcgggctgcc gctgtccgag aagctggcgg    19380
ccatcaactt ctcggtgctg agtctgggca agtactacgc taggaagatc tacaagaccc    19440
cgtacgtgcc catagacaag gaggtgaaga tcgacgggtt ttacatgcgc atgaccctga    19500
aagtgctgac cctgagcgac gatctggggg tgtaccgcaa cgacaggatg caccgcgcgg    19560
tgagcgccag caggcggcgc gagctgagcg accaggagct gatgcacagc ctgcagcggg    19620
ccctgaccgg ggccgggacc gaggggggaga gctactttga catgggcgcg gacctgcact    19680
ggcagcccag ccgccgggcc ttggaggcgg caggcggtcc ccctacata aagaggtgg    19740
acgatgaggt ggacgaggag ggcgagtacc tggaagactg atggcgcgac cgtatttttg    19800
ctagatgcaa caacagccac ctcctgatcc cgcgatgcgg gcggcgctgc agagccagcc    19860
gtccggcatt aactcctcgg acgattggac ccaggccatg caacgcatca tggcgctgac    19920
gacccgcaac cccgaagcct ttagacagca gccccaggcc aacggctct cggccatcct    19980
ggaggccgtg gtgccctcgc gctccaaccc cacgcacgag aaggtcctgg ccatcgtgaa    20040
cgcgctggtg gagaacaagg ccatccgcgg cgacgaggcc ggcctggtgt acaacgcgct    20100
gctggagcgc gtggcccgct acaacagcac caacgtgcag accaacctgg accgcatggt    20160
gaccgacgtg cgcgaggccg tgcccagcg cgagcggttc caccgcgagt ccaacctggg    20220
atccatggtg gcgctgaacg ccttcctcag cacccagccc gccaacgtgc cccggggcca    20280
ggaggactac accaacttca tcagcgccct gcgcctgatg gtgaccgagg tgccccagag    20340
cgaggtgtac cagtccgggc cggactactt cttccagacc agtcgccagg gcttgcagac    20400
cgtgaacctg agccaggcgt tcaagaactt gcagggcctg tggggcgtgc aggcccggt    20460
cggggaccgc gcgacggtgt cgagcctgct gacgccgaac tcgcgcctgc tgctgctgct    20520
ggtggcccc ttcacggaca gcggcagcat caaccgcaac tcgtacctgg gctacctgat    20580
taacctgtac cgcgaggcca tcggccaggc gcacgtggac gagcagacct accaggagat    20640
cacccacgtg agccgcgccc tgggccagga cgacccgggc aatctggaag ccaccctgaa    20700
```

```
cttttttgctg accaaccggt cgcagaagat cccgccccag tacacgctca gcgccgagga   20760
ggagcgcatc ctgcgatacg tgcagcagag cgtgggcctg ttcctgatgc aggaggggggc  20820 cacccccagc gccgcgctcg acatgaccgc gcgcaacatg gagcccagca tgtacgccag   20880
caaccgcccg ttcatcaata aactgatgga ctacttgcat cgggcggccg ccatgaactc   20940
tgactatttc accaacgcca tcctgaatcc ccactggctc ccgccgccgg ggttctacac   21000
gggcgagtac gacatgcccg accccaatga cgggttcctg tgggacgatg tggacagcag   21060
cgtgttctcc ccccgaccgg gtgctaacga gcgcccttg tggaagaagg aaggcagcga   21120
ccgacgcccg tcctcggcgc tgtccggccg cgagggtgct gccgcggcgg tgcccgaggc   21180
cgccagtcct ttcccgagct tgcccttctc gctgaacagt attcgcagca gcgagctggg   21240
caggatcacg cgcccgcgct tgctgggcga ggaggagtac ttgaatgact cgctgttgag   21300
acccgagcgg gagaagaact tccccaataa cgggatagag agcctggtgg acaagatgag   21360
ccgctggaag acgtatgcgc aggagcacag ggacgatccg tcgcagggg ccacgagccg    21420 gggcagcgcc gcccgtaaac gccggtggca cgacaggcag cggggactga tgtgggacga   21480
tgaggattcc gccgacgaca gcagcgtgtt ggacttgggt gggagtggta acccgttcgc   21540
tcacctgcgc ccccgcatcg ggcgcatgat gtaagagaaa ccgaaaataa atgatactca   21600
ccaaggccat ggcgaccagc gtgcgttcgt ttcttctctg ttgttgtatc tagtatgatg   21660
aggcgtgcgt acccggaggg tcctcctccc tcgtacgaga gcgtgatgca gcaggcgatg   21720
gcggcggcgg cggcgatgca gccccgctg gaggctcctt acgtgccccc gcggtacctg    21780
gcgcctacgg aggggcggaa cagcattcgt tactcggagc tggcacccct tgtacgatacc  21840 acccggttgt acctggtgga caacaagtcg gcggacatcg cctcgctgaa ctaccagaac   21900
gaccacagca acttcctgac caccgtggtg cagaacaatg acttcacccc cacggaggcc   21960
agcacccaga ccatcaactt tgacgagcgc tcgcggtggg gcggtcagct gaaaaccatc   22020
atgcacacca acatgcccaa cgtgaacgag ttcatgtaca gcaacaagtt caaggcgcgg   22080
gtgatggtct cccgcaagac ccccaacggg gtgacagtga cagatggtag tcaggatatc   22140
ttggagtatg aatgggtgga gtttgagctg cccgaaggca acttctcggt gaccatgacc   22200
atcgacctga tgaacaacgc catcatcgac aattacttgg cggtggggcg gcagaacggg   22260
gtcctggaga gcgatatcgg cgtgaagttc gacactagga acttcaggct gggctgggac   22320
cccgtgaccg agctggtcat gcccggggtg tacaccaacg aggccttcca ccccgatatt   22380
gtcttgctgc ccggctgcgg ggtggacttc accgagagcc gcctcagcaa cctgctgggc   22440
attcgcaaga ggcagcccct tccaggaggc ttccagatca tgtacgagga tctggagggg   22500
ggcaacatcc ccgcgctcct ggatgtcgac gcctatgaga aaagcaagga ggagagcgcc   22560
gccgcggcga ctgcagctgt agccaccgcc tctaccgagg tcaggggcga taattttgcc   22620
agccctgcag cagtggcagc ggccgaggcg gctgaaaccg aaagtaagat agtcattcag   22680
ccggtggaga aggatagcaa ggacaggagc tacaacgtgc tgccggacaa gataaacacc   22740
gcctaccgca gctggtacct ggcctacaac tatggcgacc ccgagaaggg cgtgcgctcc   22800
tggacgctgc tcaccacctc ggacgtcacc tgcggcgtgg agcaagtcta ctggtcgctg   22860
cccgacatga tgcaagaccc ggtcaccttc cgctccacgc gtcaagttag caactacccg   22920
gtggtgggcg ccgagctcct gccgtctac tccaagagct tcttcaacga gcaggccgtc   22980
tactcgcagc agctgcgcgc cttcacctcg ctcacgcacg tcttcaaccg cttccccgag   23040
```

```
aaccagatcc tcgtccgccc gcccgcgccc accattacca ccgtcagtga aaacgttcct   23100
gctctcacag atcacgggac cctgccgctg cgcagcagta tccggggagt ccagcgcgtg   23160
accgttactg acgccagacg ccgcacctgc ccctacgtct acaaggccct gggcatagtc   23220
gcgccgcgcg tcctctcgag ccgcaccttc taaaaaatgt ccattctcat ctcgcccagt   23280
aataacaccg gttggggcct gcgcgcgccc agcaagatgt acggaggcgc tcgccaacgc   23340
tccacgcaac accccgtgcg cgtgcgcggg cacttccgcg ctccctgggg cgccctcaag   23400
ggccgcgtgc ggtcgcgcac caccgtcgac gacgtgatcg accaggtggt ggccgacgcg   23460
cgcaactaca cccccgccgc cgcgcccgtc tccaccgtgg acgccgtcat cgacagcgtg   23520
gtggccgacg cgcgccggta cgcccgcgcc aagagccggc ggcggcgcat cgcccggcgg   23580
caccggagca cccccgccat gcgcgcgcg cgagccttgc tgcgcagggc caggcgcacg   23640
ggacgcaggg ccatgctcag ggcggccaga cgcgcggctt caggcgccag cgccggcagg   23700
acccggagac gcgcggccac ggcggcggca cggccatcg ccagcatgtc ccgcccgcgg   23760
cgagggaacg tgtactgggt gcgcgacgcc gccaccggtg tgccgcgtgcc cgtgcgcacc   23820
cgccccctc gcacttgaag atgttcactt cgcgatgttg atgtgtccca gcggcgagga   23880
ggatgtccaa gcgcaaattc aaggaagaga tgctccaggt catcgcgcct gagatctacg   23940
gccccgcggt ggtgaaggag gaaagaaagc cccgcaaaat caagcgggtc aaaaaggaca   24000
aaaaggaaga agatgacgat ctggtggagt ttgtgcgcga gttcgccccc cggcggcgcg   24060
tgcagtggcg cgggcggaaa gtgcacccgg tgctgagacc cggcaccacc gtggtcttca   24120
cgcccggcga gcgctccggc agcgcttcca agcgctccta cgacgaggtg tacgggacg   24180
aggacatcct cgagcaggcg gccgagcgcc tgggcgagtt tgcttacggc aagcgcagcc   24240
gccccgccct gaaggaagag gcggtgtcca tcccgctgga ccacgcaac cccacgccga   24300
gcctcaagcc cgtgaccctg cagcaggtgc tgccgagcgc agccgcgc cggggttca   24360
agcgcgaggg cgaggatctg tacccacca tgcagctgat ggtgcccaag cgccagaagc   24420
tggaagacgt gctggagacc atgaaggtgg accggacgt gcagcccgag gtcaaggtgc   24480
ggcccatcaa gcaggtggcc ccgggcctgg gcgtgcagac cgtggacatc aagatcccca   24540
cggagcccat ggaaacgcag accgagccca tgatcaagcc cagcaccagc accatggagg   24600
tgcagacgga tccctggatg ccatcggctc ctagccgaag accccggcgc aagtacggcg   24660
cggccagcct gctgatgccc aactacgcgc tgcatccttc catcatcccc acgccgggct   24720
accgcggcac gcgcttctac cgcggtcata caaccagccg ccgccgcaag accaccaccc   24780
gccgccgccg tcgccgcaca gccgctgcat ctacccctgc cgccctggtg cggagagtgt   24840
accgccgcgg ccgcgcgcct ctgacccctac cgcgcgcgcg ctaccacccg agcatcgcca   24900
tttaaacttt cgcctgcttt gcagatggcc ctcacatgcc gcctccgcgt tcccattacg   24960
ggctaccgag gaagaaaacc gcgccgtaga aggctggcgg ggaacgggat gcgtcgccac   25020
caccatcggc ggcggcgcgc catcagcaag cggttggggg gaggcttcct gcccgcgctg   25080
atccccatca tcgccgcggc gatcggggcg atcccggca ttgcttccgt ggcggtgcag   25140
gcctctcagc gccactgaga cacttggaaa acatcttgta ataaaccaat ggactctgac   25200
gctcctggtc ctgtgatgtg ttttcgtaga cagatggaag acatcaattt tcgtccctg   25260
gctccgcgac acggcacgcg gccgttcatg ggcacctgga gcgacatcgg caccagccaa   25320
ctgaacgggg gcgccttcaa ttggagcagt ctctggagcg ggcttaagaa tttcgggtcc   25380
acgcttaaaa cctatggcag caaggcgtgg aacagcacca cagggcaggc gctgagggat   25440
```

```
aagctgaaag agcagaactt ccagcagaag gtggtcgatg ggctcgcctc gggcatcaac    25500
ggggtggtgg acctggccaa ccaggccgtg cagcggcaga tcaacagccg cctggacccg    25560
gtgccgcccg ccggctccgt ggagatgccg caggtggagg aggagctgcc tccctggac    25620 aagcggggcg agaagcgacc ccgccccgac gcggaggaga cgctgctgac gcacacggac    25680
gagccgcccc cgtacgagga ggcggtgaaa ctgggtctgc ccaccacgcg gcccatcgcg    25740
cccctggcca ccggggtgct gaaacccgaa agtaataagc ccgcgaccct ggacttgcct    25800
cctcccgctt cccgcccctc tacagtggct aagcccctgc cgccggtggc cgtggcccgc    25860
gcgcgacccg ggggctccgc ccgccctcat gcgaactggc agagcactct gaacagcatc    25920
gtgggtctgg gagtgcagag tgtgaagcgc cgccgctgct attaaaccta ccgtagcgct    25980
taacttgctt gtctgtgtgt gtatgtatta tgtcgccgct gtccgccaga aggaggagtg    26040
aagaggcgcg tcgccgagtt gcaagatggc cacccatcg atgctgcccc agtgggcgta    26100
catgcacatc gccggacagg acgcttcgga gtacctgagt ccgggtctgg tgcagttcgc    26160
ccgcgccaca gacacctact tcagtctggg gaacaagttt aggaacccca cggtggcgcc    26220
cacgcacgat gtgaccaccg accgcagcca gcggctgacg ctgcgcttcg tgcccgtgga    26280
ccgcgaggac aacacctact cgtacaaagt gcgctacacg ctggccgtgg gcgacaaccg    26340
cgtgctggac atggccagca cctactttga catccgcggc gtgctggatc ggggccctag    26400
cttcaaaccc tactccggca ccgcctacaa cagcctggct cccaagggag cgcccaattc    26460
cagccagtgg gagcaaaaaa aggcaggcaa tggtgacact atggaaacac acacatttgg    26520
tgtggcccca atgggcggtg agaatattac aatcgacgga ttacaaattg gaactgacgc    26580
tacagctgat caggataaac caatttatgc tgacaaaaca ttccagcctg aacctcaagt    26640
aggagaagaa aattggcaag aaactgaaag cttttatggc ggtagggctc ttaaaaaaga    26700
cacaagcatg aaaccttgct atggctccta tgctagaccc accaatgtaa agggaggtca    26760
agctaaactt aaagttggag ctgatggagt tcctaccaaa gaatttgaca tagacctggc    26820
tttctttgat actcccggtg gcacagtgaa tggacaagat gagtataaag cagacattgt    26880
catgtatacc gaaaacacgt atctggaaac tccagacacg catgtggtat acaaaccagg    26940
caaggatgat gcaagttctg aaattaacct ggttcagcag tccatgccca atagacccaa    27000
ctatattggg ttcagagaca actttattgg gctcatgtat tacaacagta ctggcaatat    27060 ggggggtgctg gctggtcagg cctcacagct gaatgctgtg gtcgacttgc aagacagaaa    27120
caccgagctg tcataccagc tcttgcttga ctctttgggt gacagaaccc ggtatttcag    27180
tatgtggaat caggcggtgg acagttatga tcctgatgtg cgcattattg aaaaccatgg    27240
tgtggaagac gaacttccca actattgctt cccctggat gggtctggca ctaatgccgc    27300
ttaccaaggt gtgaaagtaa aaaatggtaa cgatggtgat gttgagagcg aatgggaaaa    27360
tgatgatact gtcgcagctc gaaatcaatt atgcaagggc aacattttg ccatggaaat    27420 taacctccaa gccaacctgt ggagaagttt cctctactcg aacgtggccc tgtacctgcc    27480
cgactcttac aagtacacgc cagccaacat caccctgccc accaacacca acacttatga    27540
ttacatgaac gggagagtgg tgcctcctc gctggtggac gctacatca atcgggcc    27600 gcgctggtcg ctggaccca tggacaacgt caatccttc aaccaccacc gcaacgcggg    27660
cctgcgctac cgctccatgc tcctgggcaa cgggcgctac gtgcccttcc atcccaggt    27720 gccccagaaa ttttcgcca tcaagagcct cctgctcctg ccgggtcct acacctacga    27780
```

```
gtggaacttc cgcaaggacg tcaacatgat cctgcagagc ccctcggca acgacctgcg   27840 cacggacggg gcctccatct ccttcaccag catcaacctc tacgccacct tcttccccat   27900
ggcgcacaac acggcctcca cgctcgaggc catgctgcgc aacgacacca acgaccagtc   27960
cttcaacgac tacctctcgg cggccaacat gctctacccc atcccggcca acgccaccaa   28020
cgtgcccatc tccatcccct cgcgcaactg ggccgccttc cgcggctggt ccttcacgcg   28080
cctcaagacc aaggagacgc cctcgctggg ctccggggttc gaccctact cgtctactc    28140 gggctccatc ccctacctcg acggcacctt ctacctcaac cacaccttca agaaggtctc   28200
catcaccttc gactcctccg tcagctggcc cggcaacgac cggctcctga cgcccaacga   28260
gttcgaaatc aagcgcaccg tcgacggcga gggatacaac gtggcccagt gcaacatgac   28320
caaggactgg ttcctggtcc agatgctggc ccactacaac atcggctacc agggcttcta   28380
cgtgcccgag ggctacaagg accgcatgta ctccttcttc cgcaacttcc agcccatgag   28440
ccgccaggtg gtggacgagg tcaactacaa ggactaccag gccgtcaccc tggcctacca   28500
gcacaacaac tcgggcttcg tcggctacct cgcgcccacc atgcgccagg ccagccctact 28560 cccgccaac tacccgtacc cgctcatcgg caagagcgcc gtcaccagcg tcacccagaa    28620
aaagttcctc tgcgacaggg tcatgtgcg catcccttc tccagcaact tcatgtccat     28680
gggcgcgctc accgacctcg gccagaacat gctctatgcc aactccgccc acgcgctaga   28740
catgaatttc gaagtcgacc ccatggatga gtccacccct ctctatgttg tcttcgaagt   28800
cttcgacgtc gtccgagtgc accagcccca ccgcggcgtc atcgaggccg tctacctgcg   28860
cacccccttc tcggccggta acgccaccac ctaaattgct acttgcatga tggctgagcc   28920
cacaggctcc ggcgagcagg agctcagggc catcatccgc gacctgggct gcgggccta    28980 cttcctgggc accttcgata agcgcttccc gggattcatg gcccgcaca agctggcctg    29040 cgccatcgtc aacacggccg gccgcgagac cggggcgag cactggctgg ccttcgcctg    29100
gaacccgcgc tcgaacacct gctacctctt cgaccccttc gggttctcgg acgagcgcct   29160
caagcagatc taccagttcg agtacgaggg cctgctgcgc cgtagcgccc tggccaccga   29220
ggaccgctgc gtcaccctgg aaaagtccac ccagaccgtg cagggtccgc gctcggccgc   29280
ctgcgggctc ttctgctgca tgttcctgca cgccttcgtg cactggcccg accgcccat    29340 ggacaagaac cccaccatga acttgctgac ggggtgccc aacggcatgc tccagtcgcc    29400
ccaggtggaa cccaccctgc gccgcaacca ggaggcgctc taccgcttcc tcaactccca   29460
ctccgcctac tttcgctccc accgcgcgcg catcgagaag gccaccgcct tcgaccgcat   29520
gaacaatcaa gacatgtaaa ccgtgtgtgt atgtttaaaa tatcttttaa taaacagcac   29580
tttaatgtta cacatgcatc tgagatgatt ttattttaga aatcgaaagg gttctgccgg   29640
gtctcggcat ggcccgcggg cagggacacg ttgcggaact ggtacttggc cagccacttg   29700
aactcgggga tcagcagttt gggcagcggg gtgtcgggga aggagtcggt ccacagcttc   29760
cgcgtcagct gcagggcgcc cagcaggtcg gcgcgcgaga tcttgaaatc gcagttggga   29820
cccgcgttct gcgcgcgaga gttgcggtac acgggggttgc agcactggaa caccatcagg   29880
gccgggtgct tcacgctcgc cagcaccgcc cgtcggtga tgctctccac gtcgaggtcc    29940
tcggcgttgg ccatcccgaa gggggtcatc ttgcaggtct gccttcccat ggtgggcacg   30000
cacccgggct tgtggttgca atcgcagtgc agggggatca gcatcatctg ggcctggtcg   30060
gcgttcatcc ccgggtacat ggccttcatg aaagcctcca attgcctgaa cgcctgctgg   30120
gccttggctc cctcggtgaa gaagaccccg caggacttgc tagagaactg gttggtggca   30180
```

```
cagccggcat cgtgcacgca gcagcgcgcg tcgttgttgg ccagctgcac cacgctgcgc    30240
ccccagcggt tctgggtgat cttggcccgg tcggggttct ccttcagcgc gcgctgcccc    30300
ttctcgctcg ccacatccat ctcgatcatg tgctccttct ggatcatggt ggtcccgtgc    30360
aggcaccgca gtttgccctc ggcctcggtg cacccgtgca gccacagcgc gcacccggtg    30420
cactcccagt tcttgtgggc gatctgggaa tgcgcgtgca cgaacccttg caggaagcgg    30480
cccatcatgg tcgtcaggggt cttgttgcta gtgaaggtca acgggatgcc gcggtgctcc    30540
```

```
tggcagcagt gtctggagga gcagaacctg aaagagctct gcaagctcct gcaaaagaac    32580
ctcaagggtc tgtggaccgg gttcgacgag cggaccaccg cctcggacct ggccgacctc    32640
atcttccccg agcgcctcag gctgacgctg cgcaacggcc tgcccgactt tatgagccaa    32700
agcatgttgc aaaactttcg ctctttcatc ctcgaacgct ccggaatcct gcccgccacc    32760
tgctccgcgc tgccctcgga cttcgtgccg ctgaccttcc gcgagtgccc ccgccgctg     32820
tggagccact gctacctgct gcgcctggcc aactacctgg cctaccactc ggacgtgatc    32880
gaggacgtca gcggcgaggg cctgctcgag tgccactgcc gctgcaacct ctgcacgccg    32940
caccgctccc tggcctgcaa ccccccagctg ctgagcgaga cccagatcat cggcaccttc    33000
gagttgcaag ggcccagcga gggcgaggga gccaaggggg gtctgaaact caccccgggg    33060
ctgtggacct cggcctactt gcgcaagttc gtgcccgagg attaccatcc cttcgagatc    33120
aggttctacg aggaccaatc ccagccgccc aaggccgagc tgtcggcctg cgtcatcacc    33180
caggggggcga tcctggccca attgcaagcc atccagaaat cccgccaaga attcttgctg    33240
aaaaagggcc gcggggtcta cctcgacccc cagaccggtg aggagctcaa ccccggcttc    33300
ccccaggatg ccccgaggaa caagaagct gaaagtggag ctgccgcccg tggaggattt    33360
ggaggaagac tgggagaaca gcagtcaggc agaggagatg gaggaagact gggacagcac    33420
tcaggcagag gaggacagcc tgcaagacag tctggaggaa gacgaggagg aggcagagga    33480
ggaggtggaa gaagcagccg ccgccagacc gtcgtcctcg gcggggggaga aagcaagcag    33540
cacggatacc atctccgctc cgggtcgggg tcccgctcgg ccccacagta gatgggacga    33600
gaccgggcga ttcccgaacc ccaccaccca gaccggtaag aaggagcggc agggatacaa    33660
gtcctggcgg gggcacaaaa acgccatcgt ctcctgcttg caggcctgcg ggggcaacat    33720
ctccttcacc cggcgctacc tgctcttcca ccgcggggtg aacttccccc gcaacatctt    33780
gcattactac cgtcacctcc acagccccta ctacttccaa gaagaggcag cagcagcaga    33840
aaaagaccag aaaaccagct agaaaatcca cagcggcggc agcggcaggt ggactgagga    33900
tcgcggcgaa cgagccggcg cagacccggg agctgaggaa ccggatcttt cccaccctct    33960
atgccatctt ccagcagagt cggggggcagg agcaggaact gaaagtcaag aaccgttctc    34020
tgcgctcgct caccccgcagt tgtctgtatc acaagagcga agaccaactt cagcgcactc    34080
tcgaggacgc cgaggctctc ttcaacaagt actgcgcgct cactcttaaa gagtagcccg    34140
cgcccgccca gtcgcagaaa aaggcgggaa ttacgtcacc tgtgcccttc gccctagccg    34200
cctccaccca gcaccgccat gagcaaagag attcccacgc cttacatgtg gagctaccag    34260
ccccagatgg gcctggccgc cggcgccgcc caggactact ccacccgcat gaattggctc    34320
agcgccgggc ccgcgatgat ctcacgggtg aatgacatcc gcgcccaccg aaaccagata    34380
ctcctagaac agtcagcgct caccgccacg ccccgcaatc acctcaatcc gcgtaattgg    34440
cccgccgccc tggtgtacca ggaaattccc cagcccacga ccgtactact tccgcgagac    34500
gcccaggccg aagtccagct gactaactca ggtgtccagc tggcgggcgg cgccaccctg    34560
tgtcgtcacc gccccgctca gggtataaag cggctggtga tccggggcag aggcacacag    34620
ctcaacgacg aggtggtgag ctcttcgctg ggtctgcgac ctgacggagt cttccaactc    34680
gccggatcgg ggagatcttc cttcacgcct cgtcaggcgg tcctgacttt ggagagttcg    34740
tcctcgcagc cccgctcggg cggcatcggc actctccagt tcgtggagga gttcactccc    34800
tcggtctact tcaaccccct ctccggctcc cccgccact acccgacga gttcatcccg    34860
aactttgacg ccatcagcga gtcggtggac ggctacgatt gattaattaa tcaactaacc    34920
```

```
ccttacccct ttaccctcca gtaaaaataa agattaaaaa tgattgaatt gatcaataaa   34980
gaatcactta cttgaaatct gaaaccaggt ctctgtccat gttttctgtc agcagcactt   35040
cactcccctc ttcccaactc tggtactgca ggccccggcg ggctgcaaac ttcctccaca   35100
ctctgaaggg gatgtcaaat tcctcctgtc cctcaatctt cattttatc ttctatcaga    35160 tgtccaaaaa gcgcgcgcgg gtggatgatg gcttcgaccc cgtgtacccc tacgatgcag   35220
acaacgcacc gactgtgccc ttcatcaacc ctcccttcgt ctcttcagat ggattccaag    35280
aaaagcccct gggggtgttg tccctgcgac tggccgaccc cgtcaccacc aagaatgggg   35340
ctgtcaccct caagctgggg gaggggtgg acctcgacga ctcgggaaaa ctcatctcca    35400
aaaatgccac caaggccact gcccctctca gtatttccaa cggcaccatt tcccttaaca   35460
tggctgcccc tttttacaac aacaatggaa cgttaagtct caatgtttct acaccattag   35520
cagtatttcc cacttttaac actttaggta tcagtcttgg aaacggtctt caaacttcta   35580
ataagttgct gactgtacag ttaactcatc ctcttacatt cagctcaaat agcatcacag   35640
taaaaacaga caaaggactc tatattaatt ctagtggaaa cagagggctt gaggctaaca   35700
taagcctaaa aagaggactg attttgatg gtaatgctat tgcaacatac cttggaagtg    35760
gtttagacta tggatcctat gatagcgatg ggaaaacaag acccatcatc accaaaattg   35820
gagcaggttt gaattttgat gctaataatg ccatggctgt gaagctaggc acaggtttaa   35880
gttttgactc tgccggtgcc ttaacagctg gaaacaaaga ggatgacaag ctaacacttt   35940
ggactacacc tgacccaagc cctaattgtc aattactttc agacagagat gccaaattta   36000
ccctatgtct tacaaaatgc ggtagtcaaa tactaggcac tgttgcagta gctgctgtta   36060
ctgtaggttc agcactaaat ccaattaatg acacagtaaa aagcgccata gtattcctta   36120
gatttgactc tgacggtgtg ctcatgtcaa actcatcaat ggtaggtgat tactggaact   36180
ttagggaagg acagaccacc caaagtgtgg cctatacaaa tgctgtggga ttcatgccca   36240
atctaggtgc atatcctaaa acccaaagca aaacaccaaa aatagtata gtaagtcagg    36300 tatatttaaa tggagaaact actatgccaa tgacactgac aataactttc aatggcactg   36360
atgaaaaaga cacaacacct gtgagcactt actccatgac ttttacatgg cagtggactg   36420
gagactataa ggacaagaat attaccttg ctaccaactc ctttactttc tcctacatgg    36480
cccaagaata aaccctgcat gccaaccca ttgttcccac cactatggaa aactctgaag     36540
cagaaaaaaa taaagttcaa gtgttttatt gattcaacag ttttctcaca gaaccctagt   36600
attcaacctg ccacctccct cccaacacac agagtacaca gtcctttctc cccggctggc   36660
cttaaaaagc atcatatcat gggtaacaga catattctta ggtgttatat tccacacggt   36720
ttcctgtcga gccaaacgct catcagtgat attaataaac tccccgggca gctcacttaa   36780
gttcatgtcg ctgtccagct gctgagccac aggctgctgt ccaacttgcg gttgcttaac   36840
gggcggcgaa ggagaagtcc acgcctacat ggggtagag tcataatcgt gcatcaggat    36900
agggcggtgg tgctgcagca gcgcgcgaat aaactgctgc cgccgccgct ccgtcctgca   36960
ggaatacaac atggcagtgg tctcctcagc gatgattcgc accgcccgca gcataaggcg   37020
ccttgtcctc cgggcacagc agcgcaccct gatctcactt aaatcagcac agtaactgca   37080
gcacagcacc acaatattgt tcaaaatccc acagtgcaag gcgctgtatc caaagctcat   37140
ggcggggacc acagaaccca cgtggccatc ataccacaag cgcaggtaga ttaagtggcg   37200 accccctcata aacacgctgg acataaacat tacctctttt ggcatgttgt aattcaccac   37260
```

```
ctcccggtac catataaacc tctgattaaa catggcgcca tccaccacca tcctaaacca    37320
gctggccaaa acctgcccgc cggctataca ctgcagggaa ccgggactgg aacaatgaca    37380
gtggagagcc caggactcgt aaccatggat catcatgctc gtcatgatat caatgttggc    37440
acaacacagg cacacgtgca tacacttcct caggattaca agctcctccc gcgttagaac    37500
catatcccag ggaacaaccc attcctgaat cagcgtaaat cccacactgc agggaagacc    37560
tcgcacgtaa ctcacgttgt gcattgtcaa agtgttacat tcgggcagca gcggatgatc    37620
ctccagtatg gtagcgcggg tttctgtctc aaaaggaggt agacgatccc tactgtacgg    37680
agtgcgccga gacaaccgag atcgtgttgg tcgtagtgtc atgccaaatg gaacgccgga    37740
cgtagtcata tttcctgaag caaaaccagg tgcgggcgtg acaaacagat ctgcgtctcc    37800
ggtctcgccg cttagatcgc tctgtgtagt agttgtagta tatccactct ctcaaagcat    37860
ccaggcgccc cctggcttcg ggttctatgt aaactccttc atgcgccgct gccctgataa    37920
catccaccac cgcagaataa gccacaccca gccaacctac acattcgttc tgcgagtcac    37980
acacgggagg agcgggaaga gctggaagaa ccatgattaa ctttattcca aacggtctcg    38040
gagcacttca aaatgcaggt cccggaggtg gcacctctcg cccccactgt gttggtggaa    38100
aataacagcc aggtcaaagg tgacacggtt ctcgagatgt tccacggtgg cttccagcaa    38160
agcctccacg cgcacatcca gaaacaagag gacagcgaaa gcgggagcgt tttctaattc    38220
ctcaatcatc atattacact cctgcaccat ccccagataa ttttcatttt tccagccttg    38280
aatgattcgt attagttcct gaggtaaatc caagccagcc atgataaaaa gctcgcgcag    38340
agcgccctcc accggcattc ttaagcacac cctcataatt ccaagagatt ctgctcctgg    38400
ttcacctgca gcagattaac aatgggaata tcaaaatctc tgccgcgatc cctaagctcc    38460
tccctcaaca ataactgtat gtaatctttc atatcatctc cgaaatttt agccataggg    38520
ccgccaggaa taagagcagg gcaagccaca ttacagataa agcgaagtcc tccccagtgw    38580
gcattgccaa atgtaagatt gaaataagca tgctggctag accctgtgat atcttccaga    38640
taactggaca gaaaatcagg caagcaattt ttaagaaaat caacaaaaga aaagtcgtcc    38700
aggtgcaggt ttagagcctc aggaacaacg atggaataag tgcaaggagt gcgttccagc    38760
atggttagtg ttttttttggt gatctgtaga acaaaaaata aacatgcaat attaaaccat    38820
gctagcctgg cgaacaggtg ggtaaatcac tctttccagc accaggcagg ctacggggtc    38880
tccggcgcga ccctcgtaga agctgtcgcc atgattgaaa agcatcaccg agagaccttc    38940
ccggtggccg gcatggatga ttcgagaaga agcatacact ccgggaacat tggcatccgt    39000
gagtgaaaaa aagcgaccta taaagcctcg gggcactaca atgctcaatc tcaattccag    39060
caaagccacc ccatgcggat ggagcacaaa attggcaggt gcgtaaaaaa tgtaattact    39120
cccctcctgc acaggcagca aagcccccgc tccctccaga aacacataca aagcctcagc    39180
gtccatagct taccgagcac ggcaggcgca agagtcagag aaaaggctga gctctaacct    39240
gactgcccgc tcctgtgctc aatatatagc cctaacctac actgacgtaa aggccaaagt    39300
ctaaaaatac ccgccaaaat gacacacacg cccagcacac gcccagaaac cggtgacaca    39360
ctcaaaaaaa tacgtgcgct tcctcaaacg cccaaaccgg cgtcatttcc gggttcccac    39420
gctacgtcac cgctcagcga ctttcaaatt ccgtcgaccg ttaaaaacgt cactcgcccc    39480
gcccctaacg gtcgcccttc tctcggccaa tcaccttcct cccttcccaa attcaaacgc    39540
ctcatttgca tattaacgcg cacaaaaagt ttgaggtata tatttgaatg atg           39593
```

<210> SEQ ID NO 26
<211> LENGTH: 675
<212> TYPE: DNA
<213> ORGANISM: Artificial Sequence
<220> FEATURE:
<223> OTHER INFORMATION: Polynucleotide construct for vector ChAdOx1_P1A

<400> SEQUENCE: 26

```
atgagcgaca acaagaagcc cgacaaggcc cactctggca gcggcggaga tggcgacggc     60
aacagatgta acctgctgca cagatacagc ctggaagaga tcctgcccta cctgggctgg    120
ctggtgttcg ccgtcgtgac aacaagcttc ctggccctgc agatgttcat cgacgccctg    180
tacgaggaac agtacgagag ggacgtggcc tggatcgcca gacagagcaa gagaatgagc    240
agcgtggacg aggacgagga tgatgaggac gacgaagatg actactacga cgatgaggat    300
gacgacgacg acgccttcta cgatgacgag gacgatgaag aggaagaact ggaaaacctg    360
atggacgacg agtccgagga tgaggccgag aagagatga gcgtggaaat gggcgctggc    420
gccgaagaga tgggagccgg cgctaactgt gcttgcgtgc aggacacca cctgagaaag    480
aacgaagtga agtgccggat gatctacttc ttccacgacc ccaactttct ggtgtccatc    540
cccgtgaacc ccaaagaaca gatggaatgc agatgcgaga cgccgacga gaggtggcc    600
atggaagaag aagaggaaga ggaagaagaa gaagaagagg aagaaatggg caaccccgac    660
ggcttcagcc cctga                                                    675
```

<210> SEQ ID NO 27
<211> LENGTH: 224
<212> TYPE: PRT
<213> ORGANISM: Artificial Sequence
<220> FEATURE:
<223> OTHER INFORMATION: Translated protein of ChAdOx1_P1A

<400> SEQUENCE: 27

```
Met Ser Asp Asn Lys Lys Pro Asp Lys Ala His Ser Gly Ser Gly Gly
1               5                   10                  15
Asp Gly Asp Gly Asn Arg Cys Asn Leu Leu His Arg Tyr Ser Leu Glu
            20                  25                  30
Glu Ile Leu Pro Tyr Leu Gly Trp Leu Val Phe Ala Val Val Thr Thr
        35                  40                  45
Ser Phe Leu Ala Leu Gln Met Phe Ile Asp Ala Leu Tyr Glu Glu Gln
    50                  55                  60
Tyr Glu Arg Asp Val Ala Trp Ile Ala Arg Gln Ser Lys Arg Met Ser
65                  70                  75                  80
Ser Val Asp Glu Asp Glu Asp Asp Glu Asp Asp Glu Asp Asp Tyr Tyr
                85                  90                  95
Asp Asp Glu Asp Asp Asp Asp Ala Phe Tyr Asp Asp Glu Asp Asp
            100                 105                 110
Glu Glu Glu Glu Leu Glu Asn Leu Met Asp Asp Glu Ser Glu Asp Glu
        115                 120                 125
Ala Glu Glu Glu Met Ser Val Glu Met Gly Ala Gly Ala Glu Glu Met
    130                 135                 140
Gly Ala Gly Ala Asn Cys Ala Cys Val Pro Gly His His Leu Arg Lys
145                 150                 155                 160
Asn Glu Val Lys Cys Arg Met Ile Tyr Phe Phe His Asp Pro Asn Phe
                165                 170                 175
Leu Val Ser Ile Pro Val Asn Pro Lys Glu Gln Met Glu Cys Arg Cys
            180                 185                 190
```

Glu Asn Ala Asp Glu Glu Val Ala Met Glu Glu Glu Glu Glu
              195                 200                 205

Glu Glu Glu Glu Glu Glu Glu Met Gly Asn Pro Asp Gly Phe Ser Pro
    210                 215                 220

<210> SEQ ID NO 28
<211> LENGTH: 753
<212> TYPE: DNA
<213> ORGANISM: Artificial Sequence
<220> FEATURE:
<223> OTHER INFORMATION: Polynucleotide construct for vector
      ChAdOx1_mIi_P1A

<400> SEQUENCE: 28
atgggcgctc tgtatactgg cgtgtccgtg ctggtggccc tgctgctggc tggacaggct      60
acaaccgcct acttcctgta cagcgacaac aagaagcccg acaaggccca ctctggcagc     120
ggcggagatg gcgacggcaa cagatgtaac ctgctgcaca gatacagcct ggaagagatc     180
ctgccctacc tgggctggct ggtgttcgcc gtcgtgacaa caagcttcct ggccctgcag     240
atgttcatcg acgccctgta cgaggaacag tacgagaggg acgtggcctg gatcgccaga     300
cagagcaaga gaatgagcag cgtggacgag gacgaggatg atgaggacga cgaagatgac     360
tactacgacg atgaggatga cgacgacgac gccttctacg atgacgagga cgatgaagag     420
gaagaactgg aaaacctgat ggacgacgag tccgaggatg aggccgagga agagatgagc     480
gtggaaatgg gcgctggcgc cgaagagatg ggagccggcg ctaactgtgc ttgcgtgcca     540
ggacaccacc tgagaaagaa cgaagtgaag tgccggatga tctacttctt ccacgacccc     600
aactttctgg tgtccatccc cgtgaacccc aaagaacaga tggaatgcag atgcgagaac     660
gccgacgaag aggtggccat ggaagaagaa gaggaagagg aagaagaaga agaagaggaa     720
gaaatgggca accccgacgg cttcagcccc tga                                  753

<210> SEQ ID NO 29
<211> LENGTH: 250
<212> TYPE: PRT
<213> ORGANISM: Artificial Sequence
<220> FEATURE:
<223> OTHER INFORMATION: Translated protein ChAdOx1_mIi_P1A

<400> SEQUENCE: 29

Met Gly Ala Leu Tyr Thr Gly Val Ser Val Leu Val Ala Leu Leu Leu
1               5                   10                  15

Ala Gly Gln Ala Thr Thr Ala Tyr Phe Leu Tyr Ser Asp Asn Lys Lys
            20                  25                  30

Pro Asp Lys Ala His Ser Gly Ser Gly Gly Asp Gly Asp Gly Asn Arg
        35                  40                  45

Cys Asn Leu Leu His Arg Tyr Ser Leu Glu Glu Ile Leu Pro Tyr Leu
    50                  55                  60

Gly Trp Leu Val Phe Ala Val Val Thr Thr Ser Phe Leu Ala Leu Gln
65                  70                  75                  80

Met Phe Ile Asp Ala Leu Tyr Glu Glu Gln Tyr Glu Arg Asp Val Ala
                85                  90                  95

Trp Ile Ala Arg Gln Ser Lys Arg Met Ser Ser Val Asp Glu Asp Glu
            100                 105                 110

Asp Asp Glu Asp Asp Glu Asp Tyr Tyr Asp Asp Glu Asp Asp Asp
        115                 120                 125

Asp Asp Ala Phe Tyr Asp Asp Glu Asp Asp Glu Glu Glu Leu Glu
        130                 135                 140

Asn Leu Met Asp Asp Glu Ser Glu Asp Glu Ala Glu Glu Met Ser
145                 150                 155                 160

Val Glu Met Gly Ala Gly Ala Glu Glu Met Gly Ala Gly Ala Asn Cys
            165                 170                 175

Ala Cys Val Pro Gly His His Leu Arg Lys Asn Glu Val Lys Cys Arg
            180                 185                 190

Met Ile Tyr Phe Phe His Asp Pro Asn Phe Leu Val Ser Ile Pro Val
            195                 200                 205

Asn Pro Lys Glu Gln Met Glu Cys Arg Cys Glu Asn Ala Asp Glu Glu
        210                 215                 220

Val Ala Met Glu Glu Glu Glu Glu Glu Glu Glu Glu Glu Glu Glu Glu
225                 230                 235                 240

Glu Met Gly Asn Pro Asp Gly Phe Ser Pro
            245                 250

<210> SEQ ID NO 30
<211> LENGTH: 675
<212> TYPE: DNA
<213> ORGANISM: Artificial Sequence
<220> FEATURE:
<223> OTHER INFORMATION: Polynucleotide construct for vector MVA_P1A

<400> SEQUENCE: 30
atgagcgaca acaagaagcc cgacaaggcc cactctggca gcggcggaga tggcgacggc      60
aacagatgta acctgctgca cagatacagc ctggaagaga tcctgcccta cctgggctgg     120
ctggtgttcg ccgtcgtgac aacaagcttc ctggccctgc agatgttcat cgacgccctg     180
tacgaggaac agtacgagag ggacgtggcc tggatcgcca gacagagcaa gagaatgagc     240
agcgtggacg aggacgagga tgatgaggac gacgaagatg actactacga cgatgaggat     300
gacgacgacg acgccttcta cgatgacgag gacgatgaag aggaagaact ggaaaacctg     360
atggacgacg agtccgagga tgaggccgag aagagatgaa gcgtggaaat gggcgctggc     420
gccgaagaga tgggagccgg cgctaactgt gcttgcgtgc aggacaccca cctgagaaag     480
aacgaagtga agtgccggat gatctacttc ttccacgacc ccaactttct ggtgtccatc     540
cccgtgaacc ccaaagaaca gatggaatgc agatgcgaga acgccgacga agaggtggcc     600
atggaagaag aagaggaaga ggaagaagaa gaagaagagg aagaaatggg caaccccgac     660
ggcttcagcc cctga                                                      675

<210> SEQ ID NO 31
<211> LENGTH: 224
<212> TYPE: PRT
<213> ORGANISM: Artificial Sequence
<220> FEATURE:
<223> OTHER INFORMATION: Translated protein of MVA_P1A

<400> SEQUENCE: 31

Met Ser Asp Asn Lys Lys Pro Asp Lys Ala His Ser Gly Ser Gly Gly
1               5                   10                  15

Asp Gly Asp Gly Asn Arg Cys Asn Leu Leu His Arg Tyr Ser Leu Glu
            20                  25                  30

Glu Ile Leu Pro Tyr Leu Gly Trp Leu Val Phe Ala Val Val Thr Thr
        35                  40                  45

Ser Phe Leu Ala Leu Gln Met Phe Ile Asp Ala Leu Tyr Glu Glu Gln
    50                  55                  60

Tyr Glu Arg Asp Val Ala Trp Ile Ala Arg Gln Ser Lys Arg Met Ser

```
                 65                  70                  75                  80
Ser Val Asp Glu Asp Glu Asp Glu Asp Asp Glu Asp Asp Tyr Tyr
                    85                  90                  95

Asp Asp Glu Asp Asp Asp Asp Ala Phe Tyr Asp Asp Glu Asp Asp
                100                 105                 110

Glu Glu Glu Glu Leu Glu Asn Leu Met Asp Asp Glu Ser Glu Asp Glu
            115                 120                 125

Ala Glu Glu Glu Met Ser Val Glu Met Gly Ala Gly Ala Glu Glu Met
        130                 135                 140

Gly Ala Gly Ala Asn Cys Ala Cys Val Pro Gly His His Leu Arg Lys
145                 150                 155                 160

Asn Glu Val Lys Cys Arg Met Ile Tyr Phe Phe His Asp Pro Asn Phe
                165                 170                 175

Leu Val Ser Ile Pro Val Asn Pro Lys Glu Gln Met Glu Cys Arg Cys
            180                 185                 190

Glu Asn Ala Asp Glu Glu Val Ala Met Glu Glu Glu Glu Glu Glu
            195                 200                 205

Glu Glu Glu Glu Glu Glu Glu Met Gly Asn Pro Asp Gly Phe Ser Pro
    210                 215                 220
```

VIRAL VECTORS ENCODING CANCER/TESTIS ANTIGENS FOR USE IN A METHOD OF PREVENTION OR TREATMENT OF CANCER

This invention relates to viral vector-based vaccines for the prevention or treatment of cancer, more particularly replication-defective adenovirus (Ad) and Modified Vaccinia Virus Ankara (MVA) vectors comprising a cancer vaccine antigen of interest and for administration to a mammal. The invention therefore concerns the viral particles, immunogenic compositions comprising the viral particles, and host cells containing the viral vectors. The viral vector vaccines are used to treat a subject suffering from a cancer or to prevent a subject from getting a cancer. In a preferred regime the invention involves a prime administration using an Ad vector, followed by a boost administration using an MVA vector. This invention further provides for vaccine compositions comprising the novel replication-defective adenoviral vectors of the present invention.

BACKGROUND

More than 1.6 million Americans are diagnosed with cancer every year, and approximately 600,000 people are expected to die of this disease in 2018 in the United States alone. During the last decades, significant progress has been achieved in the detection, diagnosis, and treatment of cancer. However, still only 67% of people remain alive 5 years after the onset of treatment. (See Siegel, R. L. et al. (2017) Cancer J. Clin. 67(1): 7-30.)

Current therapeutic options include surgical procedures, radiation, radiofrequency, chemotherapeutics, monoclonal antibodies, etc. Most of these approaches are associated with serious risk, toxic side effects, high cost, and doubtful efficacy.

Cancer immunotherapy though has demonstrated some significant progress in recent years and continues as a developing field of interest. The healthy normal human immune system has an innate capacity to identify and reject tumour cells based on the ability of cytolytic T lymphocytes (CTLs) to recognise tumour-associated antigens (TA). Cancer cells should normally activate an integrated immune response, both cellular and humoral. The cellular response involves CD8$^+$ and CD4$^+$ T cells which participate in the immune response. However, in the genesis of cancer and malignant cancer the normal CTL activity against tumour cells is compromised or lost. Cancer immunotherapy therefore adopts various approaches for restoring or rekindling CTL activity of the human immune system against tumour cells. The immune system of a human cancer patient can be harnessed with the goal of eradicating the malignant cells that express a tumour-associated antigen (TA).

Cytotoxic T cells express CD8 and can specifically kill cancerous cells. CD4$^+$ T cells or T helper cells support the development of the cytotoxic response, produce cytokines, and also assist in the maturation and proliferation of B cells. During the humoral response, B cells are activated, replicate, differentiate, and produce TA-specific antibodies. For more information, see Murphy, K. & Weaver, C. "Janeway's Immunobiology" 9th Edition (2016): Garland Science/Taylor & Francis: New York, NY.

Adoptive T cell therapies and immune checkpoint modulators are clinical approaches aimed at boosting the ability of the human immune system to reject tumours. However, both approaches have limitations. Adoptive T cell therapy requires expansion and transduction of effector T cells of a required specificity (see Baruch E. N. et al. (2017) Cancer 123(S11): 2154-62. This complexity currently limits the applicability of this approach. Checkpoint inhibitor treatment, a segment of immune checkpoint modulators, is based on monoclonal antibodies that release brakes on T cells in order to improve their effector functions. Whilst checkpoint inhibitors may induce long-term clinical responses in a fraction of advanced cancer patients, the side effects of autoimmune toxicity caused by this stimulation of all T cells remains a problem. Also, existing checkpoint inhibitor treatments suffer from a lack of efficacy in relation to "cold" tumours which are not infiltrated by T cells.

Another approach representing a promising alternative to the above are cancer vaccines or more specifically therapeutic cancer vaccines which are used to elicit an immune response against tumour cells. This is based on the concept that tumour cells are inherently poorly immunogenic and a vaccine should help serve to overcome this deficiency. Many different types of cancer vaccines have been studied and some have shown promising results. Sahin U. et al. (2017) Nature 547(7662): 222-226 tried personalized RNA mutanome vaccines which mobilize polyspecific therapeutic immunity against cancer. Also, Ott P. A. et al. (2017) Nature 547(7662): 217-221 tried personalized immunogenic neoantigen vaccine for patients with melanoma.

However, the potential of cancer vaccines became questionable after failure of several large scale clinical trials, including two large phase III trials by GlaxoSmithKline (GSK). These trials used vaccination approach based on a recombinant tumour-associated protein combined with an adjuvant. This vaccine platform, like many others, had proven to be able to induce good antibody and CD4$^+$ T-helper responses, but was unable to mount consistent CTL responses. Given that CTLs are key effectors of the anti-tumour immune response, this likely explains the clinical failure of those vaccines. A technical challenge is therefore the provision of a new cancer vaccine platform that induces good CD8 responses in humans.

In order to achieve some efficacy, it is believed that a cancer vaccine should have the ability to: i) target antigens that are potentially expressed or expressed solely on cancer cells and can elicit an integrated immune response; and ii) induce a robust clonal expansion and effector and memory differentiation of antigen-specific T cells (see Coulie, P. G. (2014) Nat. Rev. Cancer, 14(2): 135-146.

Traditionally, therapeutic cancer vaccines have comprised a tumour antigen (TA) protein and an adjuvant. For example, the vaccine called Stimuvax (formerly known as BLP25 liposome vaccine (L-BLP25)), is a liposome that encapsulates synthetic peptides derived from the mucin 1 (MUC1) antigen and the adjuvant MPL4, and to which U.S. Pat. No. 6,600,012 (B1) BIOMIRA INC. relates. Also, the MAGRIT vaccine which was assessed in a Phase 3 trial in patients with resected MAGE-A3-positive non-small-cell lung cancer (see Vansteenkiste, J. F. et al Lancet Oncol. 17(6): 822-835) contained the AS15 adjuvant combined with a recombinant melanoma-associated antigen MAGE-A3 protein. However, as indicated generally above, these Stimuvax and MAGRIT vaccines failed to show efficacy in large phase III trials.

The first "cancer vaccine" to be approved in the United States and Europe is PROVENGE, an autologous cellular vaccine in which patient's antigen presenting cells (APC) are incubated with the prostate acid phosphatase (PAP) antigen. Despite efficacy and an ability to activate proper T cell response, this vaccine requires to be made individually for each patient, thereby involving a complex and expensive manufacturing process. Consequently, the vaccine is of limited practical use. (See US2004/141991 (A1) LAUS et al.).

Vector-based cancer vaccines have shown great promise and have generated strong therapeutic interest with several vector technologies, adjuvants and combinations tested in the clinic. The basis for this strategy is to use recombinant viral vectors to deliver tumour antigens. The viral vectors themselves are modified to be replication-defective, and so no longer harmful to patients. The vectors express both the TA as well as other viral antigens that act as adjuvants and potentiate the induction of the immune response. An ideal viral vector should have several properties: i) being safe; ii) enabling efficient antigen presentation; iii) elicit an integrated immune response; and iv) able to be produced on a large scale (see Melief, C. J. M. et al. (2015) J. Clin. Invest. 125(9): 3401-3412.

Several viral vectors have been proposed for clinical use. For example, replication-defective adenovirus (Ad) have been studied as vaccine vector for infectious diseases such as disclosed in EP 2,130,921 B1 GLAXOSMITHKLINE BIOLOGALS SA for Human Immunodeficiency Virus (HIV)-1 or in US2012/082694 (A1) CRUCELL, for malaria.

In the field of vaccination, vaccine administration is typically followed by one or more boosting injections that are administered in the same manner as the first injection, but at a later time, or times. During the interval between the first (priming) and the following (boosting) administrations the immune system responds by eliciting both cellular and humoral response (see Woodland, D. L. (2004) Trends Immunol. 25(2): 98-104).

However, repeated administrations with the same vector (homologous boosting) failed to boost tumour antigen-specific T cell responses, because competing immunogenicity is generated against viral antigens, resulting in the production of antibodies that recognized surface antigens of the viral capsid and prevent further infection of antigen-presenting cells by the recombinant vectors. In particular, homologous boosting does not induce CD8 T cells against the inserted tumour antigens. A potential approach to circumvent this problem involves the sequential administration of vaccines that use different antigen-delivery systems such as two different viral vectors (heterologous boosting). EP 2,631,290 (A1) NATIONAL UNIVERSITY CORPORATION discloses a virus vector for prime/boost vaccines which comprises Vaccinia virus vector and Sendai virus vector. Chen, J.-L. et al. (2015) Int. J. Cancer 136(6): E590-601 describes NY-ESO-1 specific antibody and cellular responses in melanoma patients primed with NY-ESO-1 protein in ISCOMATRIX and boosted with recombinant NY-ESO-1 fowlpox virus.

Many prime/boost vaccines composed of DNA vaccines and various viral vectors have been tried. For example, WO2006/057454 (A1) JAPAN SCIENCE AND TECHNOLOGY AGENCY discloses a heterologous prime/boost HIV vaccine developed against HIV-1 gag E antigen by using a Bacillus Calmette-Guérin (BCG) vector for priming and an attenuated vaccinia virus strain DIs, for boosting. Odunsi, K. et al. (2012) Proc. Natl. Acad. Sci. U.S.A. 109(15): 5797-5802 describe a limited size phase I study using a prime-boost approach with two different orthopox vectors (vaccinia and fowlpox) and the antigen NY-ESO-1 and showed possible clinical benefits among melanoma and ovarian cancer patients.

Human adenoviruses are widely used by scientists for the development of cancer vaccines because of their properties (e.g. replication-deficiency, stability, high immunogenicity, ability to transduce numerous cell types, etc.). Natural adenoviral infection is endemic in the human population and a majority of humans seroconvert within the first five years of life. Thus, cancer vaccines derived from human adenoviruses will encounter pre-existing humoral and cellular immunity which will limit its efficacy (see Coughlan, L. (2015) et al. J. Pharm. Pharmacol. 67(3): 382-399 and U.S. Pat. No. 6,140,087 ADVEC INC entitled "Adenovirus Vectors for Gene Therapy").

U.S. Pat. No. 9,714,435 (B2) ISIS INNOVATION entitled "Simian Adenovirus and hybrid Adenoviral vectors" and EP 2,163,260 (A2) ISTITUTO RICHERCHE DI BIOLOGICA MOLECULARE entitled "Chimpanzee Adenovirus Vaccine Carriers" explain how scientists have developed replication-defective adenoviruses derived from non-human primates, that evade any pre-existing immunity in humans. Chimpanzee adenovirus (ChAd) shows several qualities: i) robust immunogenicity; ii) low seroprevalence in humans; iii) standardized manufacturing production.

Also known is an attenuated non-replicative vaccinia virus Ankara strain (MVA). This viral vector has been shown to elicit an immune response with an excellent safety profile. MVA has been attenuated by more than 570 passages in chicken embryo fibroblasts with a consequent loss of approximately 15% of its genome. Thus, MVA lacks the ability to mature virions in many mammalian cells and is associated with a strong immunogenicity and reduced risk of amplification. WO2011/128704 of Isis Innovation Limited describes a pox virus expression system, including MVA, in which a transgene is inserted into a poxvirus genome and therefore provides poxvirus vectors and uses of this to transfer genes of interest into a target cell for the purposes of vaccines against infection, cancer treatment and gene therapy. There is also EP 2044947 A1 of Isis Innovation Limited which describes MVA viral vectors used for inducing immune responses, particular T cell immune responses against influenza virus.

Aiming a cure for infectious diseases, viral vector-based vaccines in a heterologous prime-boost regime have been developed and optimised to induce strong CTL responses. This vaccine strategy employed a chimpanzee adenovirus (ChAd) for prime and boost with Modified Vaccinia Ankara (MVA) carrying the same immunogen. Coughlan L. et al. (2015) J. Pharm. Pharmacol. 67(3): 382-99 and Hui E. P. et al. (2013) Cancer Res. 73(6): 1676-88 report on the individual testing of both viral vectors in preclinical and clinical studies in infectious disease settings and how they have a very high safety profile.

EP 2,044,947 (A1) ISIS INNOVATION discloses vaccines with an adenovirus vector for priming and then MVA for boosting in the prevention of influenza.

Ewer K. J. et al. (2013) Nat. Commun. 4: 2836 and Ogwang, C. et al. (2015) Sci. Transl. Med. 7(286): 286re5 discloses vaccines with ChAd as priming and MVA as boosting for malaria.

The same prime-boost approach has been described in Cappuccini, F. et al. (2017) Oncotarget 8(29): 47474-47489 in a cancer mouse model expressing 5T4 antigen, and in Cappuccini, F. et al. (2016) Cancer Immunol. Immunother. CII 65(6): 701-713 where a cancer mouse model expressed STEAP1 which is a prostate cancer antigen. In all these studies, the heterologous prime-boost vaccine induced a strong immune response toward TA and the activation of antigen-specific $CD8^+$ T cells.

There is also WO2017/120670 A1 (Lichty, B. & Bell, J.) which describes co-administration of a replicative oncolytic rhabdovirus and an immune checkpoint inhibitor in clinically relevant cancer models results resulting in a stimulation of antigen-specific T lymphocytes and significant survival. Oncolytic rhabdovirus specifically infects, replicates in, and kills malignant cells leaving normal tissues unaffected. The oncolytic rhabdovirus (e.g. VSVdelta5 I or Mamba MG 1) expresses a tumor antigen to which the test animal has a preexisting immunity selected from MAGEA3, Human Papilloma Virus E6/E7 fusion protein, human Six-Transmembrane Epithelial Antigen of the Prostate protein, or Cancer Testis Antigen.

A successful therapeutic cancer vaccine will need to target tumour antigens that are expressed on tumours but not on normal tissues. Cancer-germline antigens are an heterologous group of proteins that are physiologically expressed in several types of cancer, but not in differentiated, normal tissues, except for germline cells that are incapable to present antigens to the immune system due to the lack of MHC I molecules. These antigens are encoded by cancer-germline genes. NY-ESO-1 and MAGE-A3 are prototypical MAGE-type antigens being two of the most representative of the group as described in Gnjatic, S. et al. (2006) Cancer Res. 95: 1-30. Also, Coulie P. G. et al. (2014) supra which describes responses shown to occur in a number of patients.

BRIEF SUMMARY OF THE DISCLOSURE

In accordance with the present invention there is provided a chimpanzee adenovirus (ChAd) vector encapsidating a nucleic acid molecule, the nucleic acid molecule comprising a polynucleotide sequence encoding (i) a MAGE cancer antigen and/or NY-ESO-1 cancer antigen, or immunogenic fragments thereof; or (ii) a MAGE cancer antigen and/or LAGE1 cancer antigen, or immunogenic fragments thereof, operably linked to expression control sequences which direct the translation, transcription and/or expression of the cancer antigen or fragment thereof in an animal cell, and an adenoviral packaging signal sequence. Advantageously such ChAd viral vectors are stable and well-studied, not neutralized by antibodies to human adenovirus and are engineered to be replication deficient. They have high capacity for inserted antigens of interest and can be produced in HEK293 cells containing the adenoviral E1 gene.

MAGE-type antigens are tumour-specific shared human tumour antigens known to induce CD8 T cells in cancer patients. They are expressed in many cancer types and are not expressed in normal tissues, except for male germline cells which have no MHC-1 molecules.

NY-ESO-1 (gene name CTAG1) induces a strong CD8 response in many cancer patients and numerous CD8 epitopes can be identified, as presented by multiple HLA class I specificities.

In a particular form the ChAd vector may be (a) ChAdOx1 as disclosed in WO2012/172277; preferably encoded by a polynucleotide of SEQ ID NO: 38 as disclosed in WO2012/172277 or a sequence of at least 80% identity therewith; or (b) ChAdOx2 as disclosed in WO2017/221031; preferably encoded by a polynucleotide of SEQ ID NO: 10 as disclosed in WO2017/221031 or a sequence of at least 80% identity therewith.

Also provided by the invention is a modified vaccinia virus Ankara (MVA) vector encapsidating a nucleic acid molecule, the nucleic acid molecule comprising a polynucleotide sequence encoding (i) a MAGE cancer antigen and/or NY-ESO-1 cancer antigen, or immunogenic fragments thereof; or (ii) a MAGE cancer antigen and/or LAGE1 cancer antigen, or immunogenic fragments thereof, operably linked to expression control sequences which direct the translation, transcription and/or expression of the cancer antigen or fragment thereof in an animal cell. Advantageously, such MVA vectors are not able to replicate in humans and have a long safety track record as smallpox vaccines. MVA provides excellent boosting after priming with ChAd. MVA has no virulence and immune system evasion factors and is highly immunogenic and is readily produced in chicken embryonic fibroblasts or immortalized duck embryonic cell lines.

An MVA vector in more particular form may be as disclosed in WO2011/128704 or EP 2044947 A1.

For the ChAd and/or MVA vectors of the invention as herein described, the MAGE antigen is preferably MAGE3A and as such has an amino acid sequence of SEQ ID NO: 1 or a sequence of at least 46%; preferably at least 69%; more preferably at least 95% identity therewith; or any immunogenic fragment thereof.

For the ChAd and/or MVA vectors of the invention as herein described, the NY-ESO-1 cancer antigen has an amino acid sequence of SEQ ID NO: 3 or a sequence of at least 75%; preferably at least 76.7% identity therewith; or any immunogenic fragment thereof.

For the ChAd and/or MVA vectors of the invention as herein described, the LAGE1 antigen has an amino acid sequence of SEQ ID NO: 5, or a sequence of at least 78%; preferably at least 97% identity therewith; or any immunogenic fragment thereof.

In preferred ChAd and/or MVA vectors of the invention, the polynucleotide sequence may further encode a human HLA class II histocompatibility antigen gamma chain (hli or li), and li may have an amino acid sequence of SEQ ID NO: 6 or a sequence of at least 79% identity therewith, or a fragment thereof, so that the cancer antigen is expressed in an animal cell as a fusion with li or fragment thereof; more preferably wherein the fragment is a transmembrane domain; even more preferably wherein the transmembrane domain comprises amino acid residues 30 to 55 or 30 to 61. In a particularly preferred embodiment the transmembrane domain has the amino acid sequence of SEQ ID NO: 7.

In alternatively preferred ChAd and/or MVA vectors of the invention, the polynucleotide sequence may further encode tPA which has an amino acid sequence of SEQ ID NO: 8 or a sequence of at least 81% identity therewith, or a fragment thereof; so that the cancer antigen is expressed in an animal cell as a fusion with tPA or a fragment thereof; more preferably wherein the fragment comprises a 21 amino acid leader sequence; even more preferably the 21 amino acid leader sequence is SEQ ID NO: 9.

Advantageously, the inclusion of li or tPA increases immunogenicity of the viral vector produced antigen. This increases the magnitude, breadth and duration of antigen-specific T cell response.

A ChAd vector of the invention may be constructed so that it has a polynucleotide sequence encoding (i) a MAGE cancer antigen or immunogenic fragment thereof and a NY-ESO-1 cancer antigen or immunogenic fragment thereof, each as herein defined; or (ii) a MAGE cancer antigen or immunogenic fragment thereof and a LAGE1 cancer antigen or immunogenic fragment thereof, each as herein defined, expressed in an animal cell as a fusion protein.

An MVA vector of the invention may be constructed so that it has a polynucleotide sequence encoding (i) a MAGE cancer antigen or immunogenic fragment thereof and/or an NY-ESO-1 cancer antigen or immunogenic fragment thereof each as herein defined; or (ii) a MAGE cancer antigen or immunogenic fragment thereof and/or a LAGE1 cancer antigen or immunogenic fragment thereof each as herein defined, expressed in an animal cell as a fusion protein, wherein at least one of the MAGE cancer antigen, NY-ESO-1 cancer antigen or LAGE1 cancer antigen is a fragment.

The inventors believe that NYESO-1 may be more immunogenic than MAGEA3 in humans. Also, in cancer patients, in certain groups of these, tumours are found more frequently to express MAGEA3 and not NY-ESO-1. Therefore, a possible concern might be in having an MVA boost vector in a prime-boost regimen of the present invention, comprising both MAGEA3 and NY-ESO-1 antigens leading to an immunodominant immune response to NY-ESO-1 and ineffective immunization against MAGEA3. Therefore, at least for such particular patient groups, or groups with higher expression of MAGEA3 compared to NY-ESO-1, an MVA vector comprising just MAGEA3 cancer antigen or immunogenic fragment thereof is preferred in the prime-boost regimen. That is to say, in certain embodiments, the invention does not include an MVA vector comprising any NY-ESO-1 cancer antigen or immunogenic fragment thereof. In a similar way, in certain embodiments, the invention does not include an MVA vector comprising any LAGE1 cancer antigen or immunogenic fragment thereof.

In preferred embodiments each of MVA vector, each of the MAGE cancer antigen and NY-ESO-1, or MAGE cancer antigen and LAGE1 are immunogenic fragments.

Where the ChAd and/or MVA vectors of the invention are constructed to yield fusions of antigens on expression, the polynucleotide sequence preferably also encodes a suitable polypeptide linker of between 5 and 9 amino acids; more preferably having the amino acid sequence GGGPGGG, which when expressed links the MAGE and NY-ESO-1 or LAGE1 cancer antigens or fragments thereof, in either order, as a fusion protein.

The invention therefore also provides an immunogenic composition comprising a ChAd or MVA vector as hereinbefore and as herein described. Such compositions may further comprise a suitable adjuvant.

The invention further provides an isolated polynucleotide comprising a sequence encoding a fusion protein contained in a ChAd vector or an MVA vector as herein described.

A preferred polynucleotide comprises the nucleic acid sequence SEQ ID NO: 10 encoding a MAGEA3/linker/NY-ESO-1 fusion protein. Also possible are polynucleotides having sequences of at least 70% identity with SEQ ID NO: 10. The translated protein sequence of 501 amino acids is as set forth in SEQ ID NO: 11 or a sequence of at least 70% identity therewith.

Another preferred polynucleotide has the nucleic acid sequence SEQ ID NO: 12 encoding a hli/MAGEA3/linker/NY-ESO-1 fusion protein. Also possible are polynucleotides having sequences of at least 70% identity with SEQ ID NO: 12. The translated protein sequence is set forth in SEQ ID NO: 13 or a sequence of at least 70% identity therewith.

Yet another preferred polynucleotide has the nucleic acid sequence SEQ ID NO: 14 encoding tPA/MAGEA3/linker/NY-ESO-1 fusion protein. Also possible are polynucleotides having sequences of at least 70% identity with SEQ ID NO: 12. The translated protein sequence is set forth in SEQ ID NO: 15 or a sequence of at least 70% identity therewith.

In particular embodiments the isolated polynucleotide consists of any of the aforementioned sequences or variants thereof.

In all aspects of the invention, the polynucleotides encoding the antigens are preferably codon optimised for expression in humans. A person of skill in the art will be familiar with a number of available software packages, including for example those described in U.S. Pat. No. 8,326,547, or Puigbo, P. et al. (2007) OPTIMIZER: A web server for optimizing the codon usage of DNA sequences: Nucleic Acids Research, 35:W126-W131. Also, commercially available services and software such as those offered by Integrated DNA Technologies or GenScript.

The invention also includes a Bacterial Artificial Chromosome (BAC) clone comprising a polynucleotide as described herein. Converting the BAC clones of the viral genomes into viruses ("rescue") can be carried out by a well-known process, as described in WO2012/172277 of Isis Innovation Limited, incorporated herein by reference.

The invention further includes an isolated host cell comprising a ChAd and/or MVA vector as described herein.

Also, the invention provides a method of preventing or treating cancer in an individual, comprising administering an effective amount or a ChAd vector as described herein, and administering an effective amount of an MVA vector as described herein, whereby the adaptive immune system of the individual is stimulated to provide an anti-cancer immune response. Advantageously the method of the invention generates a strong T cell immune response, particularly a strong $CD8^+$ immune response leading to protective immunity which is long lasting.

In a preferred method of preventing or treating cancer in accordance with the invention, the administration of the ChAd and MVA vectors is carried out separately, sequentially or simultaneously.

In particular methods of preventing or treating cancer in accordance with the invention, there is the further administration of an effective amount of one or more immune checkpoint modulators. Such checkpoint modulators may be administered simultaneously, separately or concurrently with the ChAd and MVA vectors.

In the method of preventing or treating cancer aspects of the invention, an individual who is being treated may be one who has received, is receiving or will receive a chemotherapy and/or radiotherapy treatment.

In the methods of preventing or treating cancer in accordance with the invention, the ChAd vector is preferably administered first.

In the cancer prevention or treatment methods of the invention, the ChAd and MVA vectors may be administered more than once each. In preferred aspect when the ChAd is used as a priming immunization then there is just one of these, followed by two MVA booster immunizations. Also possible is methods of cancer treatment or prevention in which the ChAd and MVA vectors are administered in alternation.

The period of time between each administration of a vector of the invention may be in the range 5 days to 8 weeks; preferably though a period of about 1 week is used between prime and subsequent boost or boosts.

In cancer prevention or treatment methods of the invention where a checkpoint modulator is administered and also forms part of the treatment regimen, the checkpoint modulator may be an inhibitor that blocks PD-1, CTLA-4 or PD-L1. Advantageously, using the vectors and immunogenic compositions of the invention together with one or more checkpoint modulators can serve to reduce the dosage of checkpoint modulators needed for equivalent effect (i.e. when used alone). The effect is not simply additive but synergistic as between the viral vector treatment regimen of the present invention and checkpoint modulators.

Particularly preferred checkpoint modulators may be selected from nivolumab (Opdivo®), pembrolizumab (Keytruda®), ipilimumab (Yervoy®), tremelimumab or atezolizumab (Tecentriq®), durvaliumab (Imfinzi®) or avelumab (Bavencio®).

Methods of preventing or treating cancer in accordance with the invention are directed to cancers expressing cancer-germline genes, preferably genes coding MAGE-type, NYESO, and LAGE antigens: preferably directed to particular cancer types, e.g. wherein the cancer is non-small cell lung cancer (NSCLC), melanoma, Hodgkin lymphoma, non-Hodgkin lymphoma, urinary tract (urothelial), esophageal, bladder, small cell lung cancer, renal, head & neck, sarcoma, or breast.

Accordingly, the invention includes a ChAd vector of the invention for use in the prevention or treatment of cancer. Also, an MVA vector of the invention for use in the prevention or treatment of cancer. In respect of such use, each of the various aspects of the method of the invention applies equally.

Further, the invention includes a ChAd vector of the invention as herein defined, and an MVA vector of the invention as herein defined, for separate, sequential or simultaneous administration to a patient for the prevention or treatment of cancer.

ChAd and MVA vectors for use in prevention or treatment of cancer as herein defined, may further including one or more modulators of cancer-immunity cycle or cancer-immunity set-points as described in Chen, D. S. and Mellman, I. (2013) Immunity 39(1):1-10, and Chen, D. S. and Mellman, I. (2017) Nature 541(7637):321-330; preferably checkpoint inhibitors for administration with the ChAd and MVA vectors for the treatment of cancer.

A large proportion of patients with advanced cancer currently do not respond to immunotherapy based on checkpoint modulators. For example, where an anti-PD1 inhibitor is used in melanoma, renal cell carcinoma, head & neck carcinoma and lung carcinoma. In one aspect the invention uses a ChAd/MVA vaccine to induce CD8 T cells against MAGE-A3 and NY-ESO-1 in combination with anti-PD1 and chemotherapy. Without wishing to be bound by any particular theory, the inventors expect that what would otherwise be "cold" tumours become infiltrated by tumour-specific CD8 T cells that will be boosted by the anti-PD1.

The inventors have also found that a triple combination of vaccine in accordance with the invention, plus chemotherapeutic agent, plus checkpoint inhibitor provides a significantly improved anti-tumour effect, and significant survival times of mice in a mouse model, when compared to vaccine alone or vaccine plus chemotherapeutic agent or vaccine plus checkpoint inhibitor. Indeed the effect of the triple combination is such that it is synergistic.

There is a significant depletion of myeloid derived suppressor cell (MDSC) achieved with the triple combination. The invention therefore also provides such a triple combination method of treatment and corresponding medical use. Also the invention provides a ChAd vector as hereinbefore defined, an MVA vector as hereinbefore defined, a chemotherapeutic agent, and a checkpoint inhibitor, for separate, sequential or simultaneous administration to a patient for the prevention or treatment of cancer.

The chemotherapeutic agent may be selected from (but not limited to) (a) carboplatin or cisplatin in combination with (b) one of paclitaxel, docetaxel, vinorelbine, gemcitabine, etoposide or pemetrexed. For the checkpoint inhibitor this may be PD-1. Such particular triple combinations may provide useful treatments for non-small cell lung cancer (NSCLC) or small cell lung cancer (SCLC) melanoma, Hodgkin lymphoma, non-Hodgkin lymphoma, urinary tract (urothelial), bladder, renal, head & neck, sarcoma or breast cancer.

Also provided as part of the invention are kits comprising ChAd and/or MVA vectors as herein described for the prevention or treatment or cancer. Such kits comprise at least one container which holds one of the ChAd and/or MVA vectors of the invention. Kits may comprise two or more, i.e. a multiplicity of containers, each with a different viral vector of the invention. Kits may include a set of instructions in the use of the vectors as a vaccine, including essential information on the vaccine regimen to be used, e.g. prime-boost, and periods between administrations. In more complex embodiments the kits may comprise any of the further therapeutic elements, e.g. checkpoint modulators, in accordance with the invention described herein.

BRIEF DESCRIPTION OF THE DRAWINGS

Embodiments of the invention are further described hereinafter with reference to the accompanying drawings, in which.

DETAILED DESCRIPTION

Figure 1A:
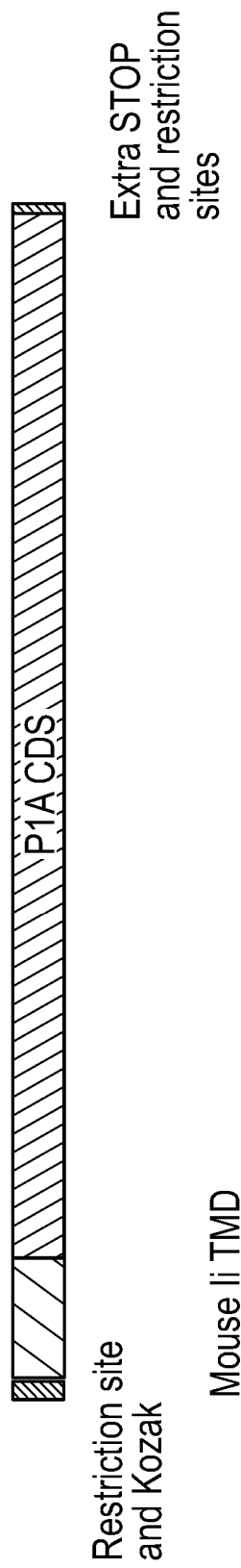
FIG. 1A shows schematically ChAdOx1 vectors which were prepared encoding mouse P1A antigen.

Suitable chimpanzee adenoviral vectors for use in accordance with the present invention are described in detail in WO2012/17277 Isis Innovations Limited, or WO 2005/071093 Istituto di Ricerche di Biologia Moleculare P. Angeletti S.p.A, or WO2017/221031 of Oxford University Innovation Limited, all of which are incorporated herein by reference.

Particularly preferred adenoviral vectors are the chimpanzee adenovirus Oxford 1 and 2 (ChAdOx1 and ChAdOx2) of Vaccitech Ltd, Oxford. ChAdOx1 is a replication-defective E1/E3 deleted chimpanzee adenovirus vector from wild-type isolate Y25 (species human adenovirus E) and is described in Dicks M. D. et al. (2012) PLoS ONE 7: e40385. ChAdOx2 is an E1/E3-deleted vaccine vector derived from ChAd68 with a modified E4 region to increase virus yields in HEK293 cells.

The ChAd vector of the invention may be (a) ChAdOx1 as disclosed in WO2012/172277; preferably encoded by a polynucleotide of SEQ ID NO: 38 as disclosed in WO2012/172277 or a sequence of at least 80% identity therewith; or (b) ChAdOx2 as disclosed in WO2017/221031; preferably encoded by a polynucleotide of SEQ ID NO: 10 as disclosed in WO2017/221031 or a sequence of at least 80% identity therewith. The skilled person will understand that ChAd vectors used in the invention may include homologues, equivalents and derivatives of all of the nucleic acid sequences, as further described herein.

Suitable Modified Vaccinia Ankara (MVA) vectors for use in accordance with the present invention are described in detail in WO2011/128704 or EP 2044947 A1, each of which are incorporated herein by reference.

The cancer antigens, whether separate or in the form of fusions with each other and optionally other polypeptides, as encoded by and expressed by any of the viral vectors of the invention are preferably immunogenic as defined herein, and this includes fragments of cancer antigens and their fusions with each other and other polypeptides.

As used herein, "antigen" generally equates with one or more epitopes of a protein or polypeptide, including fusions and fragments and variants thereof. Such fragments and variants may retain essentially the same biological activity or function as the parent antigen. By "antigenic" is usually meant that the protein or polypeptide or fragment is capable of being used to raise antibodies or T cells and so is capable of inducing an antibody or T cell response in a subject. "Immunogenic" means that a protein or polypeptide or fragment is capable of eliciting a potent and preferably a protective immune response in a subject. Thus, in the latter case, the protein or polypeptide or fragment may be capable of generating an antibody response and a non-antibody based immune response.

As used herein, whenever there is reference to a nucleic acid sequence having identity to a reference sequence, then the degree of identity may be selected from any of the following, wherein the "at least" applies to each percentage figure listed here: at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4% 99.5%, 99.6%, 99.7%, 99.8% or 99.9%. When comparing nucleic acid sequences for the purposes of determining the degree of homology or identity one can use programs such as BESTFIT and GAP (both from the Wisconsin Genetics Computer Group (GCG) software package). BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention, when discussing identity of nucleic acid sequences, the comparison is made by alignment of the sequences along their whole length. The above applied mutatis mutandis to all nucleic acid sequences disclosed in the present application.

Additionally, the skilled person will also appreciate that variation from the particular nucleic acid molecules exemplified herein will be possible in view of the degeneracy of the genetic code. Preferably, such variants have substantial identity to the nucleic acid sequences described herein over their entire length.

Having regard to any amino acid sequence described in connection with the present invention, this includes variants of these amino acid sequences. As will be well known to a person of skill in the art, for a given starting or reference sequence disclosed herein, one or more amino acid residues may be substituted, deleted or added in any combination. Preferred as changes are silent substitutions, additions and deletions, which do not alter the properties and activities of the protein of the present invention. Various amino acids have similar properties, and one or more such amino acids can be substituted by one or more other such amino acids without eliminating a desired immunogenicity or other activity of that substance. Thus, amino acids glycine, alanine, valine, leucine and isoleucine can often be substituted for one another—they have aliphatic side chains. Of these glycine and alanine are preferable used to substitute each other. Also, valine, leucine and isoleucine may be used to substitute for each another—they have larger aliphatic side chains which are hydrophobic). Phenylalanine, tyrosine and tryptophan may substitute for each other—being amino acids having aromatic side chains. Lysine, arginine and histidine may substitute for each other—being amino acids having basic side chains. Aspartate and glutamate may substitute for each other—having acidic side chains. Asparagine and glutamine may substitute for each other—having amide side chains). Cysteine and methionine may substitute for each other—having sulphur-containing side chains.

"Variants" as described herein include naturally occurring or artificial variants. Artificial variants may be generated using mutagenesis or gene engineering or gene editing techniques, including those applied to nucleic acid molecules, cells or organisms. As used herein, whenever there is reference to an amino acid sequence having identity to a reference sequence, then the degree of identity may be selected from any of the following, wherein the "at least" applies to each percentage figure listed here: at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4% 99.5%, 99.6%, 99.7%, 99.8% or 99.9%. A person of skill in the art may use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. The above applies mutatis mutandis to all amino acid sequences disclosed in the present application.

Particularly preferred MVA vectors are standard MVA produced by Anton Mayr after 570 passages in CEFs as is most commonly used in the art. This is a highly attenuated strain of vaccinia virus that was developed in connection with smallpox eradication. MVA has lost about 10% of the vaccinia genome and with it the ability to replicate efficiently in primate cells.

Regarding the MAGE human cancer antigen, the MAGE family consists of approximately 40 members. MAGE-A proteins share at least 46% of sequence identity, defined biochemical structure and properties. MAGE-A3 is significantly expressed in major forms of cancer and its expression is associated with a negative outcome. Alignment of MAGE-A3 amino acid sequences with other MAGE-A family members gave the following % identity values:

|         | Identity with MAGEA3 |
|---------|----------------------|
| MAGEA1  | 66.9%                |
| MAGEA2  | 84.4%                |
| MAGEA4  | 69.3%                |
| MAGEA5  | 71.8%                |
| MAGEA6  | 95.9%                |
| MAGEA8  | 63.7%                |
| MAGEA9  | 59.6%                |
| MAGEA10 | 47.8%                |
| MAGEA11 | 59.6%                |
| MAGEA12 | 85.4%                |

Each of the MAGE antigens noted above may be used in pursuance of the present invention, as may be defined in terms of any percentage identity with the MAGEA3 reference sequence of SEQ ID NO: 1.

Regarding NY-ESO-1 this is a known cancer antigen of 180 amino acids. The sequence has a 76.6% identity to LAGE-1. Several studies have tried to define the immunogenicity of the sequence. The main region spans from aa 79 to 173 of NY-ESO-1. Gnjatic S, et al. (2006) Adv. Cancer Res. vol 95:1-30; Sabbatini P, et al. (2012) Clin. Cancer Res. Vol 18(23): 6497-508; and Baumgaertner P, et al. (2016) Oncoimmunology vol 9:5(10) report how melanoma or ovarian cancer have highlighted specific fragments of interest. These are each options for use in any aspect of the present invention:
NY-ESO-1 79-173
NY-ESO-1 79-108
NY-ESO-1 100-129
NY-ESO-1 121-150
NY-ESO-1 42-173

LAGE1 is also a known cancer antigen and it too or fragments thereof may be used together with MAGEA3 in the viral vectors and methods and uses of the present invention.

Adjuvants may be used in compositions for the delivery of the AdCh and/or MVA vectors of the invention described herein. Advantageously these viral vectors may be engineered so that they comprise a polynucleotide construct that encodes a fusion protein between the cancer antigen or fragment and CD74, the MHC class II invariant chain (Ii). This is expected to lead to enhanced $CD8^+$ T cell immunogenicity. More detailed information about how to make such protein fusions and preferred li sequences is provided in WO2015/082922 of Isis Innovation Limited, incorporated herein by reference.

The viral vector of the invention may be designed to express the one or more antigen genes as an epitope string. Preferably, the epitopes in a string of multiple epitopes are linked together without intervening sequences such that unnecessary nucleic acid and/or amino acid material is avoided. The creation of the epitope string is preferably achieved using a recombinant DNA construct that encodes the amino acid sequence of the epitope string, with the DNA encoding the one or more epitopes in the same reading frame. Alternatively, the antigens may be expressed as separate polypeptides.

Any fragments of antigens, whether separately or in an epitope string as described, preferably comprise at least n consecutive amino acids from the sequence of the parent antigen, wherein n is preferably at least, or more than, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 57, 58, 59, 60, 70, 80, 90 or 100 amino acids. Fragments preferably include one or more epitopes of the parent antigen. A fragment may in some situations comprise or consist of just a single epitope of a parental antigen. Usually the fragment will be sufficiently similar to the parent regions or epitope(s) such that the antigenic/immunogenic properties are maintained.

One or more of the antigens or antigen genes used in the invention may be truncated at the C-terminus and/or the N-terminus. This may facilitate cloning and construction of the vectored vaccine and/or enhance the immunogenicity or antigenicity of the antigen. Methods for truncation will be known to those of skill in the art. For example, various well-known techniques of genetic engineering can be used to selectively delete the encoding nucleic acid sequence at either end of the antigen gene, and then insert the desired coding sequence into the viral vector. For example, truncations of the candidate protein are created using 3' and/or 5' exonuclease strategies selectively to erode the 3' and/or 5' ends of the encoding nucleic acid, respectively. The wild type gene sequence may be truncated such that the expressed antigen may be truncated by 1, 2, 3, 4, 5, 6, 7, 8, 9, 10, 11, 12, 13, 14, 15, 16, 17, 18, 19, 20 or more amino acids relative to the parent antigen. In some instances, the antigen gene is truncated by 10-20 amino acids (when expressed) at the C-terminus relative to the wild type antigen. In other instances the antigen gene is truncated by 13-18 amino acids (when expressed), preferably by 15 amino acids (when expressed) at the C-terminus relative to the wild type antigen.

In some situations, antigen genes may include a leader sequence and this may affect processing of the primary transcript to mRNA, translation efficiency, mRNA stability, and may enhance expression and/or immunogenicity of the antigen. In connection with the invention some preferred leader sequences which also may serve in an adjuvanting capacity are tissue plasminogen activator (tPA) or MHC II chaperone protein invariant chain (Ii). Preferably, the leader sequence is positioned N-terminal to the one or more antigens.

The invention includes a pharmaceutical or immunogenic composition comprising the viral vector or vectors of the invention; optionally in combination with one or more additional active ingredients, a pharmaceutically acceptable carrier, diluent, excipient or adjuvant. Preferably, the composition is an immunogenic and/or antigenic composition.

Suitable adjuvants are well known in the art and include incomplete Freund's adjuvant, complete Freund's adjuvant, Freund's adjuvant with MDP (muramyldipeptide), alum (aluminium hydroxide), alum plus Bordatella pertussis and immune stimulatory complexes (ISCOMs, typically a matrix of Quil A containing viral proteins).

The immunogenic and/or antigenic compositions of the invention may be prophylactic (whereby they induce immune responses which prevent a cancer from forming) or therapeutic (whereby they induce immune responses which have an anti-cancer activity).

The vectors or compositions of the invention are administered to the individual subject either as a single immunisation or multiple immunisations. Preferably, the viral vector or immunogenic composition thereof are administered as part of a single, double or triple immunisation regime. They may also be administered as part of a homologous or heterologous prime-boost immunisation regime.

The immunisation regime may include second or subsequent administrations of the viral vector or immunogenic composition of the present invention. The second administration can be administered over a short time period or over a long time period. The doses may be administered over a period of hours, days, weeks, months or years, for example up to or at least 1, 2, 3, 4, 5, 6, 7, 8, 9, or 10 or more weeks or 0.25, 0.5, 0.75, 1, 5, 10, 15, 20, 25, 30, 35 or 40 or more years after the first administration. Preferably, the second administration occurs at least 2 months after the first administration. Preferably, the second administration occurs up to 10 years after the first administration. These time intervals preferably apply mutatis mutandis to the period between any subsequent doses.

In terms of administration, the virus vectors of the invention may be administered in amounts of one or more doses of 10, 100, $10^3$, $10^4$, $10^5$, $10^6$, $10^7$, $10^8$, $10^9$, $10^{10}$, $10^{11}$, $10^{12}$, $10^{13}$, $10^{14}$ or more viral particles (vp).

Administration may be by intraperitoneal, intravenous, intra-arterial, intramuscular, intradermal, subcutaneous, or intranasal administration. In preferred embodiments, the viral vectors are administered systemically, particularly by intravascular administration, which includes injection, perfusion and the like.

Immune checkpoint modulators (agonists or inhibitors) are an immunotherapy used in the treatment of cancers. They regulate checkpoint proteins, which are proteins known to tune T cells attacking cancer cells. Checkpoint inhibitors, a segment of checkpoint modulators, for use in accordance with the invention block different checkpoint proteins including, CTLA-4 (cytotoxic T lymphocyte associated protein 4), PD-1 (programmed cell death protein 1) or PD-L1 (programmed death ligand 1). CTLA-4 and PD-1 are found on T cells, whereas PD-L1 is found on cancer cells. Suitable checkpoint inhibitors for blocking PD-1 include nivolumab (Opdivo®), pembrolizumab (Keytruda®) and may be used together with the vaccination approach of the present invention for treating patients suffering from cancers such as melanoma, Hodgkin lymphoma, non small cell lung cancer, urinary tract (urothelial), bladder. Suitable checkpoint inhibitors for blocking CTLA-4 include Ipilimumab (Yervoy®) and may be used with the present invention for treatment of melanoma. Suitable checkpoint inhibitors for blocking PD-L1 includes atezolizumab (Tecentriq®) and may be used with the present invention for treatment of cancers including lung, breast and urothelial.

Others suitable targets for immune checkpoint modulators useful in operation of the methods and uses of the invention include, for example any selected from AMHRII, B7-H3, B7-H4, BTLA, BTNL2, Butyrophilin family, CD27, CD28, CD30, CD40, CD40L, CD47, CD48, CD70, CD80, CD86, CD155, CD160, CD226, CD244, CEACAM6, CLDN6, CCR2, CTLA4, CXCR4, GD2, GGG (guanylyl cyclase G), GIRT, GIRT ligand, HHLA2, HVEM, ICOS, ICOS ligand, IFN, IL1, IL1R, IL1RAP, IL6, IL6R, IL7, IL7R, IL12, IL12R, IL15, IL15R, LAG3, LIGHT, LIF, MUC16, NKG2A family, OX40, OX40 ligand, PD1, PDL1, PDL2, Resokine, SEMA4D, Siglec family, SIRPalpha, STING, TGFbeta family, TIGIT, TIM3, TL1A, TMIGD2, TNFRSF, VISTA, 4-1 BB and 4-1 BB ligand.

A fuller review of checkpoint modulators is provided by Mahoney, A. M. et al., (2015) Nature Reviews Drug Discovery vol 14: 561-584 (see particularly FIG. 1).

The administration of a checkpoint modulators may be simultaneously together with either the prime or the one or more boost immunizations of the invention. This therefore provides a combination treatment, for prophylactic or therapeutic purposes. As a modification of a simultaneous administration the checkpoint modulator may be administered substantially following the prime and/or boost administrations, in effect at the same time. Or there may be a sequential administration delayed in time from the prime and/or boost administrations. The delay may differ relative to prime and boost administrations and may be long enough such that the checkpoint modulator is administered separately in time in between vaccine administrations. Separate administration of checkpoint modulator from the immunogenic compositions of the invention may result in equal time periods between each administration. In some instances, checkpoint modulator may be administered before the prime vaccination using the ChAd-based immunogenic composition of the invention.

A "combination treatment" in the context of one or more checkpoint modulator envisages the simultaneous, sequential or separate administration of the components of the combination. For example, simultaneous administration of a viral vector of the invention and checkpoint inhibitor. Also possible for example is a sequential administration of a viral vector of the invention and one or more checkpoint inhibitors. Further, there is the example of separate administration of a viral vector of the invention and one or more checkpoint inhibitor. Where the administration of the viral vector and checkpoint inhibitor is sequential or separate, the virus and checkpoint inhibitor may be administered within time intervals that allow that the therapeutic agents show a cooperative e.g., synergistic, effect. In preferred embodiments, a viral vector of the invention and one or more checkpoint inhibitors are administered within 1, 2, 3, 6, 12, 24, 48, 72 hours, or within 4, 5, 6 or 7 days or within 8, 9, 10, 11, 12, 13, 14, 15, 16, 17, 18, 19, 20, 21, 22, 23, 24, 25, 26, 27, 28, 29, 30 or 31 days of each other. In some embodiments, a first dose of a viral vector of the invention is administered prior to a first dose of a checkpoint inhibitor or vice versa and may include a phase where treatment with a viral vector and a checkpoint inhibitor overlap. In other embodiments, a first dose of a viral vector of the invention may be administered on or about the same time as a first dose of a checkpoint inhibitor. In other embodiments, a first dose of viral vector of the invention is administered after a first dose (or second, third or subsequent dose) of a checkpoint inhibitor and may include a phase where treatment with a viral vector and checkpoint inhibitor overlap.

EXAMPLES

Materials and Methods

Viral Vector Construction

Gene sequences for insertion into the viral vectors, codon optimised for translation efficiency, were synthesized as DNA strings or plasmids by GeneArt (ThermoFisher Scientific). For the construction of chimpanzee adenoviral vectors (ChAdOx), the DNA string inserts and a p1990 backbone (Gateway® entry vector) were digested with the restriction enzymes KpnI/NotI, and then ligated via overnight incubation. Plasmids p1990 encoding the gene sequence of interest were transformed into DH5α™ competent *E. coli* and then screened for positive clones via a PCR method. Positive cloned DNA was amplified via midiprep and then Gateway® cloning (ThermoFisher Scientific) was carried out between p1990 containing the gene insert and p2563 [SEQ ID NO: 24], a ChAdOx destination vector, using LR clonase. The p2563 destination vector DNA was amplified via bacterial transformation, maxiprep and gravity column purification. The p2563 destination vectors were digested with Pme1 to linearise the DNA before sending for virus production.

More comprehensive technical information, including nucleic acid sequences and sources of deposited biological material for generating ChAdOx1 vectors is disclosed in WO2012/172277 of Isis Innovation Limited and which is incorporated herein by reference. More comprehensive technical information, including nucleic acid sequences and sources of biological material for generating ChAdOx2 vectors is disclosed in WO2017/221031 of Oxford University Innovation Limited and which is incorporated herein by reference.

Other relevant disclosure incorporated herein by reference and providing more materials and methods information for the production of the ChAdOx viral vectors of the invention are Dicks, M. D. J., et al. (2012) "A Novel Chimpanzee Adenovirus Vector with Low Human Seroprevalence: Improved Systems for Vector Derivation and Comparative Immunogenicity" PlosOne e40385.

To generate the Modified Vaccinia Ankara (MVA) vectors, the GeneArt DNA strings or plasmids were amplified via PCR using a Phusion® polymerase (ThermoFisher Scientific) to ensure correct overhangs for an InFusion reaction. The Gene insert and p4719 [SEQ ID NO: 25], an MVA destination vector were then digested with the restriction enzyme Ale I. The amplified insert and p4719 were then ligated using an InFusion method. Ligated plasmids were transformed into DH5α™ competent E. coli. Positive clones were screened and DNA amplified via midiprep. A final digest with Xho1+Acc651 to linearise the DNA was performed before virus production.

More comprehensive technical information, including nucleic acid sequences and sources of deposited biological material for generating and reproducing the necessary MVA vectors for the present invention are disclosed in WO2011/128704 of Isis Innovation Limited and also EP 2044947 A1, each of which is incorporated in their entirety herein by reference. Other relevant disclosure incorporated herein by reference and providing more materials and methods information for the production of the MVA viral vectors of the invention Pavot V., Sebastian S., Turner A. V., Matthews J., Gilbert S. C. (2017) "Generation and Production of Modified Vaccinia Virus Ankara (MVA) as a Vaccine Vector" In: Ferran M., Skuse G. (eds) Recombinant Virus Vaccines, Methods in Molecular Biology, vol 1581 Humana Press, New York, NY Peptide Production Overlapping pools of short peptides of 15 amino acids in length covering the whole of the P1A, MAGE-A3 and NY-ESO-1 proteins were ordered from and produced by Mimotopes of Mulgrave, Victoria, Australia.

Mice

Six to eight-week-old C57BL/6, DBA/2 and CD1 mice were purchased from Envigo, UK and housed at the Functional Genomics Facility, University of Oxford, UK. Mouse care and experimental procedures were carried out in accordance with the terms of the UK Animals Scientific Procedures Act Project License 30/2947

In Vivo Studies

To assess vaccine immunogenicity, mice were administered with the produced ChAdOx1 and MVA viral vectors at doses indicated in the drawings via intramuscular (i.m.) injection in a total volume of 50 µl under general anaesthesia. Vaccinations were administered at time points according to the scheme detailed for each experiment. Immunizations with live L1210.P1A.B7-1 cells were via intra-peritoneal injection. To obtain PBMCs for ex vivo assays, blood was sampled via tail vein bleed and processed to remove red blood cells with ACK lysis buffer.

Ten different recombinant viral vaccines (see Table 1 below) were generated and antigen expressions were confirmed in infected cells.

TABLE 1

| Viral vector | Polynucleotide sequence insert | Antigen amino acid sequence |
| --- | --- | --- |
| ChAdOx_MAGEA3_NYESO | SEQ ID NO: 10 | SEQ ID NO: 11 |
| ChAdOx_Ii_MAGEA3_NYESO | SEQ ID NO: 12 | SEQ ID NO: 13 |
| ChAdOx_tPA_MAGEA3_NYESO | SEQ ID NO: 14 | SEQ ID NO: 15 |
| ChAdOx_P1A | SEQ ID NO: 26 | SEQ ID NO: 27 |
| ChAdOx_Ii_P1A | SEQ ID NO: 28 | SEQ ID NO: 29 |
| MVA_MAGEA3 | SEQ ID NO: 16 | SEQ ID NO: 17 |
| MVA_NYESO | SEQ ID NO: 18 | SEQ ID NO: 19 |
| MVA_tPA_MAGEA3 | SEQ ID NO: 20 | SEQ ID NO: 21 |
| MVA_tPA_NYESO | SEQ ID NO: 22 | SEQ ID NO: 23 |
| MVA_P1A | SEQ ID NO: 30 | SEQ ID NO: 31 |

The immunogenicity of these viral vectored vaccines expressing P1A antigen were tested in three different strains of mice including DBA/2, C57BL/6 and CD1 outbred mice.

Ex Vivo Peptide Stimulation

Isolated mouse PBMCs or splenocytes were suspended in RPMI 1640 medium supplemented with 10% FCS and added to a V-bottom 96-well plate. The cells were stimulated by adding P1A, MAGE-A3 or NY-ESO-1 peptides or DMSO control to the culture medium at a working concentration of 4 mg/ml, together with anti-CD28 antibody (2 µg/ml) and DNase (20 µg/ml). Peptide stimulated cells were incubated at 37° C. in 5% $CO_2$ for 5 hours, with the addition of Brefaldin A after 1 hour to promote intracellular cytokine accumulation.

Flow Cytometry—Intracellular Cytokine Staining

Following peptide stimulation, PBMCs were washed with PBS, and stained for surface markers/viability by incubating with Aqua live/dead fixable dye (Invitrogen) and anti-CD8/anti-CD4 antibodies in PBS for 20 minutes at 4° C. To assess the percentage of activated cells producing cytokines, cells were then fixed and permeabalized with CytoFix/CytoPerm (BD Biosciences) and incubated with anti-IFN-γ, anti-TNF-α and anti-IL-2 antibodies in 1× perm buffer (BD Biosciences) for 20 minutes at 4° C. Samples were acquired on a BD Fortessa and analysis performed using FlowJo software (Tree Star, Inc.).

Statistical Analysis

All statistical tests and analyses were performed using Graph Pad Prism software. Differences between multiple groups were determined with a Kruskal-Wallis non-parametric ANOVA and between individual groups with a Mann-Whitney non-parametric t-test.

Example 1: Induction of CD8 T Cells Against P1A by Immunization with ChAdOx/MVA

P1A is a murine MAGE-type antigen that can be used to confirm induction of CD8 responses against a non-mutated MAGE-type antigen in a syngeneic host and induce protection against P1A-expressing tumour P815. It is a surrogate for MAGE-A3 and NY-ESO-1.

Figure 1B:
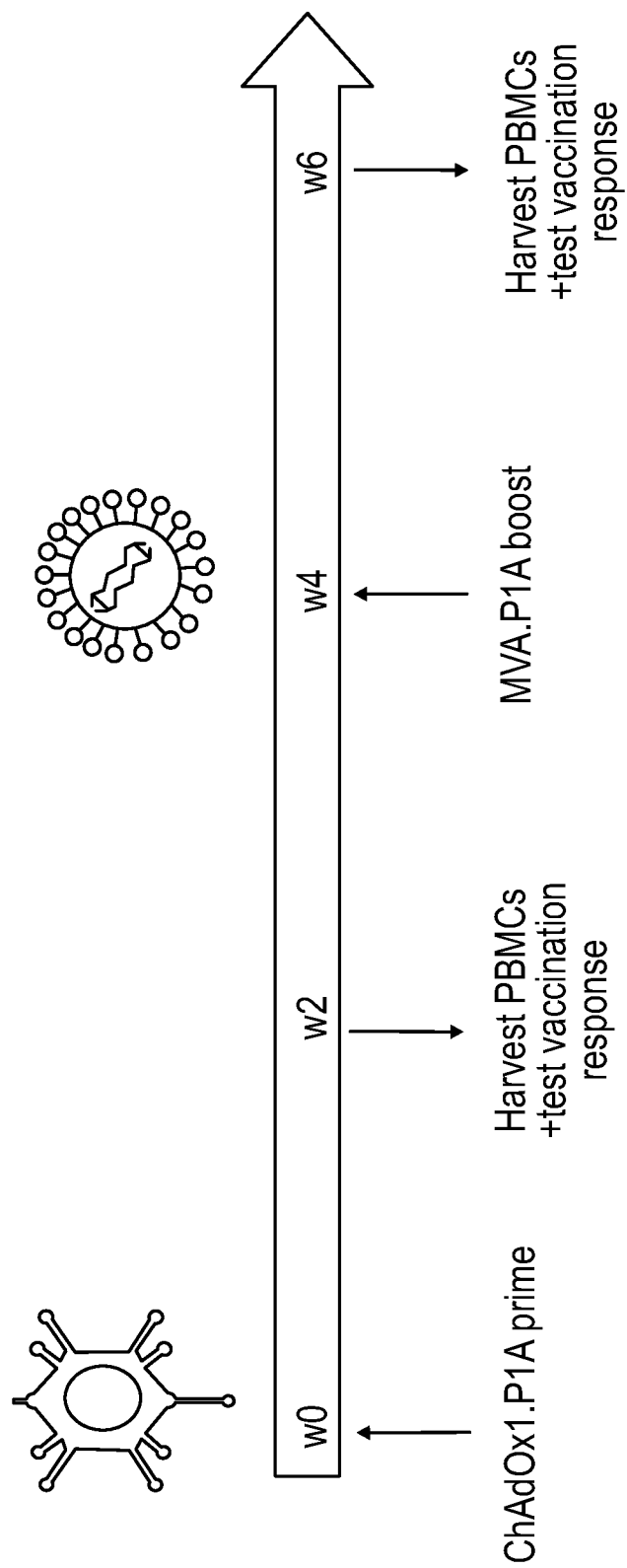
FIG. 1B shows a schematic outline of the ChAdOx1-P1A/MVA-P1A prime-boost immunization of mice from which peripheral blood mononuclear cells (PBMCs) are taken and tested for immune responses.
Figure 2:
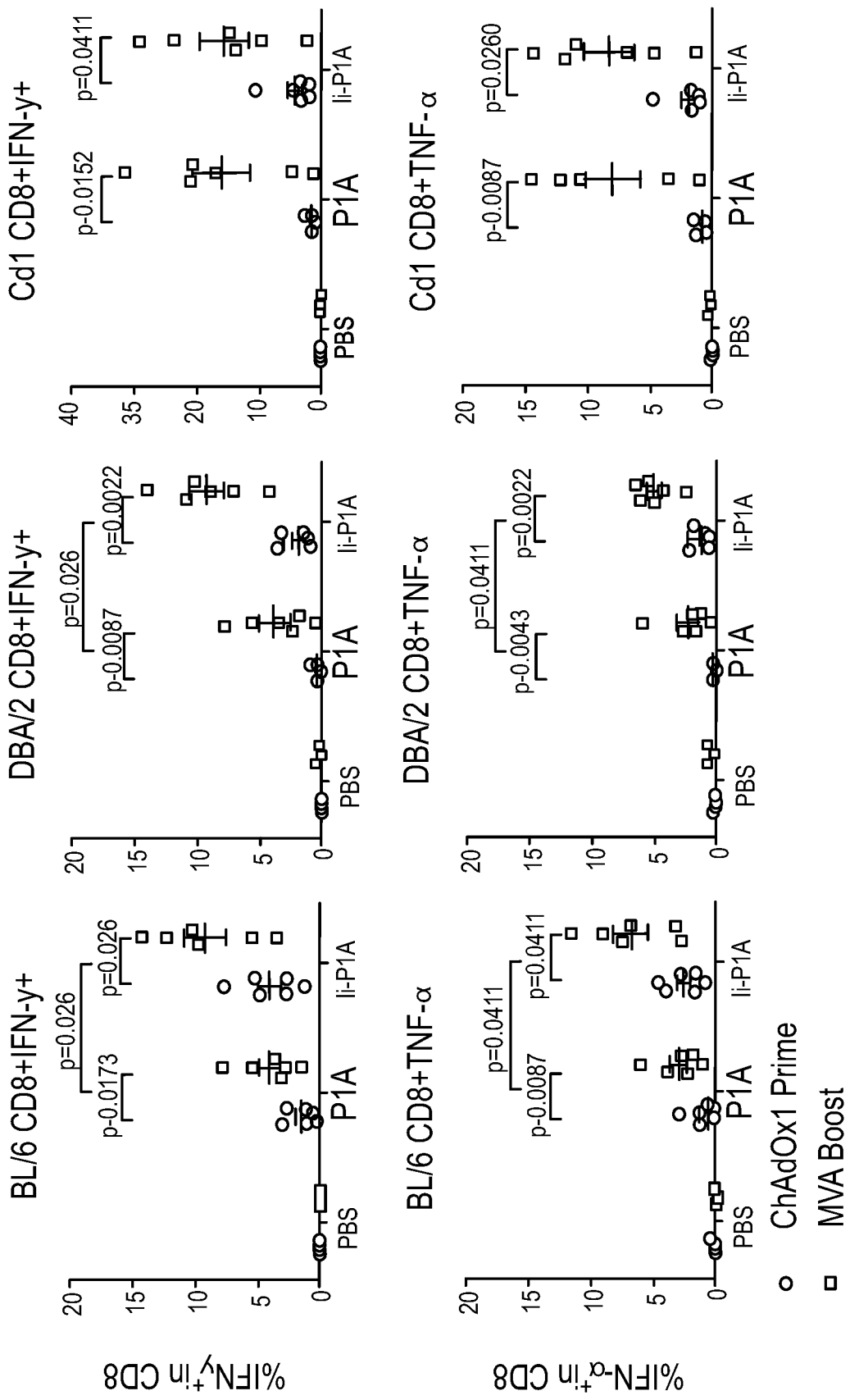
FIG. 2 shows the results of CD8$^+$ T cell response in mice immunized with ChAdOx1/MVA viral vectors encoding P1A, as noted in FIG. 1.
Figure 3:
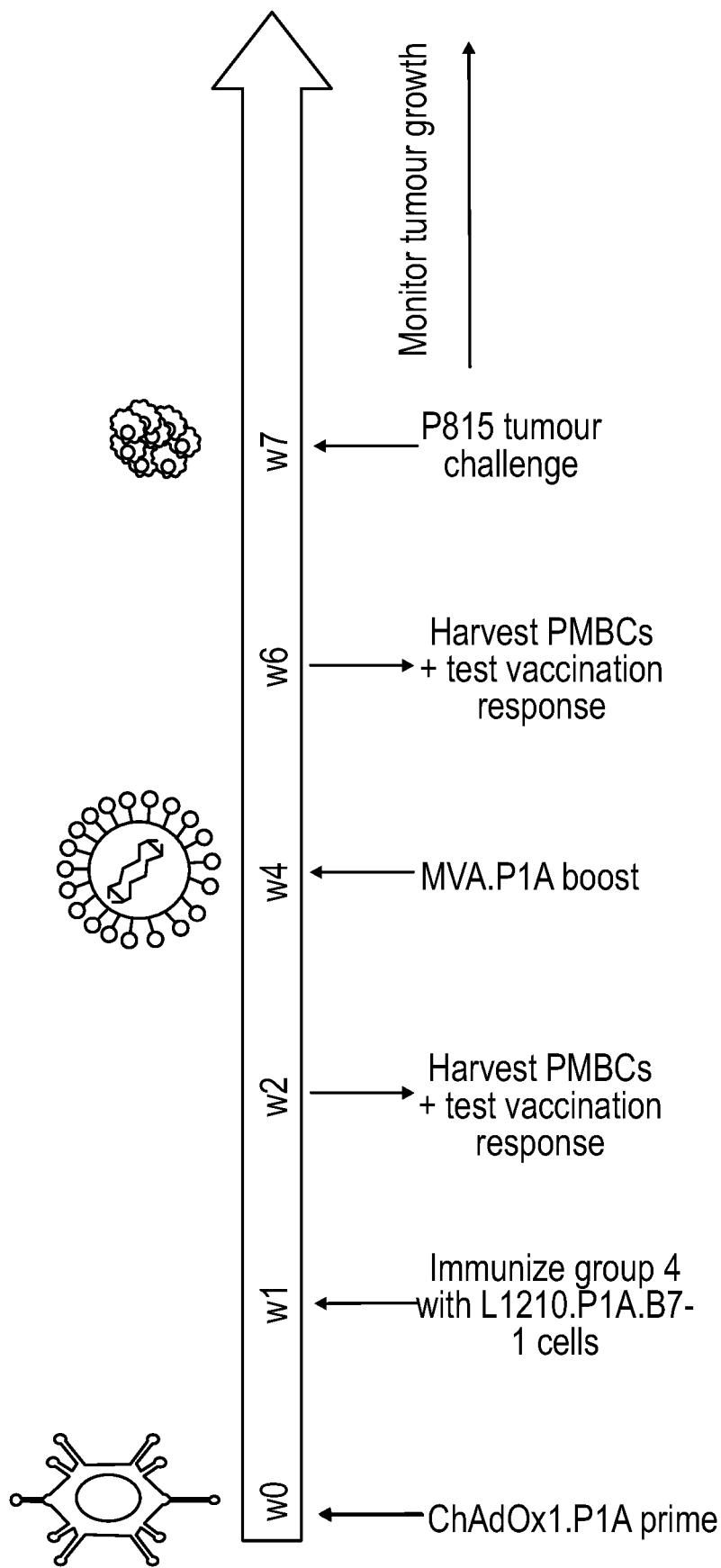
FIG. 3 shows a schematic outline of the ChAdOx1-P1A/MVA-P1A prime-boost prophylactic vaccination of mice DBA/2 mice against challenge with the syngeneic P1A-expressing cancer cell lines, P815 and 15V4T3.

FIG. 1B shows a schematic outline of the prime-boost immunization of mice from which peripheral blood mononuclear cells (PBMCs) are taken and tested for vaccination responses. FIG. 2 shows CD8$^+$ T cell response in mice vaccinated with ChAdOx1/MVA viral vectors encoding P1A. According to the vaccination scheme timeline (FIG. 1)—BL/6, DBA/2 and CD1 mice were vaccinated with either ChAdOx1.P1A or ChAdOx1.P1A-li (prime) followed by MVA.P1A (boost) 4 weeks later. To test the P1A-specific T-cell response, PMBCs were stimulated ex vivo with P1A peptide pools and the percentage cells producing type I cytokines analysed by flow cytometry. Percentage of CD8$^+$ cells producing the cytokines IFN-$\gamma$ (A) and TNF-$\alpha$ (B) (n=6 per group) was measured. The heterologous prime-boost vaccination induced a strong CD8 response against P1A in all three strains of mice (FIG. 2) as illustrated by intracellular staining of IFN-$\gamma$ and TNF-$\alpha$. The response was further enhanced when P1A was fused to the MHC II chaperone protein invariant chain (li). These results were confirmed by IFN-$\gamma$ ELISPOT assay and P1A-specific tetramer staining in DBA/2 mice (results not shown).

Overall, what was observed was very strong CD8 responses in DBA/2, B6 and outbred CD1 mice. The CD8 response was increased by adding li in the ChAdOx vector. What was found was when CD8 T cells were induced by the overlapping peptides they secreted IFN$\gamma$, IL2, and TNF$\alpha$. There was little in the way of a CD4 response against P1A (no CD4 epitope is known).

Example 2: Assessment of Protective Efficacy of ChAdOx1 and MVA Viral Vectors Carrying P1A Against Tumour Development As part of the assessment of vaccine protective efficacy against tumour challenge, mice were injected subcutaneously (s.c.) with tumour cells in serum-free cell culture media in one flank. Upon the development of palpable tumours, growth was recorded and mice euthanized once tumour size reached 10 mm in any direction. Tumour volume was measured using the formula length (mm)×width2 (mm)×0.5. Survival curves were made according to the Kaplan-Meier method and differences in survival tested using the log-rank test. P values below 0.05 were considered significant.

In more detail, DBA/2 mice were immunized with either PBS, live L1210.P1A.B7-1 cells or a ChAdOx1-P1A (±li)/MVA-P1A prime-boost given 4 weeks apart and then challenged with 1.5×10$^6$ P815 cells or 1×10$^6$ 15 V4T3 cells via subcutaneous injection in the flank. P815 and 15V4T3 are syngeneic P1A-positive mastocytoma cell lines. The 15V4T3 cells are described in Boon T, Van den Eynde B, Hirsch H, Moroni C, De Plaen E, van der Bruggen P, De Smet C, Lurquin C, Szikora J P, De Backer O. (1994) "Genes coding for tumor-specific rejection antigens" Cold Spring Harb Symp Quant Biol. 59: 617-22.

Mean tumour growth for each treatment group following P815 challenge (FIG. 4) and 15V4T3 (FIG. 7A). The Kaplan-Meier survival curves are shown for P815 (FIG. 5), 15V4T3 (FIG. 7B) n=10 per group.

Figure 4:
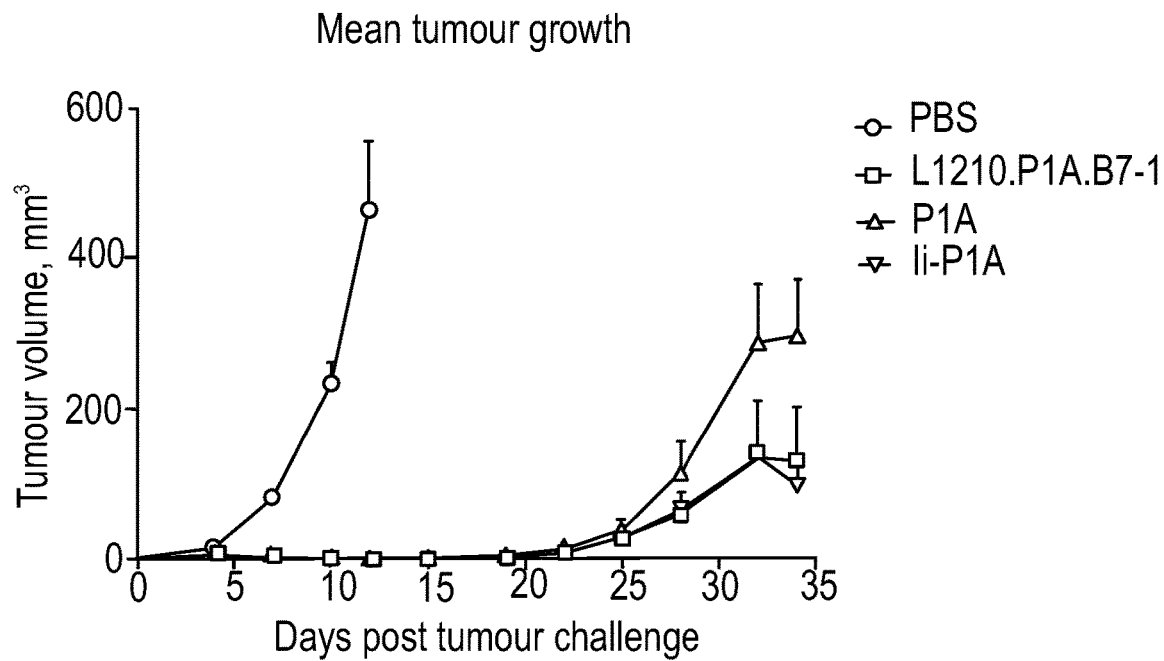
FIG. 4 shows the mean P815 tumour growth over time following prime-boost vaccination of mice as noted in FIG. 3 for three P1A antigens versus a phosphate buffered saline (PBS) control.
Figure 5:
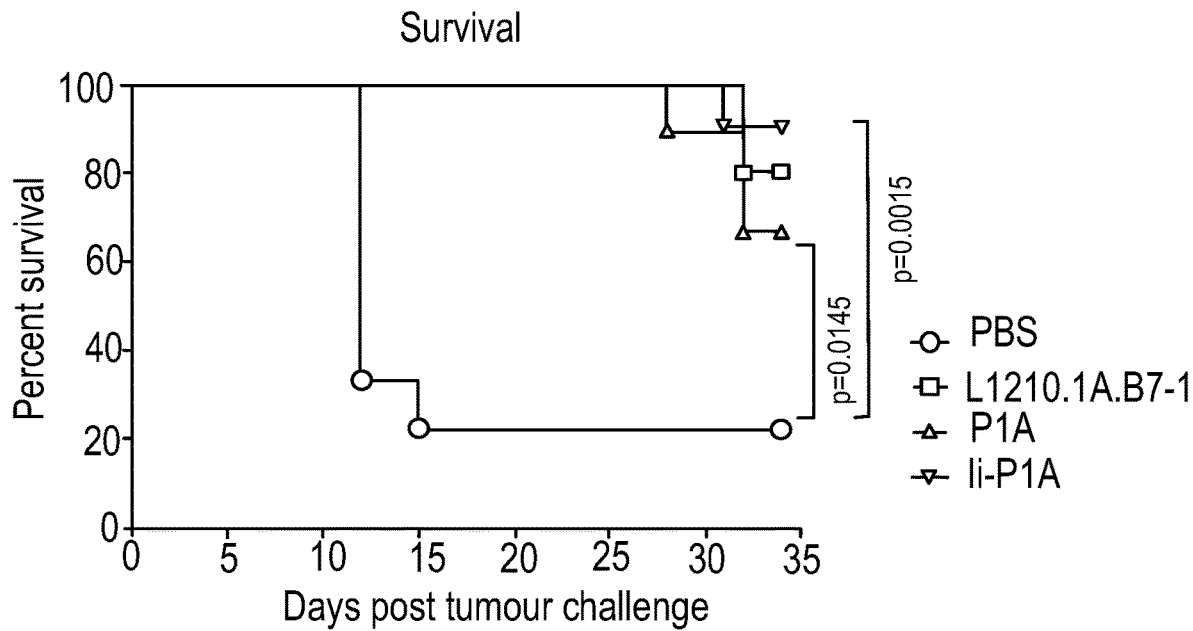
FIG. 5 shows Kaplan-Meier survival curves for the vaccinated mice noted in FIG. 4.
Figure 6A:
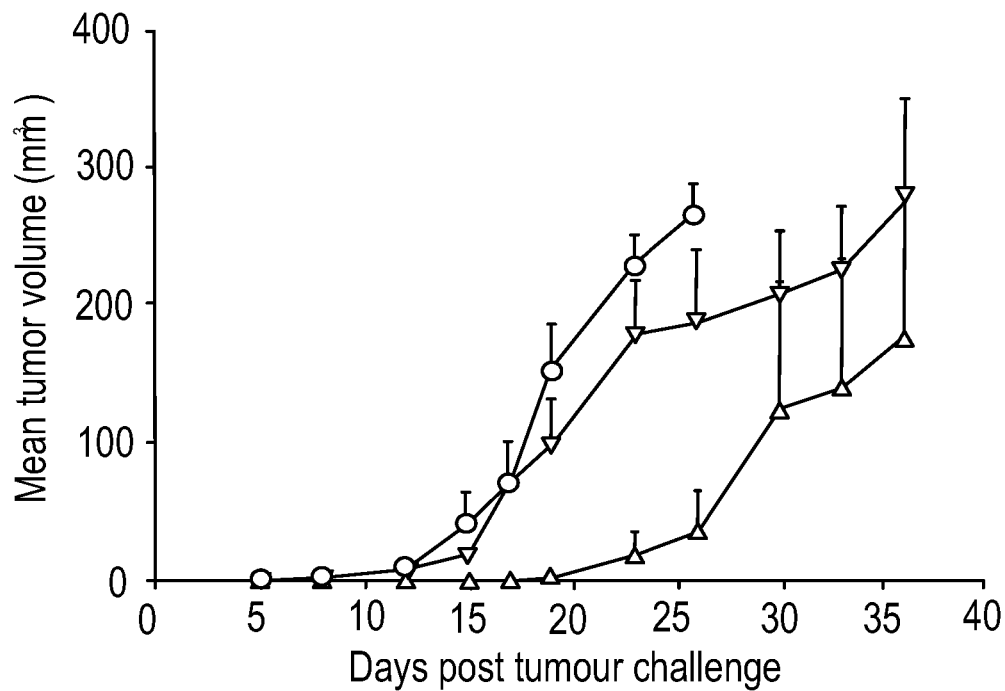
FIG. 6A shows the mean 15V4T3 tumour growth over time following prime-boost vaccination of ChAdOx1-liP1A/MVA-P1A, or immunization with the cell line L1210.P1A.B7.1 of mice as noted in FIG. 3 versus a phosphate buffered saline (PBS) control.
Figure 6B:
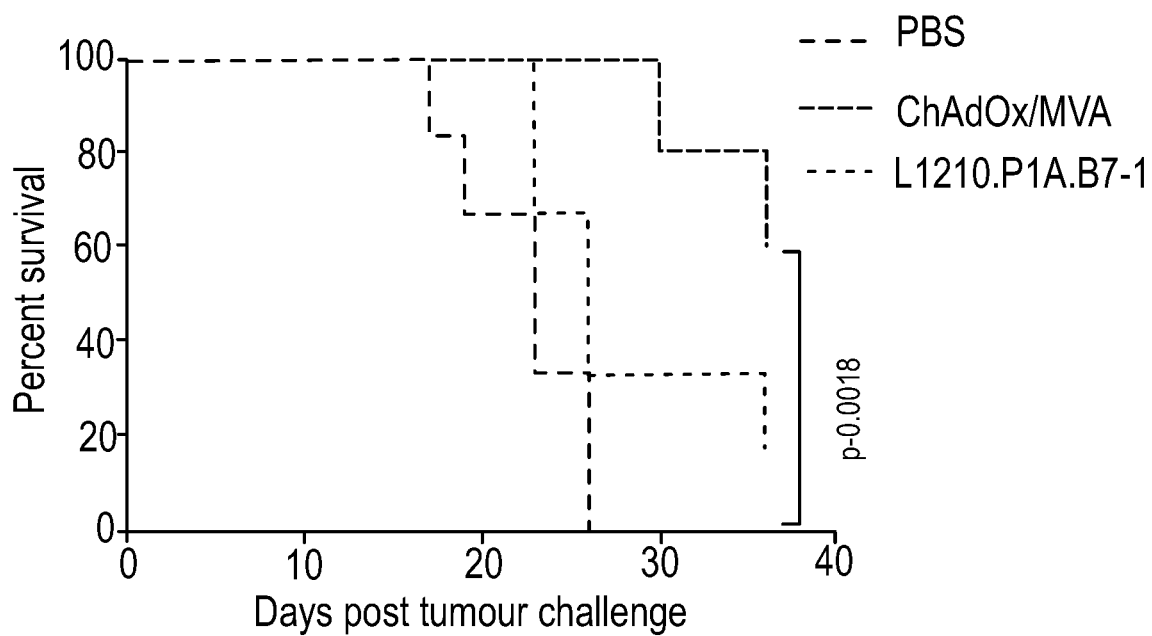
FIG. 6B shows Kaplan-Meier survival curves for the vaccinated mice noted in FIG. 6A.

As shown in FIGS. 4 and 5, adenovirus prime and MVA boost vaccination with P1A significantly reduced the tumour growth and improved survival in vaccinated mice compared to the PBS control group. Interestingly, the group vaccinated with li_P1A had smaller tumour volume and a better survival compared to the positive control group that was immunised with L1210.P1A B7.1 cells. This cell line has previously been shown to induce very strong P1A-specific cytotoxic activity and protection against P1A positive tumour challenge (see Brandle D. et al. (1998) Eur. J. Immunol. 28(12): 4010-4019 and Naslund T. I. et al. (2007) J. Immunol. 178(11): 6761-6769. This indicated that the stimulated immune response from vaccination is efficient in protecting the mice from P815 tumours. FIGS. 6A and 6B show the same results observed using the other P1A positive tumour cell line 15V4T3.

Overall, what was observed was a CD8 response associated with protection against tumour challenge and increased survival in different P1A-expressing tumour models P815 and 15V4T3 (also V4D6—data not shown). The prime-boost regimen gave better protection than with a positive control cellular vaccine. Also observed is how invariant chain (li)-P1A fusion appears better than P1A alone in the vectors. Where any tumours escape from the reduced growth effect with the treatment after a long period these have lost P1A expression (data not shown).

Figure 7:
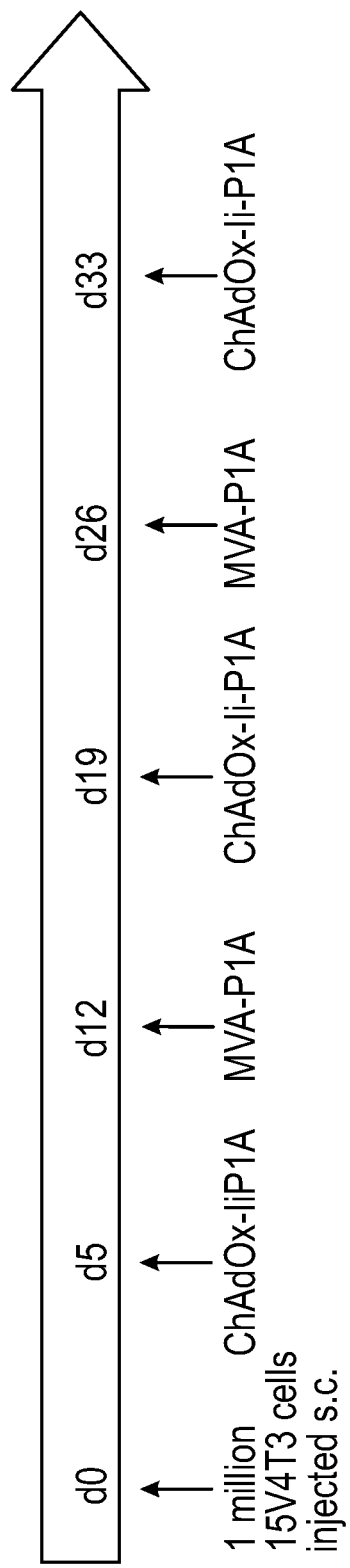
FIG. 7 shows schematically the vaccination scheme for testing the prime-boost P1A vaccine in mice in a therapeutic setting, involving rejection of established tumours.

Example 3: Assessment of Vaccine Therapeutic Efficacy of ChAdOx1 and MVA Viral Vectors Carrying P1A Experiments were performed to assess the vaccine therapeutic efficacy. Upon establishment of 15V4T3 tumours, mice were primed with ChAdOx vectors from 5 days later, and then boosted with an MVA vectors at day 26. The vaccination scheme is shown in FIG. 7. Three different vaccination schemes were tested. DBA/2 mice were challenged with 1×10$^6$ 15 V4T3 cells via subcutaneous injection in the flank and then 5 days following challenge received either a single standard dose ChAdOx-P1A (10$^8$ IU)/MVA-P1A (10$^7$ PFU) prime-boost vaccination three weeks apart, a single low dose prime-boost vaccination (ChAdOx—10$^+$ IU, MVA—10$^6$ PFU) three weeks apart, weekly alternating low dose ChAdOx-P1A/MVA-P1A vaccinations or weekly ChAdOx/MVA vaccinations encoding a control antigen, DPY. 15V4T3 tumour growth and survival in each treatment group were then monitored.

Figure 8A:
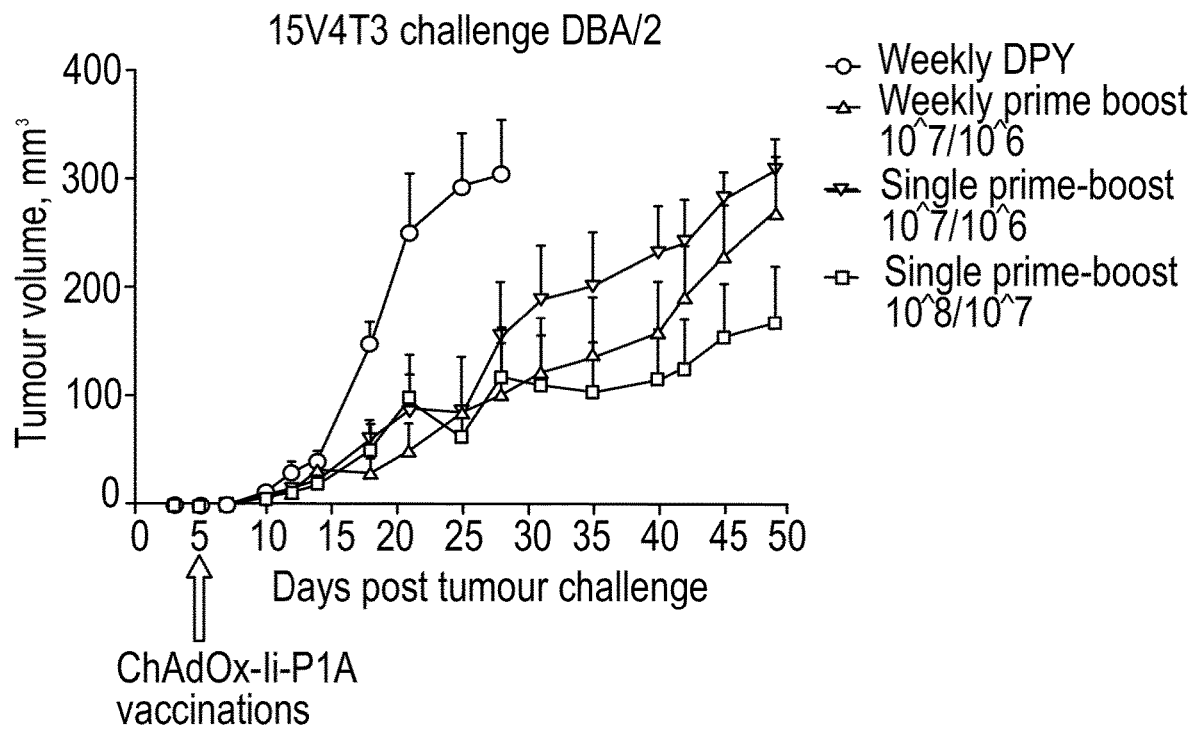
FIG. 8A shows the tumour volume growth over time post-vaccination with different ChAdOx1-P1A/MVA-P1A prime-boost vaccination regimes in DBA/2 mice in a therapeutic setting against challenge with the P1A-expressing syngeneic cancer line 15V4T3.
Figure 8B:
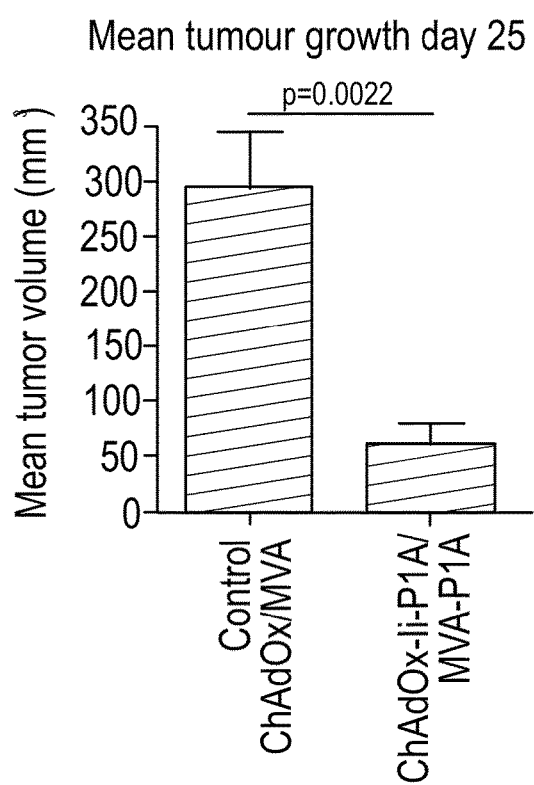
FIG. 8B shows mean tumour growth by day 25 following the prime boost vaccination scheme (single prime-boost, high dose ($10^8$ ChadOx/$10^7$ MVA).
Figure 8C:
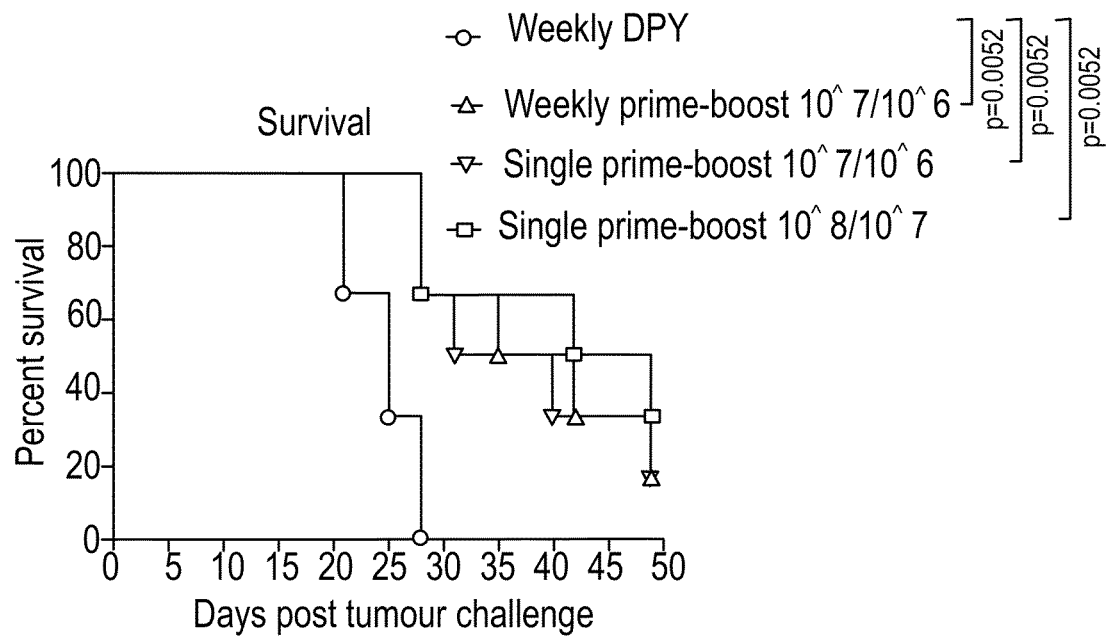
FIG. 8C shows Kaplan-Meier survival curves for the vaccinated mice noted in FIG. 8.
Figure 9:
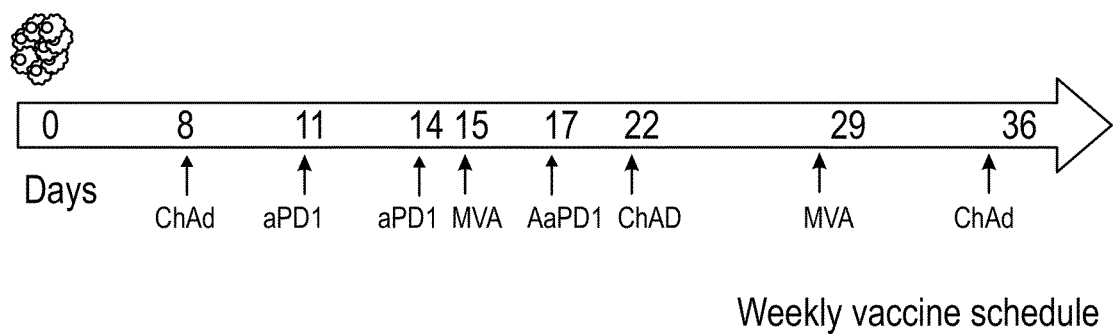
FIG. 9 shows the vaccination scheme used in the experiment to show the effect of combining the prime-boost vaccination of ChAdOx1-liP1A/MVA-P1A with an anti-PD1 checkpoint inhibitor treatment in a therapeutic setting in mice.

As shown in FIG. 8 tumour growth was remarkably delayed in vaccinated mice compared to the control group vaccinated with viral vectors expressing an irrelevant protein DPY. Moreover, the single standard dose prime-boost demonstrated the best protection and survival against the tumour challenge. However, the vaccinated mice started to lose their ability to control tumour outgrowth at the later stage (week 6).

Therapeutic efficacy was therefore observed in the 15V4T3 model.

Figure 10:
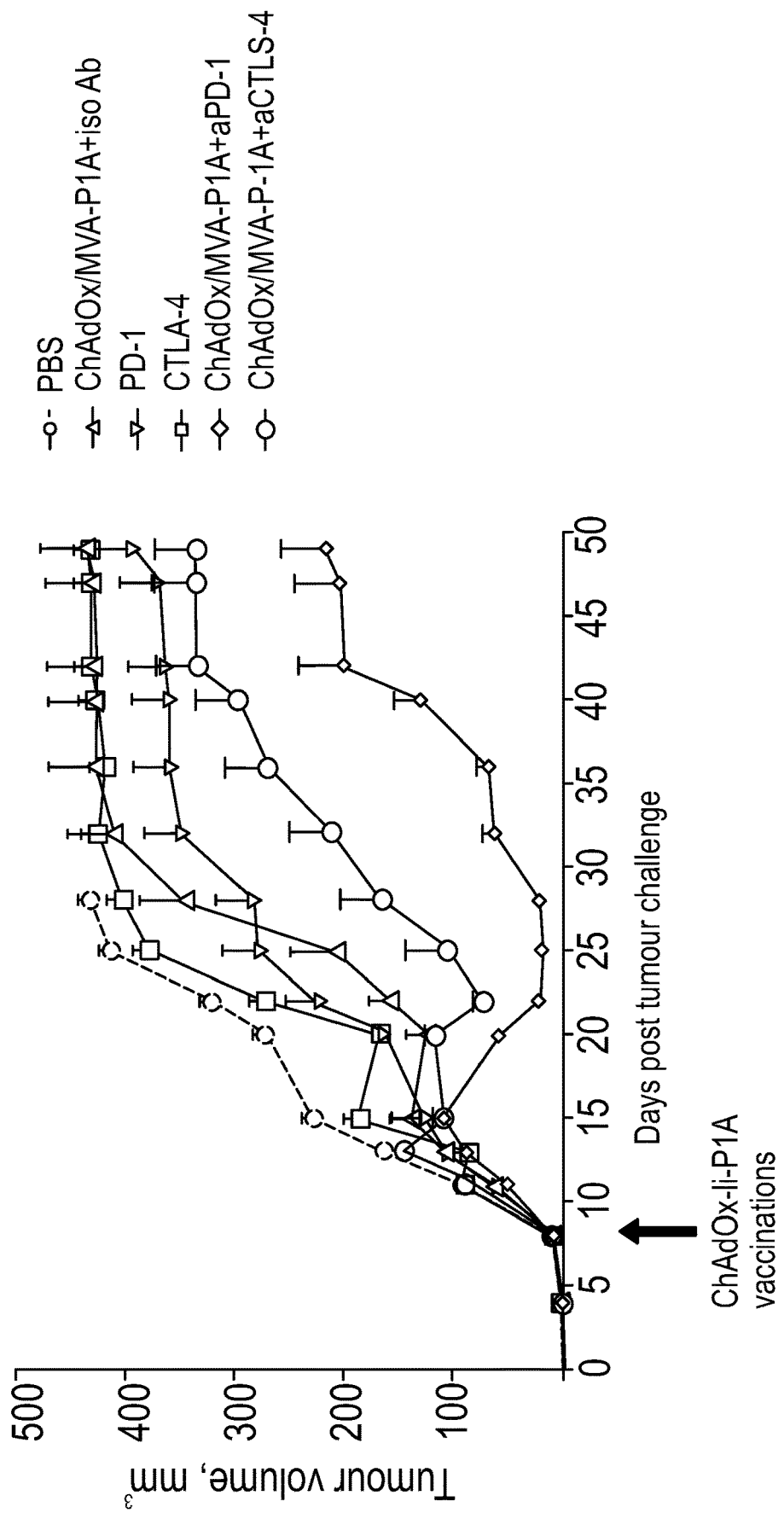
FIG. 10 shows tumour volume growth over time for ChAdOx1-liP1A/MVA-P1A prime-boost vaccination regime in combination with immune checkpoint inhibitors, in DBA/2 mice against challenge with the P1A-expressing syngeneic cancer line 15V4T3.
Figure 11:
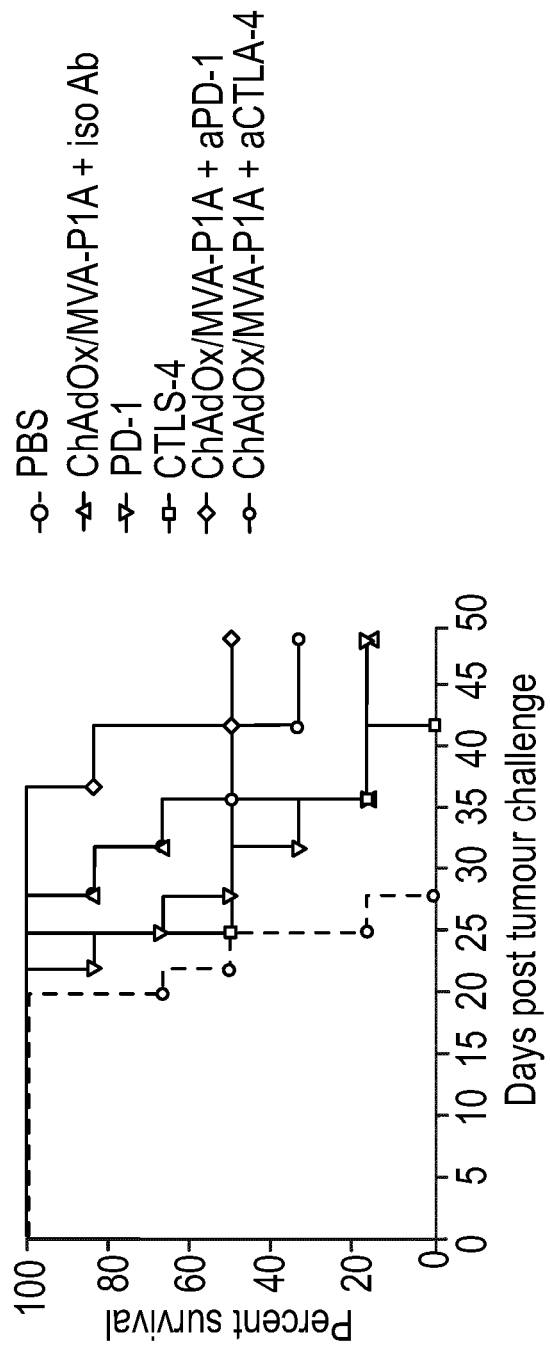
FIG. 11 shows Kaplan-Meier survival curves for the vaccinated mice in FIG. 10.

Example 4: Assessing the Therapeutic Efficacy of ChAdOx1-P1A/MVA-P1A Prime-Boost Vaccination Regime in Combination with Immune Checkpoint Inhibitors To achieve a better tumour protection and increase the vaccine efficacy, vaccines were combined with checkpoint inhibitor blocking, using the same 15V4T3 tumour model, DBA/2 mice were inoculated with P1A-expressing syngeneic 15V4T3 tumour cells. DBA/2 mice were challenged with 1×10⁶ 15 V4T3 cells via subcutaneous injection in the flank and then randomized into different treatment groups on day 8 post challenge based on tumour size. Mice received either PBS (sham) vaccinations, weekly ChAdOx/MVA vaccinations—alone or in combination with either anti-PD1 or anti-CTLA-4 antibodies (3 doses 3 days apart), or anti-PD1 or anti-CTLA-4 antibodies alone. 15V4T3 tumour growth (FIG. 10) and survival (FIG. 11) in each treatment group were monitored and recorded throughout the duration. After establishment of a palpable tumours, tumour size was measured and the mice randomized into different groups. As shown in FIG. 10 (left hand graph), the tumour growth of mice receiving the combination therapy was much delayed compared to mice in the control and single therapy groups. Also, 100% of mice receiving the combination therapy of anti-PD1 and the vaccines survived up until day 36 after tumour challenge, and 50% of mice survived in the group of anti-CTLA4 and vaccine treatment, while the other mice all had poor survival.

A synergistic effect of the vaccine+anti-PD1 was observed in the therapeutic setting of the 15V4T3 model.

Example 5: Assessing Immunogenicity of MAGE-A3 and NY-ESO-1 in CD1 Outbred Mice

Figure 12:
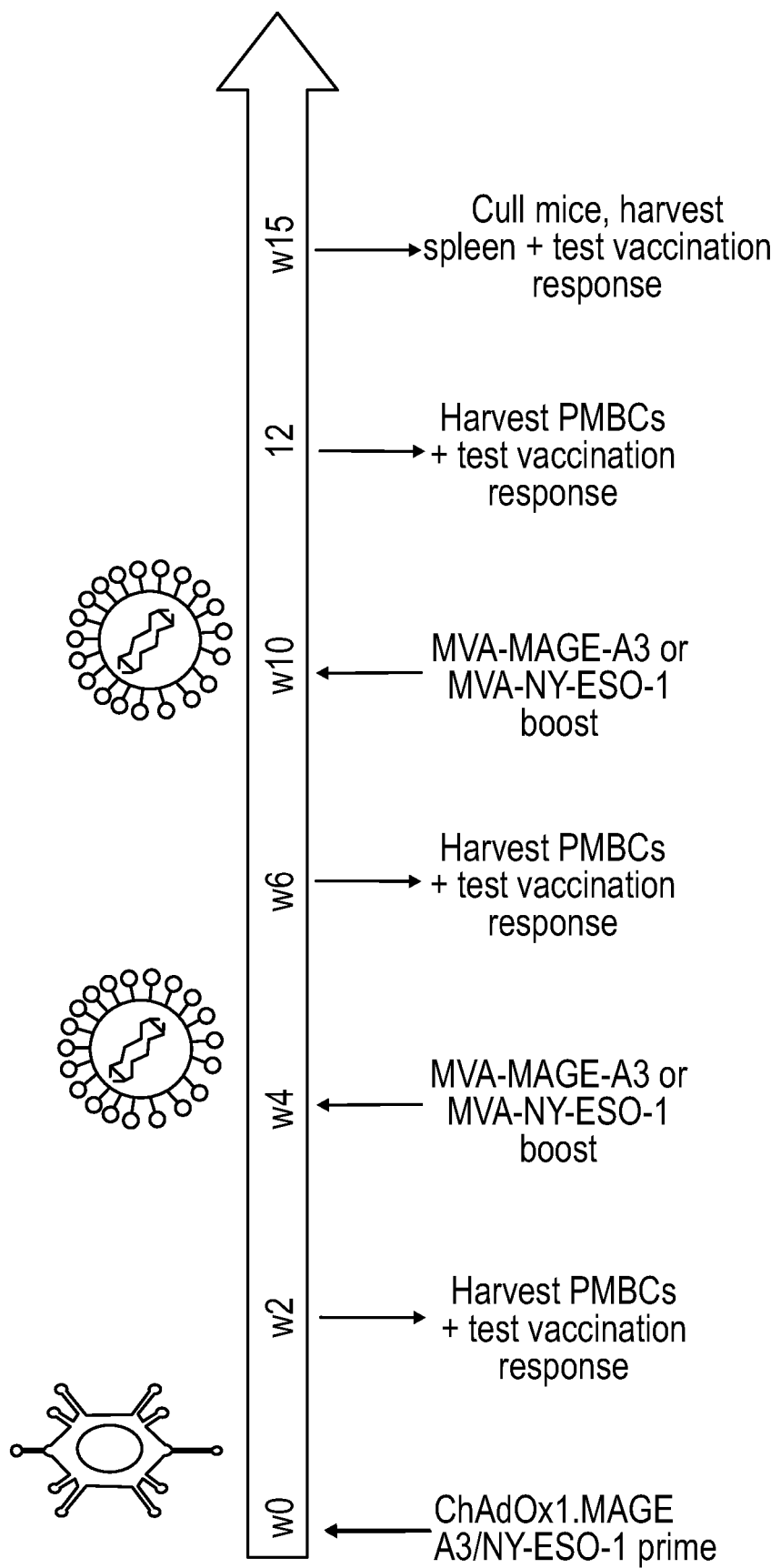
FIG. 12 shows a schematic outline for an experiment where outbred CD1 mice are vaccinated with viral vectors encoding MAGE-A3 (M) and NY-ESO-1 (NY) proteins and then the CD8$^+$ T cell responses are determined.

Having established the response from vectors encoding the mouse P1A gene, vector constructs encoding the human MAGE-type antigens were produced and tested. The immunogenicity of the different forms of the human MAGE-type antigens, MAGE-A3 and NY-ESO-1 was examined in CD1 outbred mice. MAGE-A3 and NY-ESO-1 were cloned in the Chimpanzee adenovirus vector as a fusion protein, while they were cloned in MVA individually. This is due to two main reasons. Firstly, production of adenoviral vectored vaccine is more expensive than MVA. In order to prepare for clinical setting, the aim was to minimise the cost to just include one single adenoviral vectored vaccine expressing the fusion of MAGE-A3 and NY-ESO-1. Secondly, some human tumours express either MAGE-A3 or NY-ESO-1. In order to induce a more specific response against the tumours, the particular antigen that is expressed by the tumours is targeted for boosting. In more detail, mice were vaccinated according to timeline (FIG. 12)—prime with ChAdOx1 encoding MAGE-A3-NY-ESO-1±li or tPA, followed by two boosts with MVA encoding either MAGE-A3 or NY-ESO-1, ±tPA (second MVA boost containing alternate antigen to first MVA boost). Antigen specific T-cell responses were assessed after each vaccination at the indicated time points—PBMCs were harvested and stimulated ex vivo with MAGE-A3 (blue circles) or NY-ESO-1 (red squares) peptides and the percentage of IFN-γ⁺ responding cells analysed by flow cytometry.

Figure 13:
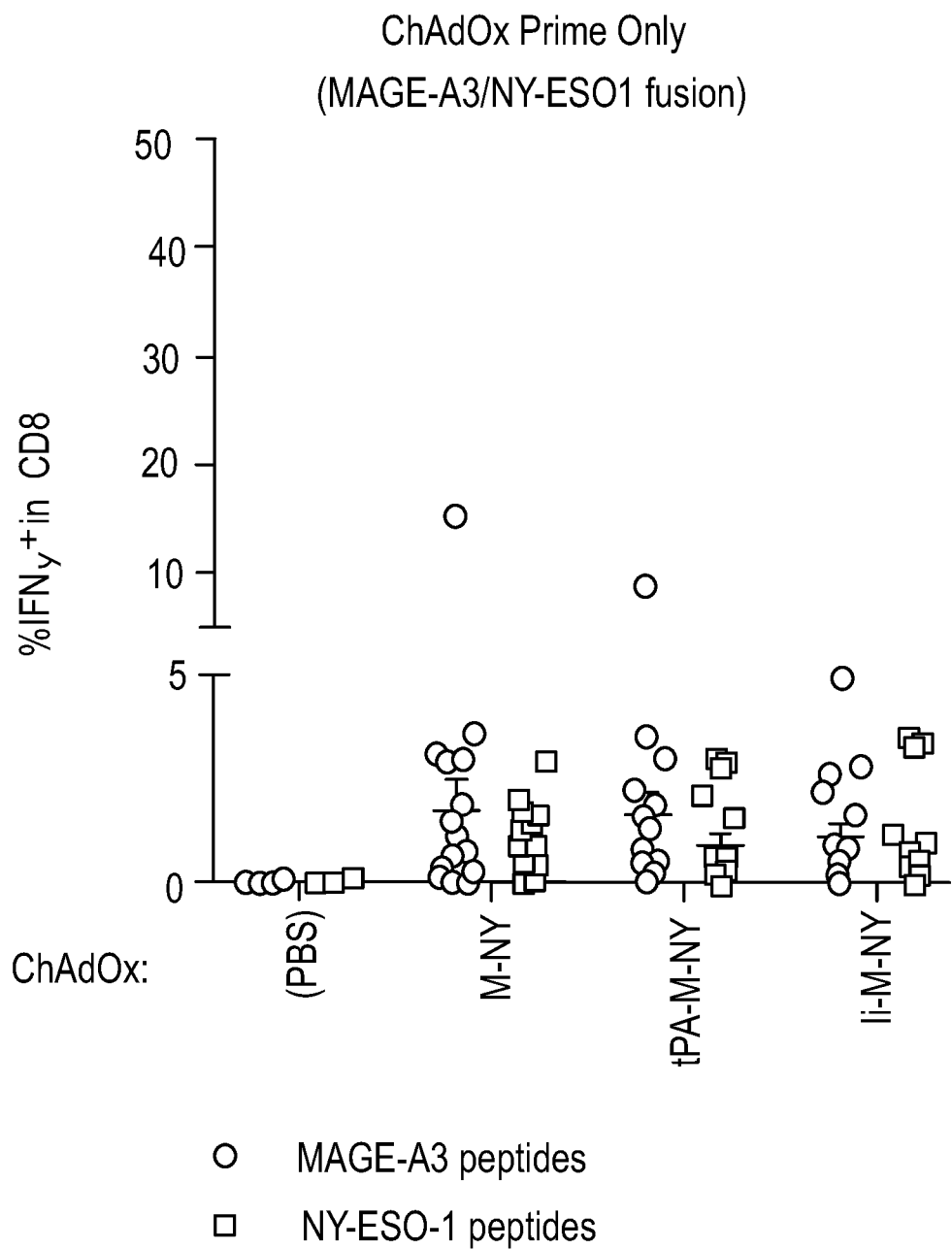
FIG. 13 shows induction of CD8 T cells (as measured by IFN$\gamma$ production) as a result of immunization of outbred CD1 mice with ChAdOx-MAGEA3/NY-ESO-1 fusion, with and without invariant chain li or tPA. Isolated PBMCs following immunization were stimulated ex vivo with overlapping MAGEA3 or overlapping NY-ESO-1 peptides.

FIG. 13 shows the induction of CD8 T cells against MAGE-A3/NY-ESO-1 following priming injection of outbred CD1 mice with ChAdOx1-MAGE-A3/NY-ESO-1 fusion (M-NY), ChAdOx1-MAGE-A3/NY-ESO-1 fusion with tPA (tPA-M-NY) and ChAdOx1-MAGE-A3/NY-ESO-1 fusion with invariant chain (li-M-NY). Two weeks later, PBMCs were isolated, and the response to MAGE-A3 overlapping peptides (red circles) and NY-ESO-1 overlapping peptides (blue squares) tested by ex vivo intracellular cytokine staining. The CD8 IFNγ responses following prime shows that a ChAdOx prime containing a fusion protein can elicit specific CD8 T cells to both antigens.

Figure 14:
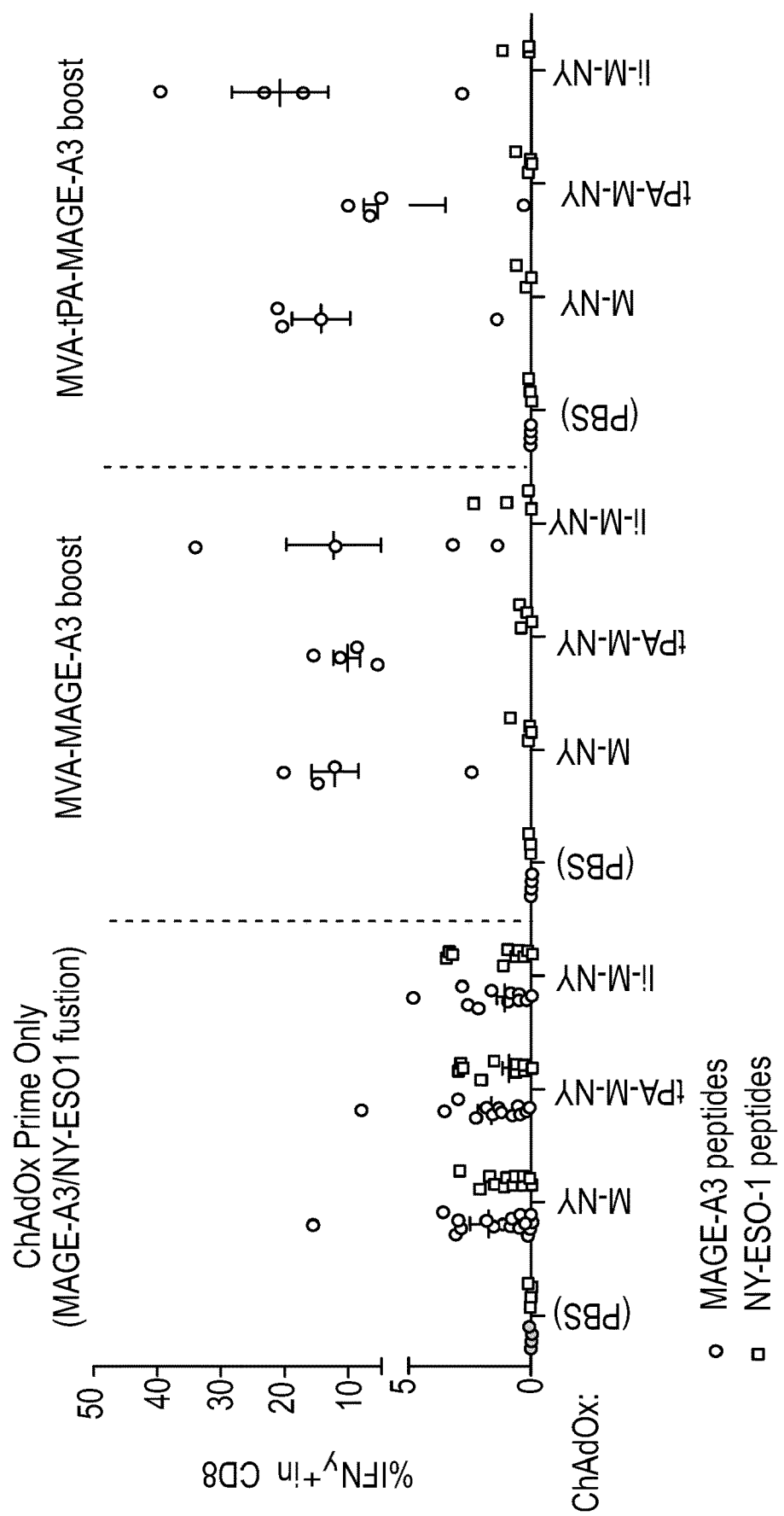
FIG. 14 shows the same as in FIG. 13 plus the results of immunisation with a boost of MVA-MAGEA3 with or without tPA.
Figure 15:
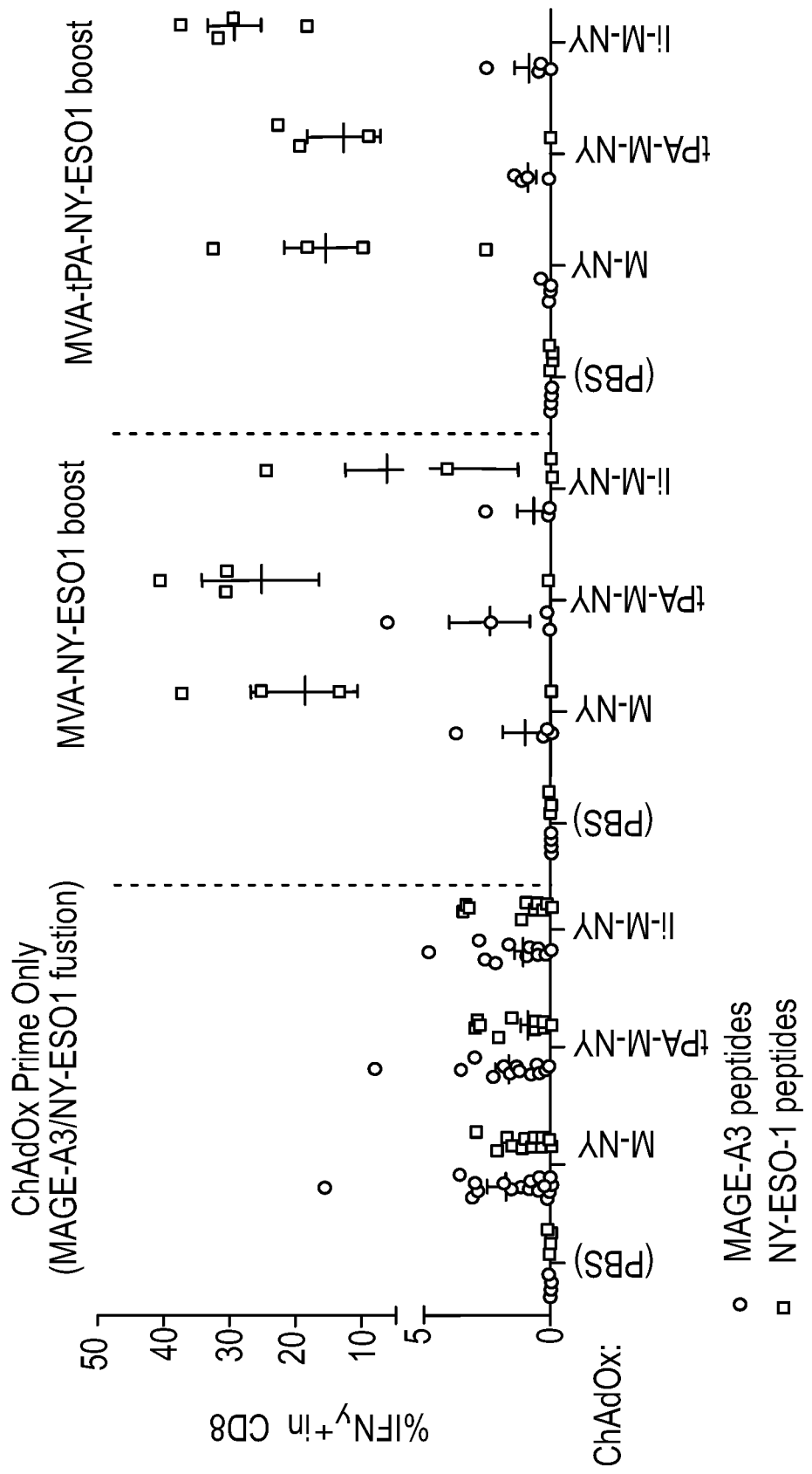
FIG. 15 shows the same as in FIG. 13 plus the results of immunisation with a boost of MVA-NY-ESO-1 with or without tPA.

Then, the ChAdOx primed mice were given booster injections with (i) MVA containing MAGEA3 with or without fusion to tPA; and (ii) MVA containing NY-ESO-1 with or without fusion to tPA. PBMCs were then again isolated from these mice and tested for MAGEA3 and NY-ESO-1 responses using ex vivo intracellular cytokine staining after stimulation with overlapping peptides. FIG. 14 shows the effect of the MVA-MAGEA3±tPA boost, and FIG. 15 shows the effect of the MVA-NY-ESO-1±tPA boost. In each of FIGS. 14 and 15, FIG. 13 is included as the left hand portion for convenient comparison of the boost results with the result of prime only. As can be seen, the initial prime responses are boosted to a much higher magnitude against either antigen of choice using MVA.

The ChAdOx-invariant chain (li) as prime and MVA-tPA appears to be the most immunogenic regime, subject to sample sizes and the use of outbred mice which have some degree of variability.

In a dual boost, initial prime responses were increased to a higher magnitude simultaneously (data not shown). The observed responses are broadly matched by other type I cytokines (data not shown).

Given how frequencies of antigen-specific T-cells appear to be boosted to much higher levels and the response directed against an antigen of choice, the invention may allow for a more personalised approach to prevention or treatment following the particular expression pattern of the individual tumour in question.

Figure 16:
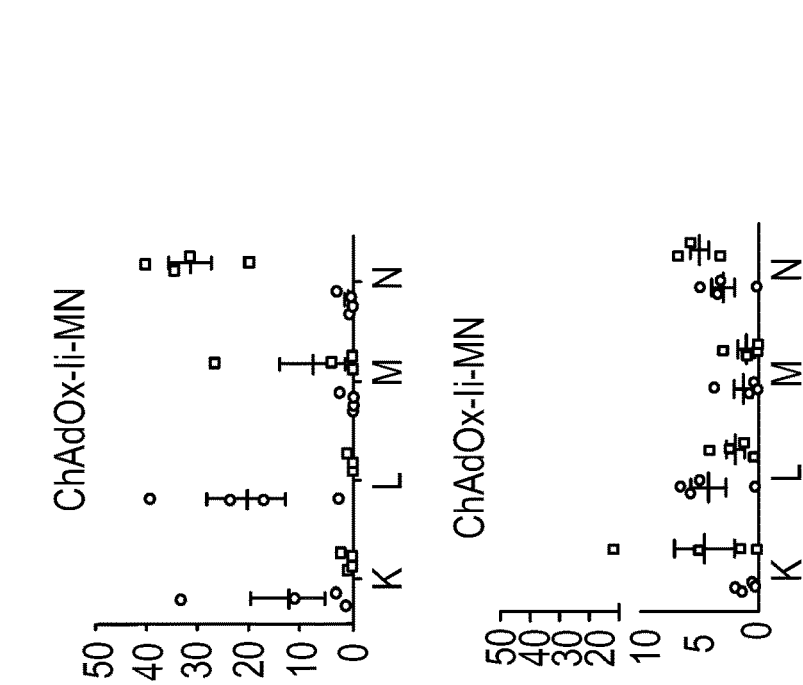
FIG. 16A shows the MAGE-A3 and NYESO specific responses in PBMCs after prime with ChAdOx-M-NY, ChAdOx-tPA-M-NY or ChAdOx-li-M-NY, and boost with MVA-M, MVA-NY MVA-tPA-M, or MVA-tPA-NY vectors.
FIG. 16B shows the MAGE-A3 and NYESO specific responses in PBMCs after second boost with either MVA-M, MVA-NY MVA-tPA-M, or MVA-tPA-NY vectors.
Figure 16:
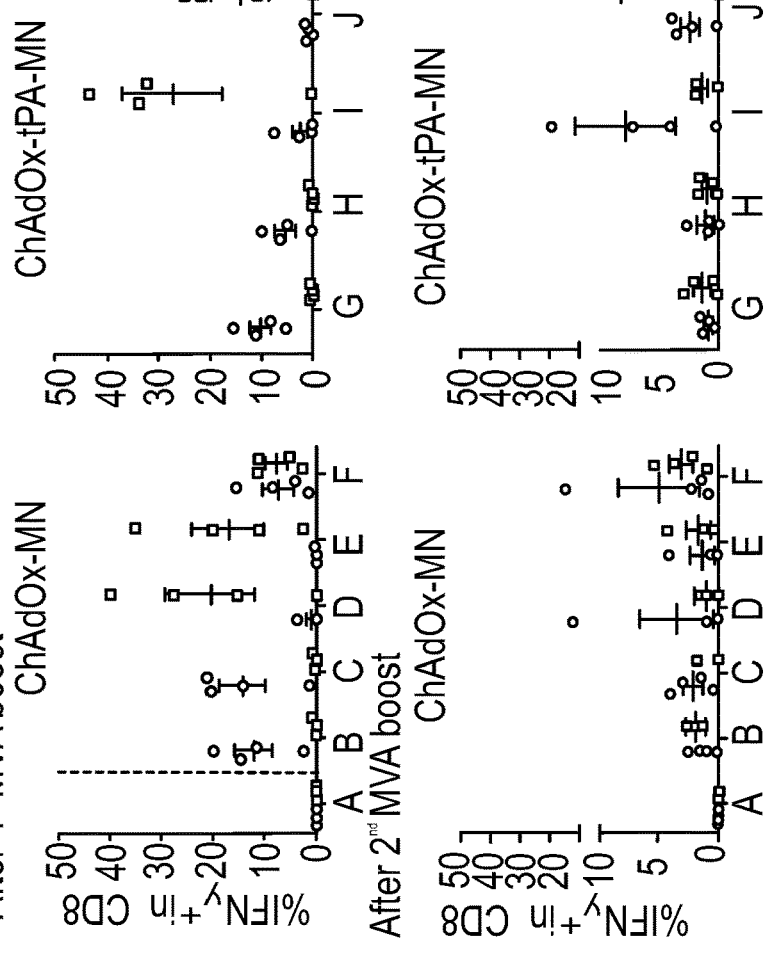
Figure 17A:
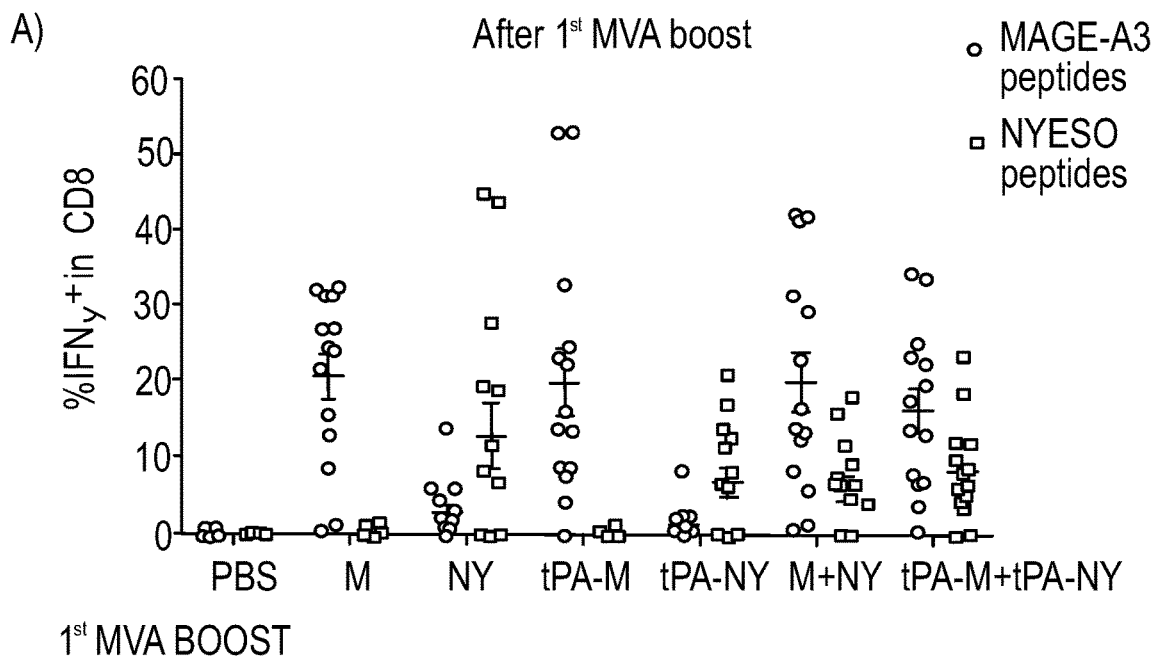
FIG. 17A shows induction of CD8 T cell responses against MAGE-A3 and NYESO in outbred CD1 mice after the immunization with ChAdOx-li-MAGEA3/NY-ESO-1 fusion, and boost with MVA-M, MVA-NY, MVA-tPA-M, or MVA-tPA-NY vectors.
Figure 17B:
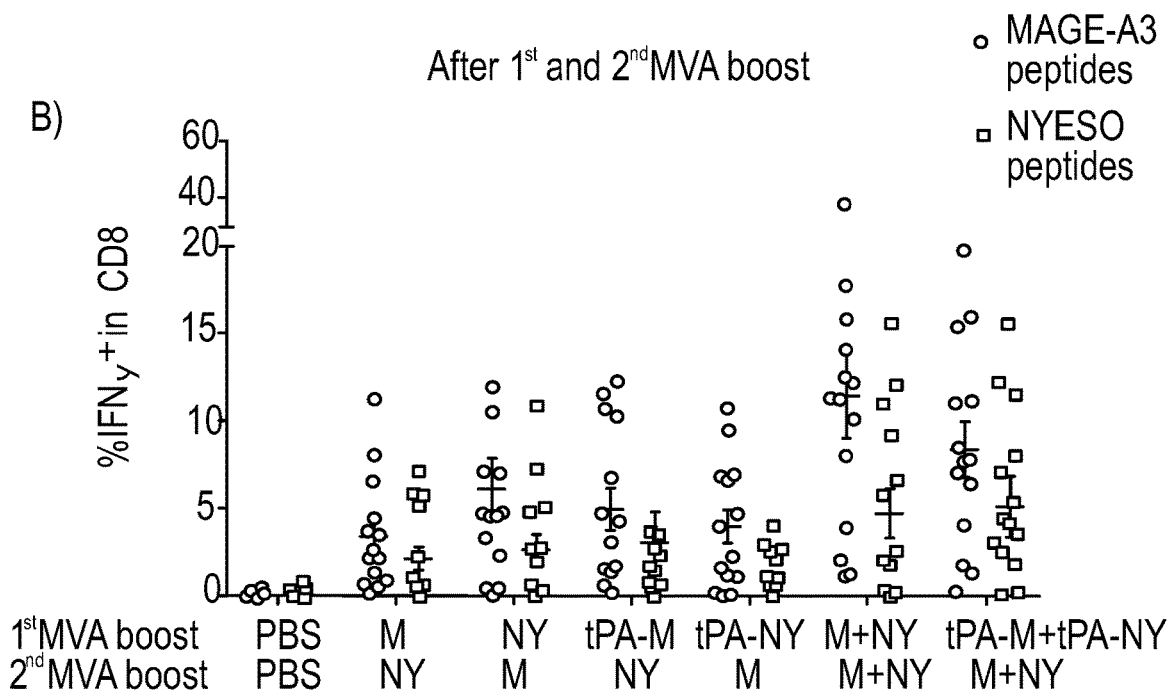
FIG. 17B shows the MAGE-A3 and NYESO-specific responses after second boost with MVA-M, MVA-NY, MVA-tPA-M, or MVA-tPA-NY vectors.

FIG. 16A shows the percentage of IFN-γ⁺ cells in CD8⁺ cells after boost with MVA-M, MVA-NY, MVA-tPA-M, or MVA-tPA-NY vectors. FIG. 16B shows the percentage of IFN-γ⁺ cells in CD8⁺ cells after second boost with either MVA-M, MVA-NY, MVA-tPA-M, or MVA-tPA-NY vectors.

When mice were primed with adenovirus expressing fusion MAGE-A3 and NY-ESO-1, and boosted with MVA either expressing MAGE-A3 or NY-ESO-1, the increased CD8 response was directed against the antigen expressed by the MVA (FIGS. 14 and 15). Also, boosting the mice with both MVAs (MVA_MAGEA3 and MVA_NYESO) induced similar levels of CD8 responses against these two antigens.

The immunogenicity of an antigen can be enhanced by fusing the gene to some molecular adjuvants as described in Bolhassani A. et al. (2011) Mol. Cancer. 10:3. Among these, the human tissue plasmogen activator (tPA) signal peptide (see Delogu G. et al. (2002) Infect. Immun. 70(1): 292-302) may increase protein expression within infected cells, thus enhance the T cell responses (e.g. Biswas S. et al. (2011) PLoS One 6(6): e20977. Also, fusing antigens to the MHC II associated li can strengthen CD8 response (Mikkelsen M. et al. (2011) Journal of Immunology 186(4): 2355-2364; and Sorensen M. R. et al. (2009) European Journal of Immunology 39(10): 2725-2736.

In summary from the various examples above, the CD8 response to P1A is enhanced when fusing the antigen to li (FIG. 2). Also shown is how the better stimulated CD8 response translated to a better tumour protection in mice (FIGS. 4 and 5). The effect of tPA fusion had not hitherto been studied in viral vectored vaccines. The examples show that unlike li, tPA fusion to MAGE antigens could not enhance CD8⁺ T cell response in a single vaccination with adenovirus. Also, an increase in CD8 response was observed when mice were primed with adenovirus expressing antigens fused to li, and boosted with MVA encoding antigens fused to tPA, in single prime boost vaccination (see FIGS. 16A and 16B). However, further analysis shows that tPA fusion to the MAGE antigens in the MVA boost could not enhance the CD8 responses.

Figure 18:
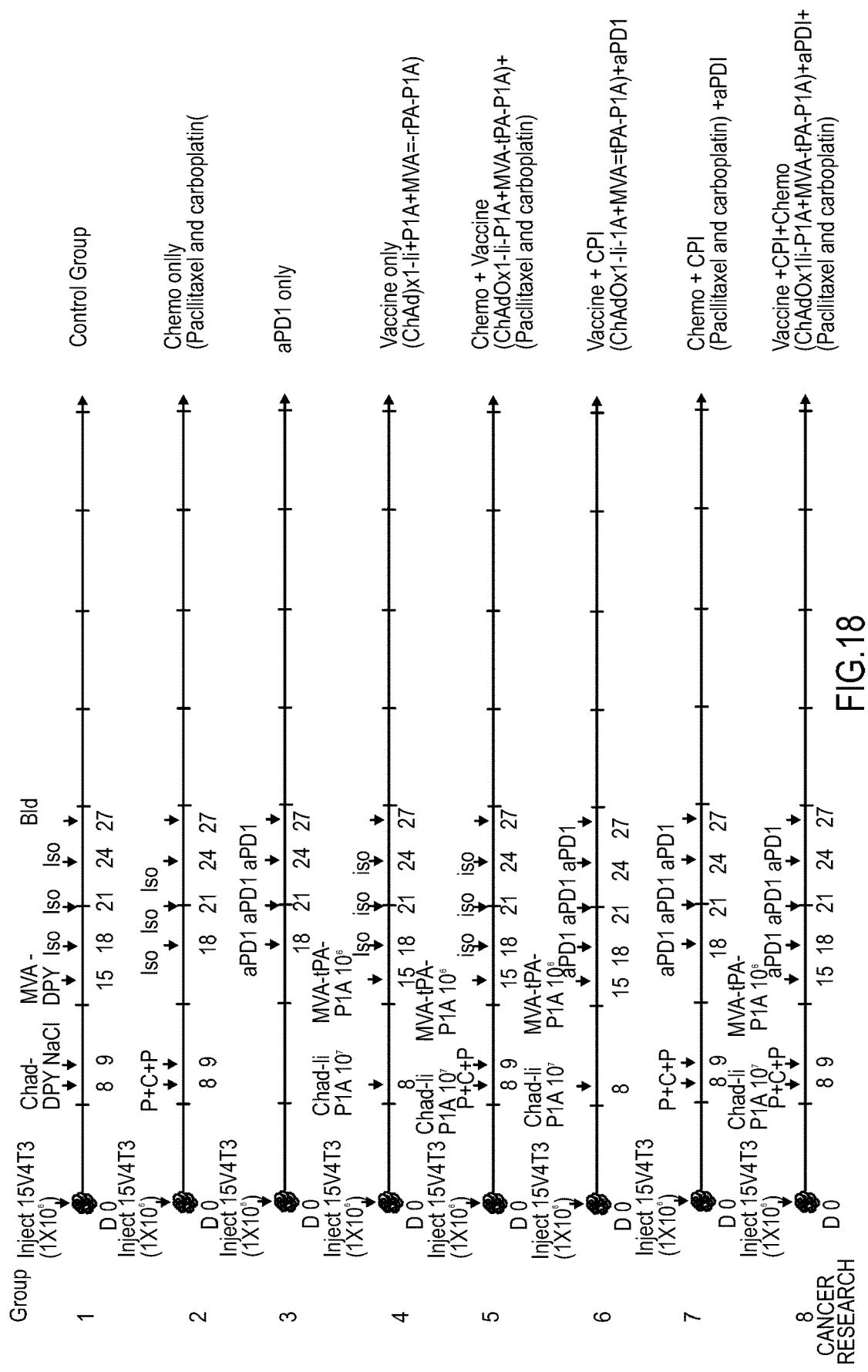
FIG. 18 shows the time lines of 15V4T3 cell injections into mice and subsequent treatment points in each of 8 experimental groups of mice.

Example 6: Triple Combination of Vaccine, Checkpoint Inhibitor and Chemotherapy in Effect on 15V4T3 Tumour in DBA/2 Mice FIG. 18 shows the experimental chronologies for vaccination of test mice together with chemotherapy and checkpoint inhibitor treatment, as well as associated control treatments. Briefly, 1 million 15V4T3 cells were injected subcutaneously into each of DBA/2 mice. The mice were randomly divided into groups based on tumour size on day 6. Treatments including any vaccinations of mice were begun on day 8 after tumour implantation. Where administered, 20 mg/kg paclitaxel and 40 mg/kg of carboplatin were given to the mice on day 8 by I.P, and 20 mg/kg of paclitaxel was given on day 9 by I.P. Where administered, 3 doses of 100 μg of αPD1 were given on days 18, 21 and 24 by I.P. The number of mice per group was 6 or 7 or 8.

Figure 19:
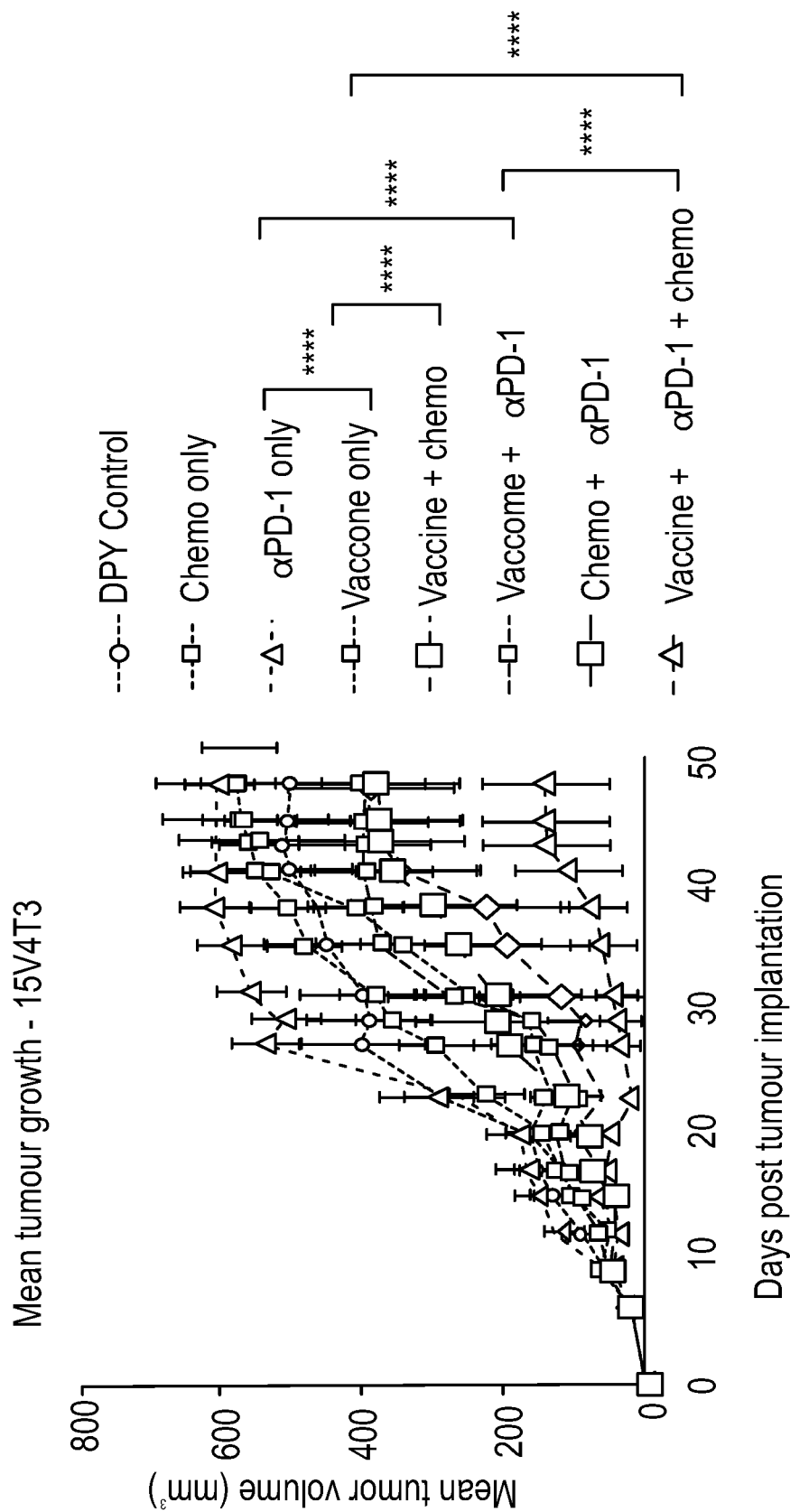
FIG. 19 shows a graph of the mean tumour growth results of the experiments shown in FIG. 18. Results are analysed by 2-way ANOVA. $*=p<0.05$. $=p<0.01$. $*=p<0.001$. $****=p<0.0001$.

FIG. 19 shows time courses of mean tumour volume in the mice for each of the experimental and control treatments.

Figure 20:
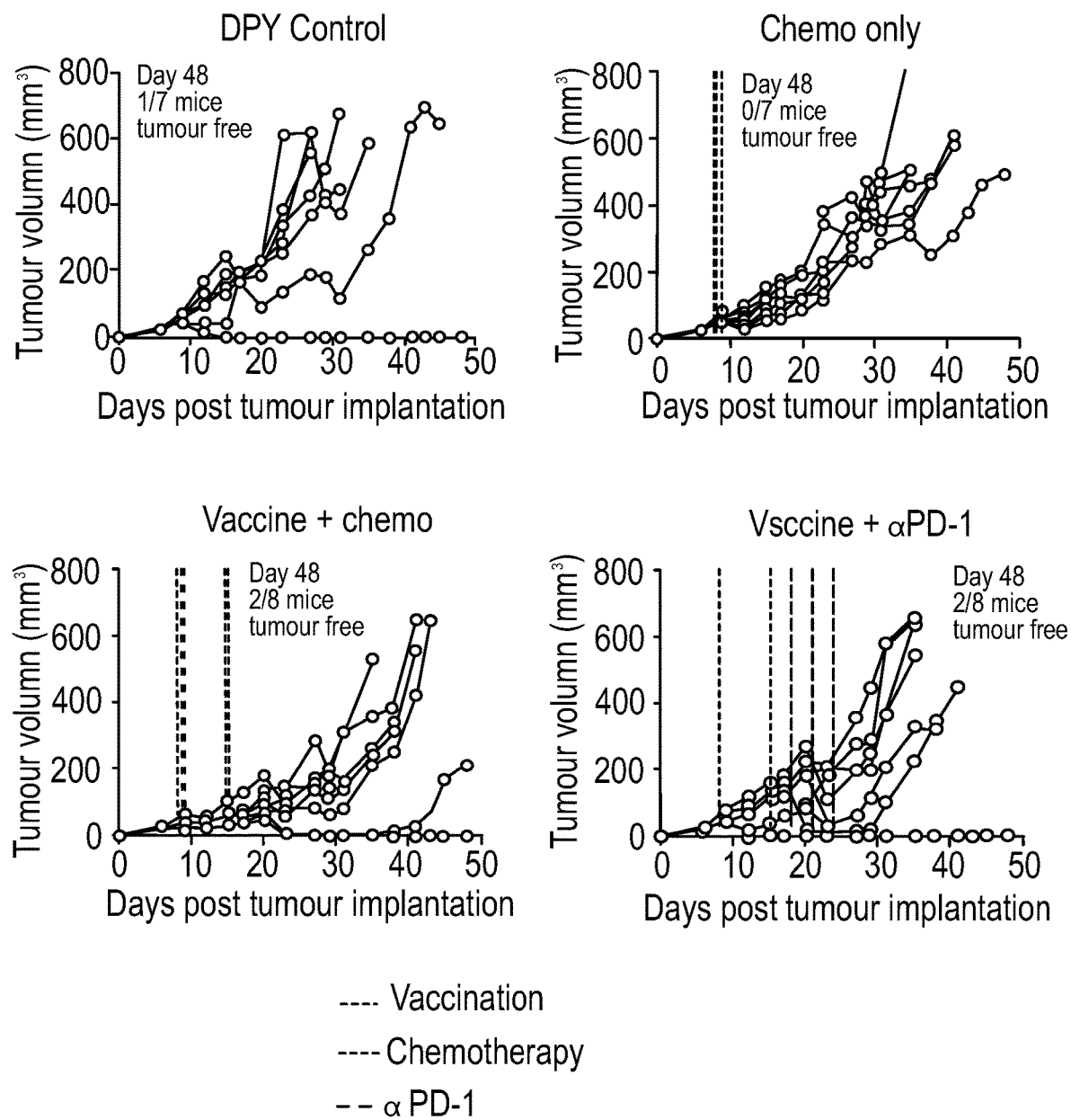
FIG. 20 shows graphs of tumour volume over time of tumour post-implantation, for each of the 8 experimental groups of mice.

FIG. 20 shows time courses for the tumour volumes of individual mice in each experimental group or control group. The times of treatment, whether vaccination and/or chemotherapy and/or checkpoint inhibitor are shown. Also indicated are the 48 day end-point numbers of mice in each group which are found to be tumour free. The triple combination of vaccination, chemotherapy and checkpoint inhibitor clearly inhibits the formation of tumours the most effectively of the various treatments.

Figure 21:
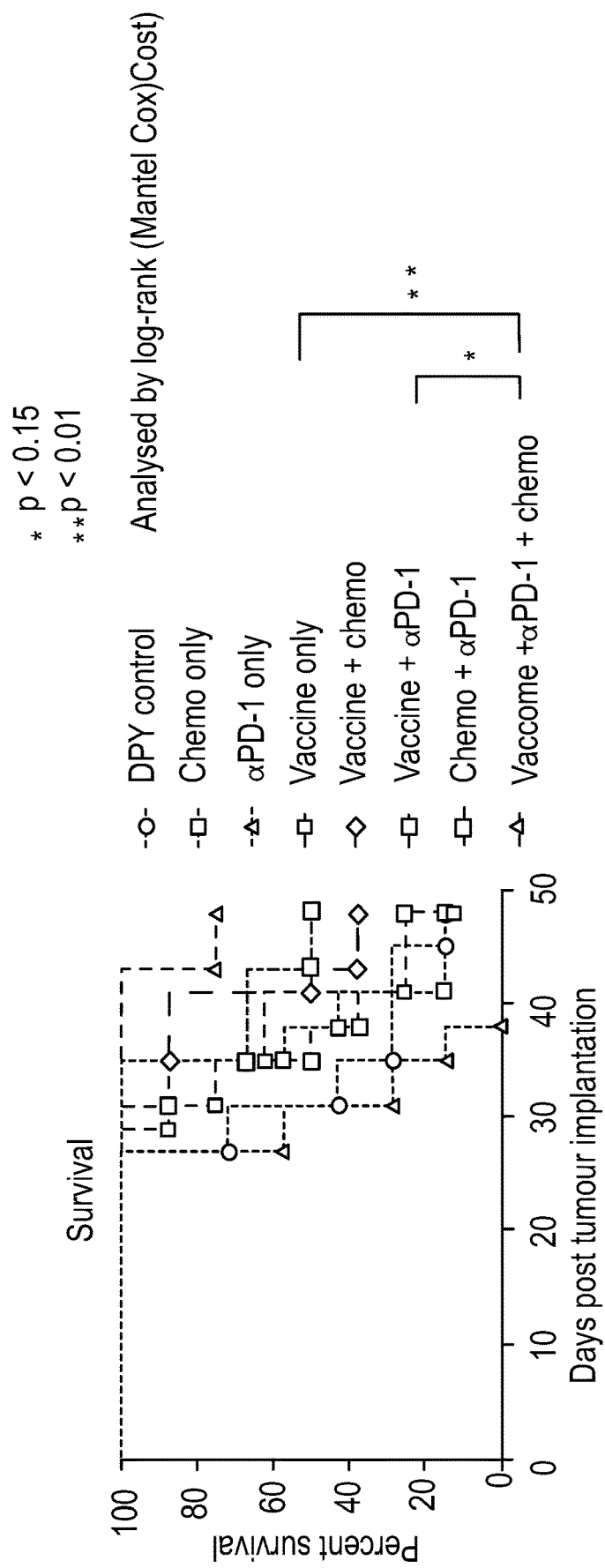
FIG. 21 shows Kaplan Meier survival plots for each of the 8 experimental groups of mice. Data was analysed by log-rank (Mantel-Cox) test. $*=p<0.05$. $**=p<0.01$.

FIG. 21 shows the survival of mice over time in each experimental and control group. The triple combination of vaccination, chemotherapy and checkpoint inhibitor clearly provides the best survival of the mice compared to the other treatments and controls.

Figure 22:
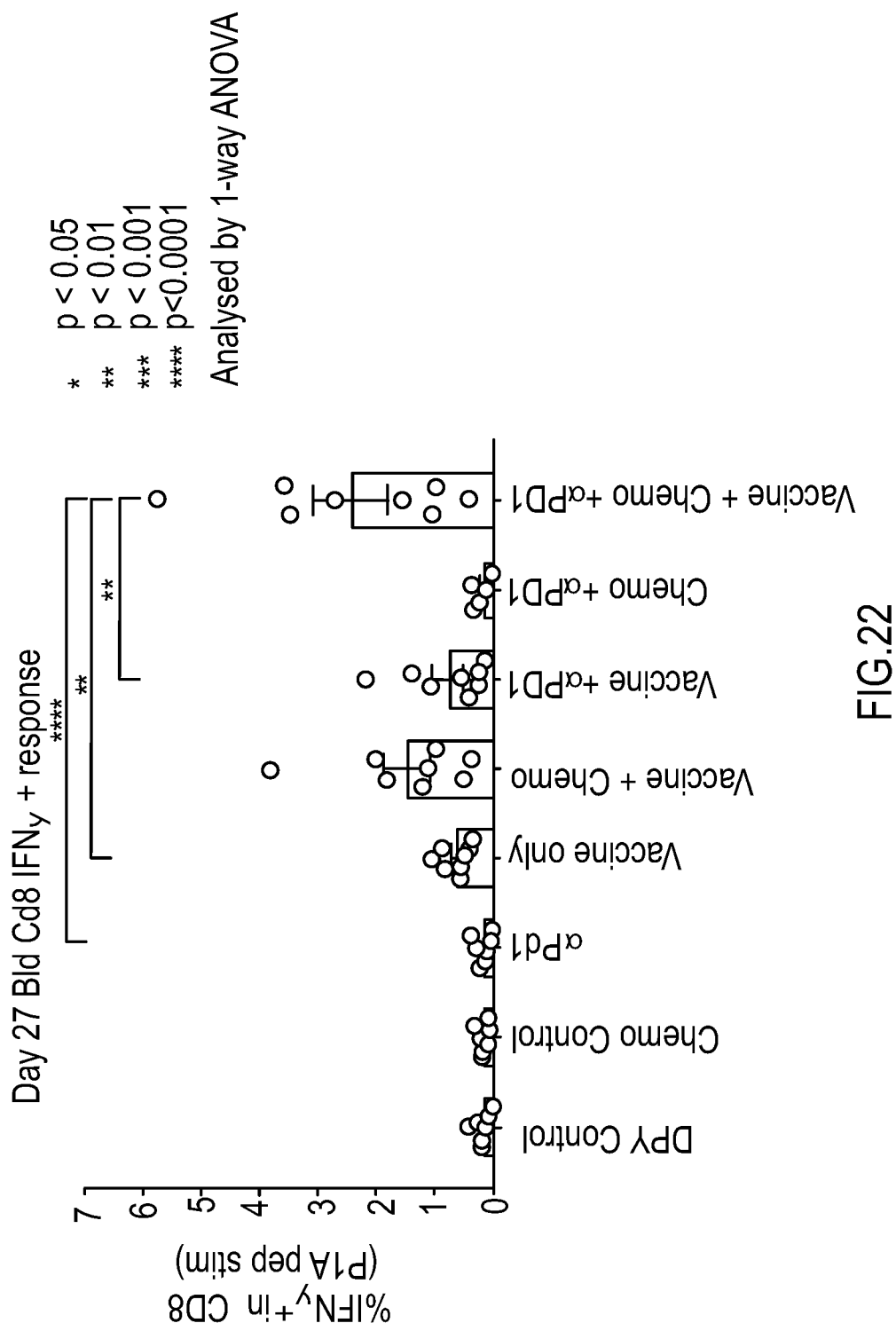
FIG. 22 is a chart showing the IFN$\gamma$ response of CD8 cells on bleed at day 27 of the 8 experimental groups of mice

The triple combination of vaccines with αPD1 and chemotherapy significantly inhibited the tumour growth compared to other groups. There were 6 out of 8 tumour-free mice on day 23 after tumour injection, and these mice remained tumour-free up till day 48. Also as shown in FIG. 22, the triple combination group also has the highest periphery P1A-specific CD8 responses on day 27 after tumour injection.

Figure 23:
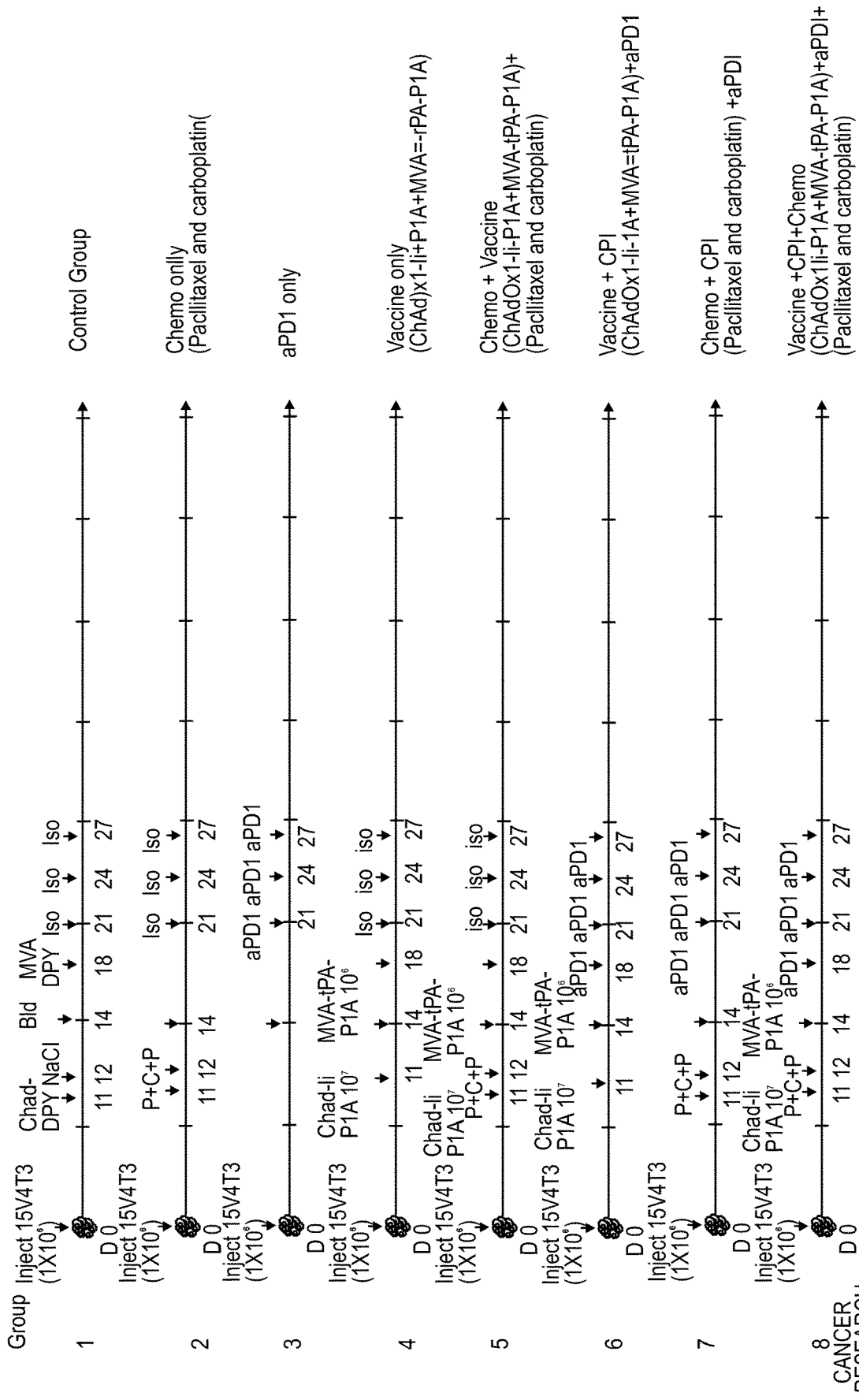
FIG. 23 shows the time lines of a repeated experiment of 15V4T3 cell injections into mice and subsequent treatment points in each of 8 experimental groups of mice.

Example 7: Triple Combination of Vaccine, Checkpoint Inhibitor and Chemotherapy in Effect on 15V4T3 Tumour in DBA/2 Mice FIG. 23 shows the time lines for each experimental group of mice and controls. 1 million 15V4T3 cells (early passage) were injected simultaneously into DBA/2 mice. Mice were randomly divided into groups based on tumour size on day 11 and vaccinations of mice begun on day 11 after tumour implantation. Where administered, 20 mg/kg paclitaxel and 40 mg/kg of carboplatin were given on day 11 by I.P, and 20 mg/kg of paclitaxel was given on day 12 by I.P. Where administered, 3 doses of 100 μg of αPD1 was given on day 21, 24 and 27 by I.P. n=6 or 7 per group. A naïve group without tumour challenge was also included in this experiment. Bleeding was carried out on day 14 and samples were used to check myeloid derived suppressor cell (MDSC) depletion.

Figure 24:
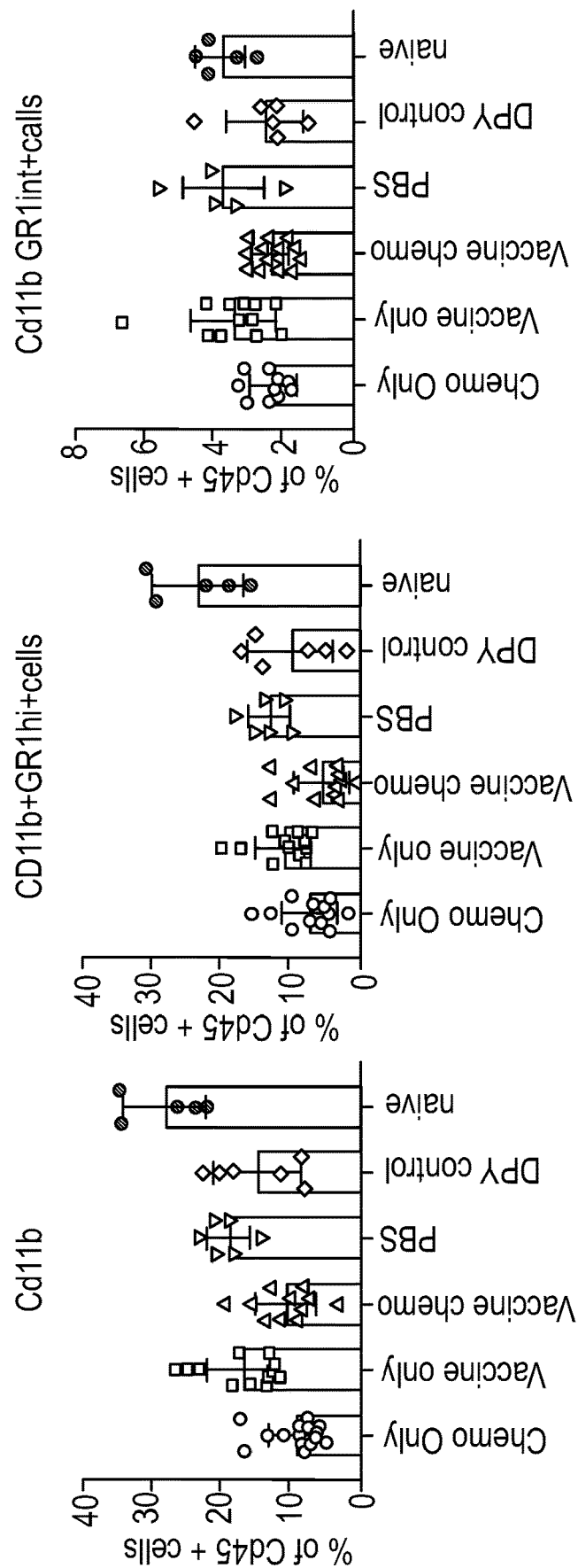
FIG. 24 shows graphs of the proportion of CD45$^+$ cells which are (a) CD11b, (b) CD11b$^+$ and GR1hi$^+$ or (c) CD11b and GR1int$^+$, for certain experimental treatments and controls.
Figure 25:
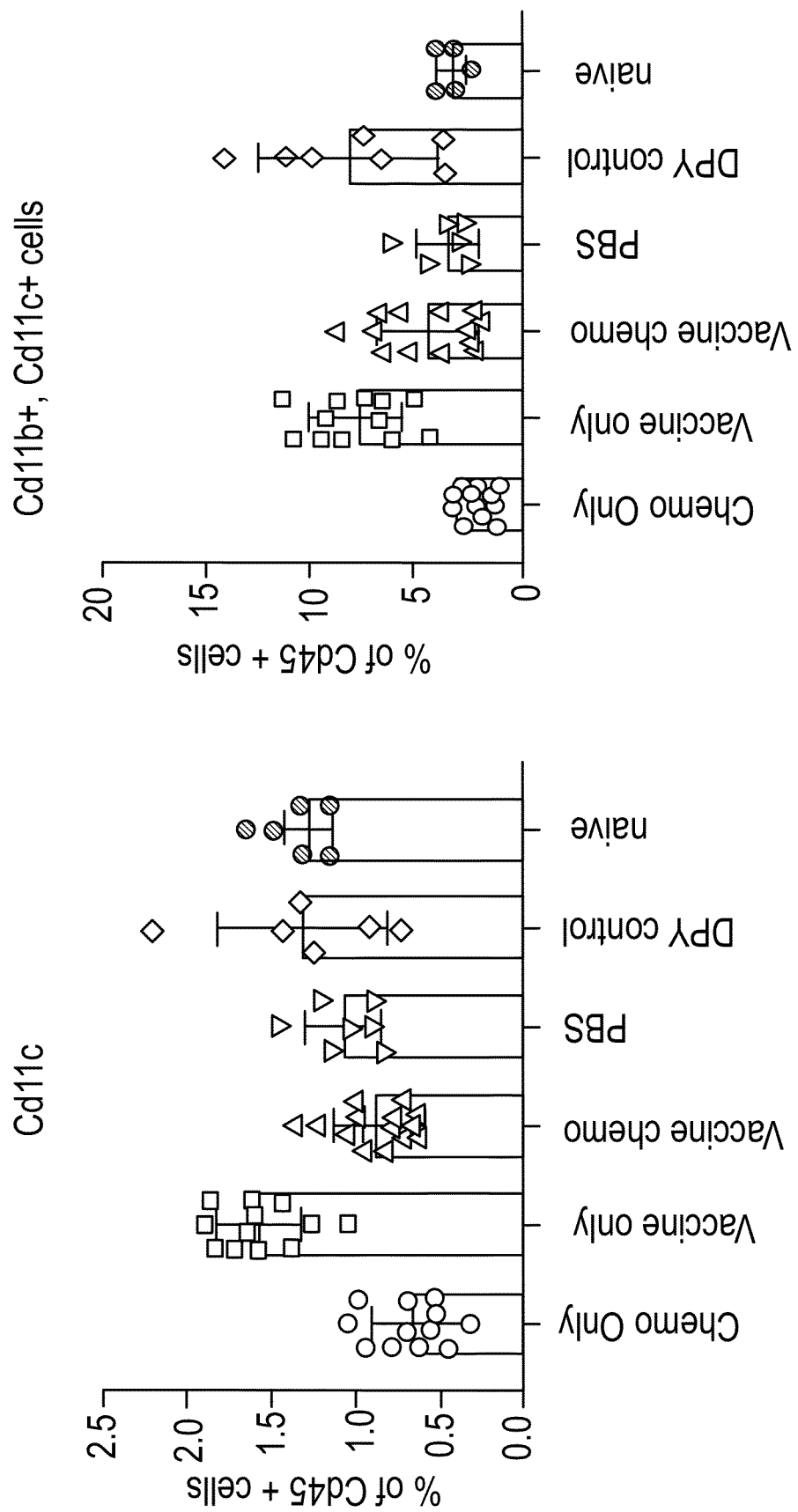
FIG. 25 shows graphs of the proportion of CD45$^+$ cells which are (a) CD11c, and (b) CD11b$^+$ and CD11c$^+$, for certain experimental treatments and controls.

FIGS. 24 and 25 show how mice treated with chemotherapy only or chemotherapy plus vaccine had lower MDSC frequency.

Figure 26:
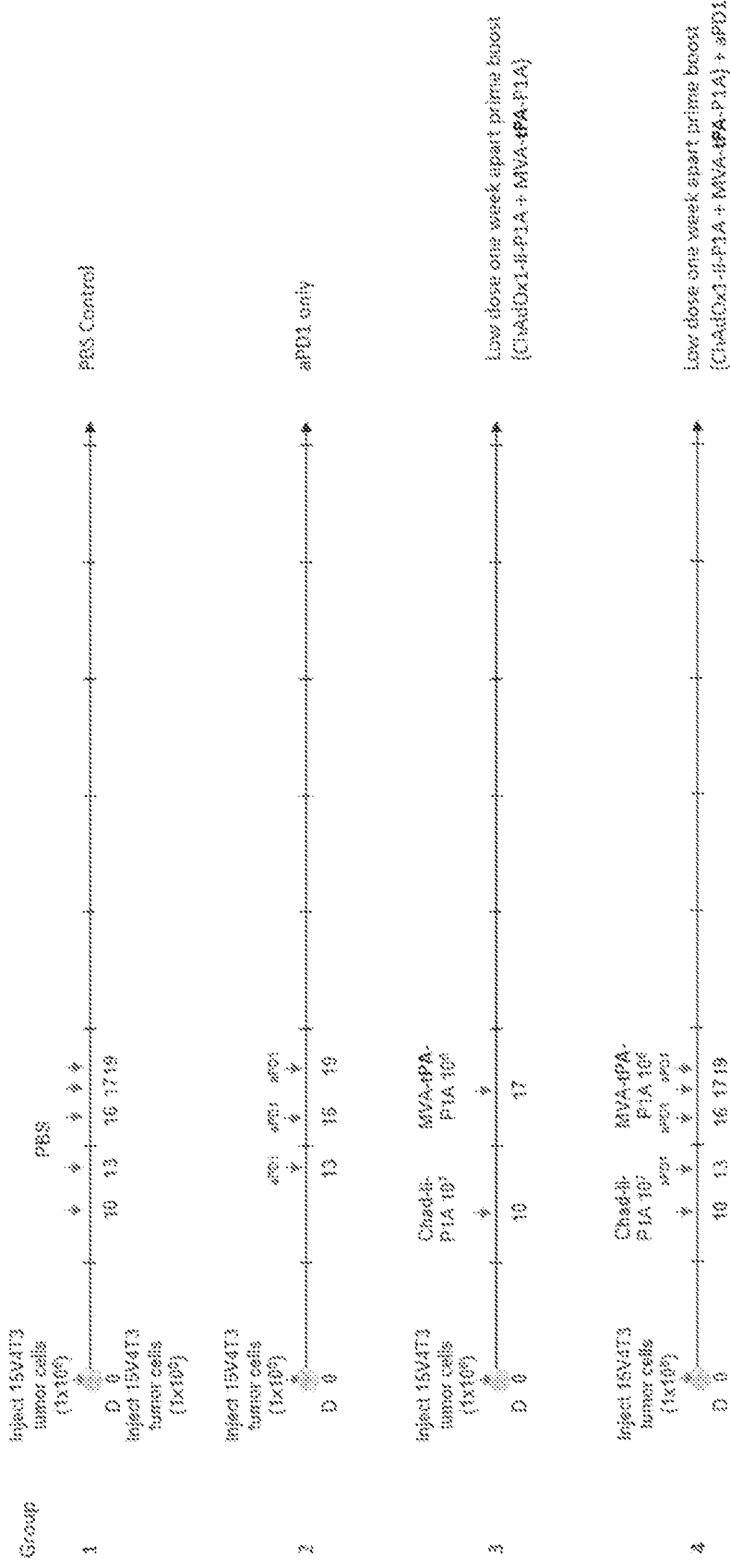
FIG. 26 shows the time line of vaccinations for PBS control, $\alpha$PD1 only, and two test groups of mice (1) a low dose one week apart prime boost (ChAdOx1-li-P1A+MVA-tPA-P1A) and (2) a low dose one week apart prime boost (ChAdOx1-li-P1A+MVA-tPA-P1A)+$\alpha$PD1.

Example 8: 15V4T3 Tumour in DBA/2 Mice—Vaccination with CPI Increases Tumour T Cell Infiltration 1 million 15V4T3 cells were injected subcutaneously in DBA/2 mice. The vaccination schedules are shown in FIG. 26 for PBS control, αPD1 only, and the two test groups of mice (1) a low dose one week apart prime boost (ChAdOx1-li-P1A+MVA-tPA-P1A) and (2) a low dose one week apart prime boost (ChAdOx1-li-P1A+MVA-tPA-P1A)+αPD1. Vaccination of mice was begun on day 10 after tumour implantation. CPI (αPD1) was given 3 days after prime, with 3 doses of 100 μg on day 13, 16 and 19 after tumour injection. All mice were bled on day 20 and sacrificed on day 21. The immune profiles of the tumour microenvironment were studied by FACS. The results are set forth in FIGS. 27-53.

Figure 27:
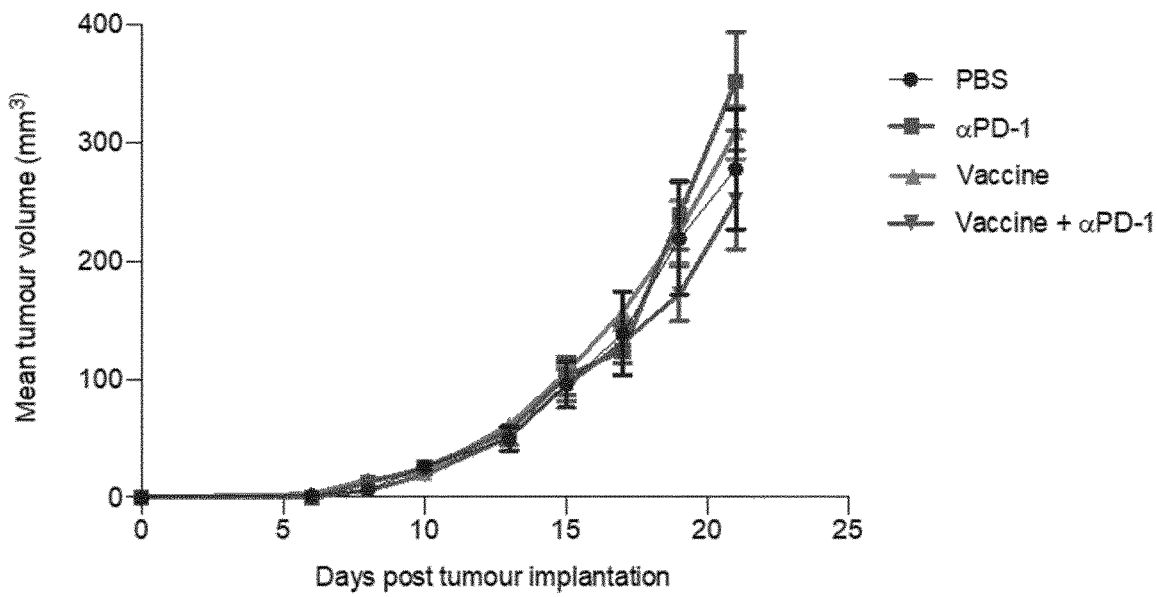
FIG. 27 shows the mean tumour volume over time for each of the experimental mice and controls shown in FIG. 26.
Figure 28:
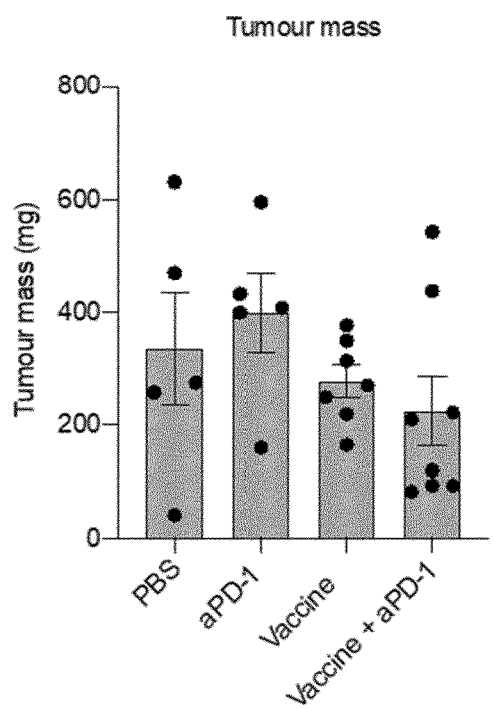
FIG. 28 is a chart showing the tumour mass for each of the experimental mice and controls shown in FIG. 26.

In more detail, FIG. 27 shows an even spread of tumour size in all groups of mice at sacrifice. FIG. 28 shows a reduction in tumour mass in a subset of mice in the vaccine+anti-PD-1 combination group, indicating beginnings of tumour clearance in these mice.

Figure 29:
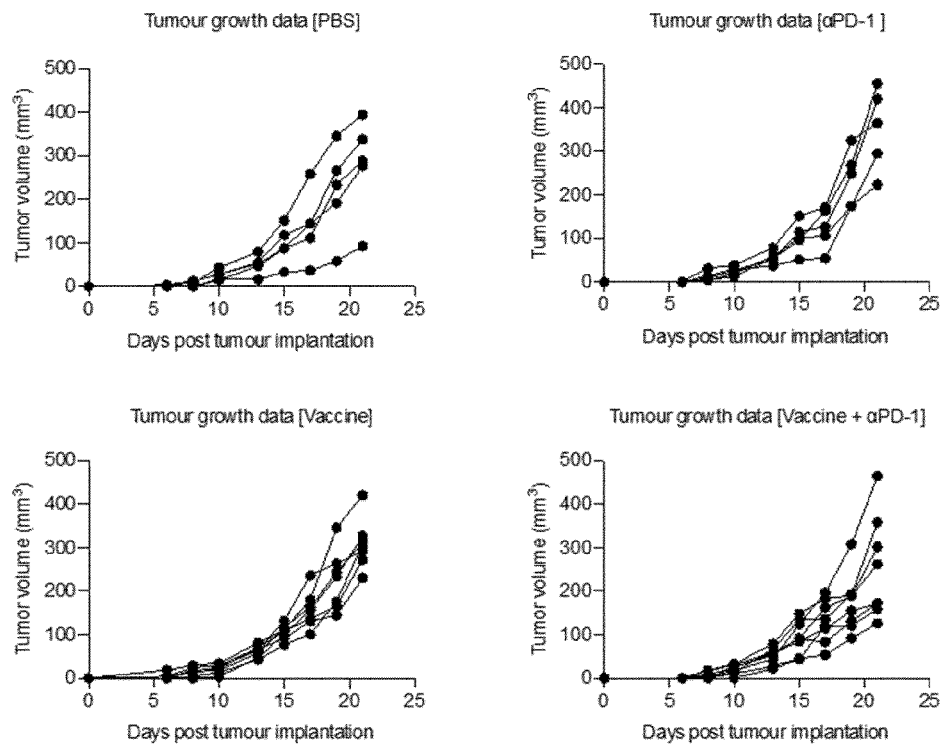
FIG. 29 are graphs of tumour growth rate data for each individual animal for each of the control and experimental groups as shown in FIGS. 25 to 28.

FIG. 29 shows individual tumour growth curves for each of the mice in each group.

Figure 30:
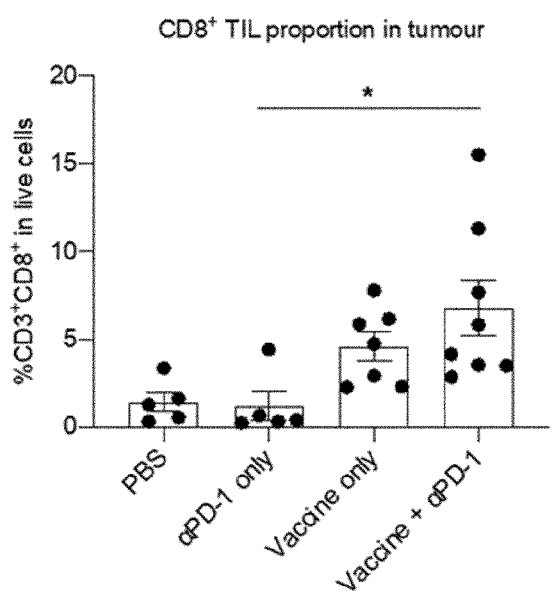
FIG. 30 is a chart showing the proportion of tumour infiltrating lymphocytes (TILs) as a proportion of total cells in tumours in each experimental and control group of mice.
Figure 31:
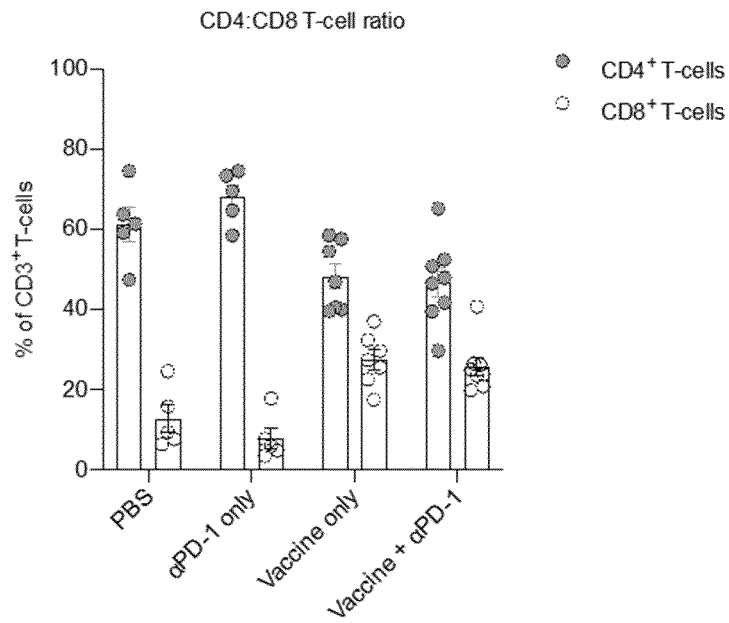
FIG. 31 is a chart showing the ratio of CD4:CD8 T cells in each of the experimental and control groups of mice.
Figure 32:
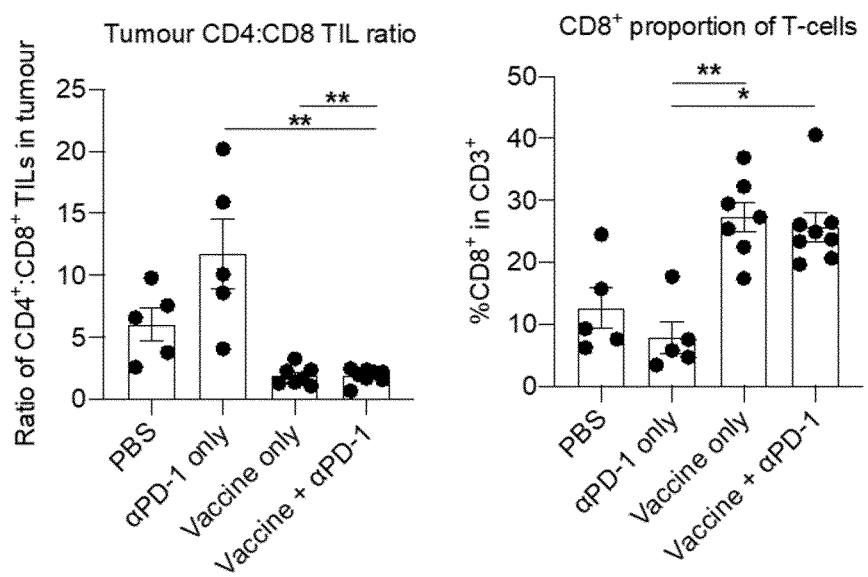
FIG. 32 shows charts of the ratio of the ratio of CD4$^+$:CD8$^+$ TILs in tumours in each of the experimental and control groups of mice (left hand chart); and the percentage of T cells which are CD8$^+$ cells (right hand chart).

FIG. 30 shows the percentage of $CD8^+$ tumour infiltrating lymphocytes (TILs) in the tumours of vaccine and control groups of mice. Vaccination increases $CD3^+CD8^+$ TILs as a proportion of total cells in the tumour.

Figure 33:
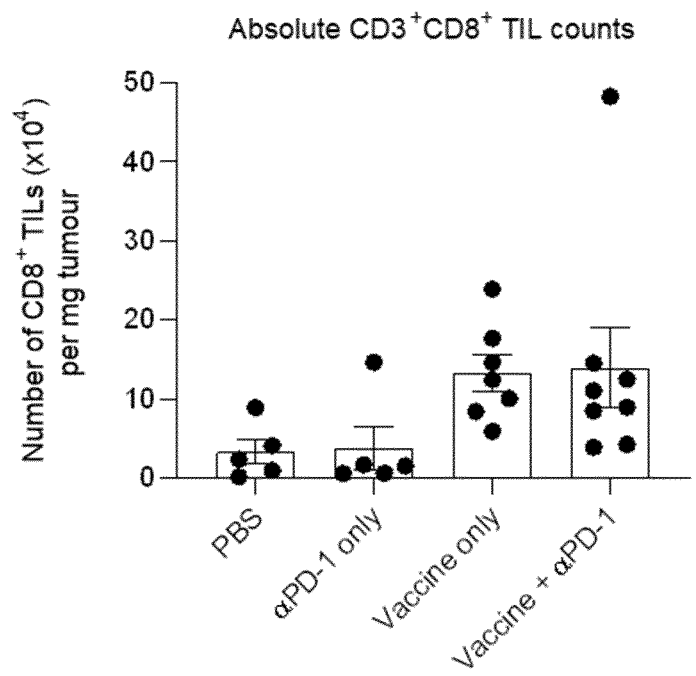
FIG. 33 is a chart showing the absolute number of CD3$^+$ CD8$^+$ TIL counts in each of the control and experimental mice groups.
Figure 34:
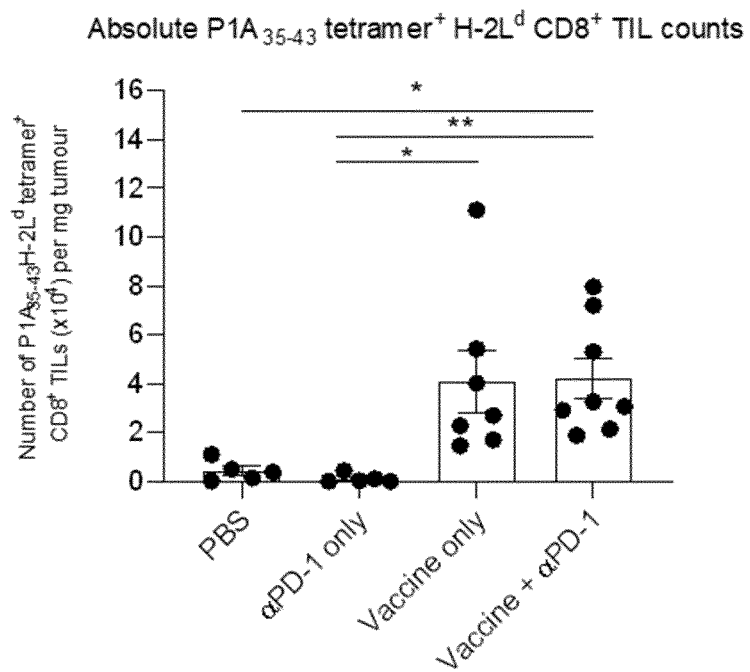
FIG. 34 is a chart showing the absolute P1A$_{35-43}$ tetramer$^+$ H-2L$^d$ CD8$^+$ TIL counts in each of the control and experimental mice groups.
Figure 35:
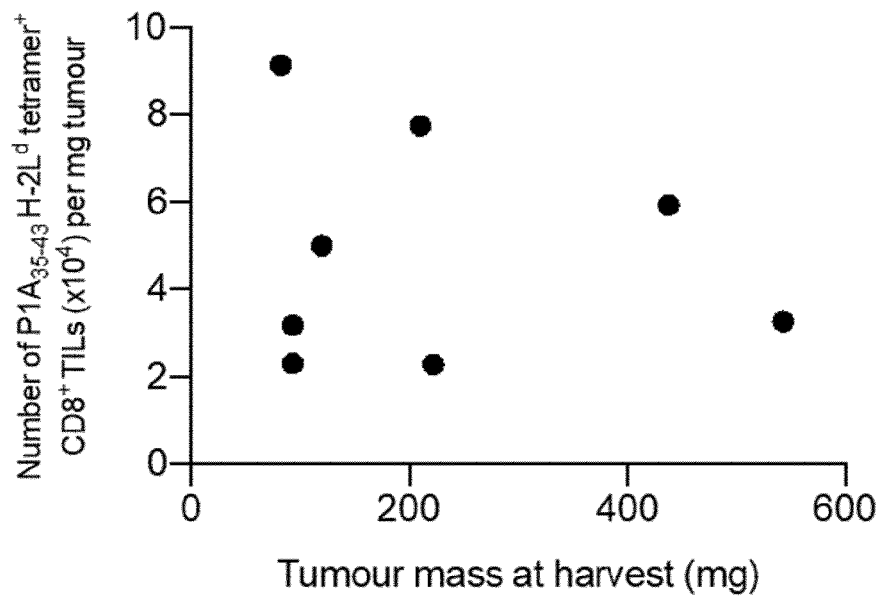
FIG. 35 is a diagram showing the correlation between P1A-specific CD8$^+$ TIL infiltrate and tumour mass at harvest.

FIGS. 33 and 34 show absolute TIL numbers calculated and normalized to cell number and tumour weight.

Figure 36:
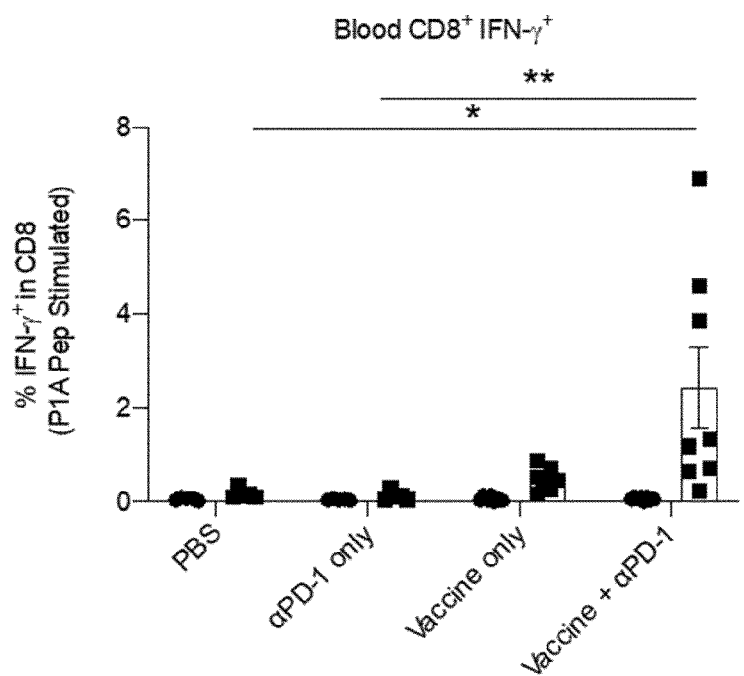
FIG. 36 and FIG. 37 are charts showing the CD8 response in blood of mice.
Figure 37:
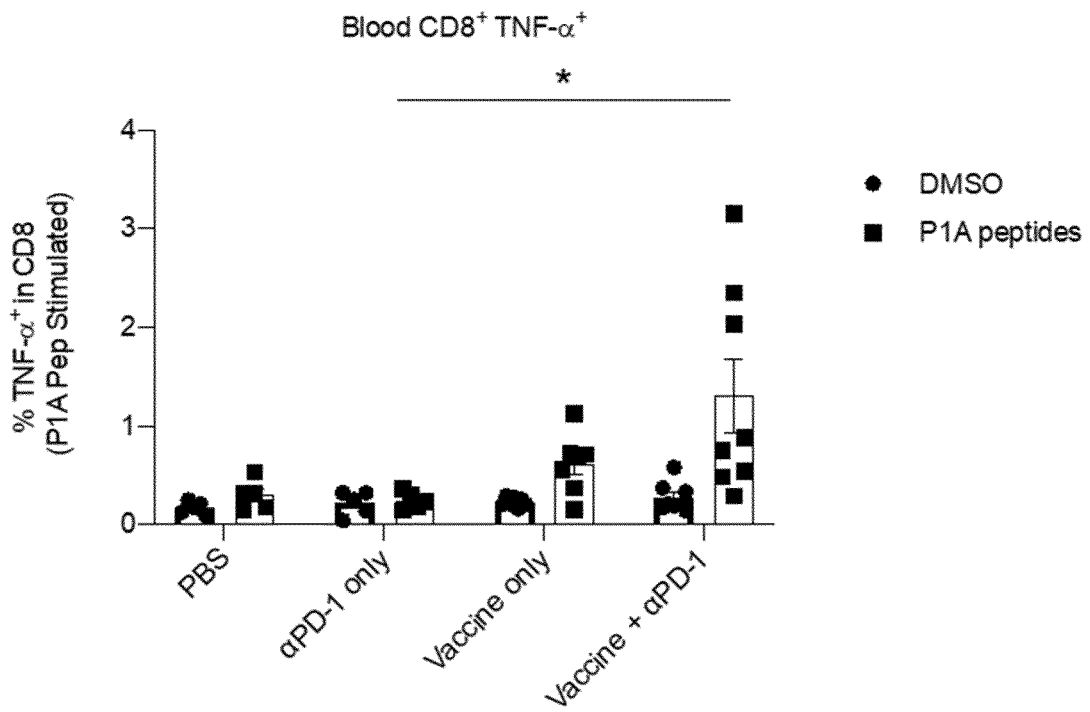
Figure 38:
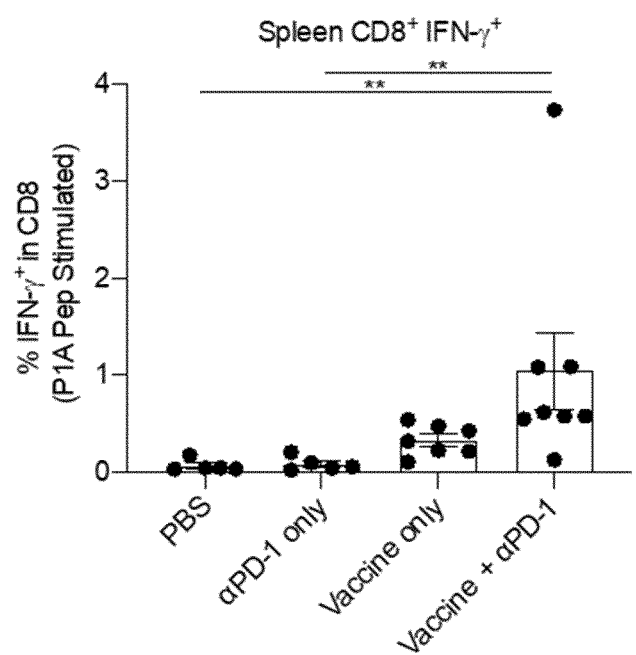
FIGS. 38-40 are charts of data showing the CD8 response in spleen of mice.
Figure 39:
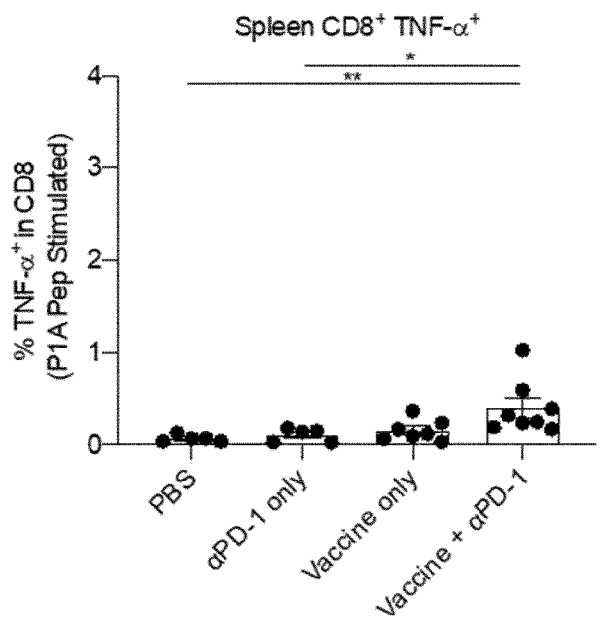
Figure 40:
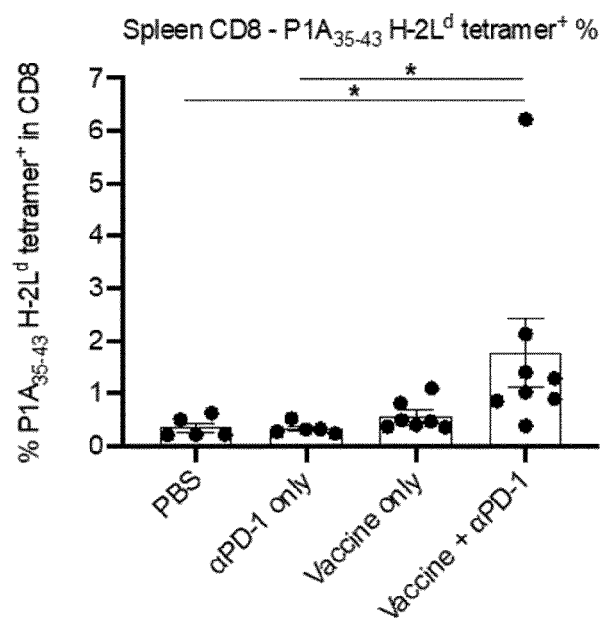
Figure 41:
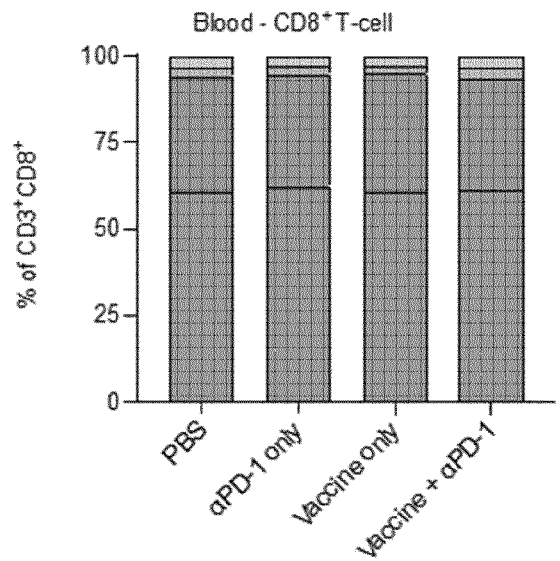
FIGS. 41-43 are bar charts of data showing T cell subset analysis. The legend to FIG. 43 applies to FIGS. 41 and 42.
Figure 42:
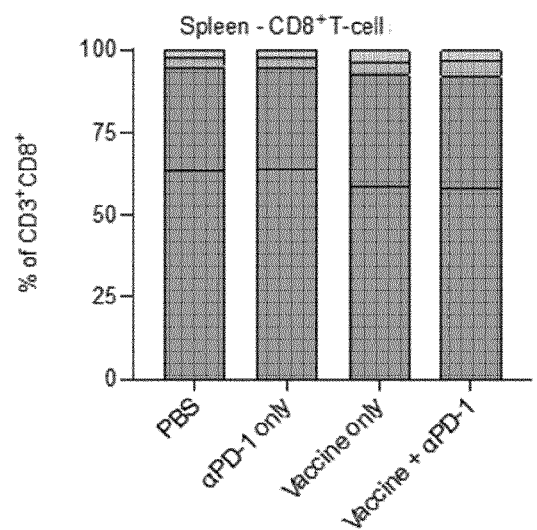
Figure 43:
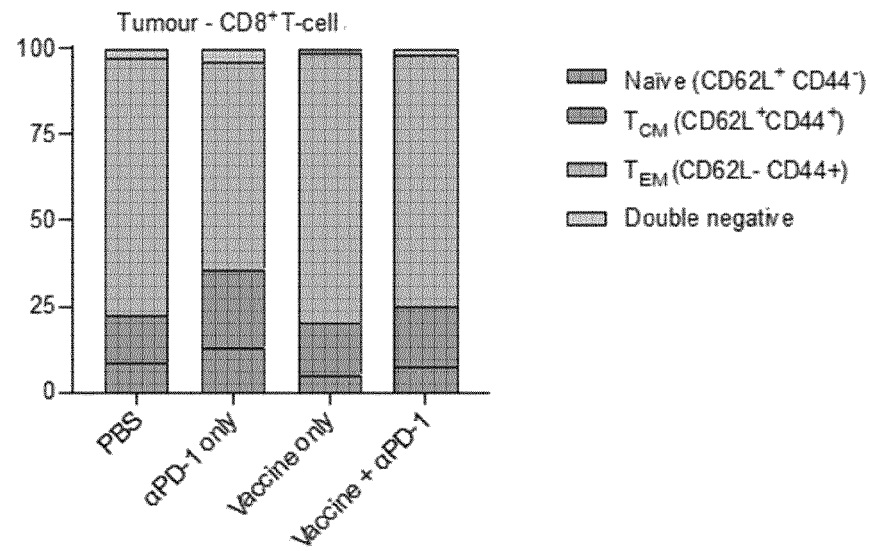
Figure 44:
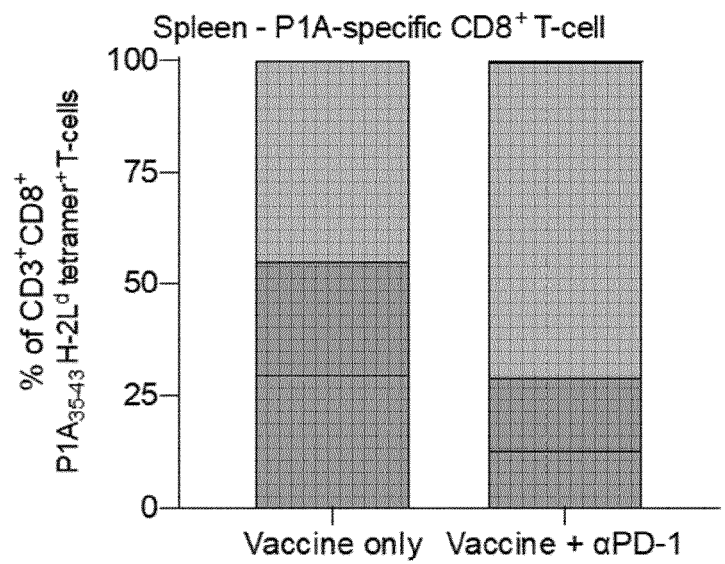
FIGS. 44 and 45 are bar charts of data showing further T cell subset analysis. The legend to FIG. 45 applies to FIG. 44.
Figure 45:
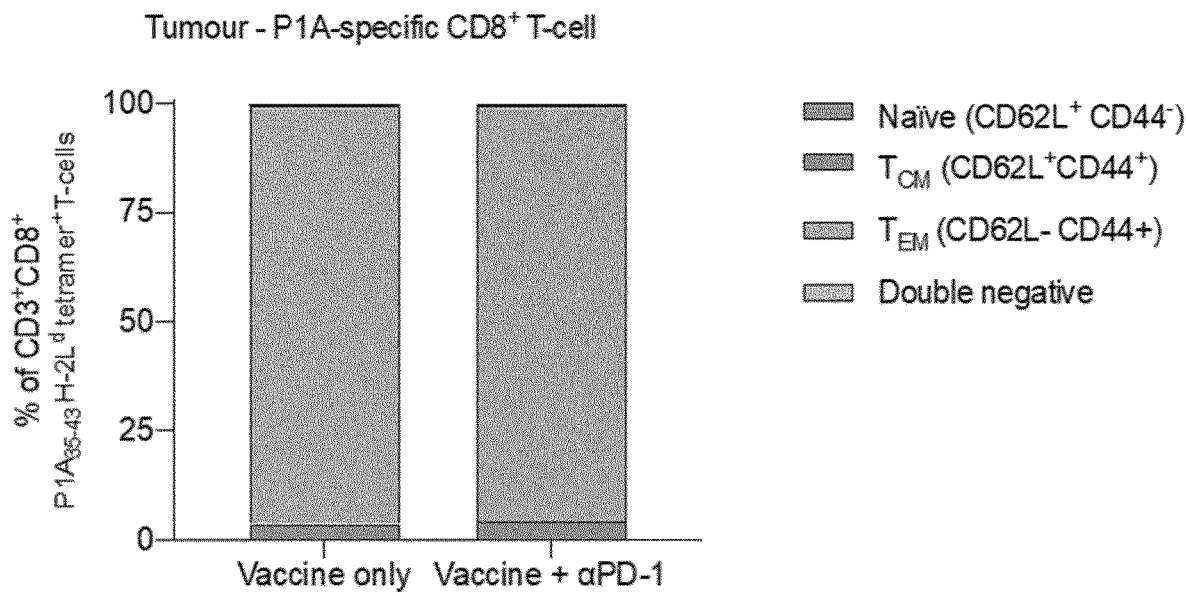

FIGS. 36 and 37 show how addition of αPD-1 treatment appears to boost P1A-specific response primed by ChAdOx/MVA vaccination when evaluated at an early time-point of day 11 post ChAdOx prime.

Figure 46:
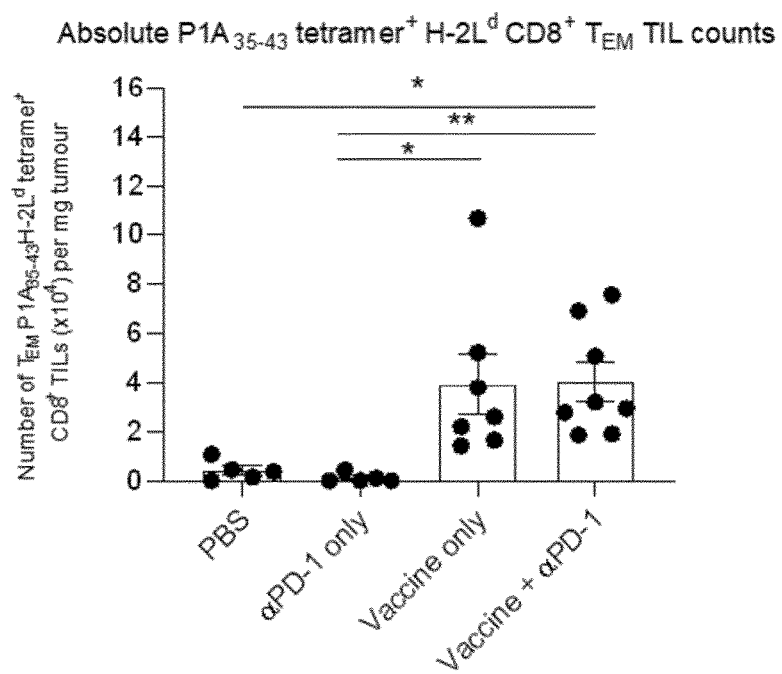
FIG. 46 shows further data of T cell-subset analysis.
Figure 47:
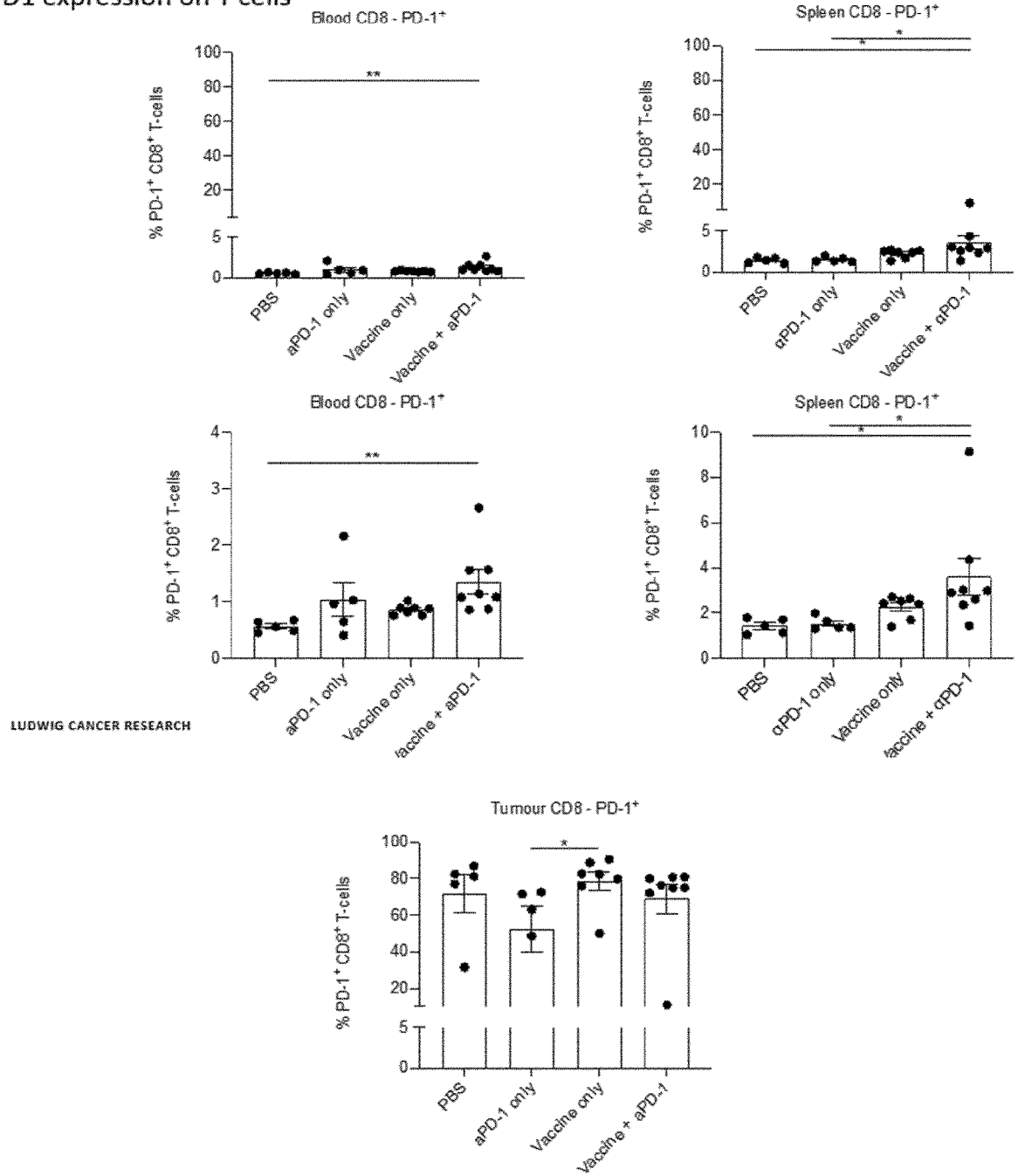
FIG. 47 shows charts of data for PD1 expression on T cells.
Figure 48:
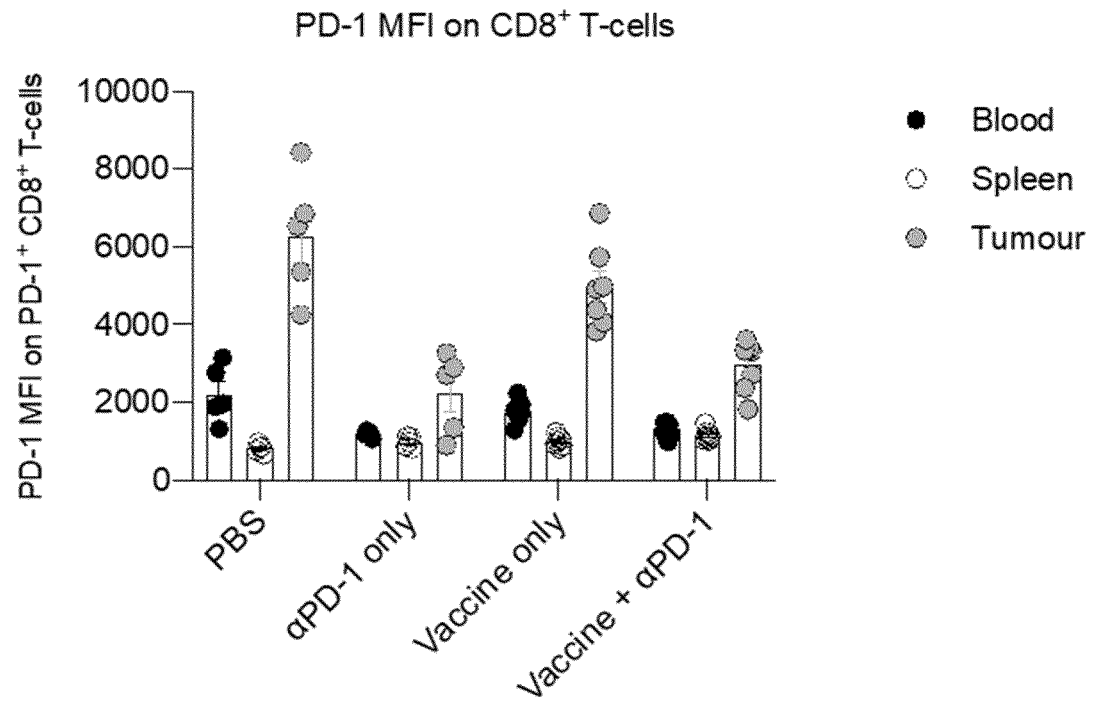
FIG. 48 shows further data for PD1 expression on T cells.
Figure 49:
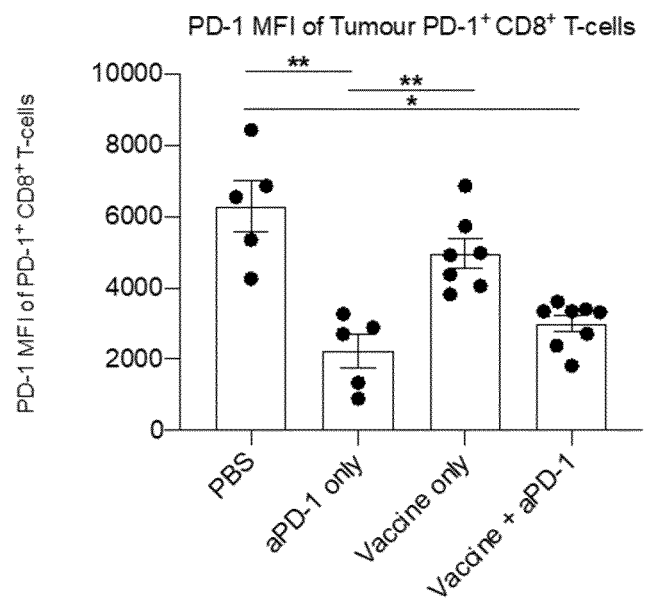
FIG. 49 shows further data for PD1 expression on T cells.
Figure 50:
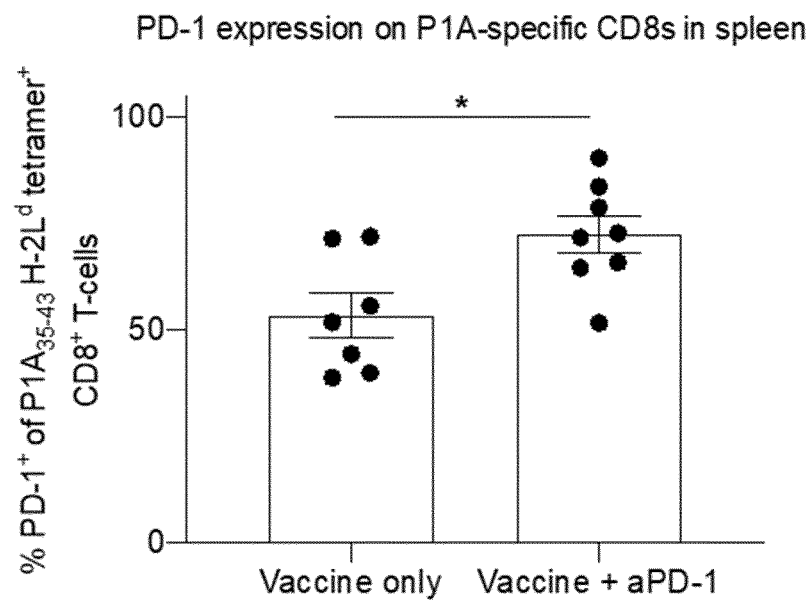
FIG. 50 shows a chart of data for PD1 expression on P1A-specific T cells.
Figure 51:
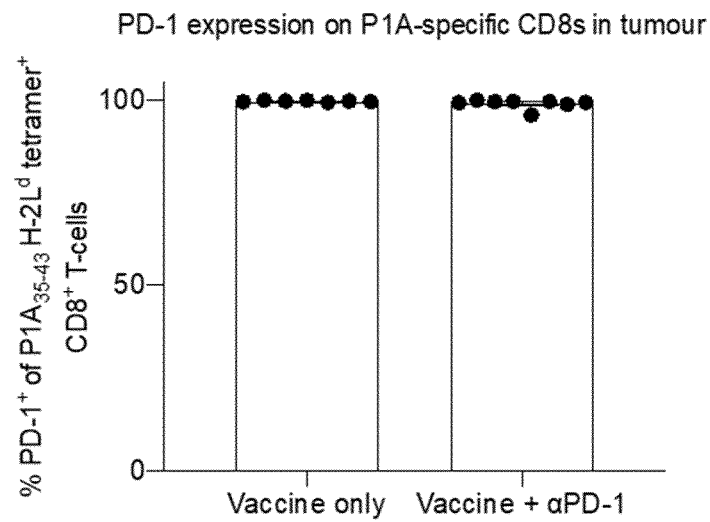
FIG. 51-53 show charts of further data for PD1 expression on P1A-specific T cells.
Figure 52:
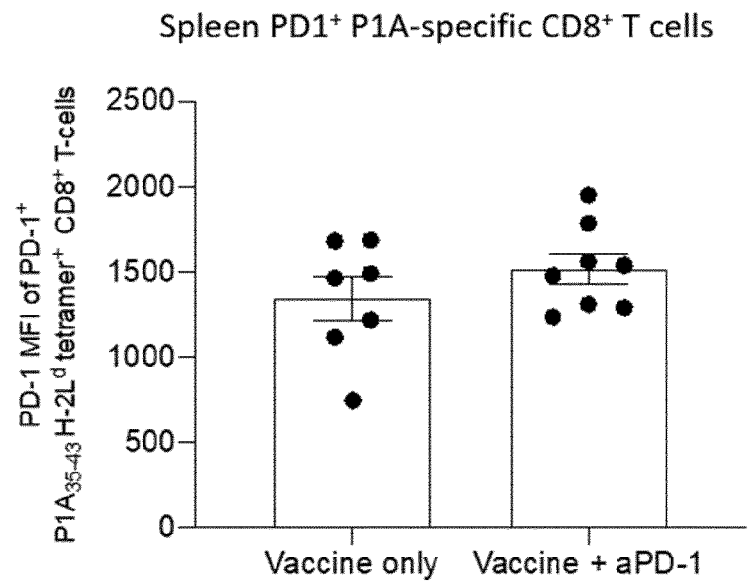
Figure 53:
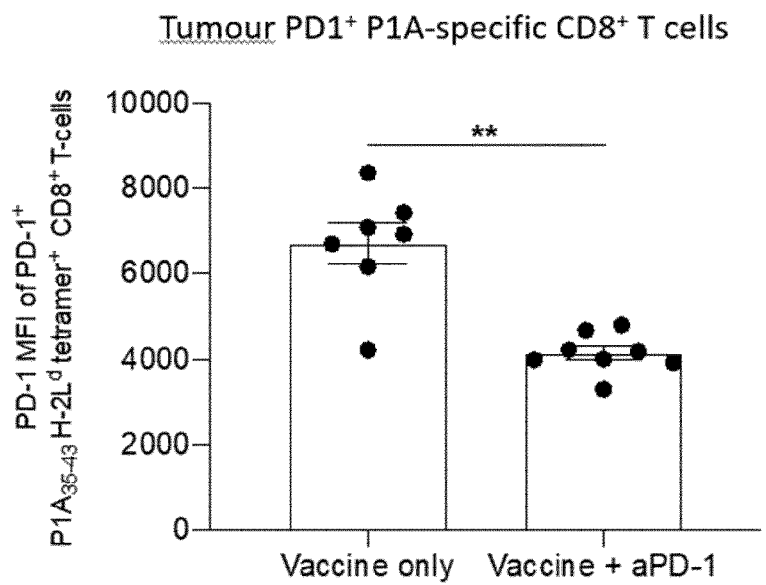

FIG. 46 shows how infiltration of P1A-specific $T_{EM}$ $CD8^+$s in the tumour follows the same pattern as P1A-specific CD8s.

Overall, the results of FIGS. 27-53 show how vaccine increases T cell infiltration of tumours, with an increase in $CD3^+CD8^+$ TIL and an increase in P1A-specific TIL in the vaccine groups of mice compared to controls.

Also, the $CD3^+CD8^+$ TIL are mainly effector memory cells $T_{EM}(CD62L^-CD44^+)$ and $T_{CM}(CD62L^+CD44^+)$.

Further, the P1A-specific TILs express PD-1 in the vaccine groups, but the expression decrease with αPD1 blockade.

Nucleotide and Amino Acid Sequences Referred to Herein

Certain proteins or polypeptides are referred to herein and reference nucleotide and/or amino acid sequences for these are provided in the accompanying sequence listing filed as part of the present description. Some of the sequences are annotated to provide further information as follows:

```
Human HLA class II histocompatibility antigen gamma chain (li)
UniProtKB/Swiss-Prot: P04233.3. The underlined sequence portions
represents the transmembrane domain used in vectors:
                                                       [SEQ ID NO: 6]
MHRRRSRSCR EDQKPVMDDQ RDLISNNEQL PMLGRRPGAP ESKCSRGALY

TGFSILVTLL LAGQATTAYF LYQQQGRLDK LTVTSQNLQL ENLRMKLPKP

PKPVSKMRMA TPLLMQALPM GALPQGPMQN ATKYGNMTED HVMHLLQNAD
```

PLKVYPPLKG SFPENLRHLK NTMETIDWKV FESWMHHWLL FEMSRHSLEQ

KPTDAPPKVL TKCQEEVSHI PAVHPGSFRP KCDENGNYLP LQCYGSIGYC

WCVFPNGTEV PNTRSRGHHN CSESLELEDP SSGLGVTKQD LGPVPM

Human Tissue-type plasminogen activator (tPA). The underlined
sequence portion shown is the leader sequence used in vectors.
[SEQ ID NO: 8]

<u>MDAMKRGLCCVLLLCGAVFVSPSQEIHARFRRGARSYQVI</u>CRDEKTQMIYQQHQSWLRP

VLRSNRVEYCWCNSGRAQCHSVPVKSCSEPRCFNGGTCQQALYFSDFVCQCPEGFAG

KCCEIDTRATCYEDQGISYRGTWSTAESGAECTNWNSSALAQKPYSGRRPDAIRLGLGN

HNYCRNPDRDSKPWCYVFKAGKYSSEFCSTPACSEGNSDCYFGNGSAYRGTHSLTESG

ASCLPWNSMILIGKVYTAQNPSAQALGLGKHNYCRNPDGDAKPWCHVLKNRRLTWEYC

DVPSCSTCGLRQYSQPQFRIKGGLFADIASHPWQAAIFAKHRRSPGERFLCGGILISSCWI

LSAAHCFQERFPPHHLTVILGRTYRVVPGEEEQKFEVEKYIVHKEFDDDTYDNDIALLQLK

SDSSRCAQESSVVRTVCLPPADLQLPDWTECELSGYGKHEALSPFYSERLKEAHVRLYP

SSRCTSQHLLNRTVTDNMLCAGDTRSGGPQANLHDACQGDSGGPLVCLNDGRMTLVGII

SWGLGCGQKDVPGVYTKVTNYLDWIRDNMRP

Polynucleotide construct for vector ChAdOx1 MAGE NYESO. MAGEA3
in underlined. Linker is in bold type. NY-ESO-1 is in italics.
[SEQ ID NO: 10]

<u>ATGCCCCTGGAACAGCGGAGCCAGCACTGCAAGCCTGAGGAAGGCCTGGAAGCCAG</u>

<u>AGGCGAAGCTCTGGGACTCGTGGGAGCACAGGCTCCAGCCACCGAAGAACAGGAAG</u>

<u>CCGCCAGCAGCAGCTCCACCCTGGTGGAAGTGACACTGGGCGAAGTGCCTGCCGCC</u>

<u>GAGTCTCCTGATCCTCCTCAGTCTCCTCAGGGCGCCAGCTCTCTGCCCACCACCATG</u>

<u>AACTACCCCCTGTGGTCCCAGTCCTACGAGGACAGCAGCAACCAGGAAGAAGAGGG</u>

<u>CCCCAGCACCTTCCCCGACCTGGAATCTGAATTCCAGGCCGCCCTGAGCCGGAAGG</u>

<u>TGGCCGAACTGGTGCACTTCCTGCTGCTGAAGTACCGGGCCAGAGAACCCGTGACC</u>

<u>AAGGCCGAGATGCTGGGCAGCGTCGTGGGCAACTGGCAGTACTTCTTCCCCGTGAT</u>

<u>CTTCTCCAAGGCCAGCTCCAGCCTGCAGCTGGTGTTCGGCATCGAGCTGATGGAAGT</u>

<u>GGACCCCATCGGACACCTGTACATCTTCGCCACCTGTCTGGGCCTGAGCTACGATGG</u>

<u>CCTGCTGGGCGACAACCAGATCATGCCCAAAGCCGGCCTGCTGATCATCGTGCTGG</u>

<u>CCATCATTGCCCGCGAGGGCGATTGTGCCCCCGAGGAAAAGATCTGGGAGGAACTG</u>

<u>AGCGTGCTGGAAGTGTTCGAGGGAAGAGAGGACTCCATCCTGGGCGACCCCAAGAA</u>

<u>GCTGCTGACCCAGCACTTCGTGCAGGAAAACTACCTGGAGTATAGACAGGTGCCCG</u>

<u>GCAGCGACCCTGCCTGCTACGAATTTCTGTGGGGCCCTAGAGCACTGGTGGAAACC</u>

<u>AGCTACGTGAAAGTGCTGCACCACATGGTCAAGATCAGCGGCGGACCCCACATCAG</u>

<u>CTACCCCCCTCTGCATGAATGGGTGCTGAGAGAGGGCGAGGAA</u>GGCGGAGGACCT

GGCGGAGGA*ATGCAGGCTGAAGGCAGAGGCACAGGCGGCTCTACAGGCGACGCTG*

*ATGGACCAGGCGGACCCGGAATTCCAGATGGCCCTGGCGGAAATGCTGGCGGGCCT*

*GGCGAAGCTGGCGCTACAGGCGGAAGAGGACCTAGAGGCGCTGGCGCCGCTAGAG*

*CTTCTGGACCAGGGGGAGGCGCTCCTAGAGGACCTCATGGCGGAGCTGCCTCTGGC*

*CTGAACGGCTGCTGTAGATGTGGCGCCAGAGGCCCCGAAAGCAGACTGCTGGAATT*

*CTACCTGGCCATGCCTTTCGCCACCCCCATGGAAGCTGAGCTGGCCAGAAGAAGCCT*

*GGCCCAGGACGCTCCTCCACTGCCTGTGCCAGGCGTGCTGCTGAAAGAATTCACCG*

```
-continued
TGTCCGGCAACATCCTGACCATCCGGCTGACAGCCGCCGACCACAGACAGCTGCAG

CTGAGCATCAGCAGCTGCCTGCAGCAGCTGTCCCTGCTGATGTGGATCACCCAGTGC

TTTCTGCCCGTGTTTCTGGCCCAGCCTCCTAGCGGACAGCGGAGATGA
```

Translated protein of ChAdOx1_MAGE_NYESO. MAGEA3 in underlined.
Linker is in bold. NY-ESO-1 is in italics:

[SEQ ID NO: 11]

MPLEQRSQHCKPEEGLEARGEALGLVGAQAPATEEQEAASSSSTLVEVTLGEVPAAESP

DPPQSPQGASSLPTTMNYPLWSQSYEDSSNQEEEGPSTFPDLESEFQAALSRKVAELVH

FLLLKYRAREPVTKAEMLGSVVGNWQYFFPVIFSKASSSLQLVFGIELMEVDPIGHLYIFAT

CLGLSYDGLLGDNQIMPKAGLLIIVLAIIAREGDCAPEEKIWEELSVLEVFEGREDSILGDPK

KLLTQHFVQENYLEYRQVPGSDPACYEFLWGPRALVETSYVKVLHHMVKISGGPHISYPP

LHEWVLREGEEGGGPGGGMQAEGRGTGGSTGDADGPGGPGIPDGPGGNAGGPGEAG

ATGGRGPRGAGAARASGPGGGAPRGPHGGAASGLNGCCRCGARGPESRLLEFYLAMP

FATPMEAELARRSLAQDAPPLPVPGVLLKEFTVSGNILTIRLTAADHRQLQLSISSCLQQLS

LLMWITQCFLPVFLAQPPSGQRR

Polynucleotide construct for vector ChAdOx1_hli_MAGE_NY-ESO-1.
li sequence in bold and italics type. MAGEA3 is underlined.
Sequence linker is in bold. NY-ESO-1 is in italics:

[SEQ ID NO: 12]

ATG *GGCGCCCTGTACACCGGCTTTAGCATCCTCGTGACCCTGCTGCTGGCCGGACA*

*GGTACCACCGCCTACTTTCTGTAC*CCCCTGGAACAGCGGAGCCAGCACTGCAAGC

CTGAGGAAGGCCTGGAAGCCAGAGGCGAAGCTCTGGGACTCGTGGGAGCACAGGC

TCCAGCCACCGAAGAACAGGAAGCCGCCAGCAGCTCTAGCACCCTGGTGGAAGTGA

CACTGGGCGAAGTGCCTGCCGCCGAGTCTCCTGATCCTCCTCAGTCTCCTCAGGGC

GCCAGCTCTCTGCCCACCACCATGAACTACCCCCTGTGGTCCCAGTCCTACGAGGAC

AGCAGCAACCAGGAAGAAGAGGGCCCCAGCACCTTCCCCGACCTGGAATCTGAATT

CCAGGCCGCCCTGAGCCGGAAGGTGGCCGAACTGGTGCACTTTCTGCTGCTGAAGT

ACCGGGCCAGAGAACCCGTGACCAAGGCCGAGATGCTGGGCAGCGTCGTGGGCAA

CTGGCAGTACTTCTTCCCCGTGATCTTCTCCAAGGCCAGCTCCAGCCTGCAGCTGGT

GTTCGGCATCGAGCTGATGGAAGTGGACCCCATCGGACACCTGTACATCTTCGCCAC

CTGTCTGGGCCTGAGCTACGATGGCCTGCTGGGCGACAACCAGATCATGCCCAAAG

CCGGCCTGCTGATCATCGTGCTGGCCATCATTGCCCGCGAGGGCGATTGTGCCCCC

GAGGAAAAGATCTGGGAGGAACTGAGCGTGCTGGAAGTGTTCGAGGGAAGAGAGGA

CTCCATCCTGGGCGACCCCAAGAAGCTGCTGACCCAGCACTTCGTGCAGGAAAACTA

CCTGGAGTATAGACAGGTGCCCGGCAGCGACCCTGCCTGCTACGAATTTCTGTGGG

GCCCTAGAGCACTGGTGGAAACCAGCTACGTGAAAGTGCTGCACCACATGGTCAAGA

TCAGCGGCGGACCCCACATCAGCTACCCCCCTCTGCATGAATGGGTGCTGAGAGAG

GGCGAGGAAGGCGGAGGACCTGGCGGAGGA*ATGCAGGCTGAAGGCAGAGGCACA*

*GGCGGCTCTACAGGCGACGCTGATGGACCAGGCGGACCCGGAATTCCAGATGGCCC*

*TGGCGGAAATGCTGGCGGGCCTGGCGAAGCTGGCGCTACAGGCGGAAGAGGACCT*

*AGAGGCGCTGGCGCCGCTAGAGCATCTGGACCAGGGGAGGCGCTCCTAGAGGAC*

*CTCATGGCGGAGCTGCCTCTGGCCTGAACGGCTGCTGTAGATGTGGCGCCAGAGGC*

*CCCGAAAGCAGACTGCTGGAATTCTACCTGGCCATGCCTTTCGCCACCCCCATGGAA*

*GCTGAGCTGGCCAGAAGAAGCCTGGCCCAGGACGCTCCTCCACTGCCTGTGCCAGG*

-continued

*CGTGCTGCTGAAAGAATTCACCGTGTCCGGCAACATCCTGACCATCCGGCTGACAGC*

*CGCCGACCACAGACAGCTGCAGCTGAGCATCAGCAGCTGCCTGCAGCAGCTGTCCC*

*TGCTGATGTGGATCACCCAGTGCTTTCTGCCCGTGTTTCTGGCCCAGCCTCCTAGCG*

*GACAGCGGAGATGA*

Translated protein sequence of ChAdOx1_hli_MAGE_NY-ESO-1.
li sequence in bold and italics type. MAGEA3 is underlined.
Linker is in bold. NY-ESO-1 is in italics:

[SEQ ID NO: 13]

M*GALYTGFSILVTLLLAGQATTAYFLY*PLEQRSQHCKPEEGLEARGEALGLVGAQAPAT

EEQEAASSSSTLVEVTLGEVPAAESPDPPQSPQGASSLPTTMNYPLWSQSYEDSSNQEE

EGPSTFPDLESEFQAALSRKVAELVHFLLLKYRAREPVTKAEMLGSVVGNWQYFFPVIFS

KASSSLQLVFGIELMEVDPIGHLYIFATCLGLSYDGLLGDNQIMPKAGLLIIVLAIIAREGDCA

PEEKIWEELSVLEVFEGREDSILGDPKKLLTQHFVQENYLEYRQVPGSDPACYEFLWGPR

ALVETSYVKVLHHMVKISGGPHISYPPLHEWVLREGEEGGGPGGG*MQAEGRGTGGSTG*

*DADGPGGPGIPDGPGGNAGGPGEAGATGGRGPRGAGAARASGPGGGAPRGPHGGAA*

*SGLNGCCRCGARGPESRLLEFYLAMPFATPMEAELARRSLAQDAPPLPVPGVLLKEFTV*

*SGNILTIRLTAADHRQLQLSISSCLQQLSLLMWITQCFLPVFLAQPPSGQRR\**

Polynucleotide construct for vector ChAdOx1_tPA_MAGE_NY-ESO-1.
tPA sequence in bold and italics type. MAGEA3 is underlined.
Linker is in bold. NY-ESO-1 is in italics:

[SEQ ID NO: 14]

ATG *GACGCCATGAAGCGGGGCCTGTGTTGCGTGCTGCTGCTGTGTGGCGCTGTGTT*

*CGTGTCCCCC*<u>CCACTGGAACAGAGAAGCCAGCACTGCAAGCCCGAGGAAGGCCTGG</u>

<u>AAGCCAGAGGCGAAGCTCTGGGACTCGTGGGAGCACAGGCTCCAGCCACCGAAGAA</u>

<u>CAGGAAGCCGCCAGCAGCTCTAGCACCCTGGTGGAAGTGACACTGGGCGAAGTGCC</u>

<u>TGCCGCCGAGTCTCCTGATCCTCCTCAGTCTCCTCAGGGCGCCAGCTCTCTGCCCAC</u>

<u>CACCATGAACTACCCCCTGTGGTCCCAGTCCTACGAGGACAGCAGCAACCAGGAAGA</u>

<u>AGAGGGCCCCAGCACCTTCCCCGACCTGGAATCTGAATTCCAGGCCGCCCTGAGCC</u>

<u>GGAAGGTGGCCGAACTGGTGCACTTCCTGCTGCTGAAGTACCGGGCCAGAGAACCC</u>

<u>GTGACCAAGGCCGAGATGCTGGGCAGCGTCGTGGGCAACTGGCAGTACTTCTTCCC</u>

<u>CGTGATCTTCTCCAAGGCCAGCTCCAGCCTGCAGCTGGTGTTCGGCATCGAGCTGAT</u>

<u>GGAAGTGGACCCCATCGGACACCTGTACATCTTCGCCACCTGTCTGGGCCTGAGCTA</u>

<u>CGATGGCCTGCTGGGCGACAACCAGATCATGCCCAAAGCCGGCCTGCTGATCATCG</u>

<u>TGCTGGCCATCATTGCCCGCGAGGGCGATTGTGCCCCCGAGGAAAAGATCTGGGAG</u>

<u>GAACTGAGCGTGCTGGAAGTGTTCGAGGGAAGAGAGGACTCCATCCTGGGCGACCC</u>

<u>CAAGAAGCTGCTGACCCAGCACTTCGTGCAGGAAAACTACCTGGAGTATAGACAGGT</u>

<u>GCCCGGCAGCGACCCTGCCTGCTACGAATTTCTGTGGGGCCCTAGAGCACTGGTGG</u>

<u>AAACCAGCTACGTGAAAGTGCTGCACCACATGGTCAAGATCAGCGGCGGACCCCACA</u>

<u>TCAGCTACCCACCTCTGCACGAATGGGTGCTGAGAGAGGGCGAAGAA</u>GGCGGAGGA

CCTGGCGGAGGA*ATGCAGGCTGAAGGCAGAGGCACAGGCGGCTCTACAGGCGACG*

*CTGATGGACCAGGCGGACCCGGAATTCCAGATGGCCCTGGCGGAAATGCTGGCGGG*

*CCTGGCGAAGCTGGCGCTACAGGCGGAAGAGGACCTAGAGGCGCTGGCGCCGCTA*

*GAGCATCTGGACCAGGGGGAGGCGCTCCTAGAGGACCTCATGGCGGAGCTGCCTCT*

*GGCCTGAATGGCTGCTGTAGATGTGGCGCCAGAGGCCCCGAAAAGCAGACTGCTGGA*

*ATTCTACCTGGCCATGCCTTTCGCCACCCCCATGGAAGCTGAGCTGGCCAGAAGAAG*

-continued

CCTGGCCCAGGACGCTCCTCCACTGCCTGTGCCAGGGGTGCTGCTGAAAGAATTCA

CCGTGTCCGGCAACATCCTGACCATCCGGCTGACAGCCGCCGACCACAGACAGCTG

CAGCTGAGCATCAGCAGCTGCCTGCAGCAGCTGTCCCTGCTGATGTGGATCACCCA

GTGCTTTCTGCCCGTGTTTCTGGCCCAGCCTCCTAGCGGACAGCGGAGATGA

Translated protein of ChAdOx1_tPA_MAGE_NY-ESO-1. tPA sequence in bold and italics type. MAGEA3 is underlined. Linker is in bold. NY-ESO-1 is in italics:

[SEQ ID NO: 15]

M*DAMKRGLCCVLLLCGAVFVSP*PLEQRSQHCKPEEGLEARGEALGLVGAQAPATEEQE

AASSSSTLVEVTLGEVPAAESPDPPQSPQGASSLPTTMNYPLWSQSYEDSSNQEEEGPS

TFPDLESEFQAALSRKVAELVHFLLLKYRAREPVTKAEMLGSVVGNWQYFFPVIFSKASS

SLQLVFGIELMEVDPIGHLYIFATCLGLSYDGLLGDNQIMPKAGLLIIVLAIIAREGDCAPEEK

IWEELSVLEVFEGREDSILGDPKKLLTQHFVQENYLEYRQVPGSDPACYEFLWGPRALVE

TSYVKVLHHMVKISGGPHISYPPLHEWVLREGEEGGGPGGG*MQAEGRGTGGSTGDAD*

*GPGGPGIPDGPGGNAGGPGEAGATGGRGPRGAGAARASGPGGGAPRGPHGGAASGL*

*NGCCRCGARGPESRLLEFYLAMPFATPMEAELARRSLAQDAPPLPVPGVLLKEFTVSGNI*

*LTIRLTAADHRQLQLSISSCLQQLSLLMWITQCFLPVFLAQPPSGQRR*

Polynucleotide construct for vector MVA_tPA_MAGEA3. tPA underlined:

[SEQ ID NO: 20]

<u>ATGGACGCCATGAAGCGGGGCCTGTGCTGCGTGCTGCTGCTGTGTGGCGCTGTGTT</u>

<u>CGTGTCCCCCC</u>ACTGGAACAGAGAAGCCAGCACTGCAAGCCCGAGGAAGGCCTGG

AAGCCAGAGGCGAAGCTCTGGGACTCGTGGGAGCACAGGCTCCAGCCACCGAAGAA

CAGGAAGCCGCCAGCAGCTCTAGCACCCTGGTGGAAGTGACACTGGGCGAAGTGCC

TGCCGCCGAGTCTCCTGATCCTCCTCAGTCTCCTCAGGGCGCCAGCTCTCTGCCCAC

CACCATGAACTACCCCCTGTGGTCCCAGTCCTACGAGGACAGCAGCAACCAGGAAGA

AGAGGGCCCCAGCACCTTCCCCGACCTGGAATCTGAATTCCAGGCCGCCCTGAGCC

GGAAGGTGGCCGAACTGGTGCACTTCCTGCTGCTGAAGTACCGGGCCAGAGAACCC

GTGACCAAGGCCGAGATGCTGGGCAGCGTCGTGGGCAACTGGCAGTACTTCTTCCC

CGTGATCTTCTCCAAGGCCAGCTCCAGCCTGCAGCTGGTGTTCGGCATCGAGCTGAT

GGAAGTGGACCCCATCGGACACCTGTACATCTTCGCCACCTGTCTGGGCCTGAGCTA

CGATGGCCTGCTGGGCGACAACCAGATCATGCCCAAAGCCGGCCTGCTGATCATCG

TGCTGGCCATCATTGCCCGCGAGGGCGATTGTGCCCCCGAGGAAAAGATCTGGGAG

GAACTGAGCGTGCTGGAAGTGTTCGAGGGAAGAGAGGACTCCATCCTGGGCGACCC

CAAGAAGCTGCTGACCCAGCACTTCGTGCAGGAAAACTACCTGGAGTATAGACAGGT

GCCCGGCAGCGACCCTGCCTGCTACGAATTTCTGTGGGGCCCTAGAGCACTGGTGG

AAACCAGCTACGTGAAAGTGCTGCACCACATGGTCAAGATCAGCGGCGGACCCCACA

TCAGCTACCCACCTCTGCACGAATGGGTGCTGCGGGAAGGCGAAGAGTGA

Translated protein of MVA_tPA_MAGEA3. tPA is underlined:

[SEQ ID NO: 21]

<u>MDAMKRGLCCVLLLCGAVFVSP</u>PLEQRSQHCKPEEGLEARGEALGLVGAQAPATEEQE

AASSSSTLVEVTLGEVPAAESPDPPQSPQGASSLPTTMNYPLWSQSYEDSSNQEEEGPS

TFPDLESEFQAALSRKVAELVHFLLLKYRAREPVTKAEMLGSVVGNWQYFFPVIFSKASS

SLQLVFGIELMEVDPIGHLYIFATCLGLSYDGLLGDNQIMPKAGLLIIVLAIIAREGDCAPEEK

-continued

IWEELSVLEVFEGREDSILGDPKKLLTQHFVQENYLEYRQVPGSDPACYEFLWGPRALVE

TSYVKVLHHMVKISGGPHISYPPLHEWVLREGEE

Polynucleotide construct for vector MVA_tPA_NYESO. tPA is
underlined:
[SEQ ID NO: 22]
<u>ATGGACGCCATGAAGCGGGGCCTGTGCTGCGTGCTGCTGCTGTGTGGCGCTGTGTT</u>

<u>CGTGAGCCCT</u>CAGGCCGAGGGAAGAGGCACAGGCGGATCTACAGGCGACGCTGAT

GGACCTGGCGGCCCTGGAATTCCTGATGGCCCAGGCGGAAATGCTGGCGGACCAG

GCGAAGCTGGCGCTACAGGCGGAAGAGGACCTAGAGGCGCTGGCGCCGCTAGAGC

TTCTGGACCTGGGGGAGGCGCTCCTAGAGGACCTCATGGCGGAGCTGCCTCTGGCC

TGAATGGCTGCTGTAGATGTGGCGCCAGAGGCCCCGAAAGCCGGCTGCTGGAATTC

TACCTGGCCATGCCCTTCGCCACCCCCATGGAAGCTGAGCTGGCCAGAAGAAGCCT

GGCCCAGGACGCTCCTCCACTGCCTGTGCCAGGGGTGCTGCTGAAAGAATTCACCG

TGTCCGGCAACATCCTGACCATCCGGCTGACAGCCGCCGACCACAGACAGCTGCAG

CTGAGCATCAGCAGCTGCCTGCAGCAGCTGTCCCTGCTGATGTGGATCACCCAGTGC

TTTCTGCCCGTGTTTCTGGCCCAGCCTCCTAGCGGCCAGCGGCGCTAA

Translated protein of MVA_tPA_NYESO. tPA is underlined:
[SEQ ID NO: 23]
<u>MDAMKRGLCCVLLLCGAVFVSPQAEGRGTGGSTGDADGPGGPGIPDGPGGNAGGPGE</u>

AGATGGRGPRGAGAARASGPGGGAPRGPHGGAASGLNGCCRCGARGPESRLLEFYLA

MPFATPMEAELARRSLAQDAPPLPVPGVLLKEFTVSGNILTIRLTAADHRQLQLSISSCLQ

QLSLLMWITQCFLPVFLAQPPSGQRR

Polynucleotide construct for vector ChAdOx1_mli_P1A. The li
sequence is underlined:
[SEQ ID NO: 28]
<u>ATGGGCGCTCTGTATACTGGCGTGTCCGTGCTGGTGGCCCTGCTGCTGGCTGGACA</u>

<u>GGCTACAACCGCCTACT</u>TCCTGTACAGCGACAACAAGAAGCCCGACAAGGCCCACTC

TGGCAGCGGCGGAGATGGCGACGGCAACAGATGTAACCTGCTGCACAGATACAGCC

TGGAAGAGATCCTGCCCTACCTGGGCTGGCTGGTGTTCGCCGTCGTGACAACAAGCT

TCCTGGCCCTGCAGATGTTCATCGACGCCCTGTACGAGGAACAGTACGAGAGGGAC

GTGGCCTGGATCGCCAGACAGAGCAAGAGAATGAGCAGCGTGGACGAGGACGAGG

ATGATGAGGACGACGAAGATGACTACTACGACGATGAGGATGACGACGACGACGCC

TTCTACGATGACGAGGACGATGAAGAGGAAGAACTGGAAAACCTGATGGACGACGAG

TCCGAGGATGAGGCCGAGGAAGAGATGAGCGTGGAAATGGGCGCTGGCGCCGAAG

AGATGGGAGCCGGCGCTAACTGTGCTTGCGTGCCAGGACACCACCTGAGAAAGAAC

GAAGTGAAGTGCCGGATGATCTACTTCTTCCACGACCCCAACTTTCTGGTGTCCATCC

CCGTGAACCCCAAAGAACAGATGGAATGCAGATGCGAGAACGCCGACGAAGAGGTG

GCCATGGAAGAAGAGAGGAAGAGGAAGAAGAAGAAGAAGAGGAAGAAATGGGCAA

CCCCGACGGCTTCAGCCCCTGA

Translated protein ChAdOx1_mli_P1A. The li sequence is underlined:
[SEQ ID NO: 29]
<u>MGALYTGVSVLVALLLAGQATTAYFLY</u>SDNKKPDKAHSGSGGDGDGNRCNLLHRYSLEE

ILPYLGWLVFAVVTTSFLALQMFIDALYEEQYERDVAWIARQSKRMSSVDEDEDDEDDED

-continued

DYYDDEDDDDDAFYDDEDDEEEELENLMDDESEDEAEEEMSVEMGAGAEEMGAGANC

ACVPGHHLRKNEVKCRMIYFFHDPNFLVSIPVNPKEQMECRCENADEEVAMEEEEEEEE

EEEEEEMGNPDGFSP

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A chimpanzee adenovirus (ChAd) vector or a modified vaccinia virus Ankara (MVA) vector encapsidating a nucleic acid molecule, the nucleic acid molecule comprising a polynucleotide sequence encoding (a) (i) a MAGE cancer antigen and/or NY-ESO-1 cancer antigen, or immunogenic fragments thereof; or (ii) a MAGE cancer antigen and/or LAGE1 cancer antigen, or immunogenic fragments thereof; and (b) a linker of between 5 and 9 amino acids which when expressed links the MAGE and NY-ESO-1, or MAGE and LAGE1 cancer antigens or fragments thereof, in either order, as a fusion protein, the polynucleotide sequence operably linked to expression control sequences which direct the translation, transcription and/or expression of the cancer antigen or fragment thereof in an animal cell as a fusion protein.

2. A ChAd or MVA vector as claimed in claim 1, wherein the MAGE antigen is MAGE A3 having an amino acid sequence of SEQ ID NO: 1 or a sequence of at least 46%; preferably at least 69%; more preferably at least 95% identity therewith; or any immunogenic fragment thereof.

3. A ChAd or MVA vector as claimed in claim 1, wherein the NY-ESO-1 cancer antigen has an amino acid sequence of SEQ ID NO: 3 or a sequence of at least 75%; preferably at least 76.7% identity therewith; or any immunogenic fragment thereof.

4. A ChAd or MVA vector as claimed in claim 1, wherein the LAGE1 cancer antigen has an amino acid sequence of SEQ ID NO: 5, or a sequence of at least 78%; preferably at least 97% identity therewith; or any immunogenic fragment thereof.

5. A ChAd or MVA vector as claimed in claim 1, wherein the polynucleotide sequence further encodes a human HLA class II histocompatibility antigen gamma chain (Ii) with an amino acid sequence of SEQ ID NO: 6 or a sequence of at least 79% identity therewith, or a fragment thereof, so that the cancer antigen is expressed in an animal cell as a fusion with Ii or fragment thereof, preferably wherein the fragment is a transmembrane domain; more preferably wherein the transmembrane domain comprises amino acid residues 30 to 55 or 30 to 61, even more preferably wherein the transmembrane domain has the amino acid sequence of SEQ ID NO: 7.

6. A ChAd or MVA vector as claimed in claim 1, wherein the polynucleotide sequence further encodes tPA with an amino acid sequence of SEQ ID NO: 8 or a sequence of at least 81% identity therewith, or a fragment thereof, so that the cancer antigen is expressed in an animal cell as a fusion with tPA or a fragment thereof, preferably wherein the fragment comprises a 21 amino acid leader sequence; more preferably the 21 amino acid leader sequence is SEQ ID NO: 9.

7. An MVA vector as claimed in claim 1, wherein the polynucleotide sequence encodes (i) a MAGE cancer antigen or immunogenic fragment thereof and/or an NY-ESO-1 cancer antigen or immunogenic fragment thereof, or (ii) a MAGE cancer antigen or immunogenic fragment thereof and/or a LAGE1 cancer antigen or immunogenic fragment thereof, expressed in an animal cell as a fusion protein, wherein at least one of the MAGE cancer antigen, NY-ESO-1 cancer antigen or LAGE1 cancer antigen is a fragment.

8. An MVA vector as claimed in claim 7, wherein the MAGE cancer antigen and NY-ESO-1 or MAGE cancer antigen and LAGE1 are immunogenic fragments.

9. A ChAd or MVA vector as claimed in claim 1, wherein the linker has the amino acid sequence GGGPGGG.

10. An immunogenic composition comprising a ChAd or MVA vector as claimed in claim 1.

11. A composition of claim 10 further comprising an adjuvant.

12. An isolated polynucleotide comprising a sequence encoding a ChAd or MVA vector of claim 1.

13. An isolated polynucleotide as claimed in claim 12, codon optimised for human codon usage.

14. A Bacterial Artificial Chromosome (BAC) clone comprising a polynucleotide of claim 12.

15. An isolated host cell comprising a ChAd and/or MVA vector as set forth in claim 1.

16. A method of preventing or treating cancer in an individual, comprising administering an effective amount of a ChAd vector and an MVA vector as set forth in claim 1, whereby the adaptive immune system of the individual is stimulated to provide an anti-cancer immune response.

17. A method of preventing or treating cancer as claimed in claim 16, wherein the administration of the ChAd and MVA vectors is carried out separately, sequentially or simultaneously.

18. A method as claimed in claim 16, further comprising administration of an effective amount of one or more checkpoint inhibitors.

19. A method as claimed in claim 18, wherein the checkpoint inhibitor is administered simultaneously, separately or concurrently with the ChAd and MVA vectors.

20. A method as claimed in claim 16, wherein the individual has received, is receiving or will receive a chemotherapy and/or radiotherapy treatment.

21. A method as claimed in claim 16, wherein the ChAd vector is administered first.

22. A method as claimed in claim 16, wherein the ChAd and MVA vectors are administered more than once each.

23. A method as claimed in claim 16, wherein the ChAd and MVA vectors are administered in alternation.

24. A method as claimed in claim 16, wherein the period of time between each administration of a vector is in the range 5 days to 8 weeks; preferably 1 week.

25. A method as claimed in claim 18, wherein the checkpoint inhibitor blocks PD-1, CTLA-4 or PD-L1.

26. A method as claimed in claim 18, wherein the checkpoint inhibitor is selected from nivolumab, pembrolizumab, ipilimumab, tremelimumab or atezolizumab, durvaliumab or avelumab.

27. A method as claimed claim 18, wherein the cancer is non-small cell lung cancer (NSCLC), melanoma, Hodgkin lymphoma, non-Hodgkin lymphoma, urinary tract (urothelial), bladder, small cell lung cancer, renal, head & neck, sarcoma, or breast.

28. The ChAd vector of claim 1 further comprising an adenoviral packaging signal sequence.

\* \* \* \* \*